United States Patent
Martin et al.

(10) Patent No.: US 9,267,130 B2
(45) Date of Patent: *Feb. 23, 2016

(54) POLYPEPTIDES HAVING NUCLEIC ACID BINDING ACTIVITY AND COMPOSITIONS AND METHODS FOR NUCLEIC ACID AMPLIFICATION

(75) Inventors: Patrick K. Martin, Redwood City, CA (US); David A. Simpson, Redwood City, CA (US); Christine D. Hardy, Hayward, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,476

(22) Filed: Sep. 13, 2012

(65) Prior Publication Data

US 2013/0089895 A1 Apr. 11, 2013

Related U.S. Application Data

(63) Continuation of application No. 12/545,782, filed on Aug. 21, 2009, now abandoned, which is a continuation of application No. 11/327,845, filed on Jan. 6, 2006, now abandoned.

(60) Provisional application No. 60/641,987, filed on Jan. 6, 2005, provisional application No. 60/699,975, filed on Jul. 15, 2005.

(51) Int. Cl.
| | |
|---|---|
| *C12N 9/96* | (2006.01) |
| *C07K 14/195* | (2006.01) |
| *C12N 9/12* | (2006.01) |
| *C12Q 1/68* | (2006.01) |

(52) U.S. Cl.
CPC ............... *C12N 9/96* (2013.01); *C07K 14/195* (2013.01); *C12N 9/1252* (2013.01); *C12Q 1/6813* (2013.01); *C12Q 1/6844* (2013.01); *C12Q 1/6846* (2013.01); *C07K 2319/71* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,118,801 A | 6/1992 | Lizardi et al. | |
| 5,185,444 A | 2/1993 | Summerton et al. | |
| 5,188,934 A | 2/1993 | Menchen et al. | |
| 5,312,728 A | 5/1994 | Lizardi et al. | |
| 5,366,860 A | 11/1994 | Bergot et al. | |
| 5,378,841 A | 1/1995 | Summerton | |
| 5,436,149 A | 7/1995 | Barnes | |
| 5,449,603 A | 9/1995 | Nielson et al. | |
| 5,466,591 A | 11/1995 | Abramson et al. | |
| 5,470,967 A | 11/1995 | Huie | |
| 5,538,848 A | 7/1996 | Livak et al. | |
| 5,605,824 A | 2/1997 | Nielson et al. | |
| 5,614,365 A | 3/1997 | Tabor et al. | |
| 5,646,019 A | 7/1997 | Nielson et al. | |
| 5,677,152 A | 10/1997 | Birch et al. | |
| 5,693,502 A | 12/1997 | Gold et al. | |
| 5,698,685 A | 12/1997 | Summerton et al. | |
| 5,719,262 A | 2/1998 | Buchardt et al. | |
| 5,763,173 A | 6/1998 | Gold et al. | |
| 5,773,257 A | 6/1998 | Nielson et al. | |
| 5,773,258 A * | 6/1998 | Birch et al. | 435/91.2 |
| 5,795,762 A | 8/1998 | Abramson et al. | |
| 5,800,996 A | 9/1998 | Lee et al. | |
| 5,817,781 A | 10/1998 | Swaminathan | |
| 5,834,285 A | 11/1998 | Comb et al. | |
| 5,847,162 A | 12/1998 | Lee et al. | |
| 5,863,727 A | 1/1999 | Lee et al. | |
| 5,874,557 A | 2/1999 | Gold et al. | |
| 5,925,517 A | 7/1999 | Tyagi et al. | |
| 5,936,087 A | 8/1999 | Benson et al. | |
| 5,945,526 A | 8/1999 | Lee et al. | |
| 5,948,666 A | 9/1999 | Callen et al. | |

(Continued)

FOREIGN PATENT DOCUMENTS

| | | |
|---|---|---|
| EP | 1154017 | 11/2001 |
| EP | 0547359 | 3/2002 |
| EP | 0745676 | 7/2003 |
| EP | 1934372 | 9/2006 |
| EP | 1934372 | 2/2013 |
| EP | 2208796 | 6/2014 |
| EP | 2813581 | 12/2014 |
| JP | 2009-520461 | 3/2009 |
| WO | 92/20702 | 11/1992 |
| WO | 97/45539 | 12/1997 |

(Continued)

OTHER PUBLICATIONS

Mai VQ et al. Small Abundant DNA Binding Proteins form the Thermoacidophilic Arachaeon Sulfolobus shibatae Constrain Negative DNA Supercoils. 1998. Journal of Bacteriology. 180(9):2560-2563.*

(Continued)

Primary Examiner — David J Steadman
Assistant Examiner — Paul Holland

(57) ABSTRACT

Polypeptides having nucleic acid binding activity are provided. Methods of using polypeptides having nucleic acid binding activity are provided. Fusion proteins and methods of using fusion proteins are provided. Fusion proteins comprising a polymerase and a nucleic acid binding polypeptide are provided. Fusion proteins comprising a reverse transcriptase and a nucleic acid binding polypeptide are provided. Methods are provided for amplifying a nucleic acid sequence using a fusion protein comprising a nucleic acid binding polypeptide and a polymerase. Methods are provided for amplifying a nucleic acid sequence using a fusion protein comprising a nucleic acid binding polypeptide and a reverse transcriptase.

18 Claims, 3 Drawing Sheets

(56) References Cited

U.S. PATENT DOCUMENTS

Figure 1:
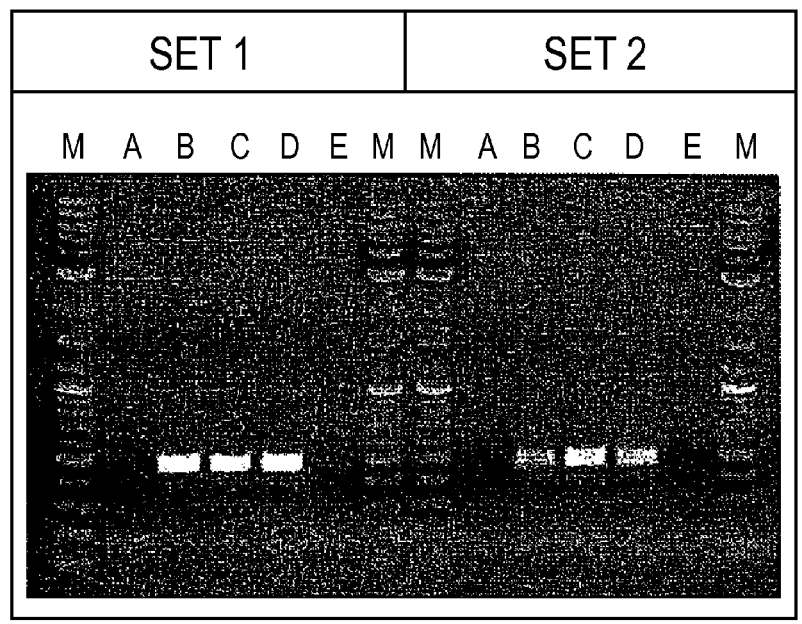

| | | | |
|---|---|---|---|
| 5,972,603 | A | 10/1999 | Bedford et al. |
| 5,990,479 | A | 11/1999 | Weiss et al. |
| 6,008,379 | A | 12/1999 | Benson et al. |
| 6,020,130 | A | 2/2000 | Gold et al. |
| 6,020,481 | A | 2/2000 | Benson et al. |
| 6,051,719 | A | 4/2000 | Benson et al. |
| 6,127,121 | A | 10/2000 | Meyer et al. |
| 6,140,500 | A | 10/2000 | Yan et al. |
| 6,143,877 | A | 11/2000 | Meyer et al. |
| 6,174,670 | B1 | 1/2001 | Wittwer et al. |
| 6,180,372 | B1 | 1/2001 | Franzen |
| 6,183,967 | B1* | 2/2001 | Jayasena et al. ............... 435/5 |
| 6,183,997 | B1 | 2/2001 | Hogrefe |
| 6,183,998 | B1 | 2/2001 | Ivanov et al. |
| 6,191,278 | B1 | 2/2001 | Lee et al. |
| 6,207,392 | B1 | 3/2001 | Weiss et al. |
| 6,214,557 | B1 | 4/2001 | Barnes et al. |
| 6,265,193 | B1 | 7/2001 | Brandis et al. |
| 6,270,967 | B1 | 8/2001 | Whitcombe et al. |
| 6,271,024 | B1 | 8/2001 | Sve et al. |
| 6,316,202 | B1 | 11/2001 | Barnes et al. |
| 6,333,159 | B1 | 12/2001 | Barnes et al. |
| 6,333,183 | B1 | 12/2001 | Evans et al. |
| 6,472,186 | B1 | 10/2002 | Quintanar et al. |
| 6,482,615 | B2 | 11/2002 | Tal et al. |
| 6,489,150 | B1 | 12/2002 | Mathur |
| 6,492,511 | B2 | 12/2002 | Callen et al. |
| 6,503,729 | B1 | 1/2003 | Bult et al. |
| 6,509,157 | B1 | 1/2003 | Martinez |
| 6,524,830 | B2 | 2/2003 | Kopf-Sill |
| 6,569,627 | B2 | 5/2003 | Wittwer |
| 6,627,424 | B1* | 9/2003 | Wang ............... 435/194 |
| 6,640,891 | B1 | 11/2003 | Oldenburg |
| 6,673,585 | B1 | 1/2004 | Querellou et al. |
| 6,787,338 | B2 | 9/2004 | Wittwer et al. |
| 6,814,934 | B1 | 11/2004 | Higuchi |
| 6,852,832 | B1 | 2/2005 | Kowalczykowski et al. |
| 7,541,170 | B2 | 6/2009 | Wang et al. |
| 7,666,591 | B2 | 2/2010 | Kowalczykowski et al. |
| 8,828,700 | B2 | 9/2014 | Lee et al. |
| 2002/0055149 | A1 | 5/2002 | Kopf-Sill |
| 2003/0022162 | A1 | 1/2003 | Hatakeyama |
| 2003/0092018 | A1 | 5/2003 | Chatterjee et al. |
| 2003/0162201 | A1 | 8/2003 | Chatterjee et al. |
| 2003/0180741 | A1* | 9/2003 | Hogrefe et al. ............... 435/6 |
| 2003/0207266 | A1 | 11/2003 | Chen et al. |
| 2003/0228616 | A1* | 12/2003 | Arezi et al. ............... 435/6 |
| 2004/0002076 | A1 | 1/2004 | Wang et al. |
| 2004/0005573 | A1 | 1/2004 | Fuller et al. |
| 2004/0180342 | A1 | 9/2004 | Haseltine et al. |
| 2004/0219558 | A1 | 11/2004 | Vander Horn et al. |
| 2005/0164265 | A1 | 7/2005 | Kowalczykowski et al. |
| 2007/0059713 | A1 | 3/2007 | Lee et al. |
| 2007/0092896 | A1 | 4/2007 | Shigemori et al. |
| 2010/0075382 | A1 | 3/2010 | Lee et al. |
| 2013/0089895 | A1 | 4/2013 | Martin et al. |
| 2014/0377810 | A1 | 12/2014 | Lee et al. |

FOREIGN PATENT DOCUMENTS

| | | |
|---|---|---|
| WO | 98/22489 | 5/1998 |
| WO | 99/14226 | 3/1999 |
| WO | 98/39352 | 7/2000 |
| WO | 00/55307 | 9/2000 |
| WO | 01/14568 | 3/2001 |
| WO | 01/38584 | 5/2001 |
| WO | 01/92501 A1 | 12/2001 |
| WO | 03/046149 | 6/2003 |
| WO | 2004/042086 | 5/2004 |
| WO | 2004/087868 | 10/2004 |
| WO | 2005/098042 | 10/2005 |
| WO | 2007/029200 A2 | 3/2007 |
| WO | 2007/029200 A9 | 3/2007 |
| WO | 2007/050125 A2 | 5/2007 |

OTHER PUBLICATIONS

Kellogg DE et al. TaqStart Antibody™: "Hot Start"PCR Facilitated by a Neutralizing Monoclonal Antibody Directed Against Taq DNA Polymerase. 1994. Biotechniques. vol. 16, No. 6. p. 1134-1137.*
Li Y et al. Structure-based design of Taq DNA polymerases with improved properties of dideoxynucleotide incorporation. 1999. Proc. Natl. Acad. Sci. vol. 96. p. 9491-9496.*
Bohlke K et al. Structure-based design of Taq DNA polymerases with improved properties of dideoxynucleotide incorporation. 2000. Nucleic Acids Research. vol. 28, No. 20. p. 3910-3917.*
ExPASy ProtParam Tool. Accessed Jan. 30, 2014. p. 1-2.*
Berg, JM et al. Biochemistry Fifth Edition, W.H. Freeman and Company, New York, 2002, pp. 176-177.*
UNIPROT:Q8ZSL4 Database accession No. Q8ZSL4 & Fitz-Gibbon et al: "Genome sequence of the hyperthermophilic crenarchaeon Pyrobaculum aerophilum" PNAS, National Academy of Science, US, vol. 99, No. 2, Jan. 22, 2002, Mar. 1, 2002, 1 page.
Afonina, I.A. et al., "Minor Groove Binder-Conjugated DNA Probes for Quantitative DNA Detection by Hybridization-Triggered Fluorescence", *BioTechniques*, vol. 32, 2002, 940-949.
Alba, et al., "Protein family review: Replicative DNA polymerases", *Genome Biology*, vol. 2, No. 1, Jan. 12, 2001, 3002.1-3002.4.
Antony, T. et al., "Selectivity of Polyamines on the Stability of RNA-DNA Hybrids Containing Phosphodiester and Phosphorothioate Oligodeoxyribonucleotides", *Biochemistry*, vol. 38, No. 33, American Chemical Society, Aug. 17, 1999, 10775-10784.
Arezi, Bahram et al., "Amplification efficiency of thermostable DNA polymerases" *Analytical Biochemistry*, vol. 321, Issue 2, Oct. 15, 2003, 226-235.
Balandina, A. et al., "The Bacterial Histone-like Protein HU specifically recognizes similar structures in all nucleic acids DNA, RNA, and their hybrids", *The Journal of Biological Chemistry*, vol. 277, No. 31, Society for Biochemistry and Molecular Biology, Inc., USA, Aug. 2, 2002, 27622-27628.
Barnes, "The Fidelity of Taq Polymerase Catalyzing PCR is Improved by an N-Terminal Deletion", *Gene*, vol. 112, No. 1, Mar. 1, 1992, 29-35.
Baumann, Herbert et al., "Solution structure and DNA-binding properties of a thermostable protein from the archaeon Sulfolobus solfataricus", *Nature Structural & Molecular Biology*, vol. 1, 1994, 808-819.
Blain, et al., "Nuclease Activities of Moloney Murine Leukemia Virus Reverse Transcriptase", *The Journal of Biological Chemistry*, vol. 268, No. 31, Nov. 5, 1993, 23585-23592.
Bochkarev, A. et al., "Structure of single-stranded-DNA-binding domain of replication protein A bound to DNA", *Nature*, vol. 385, Nature Publishing Group, 1997, 176-181.
Bochkareva, E. et al., "The RPA32 Subunit of Human Replication Protein A contains a Single-Stranded DNA-binding Domain", *J. Bio. Chem.*, vol. 273, American Society for Biochemistry and Molecular Biology, 1998, 3932-3947.
Braithwaite, D.K. et al., "Compilation, alignment, and phylogenetic relationships of DNA polymerases", *Nucleic Acids Research*, vol. 21, No. 4, Feb. 25, 1993, 787-802.
Briselden, Ann Marie et al., "Evaluation of Affirm VP Microbial Identification Test for Gardnerella vaginalis and Trichomonas vaginalis", *Journal of Clinical Microbiology*, vol. 32, No. 1, Jan. 1994, 148-152.
Bult, C.J., "NCBI Entrez, GenBank Report, accession No. F64444", 1996.
Bult, C.J. et al., "Complete Genome Sequence of the Methanogenic Archaeon, Methanococcus jannaschii", *Science*, vol. 273, American Association for the Advancement of Science, 1996, 1058-1073.
Büning, H. et al., "The histidine tail of recombinant DNA binding proteins may influence the quality of interaction with DNA", *Analytical Biochemistry*, vol. 234, Issue 2, Feb. 15, 1996, 227-230.
Chedin, Frederic et al., "Novel Homologs of Replication Protein A in Archaea: Implications for the Evolution of ssDNA-Bindeing Proteins", *Trends in Biochemical Science (TIBS)*, vol. 23, No. 8, Elsevier Science, Ltd.,, Aug. 1998, pp. 273-277.

(56) References Cited

OTHER PUBLICATIONS

Conrad, C. et al., "Both N-terminal catalytic and C-terminal RNA binding domain contribute to substrate specificity and cleavage site selection of RNase III", *FEBS Letters*, vol. 509, No. 1, Elsevier Science B.V., Nov. 30, 2001, 53-58.
Constans, A, "Some Like it Hot: A Thermal Cycler Roundup", *The Scientist*, vol. 15, Issue 24, Dec. 10, 2001, 4 pages.
Crasto, Chiquito J. et al., "LINKER: a program to generate linker sequences for fusion proteins", *Protein Engineering Design & Selection*, vol. 13, Issue 5, Oxford University Press, May 2000, 309-312.
Cubeddu, L. et al., "Structural and functional characterisatiion of Sulfolobus Solfataricus SSB and its interaction with DNA", *FASEB Summer Research Conference*, Federation of American Societies for Experimental Biology, 2002, 14.
Cubeddu, L. et al., "Structural and calorimetric studies of an archael single-stranded DNA binding protein", *European Conference of Current Trends in Microcalorimetry*, Applications of Biocaloimetry (ABC III) abstract, 1 pg., Dublin, Ireland, Aug. 27-30, 2002, 1.
Daimon, K. et al., "Three Proliferating Cell Nuclear Antigen-Like Proteins Found in the Hyperthermophilic Archaeon Aeropyrum pernix: Interactions with the Two DNA Polymerases", *Journal of Bacteriology*, vol. 184, No. 3, American Society for Microbiology, Feb. 2002, 687-694.
Derbyshire, Victoria et al., "[28] Structure-function analysis of 3'→5'-exonuclease of DNA polymerases", Methods in Enzymology, vol. 262, Academic Press, Inc., 1995, 363-385.
Dostal, L. et al., "Partial B-to-A DNA Transition upon Minor Groove Binding of Protein Sac7d Monitored by Raman Spectroscopy", *Biochemistry*, vol. 43, No. 30, American Chemical Society, Aug. 3, 2004, 9600-9609.
EP06795956.9; Extended European Search Report mailed Sep. 16, 2009, 8 pages.
EP09016058.1; Extended European Search Report mailed Oct. 4, 2010, 18 pages.
EP09016058.1; Partial European Search Report mailed Jun. 11, 2010, 6 pages.
Fairman, M.P. et al., "Cellular factors required for multiple stages of SV40 DNA replication in vitro", *The EMBO Journal*, vol. 7, IRL Press Ltd., 1988, 1211-1218.
Filee, et al., "Evolution of DNA Polymerase Familes: Evidences for Multiple Gene Exchange Between Cellular and Viral problems", *Journal of Molecular Evolution*, vol. 54, No. 6, 2002, 763-773.
Fitz-Gibbon, S. et al., "Genome Sequence of the Hyphertherophilic Crenarchaeon Pyrobaculum Aerophilum", *PNAS*. vol. 99, No. 2, Jan. 22, 2002, 984-989.
Fogg, Mark J. et al., "Structural basis for uracil recognition by archaeal family B DNA polymerases", *Nature Structural Biology*, vol. 9, No. 12, Dec. 2002, 922-927.
Freier, S. et al., "The ups and downs of nucleic acid duplex stability: structure-stability studies on chemically-modified DNA:RNA duplexes", *Nucleic Acids Research*, vol. 25, No. 22, 1997, 4429-4443.
Fujimori, Shizuyoshi et al., "Enantio-DNA Recognizes Complimentary RNA but Not Complementary DNA", *J. Am. Chem. Soc.*, vol. 112, 1990, pp. 7436-7438.
Gao, Yi-Gui et al., "The crystal structure of the hyperthermophile chromosomal protein Sso7d bound to DNA", *Nature Structural Biology*, vol. 5, No. 9, Nature America Inc., Sep. 1998, 782-786.
Garbesi, Anna et al., "L-DNAs as potential antimessenger oligonucleotides: a reassessment", *Nucleic Acids Research*, vol. 21, No. 18, 1993, 4159-4165.
Genbank, "paREP4 [Pyrobaculum aerophilum str. IM2].", Accession No. AAL64814, Downloaded at URL: http://www.ncbi.nlm.nih.gov/protein/AAL64814 on Feb. 21, 2013, Feb. 25, 2009, 1 page.
Gomes, X.V. et al., "Functional Domains of the 70-Kilodalton Subunit of Human Replication Protein A", *Biochemistry*, vol. 35, 1996, 10558-10568.
Grönlund, Hans, "Formation of disulfide bonds and homodimers of the major cat allergen Fel d 1 equivalent to the natural allergen by expression in *Escherichia coli*", *The Journal of of Biological Chemistry*, vol. 278, No. 41, The American Society for Biochemistry and Molecular Biology, Inc., Oct. 10, 2003, 40144-40151.
Guagliardi, A. et al., "Annealing of Complementary DNA Strands Above the Melting Point of the Duplex Promoted by an Archael Protein", *Journal of Molecular Biology*, vol. 267, No. 4. London, Great Britain, Apr. 11, 1997, 841-848.
Han, M. et al., "Quantum-dot-tagged microbeads for multiplexed optical coding of biomolecules", *Nature Biotechnology*, vol. 19, Jul. 2001, 631-635.
Hardy, C. et al., "Biochemical characterization of DNA-binding proteins from Pyrobaculum aerophilum and Aeropyrum pernix", *Extremophiles: Life Under Extreme Conditions*, vol. 12, No. 2, Mar. 2008, 235-246.
Haseltine, C.A. et al., "A Distinctive Single-Stranded DNA Binding Protein from the Archaeon Sulfolobus Solfataricus", *Mol. Microbiol.*, vol. 43, No. 6, 2002, 1505-1515.
Heid, et al., "Real Time Quantitative PCR", *Genome Research*, vol. 6, No. 10, Cold Spring Harbor Laboratory Press, Woodbury, NY, Oct. 1996, 986-994.
Henricksen, C. A. et al., "Phosphorylation of human replication protein A by the DNA-dependent protein kinase is involved in the modulation of DNA replication", *Nucleic Acids Research*, vol. 24, 1996, 3107-3112.
Hopfner, et al., "UniProt Accession P56689", Oct. 2004.
Ignatov, K.B. et al., "Substitution of Asn for Ser543 in the large fragment of Taq DNA polymerase increases for efficiency of synthesis of long DNA molecules", *FEBS Letters*, vol. 425, Federation of European Biochemical Societies, 1998, 249-250.
Inoue, Jin et al., "Improvements of Rolling Circle Amplification (RCA) Efficiency and Accuracy Using Thermus Thermophilus SSB Mutant Protein", *Nucleic Acids Research*, vol. 34, No. 9 e69, Apr. 19, 2006, 1-9.
Ito, et al., "Compilation and alignment of DNA polymerase sequences", *Nucleic Acids Research*, vol. 19, No. 15,, 1991, 4045-4057.
Jones, et al., "Synthesis and Binding Properties of Pyrimidine Oligodeoxynucleoside Analogs Containing Neutral Phosphodiester Replacements.", *J. Org. Chem.*, vol. 58, 1993, 2983-2991.
Kaiser, M.W. "A Comparison of Eubacterial and Archaeal Struture-specific 5'-Exonucleases", *The Journal of Biological Chemistry*, vol. 274, No. 30, The American Society for Biochemistry and Molecular Biology, Inc., USA, 1999, 21387-21394.
Kamashev, D. et al., "The histone-like protein HU binds specifically to DNA recombination and repair intermediates", *The EMBO Journal*, vol. 19, No. 23, European Molecular Biology Organization, Dec. 1, 2000, 6527-6535.
Kawarabayasi, Y. et al., "Complete Genome Sequence of an Aerobic Hyper-thermophilic Crenarchaeon, Aeropyrum pernix K1", *DNA Research*, vol. 6, No. 2, Universal Academy Press, Japan, Apr. 30, 1999, 83-101.
Kawasaki, A.M. et al., "Uniformly Modified 2'-Deoxy-2'-fluroro Phosphorothioate Oligonucleotides as Nuclease-Resistant Antisense Compounds with High Affinity and Specificity for RNA Targets", *Journal of Medicinal Chemistry*, vol. 36, No. 7, Apr. 2, 1993, 831-841.
Kelly, Thomas J. et al., "Identification and Characterization of a Single-Stranded DNA-Binding Protein From the Archaeon Methanococcus Jannaschii", *Proceedings of the National Academy of Sciences (PNAS)*, vol. 95, National Academy of Sciences of the USA, Dec. 1998, 14634-14639.
Kermekchiev, Milko B. et al., "Cold-sensitive mutants of Taq DNA polymerase provide a hot start for PCR", *Nucleic Acids Research*, vol. 31, No. 21, Oxford University Press, Nov. 1, 2003, 6139-6147.
Kerr, I.D. et al., "Insights into ssDNA recognitionby OB fold from a structural and thermodynamic study of Sulfolobus SSB protein", *EMBO J.*, vol. 22, Oxford University Press, 2003, 2561-2570.
Kerr, I.D. et al., "Overexpression,purification, crystallization and data collection of a single-stranded DNA-binding protein from Sulfolobus solfataricus", *Acta Cryst. D Biol. crystallogr.*, vol. 57, International Union of Crystallography, 2001, 1290-1292.
Kim, C. et al., "Binding Properties of Replication Protein A from Human and Yeast Cells", *Mol. Cell. Biol.*, vol. 12, American Society for Microbiology, 1992, 3050-3059.

(56) References Cited

OTHER PUBLICATIONS

Kim, C. et al., "Interactions of Human Replication Protein A with Oligonucleotides", *Biochemistry*, vol. 33, American Chemical Society, 1994, 14197-14206.

Klenk, H.P. et al., "The Complete Genome Sequence of the Hyperthermophilic, Sulphate-Reducing Archaeon Archaeoglobus Fulgidus", *Nature*, vol. 390, 1997, 364-370.

Kong, Huimin et al., "Characterization of a DNA polymerase from the hyperthermophile archaea Thermococcus litoralis Vent DNA polymerase, steady state kinetics, thermal stability, processivity, strand displacement, and exonuclease activities", *The Journal of Biological Chemistry*, vol. 268, No. 3, The American Society for Biochemistry and Molecular Biology, Inc, Jan. 25, 1993, 1965-1975.

Kricka, Larry, "Nucleic Acid Hybridization Test Formats: Strategies and Applications", *Nonisotopic DNA Probe Techniques*, Academic Press, Inc., 1992, 3-28.

Kuroita, et al., "Structural mechanism for coordination of proofreading and ploymerase activities in archael DNA polymerases", *Journal of Molecular Biology*, vol. 351, Issue 2, Aug. 12, 2005, 291-298.

Lawyer, et al., "Isolation, Characterization, and Expression in *Escherichia coli* of the DNA Polymerase Gene from Thermus aquaticus", *The Journal of Biological Chemistry*, vol. 264, No. 11, Apr. 15, 1989, 6427-6437.

Lin, Yi-Ling et al., "The Evolutionarily Conserved Zinc Finger Motif in the Largest Subunit of Human Replication Protein A is Required for DNA Replication and Mismatch Repair but not Nucleotide Excision Repair", *The Journal of Biological Chemistry*, vol. 273, American Society for Biochemistry and Molecular Biology, Jan. 15, 1998, 1453-1461.

Lin, Z. et al., "Multiplex Genotype Determination at a Large Number of Gene Loci", *Proceedings of the National Academy of Sciences of the United States*, vol. 93, No. 6, Genetics, USA,, Mar. 1996, 2582-2587.

Livak, Kenneth J. et al., "Oligonucleotides with Fluorescent Dyes at Opposite Ends Provide a Quenched Probe System Useful for Detecting PCR Product and Nucleic Acid Hybridization", *PCR Methods and Applications*, vol. 4, No. 6, Jun. 1995, 357-362.

Lohman, T.M. et al., "*Escherichia coli* Single-stranded DNA-Binding protein: Multiple DNA-Binding Modes and Cooperativities", *Annu. Rev. Biochem.*, vol. 63, 1994, 527-570.

Mai, Viet Q. et al., "Small Abundant DNA Binding Proteins from the Thermoacidophilic Archaeon Sulfolobus shibatae Constrain Negative DNA Supercoils", *Journal of Bacteriology*, vol. 180, No. 9, American Society for Microbiology, May 1998, 2560-2563.

McAfee, James G. et al., "Gene Cloning, Expression, and Characterization of the Sac7 Proteins from the Hyperthermophile Sulfolobus acidocaldarius", *Biochemistry*, vol. 34, No. 31, American Chemical Society, 1995, 10063-10077.

Medintz, Igor L. et al., "Quantum dot bioconjugates for imaging, labelling and sensing", *Nature Materials*, vol. 4, Jun. 2005, 435-446.

Mittal, Vivek, "Appendix 10: DNA Array Technology", *Molecular Cloning: A Laboratory Manual*, Third Edition, vol. 3, Cold Spring Harbor Laboratory Press, New York, 2001, A10.1-A10.19.

Moore, Pete, "PCR: Replicating success", *Nature*, vol. 435, May 12, 2005, 235-238.

Motz, M. et al., "Elucidation of an Archaeal Replication Protein Network to Generate Enhanced PCR Enzymes", *The Journal of Biological Chemistry*, vol. 277, No. 18, The American Society for Biochemistry and Molecular Biology, Inc., May 3, 2002, 16179-16188.

Ngo, J. et al., "Computational Complexity, Protein Structure Prediction, and the Levinthal Paradox", *in The Protein Folding Problem and Tertiary Structure Prediction*, Mertz et al., (editors), Birkhauser, 1994, 433, 492-495.

Nielsen, P. et al., "Sequence-Selective Recognition of DNA by Strand Displacement with a Thymine-Substituted Polyamide", *Science*, vol. 254, Dec. 6, 1991, 1497-1500.

Oshima, R.G., "Single-Stranded DNA Binding Protein Facilitates Amplification of Genomic Sequences by PCR", *BioFeedback*, vol. 13, No. 128, Circle Reader Service, Jan. 1, 1992, 188.

Pavlov, et al., "Recent developments in the optimization of thermostable DNA polymerases for efficient applications", *Trends in Biotechnology*, vol. 22, Issue 5, May 2004, 253-260.

PCT/US2006/000191; Invitation to pay Additional Fees mailed Sep. 26, 2006 with Annex to Form PCT/ISA/206 Communication Relating to the Results of the Partial International Search, 6 pages.

PCT/US2006/000191; International Preliminary Report on Patentability mailed Jul. 19, 2007, 16 pages.

PCT/US2006/000292; International Preliminary Report on Patentability mailed Jul. 19, 2007, 11 pages.

Pereira, Suzette et al., "Archaeal nucleosomes", *Proceedings of the National Academy of Sciences of the United States of America*, Microbiology, vol. 94, No. 23, Nov. 11, 1997, 12633-12637.

Philipova, D. et al., "A hierarchy of SSB promoters in replication protein A"*Genes Dev. 10:*, Cold Spring Harbor Laboratory Press, 1996, 2222-2233.

Pritham, et al., "Continuous Flouresecent Monitoring of Rapid Cycle Polymerase Chain Reaction", *Clinical Ligand Assay*, vol. 21, No. 4, 1998, 404-412.

Promega Corporation, "PCR Master Mix", Product Sheet, Part No. 9PIM750, USA, Apr. 2004, 2 pages.

Robinson, Howard et al., "The hyperthermophile chromosomal protein Sac7d sharply kinks DNA", *Nature*, vol. 392, Macmillan Publishers Ltd, Mar. 12, 1998, 202-205.

Rychlik, W. et al., "Optimization of the annealing temperature for DNA amplification in vitro", *Nucelic Acids Research*, vol. 18, No. 21, Oxford University Press, Nov. 11, 1990, 6409-6412.

Sambrook, Joseph et al., *Molecular Cloning: A Laboratory Manuel*, Third Edition, vol. 1, Cold Spring Harbor Laboratory Press, New York, 2001, 6.33-6.58.

Sambrook, Joseph et al., *Molecular Cloning: A Laboratory Manual*, Third Edition, vol. 2, Chapter 9, Protocols 13-16, Cold Spring Harbor Laboratory Press, New York, 2001, 9.62-9.75.

Sambrook, Joseph et al., "Cycle Sequencing: Dideoxy-mediated Sequencing Reactions Using PCR and End-labeled Primers", *Molecular Cloning: A Laboratory Manual*, Third Edition, vol. 2, Chapter 12, Protocol 6, Cold Spring Harbor Laboratory Press, New York, 2001, 12.51-12.60 and 12.94-12.114.

Sambrook, Joseph et al., "In Vitro Amplification of DNA by the Polymerase Chain Reaction", *Molecular Cloning: A Laboratory Manual*, Third Edition, vol. 2, Chapter 8, Cold Spring Harbor Laboratory Press, New York, 2001, 8.1-8.126.

Sancar, A. et al., "Sequences of the ssb gene and protein", *Proceedings of the National Academy of Sciences (PNAS)*, vol. 78, National Academy of Sciences, 1981, 4274-4278.

Santalucia, John, "A unified view of polymer, dumbbell, and oligonucleotide DNA nearest-neighbor thermodynamics", *Biochemistry*, vol. 95, Proceedings of the National Academy of Sciences, USA, Feb. 1998, 1460-1465.

Shamoo, Y. et al., "Crystal structure of a replication fork single-stranded DNA binding protein (T4 gp32) complexed to DNA", *Nature*, vol. 376, Nature Publishing Group, 1995, 362-366.

Shandilya, H. et al., "Thermophilic bacterial DNA polymerases with reverse-transcriptase activity", *Extremophiles*, vol. 8, No. 3, Springer-Verlag, Apr. 9, 2004, 243-251.

She, et al., "GenBank Accession AAK42515", Jun. 2004.

She, Q. et al., "The complete genome of the crenarchaeon Sulfolobus Solfataricus P2", *Proceedings of the National Academy of Sciences (PNAS)*, vol. 98, No. 14, Jul. 3, 2001, 7835-7840.

Shehi, Erlet et al., "Thermal Stability and DNA Binding Activity of a Variant Form of the Sso7d Protein from the Archeon Sulfolobus solfataricus Truncated at Leucine 54", *Biochemistry*, vol. 42, No. 27, American Chemical Society, Jul. 15, 2003, 8362-8368.

Shi, M. et al., "Enabling Large-Scale Pharmacogenetic Studies by High-Throughput Mutation Detection and Genotyping Technologies", *Clinical Chemistry*, vol. 47, No. 2, 2001, 164-172.

Shuttleworth, G. et al., "Recognition of the pro-mutagenic base uracil by family B DNA polymerases from archaea", *Journal of Molecular Biology*, vol. 337, Issue 3, Mar. 26, 2004, 621-634.

Singer, "UV spectral characteristics and acidic dissociation constants of 280 alkyl bases, nucleosides, and nucleotides", *Practical Handbook of Biochemistry and Molecular Biology*, 1989, 385-394.

(56) References Cited

OTHER PUBLICATIONS

Singleton, M.R. et al., "Conformational Changes Induced by Nucleotide Binding in Cdc6/ORC From Aeropyrum pernix", *Journal of Molecular Biology* vol. 343, No. 3, Elsevier Ltd., London, GB, Oct. 22, 2004, 547-557.

Smith, D.R. et al., "Complete Genome Sequence of Methanobacterium thermoautotrophicum ∆H: Functional Analysis and Comparative Genomics", *J. Bacteriol.*, vol. 179, American Society for Microbiology, 1996, 7135-7155.

Southworth, M. et al., "Cloning of thernostable DNA polymerases from hyperthermophilic marine Archaea with emphasis on *Thermococcus* sp. 9°N-7 and mutations affecting 3'-5' exonuclease activity", *Proceedings of the National Academy of Sciences of the United Staes of America*, Biochemistry, vol. 93, No. 11, May 28, 1996, 5281-5285.

Sreenivas, K. et al., "An Archaeal DNA Binding Protein from Thermophilic Sulfolobus Acidocaldarius Forms Diffrent Types of Complexes with DNA", *Biochem.Mol. Biol. Int.*, vol. 44, Academic Press Australia, 1998, 269-282.

Steitz, Thomas , "DNA Polymerases: Structural Diversity amd Common Mechanisms", *The Journal of Biological Chemistry*, vol. 274, No. 25, 1999, 17395-17398.

Stemmer, W.P. et al., "Single-Step Assembly of a Gene and Entire Plasmid from Large Numbers of Oligodeoxyribonucleotides", *Gene*, vol. 164, 1995, 49-53.

Stirchak, Eugene et al., "Uncharged Stereoregular Nucleic Acid Analogues. 1. Synthesis of a Cytosine-Containing Oligomer with Carbamate Internucleoside Linkages", *The Journal of Organic Chemistry*, vol. 52, No. 19, American Chemical Society, 1987, 4202-4206.

Sun, S. et al., "Biochemical and Structural Characterization of Interactions between DNA Polymerase and Single-Stranded DNA Binding Protein in Bacteriophage RB69", at URL=http://aca.hwi.buffalo.edu/ACA05/abstracts/text/W0359.pdf, downloaded Sep. 2, 2009, May 29, 2009, 1 page.

Sun, S. et al., "Biochemical Characterization of Interactions between DNA Polymerase and Single-stranded DNA-binding Protein in Bacteriophage RB69", *The Journal of Biological Chemistry*, vol. 278, No. 6, The American Society for Biochemistry and Molecular Biology, Inc., USA, Feb. 7, 2003, 3876-3881.

Sun, S. et al., "Structure and Enzymatic Properties of a Chimeric Bacteriophage RB69 DNA Polymerase and Single-Stranded DNA Binding Protein With Increased Processivity", *PROTEINS: Structure, Function and Bioinformatics*, vol. 65, No. 1, Wiley InterScience, Oct. 1, 2006, 231-238.

Takagi, Masahiro et al., "Characterization of DNA polymerase from *Pyrococcus* sp. strain KOD1 and its application to PCR", *Applied and Environmental Microbiology*, vol. 63, No. 11, American Society for Microbiology, Nov. 1997, 4504-4510.

Tatusova, Tatiana et al., "Erratum to "BLAST 2 Sequences, a new tool for comparing protein and nucleotide sequences"", *FEMS Microbiology Letters*, vol. 177, issue 1, Blackwell Publishing Ltd. Aug. 1, 1999, 187-188.

Telesnitsky, et al., "RNase H domain mutations affect the interaction between Moloney murine leukemia virus reverse transcriptase amd its primer-template", *Proceedings of the National Academy of Sciences*, vol. 90, No. 4, Feb. 15, 1993, 1276-1280.

Urata, Hidehito et al., "Spectroscopic Characterization of Heterochiral DNAs", *Nucleic Acids Synposium Series No. 29*, No. 29, 1993, 69-70.

Vainshtein, et al., "Peptide rescue of an N-terminal truncation of the Stoffel fragment of Taq DNA polymerase", *Protein Science*, vol. 5, Issue 9, The Protein Society, Sep. 1996, 1785-1792.

Vasseur, Jean et al., "Oligonucleosides: Synthesis of a Novel Methylhydroxylamine-Linked Nucleoside Dimer and Its Incorporation into Antisense Sequences", *Journal of the American Chemical Society*, vol. 114, American Chemical Society, May 1992, 4006-4007.

Wadsworth, R.I. et al., "Identification and properties of the crenarchaeal single-stranded DNA binding protein from Sulfolobus solfataricus", *Nucl. Acids Res.*, vol. 29, 2001, 914-920.

Walsh, P. et al., "Sequence analysis and characterization of stutter products at the tetranucleotide repeat locus vWA", *Nucleic Acids Research*, vol. 24, No. 14, 1996, 2807-2812.

Wang, Y. et al., "A novel strategy to engineer DNA polymerases for enhanced processivity and improved performance in vitro", *Nucleic Acids Research*, vol. 32, No. 3, Oxford University Press, Jan. 1, 2004, 1197-1207.

Whitcombe, D. et al., "Detection of PCR products using self probing amplicons and fluorescence", *Nature Biotechnology*, vol. 17, No. 8, Nature Publishing Group, Aug. 1999, 804-807.

White, M.F. et al., "Holding it together: chromatin in the Archaea", *TRENDS in Genetics*, vol. 18, No. 12, Elsevier Science, B.V. Amsterdam, NL, Dec. 2002, 621-626.

Witt, Armin et al., "DNA Hybridization Test: Rapid Diagnostic Tool for Excluding Bacterial Vaginosis in Pregnant Women with Symptoms Suggestive of Infection", *Journal of Clinical Microbiology*, vol. 40, No. 8, American Society for Microbiology, Aug. 2002, 3057-3059.

Wold, M.S. et al., "Replication Protein A: A Heterotrimeric, Single-Stranded DNA-Binding protein Required for Eukaryotic DNA Metabolism", *Annu. Rev. Biochem.*, vol. 66, Annual Reviews, Inc., 1997, 61-92.

EP14172370 ; European Search Report mailed Nov. 14, 2014, 19 Pages.

Fitz-Gibbon, S. et al., "SubName: Full=PaREP4", Mar. 1, 2002, 1 page.

Kainz, Peter et al., "Specificity-Enhanced Hot-Start PCR: Addition of Double-Stranded DNA Fragments Adapted to the Annealing Temperature", *BioTechniques*, vol. 28, No. 2: BPA International, 2000 ; pp. 278-282.

\* cited by examiner

Lanes: (pH) 1: 7.55, 2: 7.7, 3: 8.2, 4: 8.6, 5: 8.7, 6: 9.07, 7: 9.3
AT=AmpliTaq

POLYPEPTIDES HAVING NUCLEIC ACID BINDING ACTIVITY AND COMPOSITIONS AND METHODS FOR NUCLEIC ACID AMPLIFICATION

This application is a continuation of U.S. Application No. 12/545,782, filed Aug. 21, 2009 now abandoned, which is a continuation of U.S. Application No. 11/327,845, filed Jan. 6, 2006 (now abandoned) which claims the benefit of U.S. Provisional Application No. 60/641,987, filed Jan. 6, 2005; and U.S. Provisional Application No. 60/699,975, filed Jul. 15, 2005.

I. FIELD

Polypeptides having nucleic acid binding activity are provided. Methods of using polypeptides having nucleic acid binding activity are provided. Fusion proteins and methods of using fusion proteins are provided. Fusion proteins comprising a polymerase and a nucleic acid binding polypeptide are provided. Fusion proteins comprising a reverse transcriptase and a nucleic acid binding polypeptide are provided. Methods of using fusion proteins to increase the efficiency of primer extension reactions, such as PCR, are provided. Methods of performing PCR using rapid amplification cycles are provided.

II. INTRODUCTION

Polypeptides with nucleic acid binding activity are present in lower organisms, such as archaea, and higher organisms, such as eukaryotes. See, e.g., Pereira et al. (1997) *Proc. Nat'l Acad. Sci. USA* 94:12633-12637; and Motz et al. (2002) *J. Biol. Chem.* 277:16179-16188. Polypeptides with nucleic acid binding activity have various functions. For example, certain polypeptides with nucleic acid binding activity, such as histones and histone-like proteins, are involved in the packaging of chromatin into higher order structures. See, e.g., Pereira et al. (1997) *Proc. Nat'l Acad. Sci. USA* 94:12633-12637. Certain other polypeptides with nucleic acid binding activity may play a role as processivity factors in DNA replication. See, e.g., Motz et al. (2002) *J. Biol. Chem.* 277: 16179-16188.

Various methods can be used to amplify nucleic acids. One commonly used method is the polymerase chain reaction (PCR). See, e.g., U.S. Pat. Nos. 4,683,195, 4,683,202, and 4,800,159. PCR typically comprises multiple cycles in which nucleic acid synthesis is initiated from at least two primers annealed to opposite strands of a target nucleic acid. This process allows exponential amplification of the target nucleic acid.

III. SUMMARY

In certain embodiments, a method of amplifying a nucleic acid sequence is provided. In certain embodiments, the method comprises subjecting a reaction mixture to at least one amplification cycle, wherein the reaction mixture comprises a double-stranded nucleic acid, at least two primers capable of annealing to complementary strands of the double-stranded nucleic acid, and a fusion protein comprising a thermostable DNA polymerase and a nucleic acid binding polypeptide. In certain embodiments, the at least one amplification cycle comprises denaturing the double-stranded nucleic acid, annealing the at least two primers to complementary strands of the denatured double-stranded nucleic acid, and extending the at least two primers.

In certain embodiments, the time to complete one amplification cycle is 20 seconds or less. In certain embodiments, the time to complete one amplification cycle is 15 seconds or less. In certain embodiments, the time to complete one amplification cycle is 10 seconds or less.

In certain embodiments, the annealing occurs at an annealing temperature that is greater than the predicted Tm of at least one of the primers. In certain embodiments, the annealing temperature is at least about 5° C. greater than the predicted Tm of at least one of the primers. In certain embodiments, the annealing temperature is at least about 10° C. greater than the predicted Tm of at least one of the primers. In certain embodiments, the annealing temperature is at least about 15° C. greater than the predicted Tm of at least one of the primers. In certain embodiments, the annealing temperature is from about 62° C. to about 75° C. In certain embodiments, the annealing temperature is from about 65° C. to about 72° C.

In certain embodiments, the extending occurs at the annealing temperature. In certain embodiments, the reaction mixture is held at the annealing temperature for 1 second or less.

In certain embodiments, the denaturing occurs at a denaturing temperature that is sufficient to denature the double-stranded nucleic acid. In certain embodiments, the denaturing temperature is from about 85° C. to about 100° C. In certain embodiments, the reaction mixture is held at the denaturing temperature for 1 second or less. In certain embodiments, the reaction mixture is held at the denaturing temperature for 1 second or less and the annealing temperature for 1 second or less. In certain embodiments, the denaturing comprises bringing the reaction mixture to the denaturing temperature without holding the reaction mixture at the denaturing temperature after the denaturing temperature is reached, and bringing the reaction mixture to the annealing temperature without holding the reaction mixture at the annealing temperature after the annealing temperature is reached.

In certain embodiments, the nucleic acid binding polypeptide comprises an amino acid sequence of a nucleic acid binding polypeptide from a thermophilic microbe. In certain embodiments, the nucleic acid binding polypeptide comprises an amino acid sequence of a nucleic acid binding polypeptide from *Sulfolobus*. In certain embodiments, the nucleic acid binding polypeptide is a Crenarchaeal nucleic acid binding polypeptide. In certain embodiments, the nucleic acid binding polypeptide comprises a sequence selected from: a) SEQ ID NO:20, b) a sequence having at least 80% identity to SEQ ID NO:20, c) SEQ ID NO:6, d) a sequence having at least 80% identity to SEQ ID NO:6, e) SEQ ID NO:1, and f) a sequence having at least 80% identity to SEQ ID NO:1.

In certain embodiments, the thermostable DNA polymerase comprises an archaeal family B polymerase or a fragment or variant of an archaeal family B polymerase having polymerase activity. In certain embodiments, the thermostable DNA polymerase comprises Pfu polymerase or a fragment or variant of Pfu polymerase having polymerase activity.

In certain embodiments, the reaction mixture further comprises a polypeptide having 5' to 3' exonuclease activity.

In certain embodiments, the thermostable DNA polymerase comprises a bacterial family A polymerase or a fragment or variant of a bacterial family A polymerase having polymerase activity. In certain embodiments, the thermostable DNA polymerase comprises Taq DNA polymerase or a fragment or variant of Taq DNA polymerase having polymerase activity. In certain embodiments, the thermostable DNA polymerase comprises a fragment of Taq DNA polymerase lacking 5' to 3' exonuclease activity. In certain embodiments, the thermostable DNA polymerase comprises a cold-sensitive mutant of Taq polymerase. In certain embodiments, the thermostable DNA polymerase comprises a variant of Taq DNA polymerase having increased processivity relative to naturally occurring Taq DNA polymerase.

In certain embodiments, the reaction mixture further comprises an indicator molecule that indicates the amount of nucleic acid in the reaction mixture.

In certain embodiments, the reaction mixture further comprises an indicator probe capable of selectively hybridizing to a strand of the double-stranded nucleic acid. In certain embodiments, the indicator probe is a 5'-nuclease probe comprising a signal moiety capable of producing a detectable signal, and wherein extension of at least one of the at least two primers results in cleavage of the 5'-nuclease probe. In certain embodiments, cleavage of the 5'-nuclease probe increases the detectable signal from the signal moiety.

In certain embodiments, the indicator probe comprises a hybridization-dependent probe. In certain embodiments, the hybridization-dependent probe is a hairpin probe comprising a signal moiety capable of producing a detectable signal. In certain embodiments, hybridization of the hairpin probe to a strand of the double-stranded nucleic acid increases the detectable signal from the signal moiety.

In certain embodiments, the method further comprises detecting the absence or presence of an extension product from at least one of the at least two primers during at least one of the at least one amplification cycle.

In certain embodiments, the reaction mixture is subjected to up to 25 amplification cycles. In certain embodiments, the reaction mixture is subjected to up to 30 amplification cycles. In certain embodiments, the reaction mixture is subjected to up to 40 amplification cycles.

In certain embodiments, the number of amplified molecules produced in at least one of the at least one amplification cycle is from 1.6-fold to 2-fold the number of molecules present at the start of the at least one of the at least one amplification cycle. In certain embodiments, the amplification efficiency of the fusion protein in at least one of the at least one amplification cycle is from 0.8 to 1.0.

In certain embodiments, a method of stabilizing an DNA:RNA duplex is provided, wherein the method comprises combining the DNA:RNA duplex with a polypeptide comprising an amino acid sequence of a nucleic acid binding polypeptide or a fragment thereof having nucleic acid binding activity.

In certain embodiments, a method of promoting the annealing of complementary DNA and RNA strands is provided, wherein the method comprises combining the complementary DNA and RNA strands with a polypeptide comprising an amino acid sequence of a nucleic acid binding polypeptide or a fragment thereof having nucleic acid binding activity.

In certain embodiments, a method of generating DNA from an RNA template is provided, wherein the method comprises exposing the RNA template to at least one primer and a fusion protein comprising a nucleic acid binding polypeptide and a polymerase, wherein the polymerase is a family B polymerase, a fragment of a family B polymerase, or a polypeptide having at least 80% identity to a family B polymerase, wherein the fusion protein has reverse transcriptase activity.

In certain embodiments, a method of amplifying an RNA template is provided, wherein the method comprises subjecting a reaction mixture to a primer extension reaction, wherein the reaction mixture comprises the RNA template, at least one primer, and a fusion protein comprising a nucleic acid binding polypeptide and a polymerase, wherein the polymerase is a family B polymerase, a fragment of a family B polymerase, or a polypeptide having at least 80% identity to a family B polymerase, wherein the fusion protein has reverse transcriptase activity.

In certain embodiments, a method of amplifying a nucleic acid sequence is provided, wherein the method comprises subjecting a reaction mixture to a primer extension reaction, wherein the reaction mixture comprises the nucleic acid sequence, at least one primer, and a fusion protein comprising a nucleic acid binding polypeptide and a polymerase, wherein the reaction mixture has a pH equal to or greater than 8.5.

In certain embodiments, a fusion protein is provided, wherein the fusion protein comprises: a polypeptide comprising an amino acid sequence of a nucleic acid binding polypeptide or a fragment thereof having nucleic acid binding activity; and a reverse transcriptase.

In certain embodiments, a method of generating DNA from an RNA template is provided, wherein the method comprises exposing the RNA template to at least one primer and a fusion protein that comprises: a polypeptide comprising an amino acid sequence of a nucleic acid binding polypeptide or a fragment thereof having nucleic acid binding activity; and a reverse transcriptase.

IV. BRIEF DESCRIPTION OF THE DRAWINGS

FIG. 1 shows agarose gel electrophoresis of two sets of reaction mixtures subjected to "fast" PCR in which the annealing temperatures exceeded the predicted Tm of the primers, according to the work described in Example D. In sets 1 and 2, lanes B, C, and D, the amplification reaction mixture included a fusion protein comprising a nucleic acid binding polypeptide and a thermostable DNA polymerase. In sets 1 and 2, lanes A and E, the amplification reaction mixture included a thermostable DNA polymerase, and did not include a fusion protein comprising a nucleic acid binding polypeptide and a thermostable DNA polymerase. Reaction conditions are described in detail in Example D.

Figures 2A, 2B:
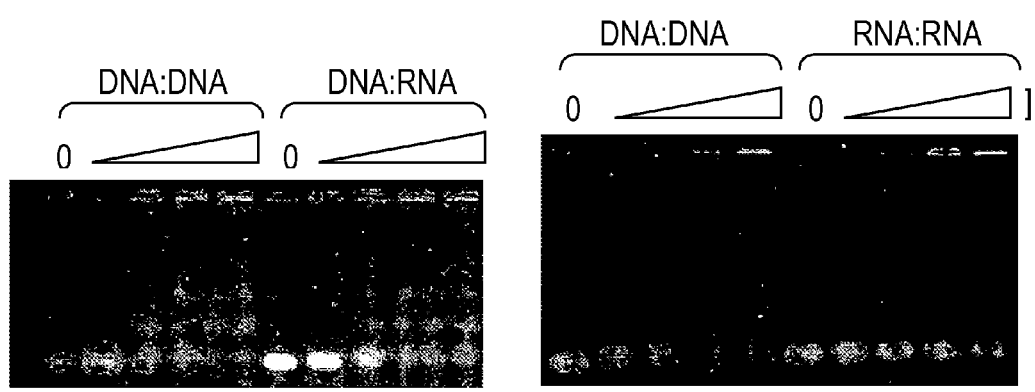

FIG. 2 shows agarose gel electrophoresis of gel-shift experiments described in Example K. FIG. 2A shows the results for the DNA:DNA duplex and the DNA:RNA duplex. FIG. 2B shows the results for the DNA:DNA duplex and the RNA:RNA duplex.

Figure 3:

FIG. 3 shows agarose gel electrophoresis of reaction mixtures subjected to RT-PCR reactions described in Example L.

Figure 4:
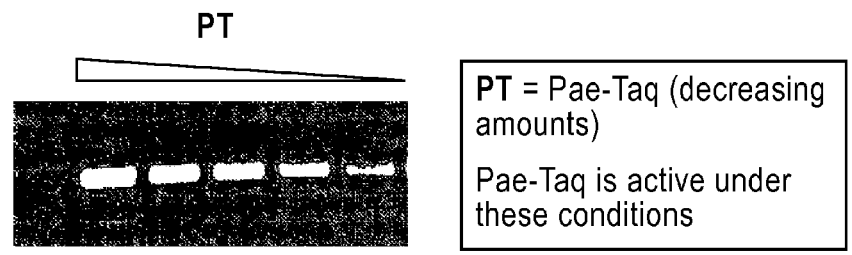

FIG. 4 shows agarose gel electrophoresis of reaction mixtures subjected to PCR reactions described in Example M. The lanes from left to right show results with decreasing amount of enzyme as described in Example M. The designation Pae-Taq is for 10His-Pae3192-Taq.

Figure 5:
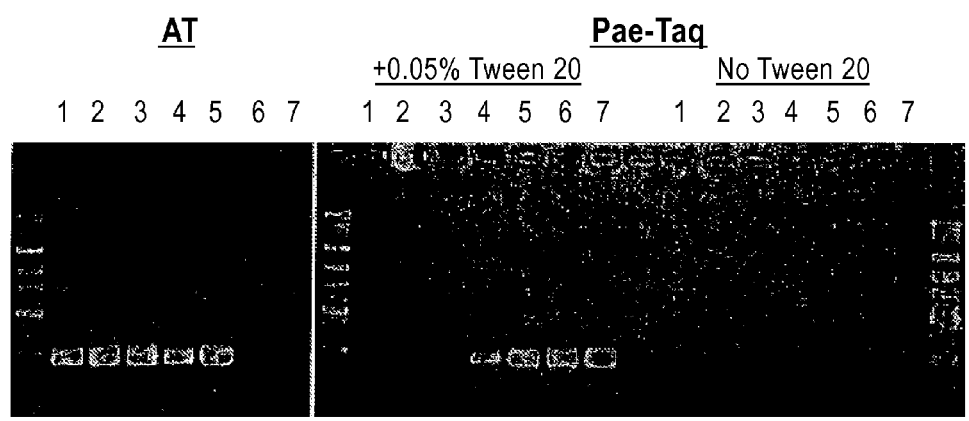

FIG. 5 shows agarose gel electrophoresis of reaction mixtures subjected to PCR reactions described in Example M. The designation AT is for AmpliTaq. The designation Pae-Taq is for 10His-Pae3192-Taq. Lanes 1 to 7 had the following pH values tested as described in Example M: Lane 1; pH 7.55; Lane 2; pH 7.7; Lane 3; pH 8.2; Lane 4; pH 8.6; Lane 5; pH 8.7; Lane 6; pH 9.07; and Lane 7; pH 9.3.

Figure 6:
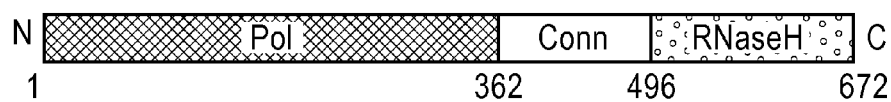

FIG. 6 shows the domain diagram for MMLV reverse transcriptase.

V. DETAILED DESCRIPTION OF VARIOUS EMBODIMENTS

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

Certain Definitions

A "nucleic acid binding polypeptide" refers to a polypeptide that has a molecular weight of about 6 to 11 kilodaltons and a predicted isoelectric point of about 9 to 11; that comprises less than or equal to 4 arginine residues and less than or equal to 15 lysine residues; and that has nucleic acid binding activity.

"Crenarchaeal nucleic acid binding polypeptide" refers to a naturally occurring Crenarchaeal polypeptide that has a molecular weight of about 6 to 11 kilodaltons and a predicted isoelectric point of about 9 to 11; that comprises less than or equal to 4 arginine residues and less than or equal to 15 lysine residues; that has nucleic acid binding activity; and that has an amino acid sequence that is less than 50% identical to the amino acid sequence of Sso7d (SEQ ID NO:20). The Crenarchaea include, but are not limited to, members of the genus *Pyrobaculum, Thermoproteus, Thermocladium, Caldivirga, Thermofilum, Staphylothermus, Ignicoccus, Aeropyrum, Pyrodictium, Pyrolobus, Sulfolobus*, and *Metallosphaera*. See, e.g., Fitz-Gibbon et al. (2002) *Proc. Nat'l Acad. Sci. USA* 99:984-989.

"Nucleic acid binding activity" refers to the activity of a polypeptide in binding nucleic acid in at least one of the following two band-shift assays. In the first assay (based on the assay of Guagliardi et al. (1997) *J. Mol. Biol.* 267:841-848), double-stranded nucleic acid (the 452-bp HindIII-EcoRV fragment from the *S. solfataricus* lacS gene) is labeled with $^{32}$P to a specific activity of at least about $2.5 \times 10^7$ cpm/ug (or at least about 4000 cpm/fmol) using standard methods. See, e.g., Sambrook et al. (2001) *Molecular Cloning: A Laboratory Manual* (3$^{rd}$ ed., Cold Spring Harbor Laboratory Press, NY) at 9.63-9.75 (describing end-labeling of nucleic acids). A reaction mixture is prepared containing at least about 0.5 µg of the polypeptide in about 10 µl of binding buffer (50 mM sodium phosphate buffer (pH 8.0), 10% glycerol, 25 mM KCl, 25 mM MgCl$_2$). The reaction mixture is heated to 37° C. for ten minutes. About $1 \times 10^4$ to $5 \times 10^4$ cpm (or about 0.5-2 ng) of the labeled double-stranded nucleic acid is added to the reaction mixture and incubated for an additional ten minutes. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture.

In the second assay (based on the assay of Mai et al. (1998) *J. Bacteriol.* 180:2560-2563), about 0.5 µg each of negatively supercoiled circular pBluescript KS(−) plasmid and nicked circular pBluescript KS(−) plasmid (Stratagene, La Jolla, Calif.) are mixed with a polypeptide at a polypeptide/DNA mass ratio of about ≥2.6. The mixture is incubated for 10 minutes at 40° C. The mixture is subjected to 0.8% agarose gel electrophoresis. DNA is visualized using an appropriate dye. Any detectable decrease in the mobility of the negatively supercoiled circular plasmid and/or nicked circular plasmid indicates formation of a binding complex between the polypeptide and the plasmid.

"Fusion protein" refers to a protein comprising two or more domains joined either covalently or noncovalently, wherein two or more of the domains do not naturally occur in a single protein.

"Nucleic acid polymerase" or "polymerase" refers to any polypeptide that catalyzes the synthesis of a polynucleotide using an existing polynucleotide as a template.

"Polymerase activity" refers to the activity of a nucleic acid polymerase in catalyzing the template-directed synthesis of a new polynucleotide. Polymerase activity is measured using the following assay, which is based on that of Lawyer et al. (1989) *J. Biol. Chem.* 264:6427-647. Serial dilutions of polymerase are prepared in dilution buffer (20 mM Tris.Cl, pH 8.0, 50 mM KCl, 0.5% NP 40, and 0.5% Tween-20). For each dilution, 5 µl is removed and added to 45 µl of a reaction mixture containing 25 mM TAPS (pH 9.25), 50 mM KCl, 2 mM MgCl$_2$, 0.2 mM dATP, 0.2 mM dGTP, 0.2 mM dTTP, 0.1 mM dCTP, 12.5 µg activated DNA, 100 µM [α-$^{32}$P] dCTP (0.05 µCi/nmol) and sterile deionized water. The reaction mixtures are incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot is removed from each reaction mixture. Unincorporated radioactively labeled dCTP is removed from each aliquot by gel filtration (Centri-Sep, Princeton Separations, Adelphia, N.J.). The column eluate is mixed with scintillation fluid (1 ml). Radioactivity in the column eluate is quantified with a scintillation counter to determine the amount of product synthesized by the polymerase. One unit of polymerase activity is defined as the amount of polymerase necessary to synthesize 10 nmole of product in 30 minutes.

"DNA polymerase" refers to a nucleic acid polymerase that catalyzes the synthesis of DNA using an existing polynucleotide as a template.

"Thermostable DNA polymerase" refers to a DNA polymerase that, at a temperature higher than 37° C., retains its ability to add at least one nucleotide onto the 3' end of a primer or primer extension product that is annealed to a target nucleic acid sequence. In certain embodiments, a thermostable DNA polymerase remains active at a temperature greater than about 37° C. In certain embodiments, a thermostable DNA polymerase remains active at a temperature greater than about 42° C. In certain embodiments, a thermostable DNA polymerase remains active at a temperature greater than about 50° C. In certain embodiments, a thermostable DNA polymerase remains active at a temperature greater than about 60° C. In certain embodiments, a thermostable DNA polymerase remains active at a temperature greater than about 70° C. In certain embodiments, a thermostable DNA polymerase remains active at a temperature greater than about 80° C. In certain embodiments, a thermostable polymerase remains active at a temperature greater than about 90° C.

A "cold-sensitive mutant" of a thermostable DNA polymerase refers to a variant of a thermostable DNA polymerase that exhibits substantially reduced activity at 25° C. to 42° C. relative to its activity at 65° C. to 72° C. In certain embodiments, activity is reduced by at least 50%, 75%, or 95%.

"Reverse transcriptase" refers to a nucleic acid polymerase that catalyzes the synthesis of DNA using an existing RNA as a template.

"Reverse transcriptase activity" refers to the activity of a nucleic acid polymerase in catalyzing the synthesis of DNA using an existing RNA as a template.

"Thermostable reverse transcriptase" refers to a reverse transcriptase that, at a temperature higher than 37° C., retains its ability to add at least one nucleotide onto the 3' end of a primer or primer extension product that is annealed to a target nucleic acid sequence. In certain embodiments, a thermostable reverse transcriptase remains active at a temperature greater than about 37° C. In certain embodiments, a thermostable reverse transcriptase remains active at a temperature greater than about 42° C. In certain embodiments, a thermostable reverse transcriptase remains active at a temperature greater than about 50° C. In certain embodiments, a thermostable reverse transcriptase remains active at a temperature greater than about 60° C. In certain embodiments, a thermostable reverse transcriptase remains active at a temperature greater than about 70° C. In certain embodiments, a thermostable reverse transcriptase remains active at a temperature greater than about 80° C. In certain embodiments, a thermostable preverse transcriptase remains active at a temperature greater than about 90° C.

"Processivity" refers to the extent of polymerization by a nucleic acid polymerase during a single contact between the polymerase and its template. The extent of polymerization refers to the number of nucleotides added by the polymerase during a single contact between the polymerase and its template.

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) *FEMS Microbiol Lett.* 174:247-250. The BLAST engine (version 2.2.10) is provided to the public by the National Center for Biotechnology Information (NCBI), Bethesda, Md. To align two polynucleotide sequences, the "Blast 2 Sequences" tool is used, which employs the "blastn" program with parameters set at default values as follows:
  Matrix: not applicable
  Reward for match: 1
  Penalty for mismatch: −2
  Open gap: 5 penalties
  Extension gap: 2 penalties
  Gap_x dropoff: 50
  Expect: 10.0
  Word size: 11
  Filter: on "Percent identity" or "% identity," with reference to polypeptide sequences, refers to the percentage of identical amino acids between at least two polypeptide sequences aligned using the Basic Local Alignment Search Tool (BLAST) engine. See Tatusova et al. (1999) *FEMS Microbiol Lett.* 174:247-250. The BLAST engine (version 2.2.10) is provided to the public by the National Center for Biotechnology Information (NCBI), Bethesda, Md. To align two polypeptide sequences, the "Blast 2 Sequences" tool is used, which employs the "blastp" program with parameters set at default values as follows:
  Matrix: BLOSUM62
  Open gap: 11 penalties
  Extension gap: 1 penalty
  Gap_x dropoff: 50
  Expect: 10.0
  Word size: 3
  Filter: on The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide. Exemplary conservative substitutions include, but are not limited to, those set forth below:

TABLE 1

Exemplary Amino Acid Substitutions

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

"Nucleic acid modification enzyme" refers to an enzymatically active polypeptide that acts on a nucleic acid substrate. Nucleic acid modification enzymes include, but are not limited to, nucleic acid polymerases (such as DNA polymerases and RNA polymerases), nucleases (including endonucleases, such as restriction endonucleases, and exonucleases, such as 3' or 5' exonucleases), gyrases, topoisomerases, methylases, and ligases. In certain embodiments, a nucleic acid modification enzyme is a reverse transcriptase.

"Melting temperature" or "Tm" refers to the temperature at which 50% of the base pairs in a double-stranded nucleic acid have denatured. "Predicted Tm" refers to the Tm calculated for a nucleic acid of >50 bases in length using the following equation:

$$Tm = 81.5° C. + 16.6 \log_{10}[M^+] + 0.41(\%[G+C]) - 675/n$$

where $[M^+]$ is the monovalent cation concentration and n is the length of the nucleic acid in bases. See Rychlik et al. (1990) *Nucleic Acids Res.* 18:6409-6412. For an oligonucleotide of ≤50 bases in length, the following equation is used to calculate Tm based on nearest neighbor thermodynamics:

$$Tm = \frac{\epsilon H° \times 1000}{\epsilon S° + R \times \ln(C_T/4)} - 273.15 + 16.6\log_{10}[M+]$$

where $\epsilon H°$ is the sum of the nearest neighbor enthalpy changes (kcal/mol), $\epsilon S°$ is the sum of the nearest neighbor entropy changes (cal/K·mol), R is the molar gas constant (1.987 cal/K·mol); $C_T$ is the total molar concentration of oligonucleotide strands; and $M^+$ is the monovalent cation concentration. SantaLucia (1998) *Proc. Natl. Acad. Sci. USA* 95:1460-1465. Values for nearest neighbor enthalpy and entropy changes are found in SantaLucia et al., supra.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2 ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman (1989) *Practical Handbook of Biochemistry* and *Molecular Biology*, pages 385-394, (CRC Press, Boca Raton, Fla.) and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

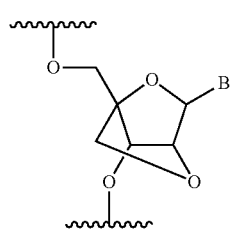

2'-4' LNA

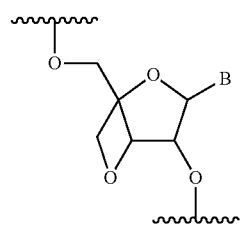

3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) *Nucl. Acids Res.* 21:4159-65; Fujimori (1990) *J. Amer. Chem. Soc.* 112:7435; Urata, (1993) *Nucleic Acids Symposium* Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, $2^{nd}$ Ed., Freeman, San Francisco, Calif.).

One or more of the pentose carbons of a nucleotide may be substituted with a phosphate ester having the formula:

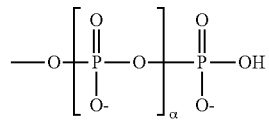

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and is sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see Shabarova, Z. and Bogdanov, A. *Advanced Organic Chemistry of Nucleic Acids*, VCH, New York, 1994.

The term "nucleotide analog," as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers that can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide," "oligonucleotide," and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-50 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, "T" denotes thymidine or an analog thereof, and "U" denotes uridine or an analog thereof, unless otherwise noted.

Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids include, but are not limited to, synthetic or in vitro transcription products.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

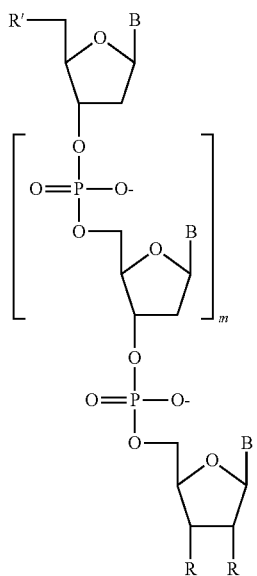

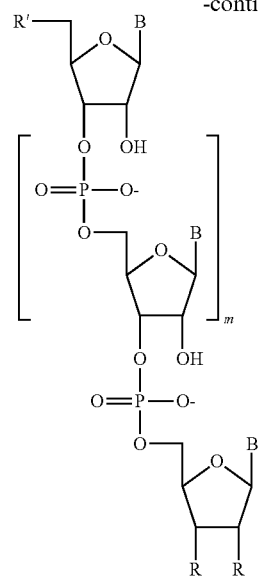

wherein each B is independently the base moiety of a nucleotide, e.g., a purine, a 7-deazapurine, a pyrimidine, or an analog nucleotide; each m defines the length of the respective nucleic acid and can range from zero to thousands, tens of thousands, or even more; each R is independently selected from the group comprising hydrogen, halogen, —R", —OR", and —NR"R", where each R" is independently (C1-C6) alkyl or (C5-C14) aryl, or two adjacent Rs are taken together to form a bond such that the ribose sugar is 2',3'-didehydroribose; and each R' is independently hydroxyl or

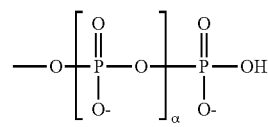

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid," "polynucleotide," and "oligonucleotide" may also include nucleic acid analogs, polynucleotide analogs, and oligonucleotide analogs. The terms "nucleic acid analog", "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254:1497-1500; WO 92/20702; U.S. Pat. Nos. 5,719,262; 5,698,685); morpholinos (see, e.g., U.S. Pat. Nos. 5,698,685; 5,378,841; 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114:4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) *Science* 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

A "target," "target nucleic acid," or "target nucleic acid sequence" is a nucleic acid in a sample. In certain embodiments, a target nucleic acid sequence serves as a template for amplification in a primer extension reaction, such as PCR. In certain embodiments, a target nucleic acid sequence is an amplification product. Target nucleic acid sequences may include both naturally occurring and synthetic molecules.

In this application, a statement that one sequence is the same as or is complementary to another sequence encompasses situations where both of the sequences are completely the same or complementary to one another, and situations where only a portion of one of the sequences is the same as, or is complementary to, a portion or the entirety of the other sequence. Here, the term "sequence" encompasses, but is not limited to, nucleic acid sequences, polynucleotides, oligonucleotides, probes, and primers.

In this application, a statement that one sequence is complementary to another sequence encompasses situations in which the two sequences have mismatches. Here, the term "sequence" encompasses, but is not limited to, nucleic acid sequences, polynucleotides, oligonucleotides, probes, and primers. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 70% of the particular identical sequences. In certain embodiments, "a substantial portion of the particular identical sequences" means at least 80% of the particular identical sequences. In certain embodiments, "a substantial portion of the particular identical sequences" means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, the more complex the composition, the more likely undesired sequences will hybridize. For example, in certain embodiments, with a given number of mismatches, a probe may more likely hybridize to undesired sequences in a composition with the entire genomic DNA than in a composition with fewer DNA sequences, when the same hybridization and wash conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, and primers.

The term "primer" refers to a polynucleotide that anneals to a target polynucleotide and allows the synthesis from its 3' end of a sequence complementary to the target polynucleotide.

The term "primer extension reaction" refers to a reaction in which a polymerase catalyzes the template-directed synthesis of a nucleic acid from the 3' end of a primer. The term "primer extension product" refers to the resultant nucleic acid. A non-limiting exemplary primer extension reaction is the polymerase chain reaction (PCR). The terms "extending" and "extension" refer to the template-directed synthesis of a nucleic acid from the 3' end of a primer, which is catalyzed by a polymerase.

The term "amplifying" encompasses both linear and exponential amplification of nucleic acid using, for example, any of a broad range of primer extension reactions. Exemplary primer extension reactions include, but are not limited to, PCR.

The term "probe" comprises a polynucleotide that comprises a specific portion designed to hybridize in a sequence-specific manner with a complementary region of a specific nucleic acid sequence, e.g., a target polynucleotide. In certain embodiments, the specific portion of the probe may be specific for a particular sequence, or alternatively, may be degenerate, e.g., specific for a set of sequences. In certain embodiments, a probe is capable of producing a detectable signal.

The terms "annealing" and "hybridization" are used interchangeably and mean the base-pairing interaction of one nucleic acid with another nucleic acid that results in the formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

The terms "denature" and "denaturing" refer to converting at least a portion of a double-stranded nucleic acid into nucleic acid strands that are no longer base-paired.

The term "thermophilic microbe" refers to a microbe that grows optimally at a temperature greater than 40° C.

The term "plurality" refers to "at least two."

The term "label" refers to any molecule that can be detected. In certain embodiments, a label can be a moiety that produces a signal or that interacts with another moiety to produce a signal. In certain embodiments, a label can interact with another moiety to modify a signal of the other moiety. In certain embodiments, the signal from a label joined to a probe increases when the probe hybridizes to a complementary target nucleic acid sequence. In certain embodiments, the signal from a label joined to a probe increases when the probe is cleaved. In certain embodiments, the signal from a label joined to a probe increases when the probe is cleaved by an enzyme having 5' to 3' exonuclease activity.

Exemplary labels include, but are not limited to, light-emitting or light-absorbing compounds which generate or quench a detectable fluorescent, chemiluminescent, or bioluminescent signal (see, e.g., Kricka, L. in *Nonisotopic DNA Probe Techniques* (1992), Academic Press, San Diego, pp. 3-28). Fluorescent reporter dyes useful as labels include, but are not limited to, fluoresceins (see, e.g., U.S. Pat. Nos. 5,188, 934; 6,008,379; and 6,020,481), rhodamines (see, e.g., U.S. Pat. Nos. 5,366,860; 5,847,162; 5,936,087; 6,051,719; and 6,191,278), benzophenoxazines (see, e.g., U.S. Pat. No. 6,140,500), energy-transfer fluorescent dyes comprising pairs of donors and acceptors (see, e.g., U.S. Pat. Nos. 5,863, 727; 5,800,996; and 5,945,526), and cyanines (see, e.g., Kubista, WO 97/45539), as well as any other fluorescent moiety capable of generating a detectable signal. Examples of fluorescein dyes include, but are not limited to, 6-carboxyfluorescein; 2',4',1,4,-tetrachlorofluorescein; and 2',4',5',7',1,4-hexachlorofluorescein.

Exemplary labels include, but are not limited to, quantum dots. "Quantum dots" refer to semiconductor nanocrystalline compounds capable of emitting a second energy in response to exposure to a first energy. Typically, the energy emitted by a single quantum dot always has the same predictable wavelength. Exemplary semiconductor nanocrystalline compounds include, but are not limited to, crystals of CdSe, CdS, and ZnS. Suitable quantum dots according to certain embodiments are described, e.g., in U.S. Pat. Nos. 5,990,479 and 6,207,392 B1; Han et al. (2001) *Nature Biotech.* 19:631-635; and Medintz et al. (2005) *Nat. Mat.* 4:435-446.

Exemplary labels include, but are not limited to, phosphors and luminescent molecules. Exemplary labels include, but are not limited to, fluorophores, radioisotopes, chromogens, enzymes, antigens, heavy metals, dyes, magnetic probes, phosphorescence groups, chemiluminescent groups, and electrochemical detection moieties. Exemplary fluorophores include, but are not limited to, rhodamine, cyanine 3 (Cy 3), cyanine 5 (Cy 5), fluorescein, Vic™, Liz™, Tamra™, 5-Fam™, 6-Fam™ and Texas Red (Molecular Probes, Eugene, Oreg.). (Vic™, Liz™, Tamra™, 5-Fam™, and 6-Fam™ are all available from Applied Biosystems, Foster City, Calif.) Exemplary radioisotopes include, but are not limited to, $^{32}P$, $^{33}P$, and $^{35}S$. Exemplary labels also include elements of multi-element indirect reporter systems, e.g., biotin/avidin, antibody/antigen, ligand/receptor, enzyme/substrate, and the like, in which the element interacts with other elements of the system in order to effect a detectable signal. One exemplary multi-element reporter system includes a biotin reporter group attached to a primer and an avidin conjugated with a fluorescent label.

Exemplary detailed protocols for certain methods of attaching labels to oligonucleotides and polynucleotides can be found in, among other places, Hermanson, *Bioconjugate Techniques*, Academic Press, San Diego, Calif. (1996) and Beaucage et al., *Current Protocols in Nucleic Acid Chemistry*, John Wiley & Sons, New York, N.Y. (2000). Certain exemplary non-radioactive labeling methods, techniques, and reagents are reviewed in: Garman *Non-Radioactive Labelling, A Practical Introduction*, Academic Press, San Diego (1997).

The term "indicator molecule" refers to any molecule that is capable of producing or effecting a detectable signal when a target nucleic acid is present in a sample. Exemplary indicator molecules include, but are not limited to, SYBR® Green I, SYBR® Gold, and the like.

The term "indicator probe" refers to a probe that is capable of producing or effecting a detectable signal when a target nucleic acid is present in a sample. In certain embodiments, selective hybridization of an indicator probe to a target nucleic acid results in the production of a detectable signal. In certain embodiments, an indicator probe is not extendable by a polymerase. In certain embodiments, an indicator probe is extendable by a polymerase.

The term "interaction probe" refers to a probe comprising at least two moieties that can interact with one another, wherein at least one of the moieties is capable of producing a detectable signal, and wherein the detectable signal from the moiety increases or decreases depending upon its proximity to the other moiety. In certain embodiments employing interaction probes, the proximity of the two moieties to one another depends upon whether a target nucleic acid is present or absent in a sample. In certain embodiments, the at least two moieties comprise a signal moiety and a quencher moiety. In certain embodiments, the at least two moieties comprise a signal moiety and a donor moiety. Exemplary interaction probes include, but are not limited to, TAQ MAN® probes, molecular beacons, ECLIPSE™ probes, SCORPION® primers, and the like.

The term "5'-nuclease probe" refers to a probe that comprises a signal moiety linked to a quencher moiety or a donor moiety through a short oligonucleotide link element. When the 5'-nuclease probe is intact, the quencher moiety or the donor moiety influences the detectable signal from the signal moiety. According to certain embodiments, the 5'-nuclease probe selectively hybridizes to a target nucleic acid sequence and is cleaved by a polypeptide having 5' to 3' exonuclease activity, e.g., when the probe is replaced by a newly polymerized strand during a primer extension reaction, such as PCR.

When the oligonucleotide link element of the 5'-nuclease probe is cleaved, the detectable signal from the signal moiety changes when the signal moiety becomes further separated from the quencher moiety or the donor moiety. In certain embodiments that employ a quencher moiety, the detectable signal from the signal moiety increases when the signal moiety becomes further separated from the quencher moiety. In certain embodiments that employ a donor moiety, the detectable signal from the signal moiety decreases when the signal moiety becomes further separated from the donor moiety.

The term "hybridization-dependent probe" refers to a probe comprising a signal moiety linked to a quencher moiety or a donor moiety through an oligonucleotide link element. When the hybridization-dependent probe is not hybridized to a target nucleic acid, the probe adopts a conformation that allows the quencher moiety or donor moiety to come into sufficiently close proximity to the signal moiety, such that the quencher moiety or donor moiety influences a detectable signal from the signal moiety.

The term "hairpin probe" refers to a hybridization-dependent probe that comprises a signal moiety linked to a quencher moiety or a donor moiety through an oligonucleotide capable of forming a hairpin, or stem-loop, structure.

In certain embodiments of a hairpin probe, the signal moiety and quencher moiety are sufficiently close when the probe assumes a hairpin conformation, such that the quencher moiety decreases the detectable signal from the signal moiety. When the probe is not in a hairpin conformation (e.g., when the hairpin probe is denatured or is hybridized to a target nucleic acid sequence), the proximity of the quencher moiety and the signal moiety decreases relative to their proximity in the hairpin conformation. The decrease in proximity produces an increase in the detectable signal from the signal moiety.

In certain embodiments of a hairpin probe, the signal moiety and donor moiety are sufficiently close when the probe assumes a hairpin conformation, such that the donor moiety increases the detectable signal from the signal moiety. When the probe is not in a hairpin conformation (e.g., when the hairpin probe is denatured or is hybridized to a target nucleic acid sequence), the proximity of the donor moiety and the signal moiety decreases relative to their proximity in the hairpin conformation. The decrease in proximity produces an decrease in the detectable signal from the signal moiety.

The term "quencher moiety" refers to a moiety that causes the detectable signal of a signal moiety to decrease when the quencher moiety is sufficiently close to the signal moiety.

The term "donor moiety" refers to a moiety that causes the detectable signal of a signal moiety to increase when the donor moiety is sufficiently close to the signal moiety.

The term "signal moiety" refers to a moiety that is capable of producing a detectable signal.

The term "detectable signal" refers to a signal that is capable of being detected under certain conditions. In certain embodiments, a detectable signal is detected when it is present in a sufficient quantity.

A. Certain Nucleic Acid Binding Polypeptides

In certain embodiments, a nucleic acid binding polypeptide comprises a naturally occurring nucleic acid binding polypeptide derived from a thermophilic microbe. In certain embodiments, a nucleic acid binding polypeptide comprises a naturally occurring nucleic acid binding polypeptide derived from a hyperthermophilic archaeote. In certain such embodiments, the hyperthermophilic archaeote is of the genus *Sulfolobus*. Certain small, basic nucleic acid binding polypeptides from *Sulfolobus solfataricus* and *Sulfolobus acidocaldarius* are known to those skilled in the art. See Gao et al. (1998) *Nature Struct. Biol.* 5:782-786; Robinson et al. (1998) *Nature* 392:202-205; McAfee et al. (1995) *Biochem.* 34:10063-10077; and Baumann et al. (1994) *Nature Struct. Biol.* 1:808-819. Certain such polypeptides include, but are not limited to, Sso7d and Sac7d, which bind DNA in a sequence non-specific manner. See Gao et al. (1998) *Nature Struct. Biol.* 5:782-786; Robinson et al. (1998) *Nature* 392: 202-205; McAfee et al. (1995) *Biochem.* 34:10063-10077; and Baumann et al. (1994) *Nature Struct. Biol.* 1:808-819.

Sso7d and Sac7d are of relatively low molecular weight (about 7 kDa) and are rich in lysine residues. Id. Certain lysine residues are believed to be involved in DNA binding. See Gao et al. (1998) *Nature Struct. Biol.* 5:782-786. Both protect double-stranded DNA from thermal denaturation by increasing its melting temperature (Tm) by about 40° C. Id.; Robinson et al. (1998) *Nature* 392:202-205. Sso7d also promotes the annealing of complementary DNA strands at temperatures exceeding the predicted Tm of the resulting duplex. See Guagliardi et al. (1997) *J. Mol. Biol.* 267:841-848. Sso7d exhibits a strong preference for DNA strands that are complementary without any mismatches over DNA strands that contain even a single mismatch. See id.; U.S. Patent Application Publication No. US 2003/0022162 A1. It is postulated that small, basic polypeptides such as Sso7d. and Sac7d protect the DNA of hyperthermophiles from denaturation and degradation in the hyperthermophilic environment, where temperatures approach or exceed 100° C. See Guagliardi et al. (1997) *J. Mol. Biol.* 267:841-848.

In certain embodiments, a nucleic acid binding polypeptide comprises the amino acid sequence of Sso7d (SEQ ID NO:20). Sso7d is encoded by SEQ ID NOs:44 and 45. Sso7d is 64 amino acids in length with a predicted isoelectric point of 10.2. A exemplary variant of Sso7d having four additional amino acids at its N-terminus is shown in SEQ ID NO:21. That variant is encoded by SEQ ID NO:46.

In certain embodiments, a nucleic acid binding polypeptide comprises a Crenarchaeal nucleic acid binding polypeptide. In certain embodiments, a Crenarchaeal nucleic acid binding polypeptide comprises a naturally occurring polypeptide from the crenarchaeon *Pyrobaculum aerophilum*. In certain embodiments, a Crenarchaeal nucleic acid binding polypeptide comprises the amino acid sequence of Pae3192 (SEQ ID NO:1), which can be found at GenBank accession numbers AAL64739 and AAL64814. Pae3192 is encoded by the open reading frames "PAE3192" (SEQ ID NO:2) and "PAE3289" (SEQ ID NO:3), which are unannotated open reading frames identified in the complete genome sequence of *P. aerophilum*. See GenBank accession no. AE009441.

In certain embodiments, a Crenarchaeal nucleic acid binding polypeptide comprises the amino acid sequence of Pae0384 (SEQ ID NO:4), which can be found at GenBank accession number AAL62754. Pae0384 is encoded by the open reading frame "PAE0384" (SEQ ID NO:5), which is an unannotated open reading frame identified in the complete genome sequence of *P. aerophilum*. See GenBank accession no. AE009441.

SEQ ID NOs:1 and 4 are low molecular weight, basic proteins of 57 and 56 amino acids in length, respectively, with a predicted isoelectric point of about 10.5. SEQ ID NO:1 contains 12 lysine residues and 2 arginine residues. SEQ ID NO:4 contains 11 lysine residues and 2 arginine residues. SEQ ID NOs:1 and 4 are about 97% identical to each other. SEQ ID NOs:1 and 4 are similar in size and charge to Sso7d, but they are not significantly identical to the amino acid sequence of Sso7d.

Additionally, SEQ ID NO:1 contains a "KKQK" motif near its N-terminus (residues 3 to 6 of SEQ ID NO:1). This motif resembles the "KQKK" motif found at the C-terminus of Sso7d (residues 61-64 of SEQ ID NO:20). The location of these motifs at opposite termini of SEQ ID NO:1 and Sso7d may have resulted from gene rearrangements during the divergence of the different Crenarchaeal species. The KQKK motif of Sso7d is discussed in Shehi et al. (2003) *Biochem.* 42:8362-8368.

In certain embodiments, a Crenarchaeal nucleic acid binding polypeptide comprises a naturally occurring polypeptide from the crenarchaeon *Aeropyrum pernix*. In certain embodiments, a Crenarchaeal nucleic acid binding polypeptide comprises the amino acid sequence of Ape3192 (SEQ ID NO:6). SEQ ID NO:6 is 55 amino acids in length with a predicted isoelectric point of about 10.5. It contains 13 lysine residues and 3 arginine residues. SEQ ID NO:6 is similar in size and charge to Sso7d, but it is not significantly identical to the amino acid sequence of Sso7d.

In certain embodiments, a nucleic acid binding polypeptide comprises a fragment of a naturally occurring nucleic acid binding polypeptide. In certain such embodiments, the fragment has at least one activity of the naturally occurring nucleic acid binding polypeptide. Exemplary activities of a naturally occurring nucleic acid binding polypeptide include, but are not limited to, the ability to bind nucleic acid, stabilize nucleic acid duplexes from thermal denaturation, increase the Tm of primers, and increase the processivity of a polymerase. Other exemplary activities of a naturally occurring nucleic acid binding polypeptide include, but are not limited to the ability to promote annealing of complementary nucleic acid strands, stabilize nucleic acid duplexes, and enhance the activity of a nucleic acid modification enzyme. In certain embodiments, the fragment has a predicted isoelectric point of about 9-11.

In certain embodiments, a nucleic acid binding polypeptide comprises a fragment of a polypeptide comprising an amino acid sequence selected from SEQ ID NOs:1, 4, 6, 20, and 21. In certain such embodiments, the fragment lacks N-terminal amino acids. In certain such embodiments, the fragment lacks up to the first 12 N-terminal amino acids of an amino acid sequence selected from SEQ ID NOs:1, 4, 6, 20, and 21. In certain embodiments, the fragment lacks C-terminal amino acids. In certain such embodiments, the fragment lacks up to the last 12 C-terminal amino acids of an amino acid sequence selected from SEQ ID NOs:1, 4, 6, 20, and 21.

In certain embodiments, a nucleic acid binding polypeptide comprises a variant of a naturally occurring nucleic acid binding polypeptide. In certain such embodiments, the variant has at least one activity of a naturally occurring nucleic acid binding polypeptide.

In certain embodiments, a nucleic acid binding polypeptide comprises a variant of a polypeptide comprising an amino acid sequence selected from SEQ ID NOs:1, 4, 6, 20, and 21. In certain such embodiments, the variant comprises an amino acid sequence having from about 60% to about 99% identity to an amino acid sequence selected from SEQ ID NOs:1, 4, 6, 20, and 21. For example, in certain embodiments, the variant comprises an amino acid sequence having at least 60%, 65%, 70%, 75%, 80%, 85%, 90%, 95%, 97%, 98%, or 99% identity to an amino acid sequence selected from SEQ ID NOs:1, 4, 6, 20, and 21. In certain such embodiments, lysine and arginine residues are not substituted or deleted in the variant.

In certain embodiments, a variant of a Crenarchaeal nucleic acid binding polypeptide is provided. In certain embodiments, one or more amino acids that are not conserved among Crenarchaeal nucleic acid binding polypeptides may be substituted or deleted to create a suitable variant. For example, the first of the two alignments below demonstrates that SEQ ID NOs:1 and 6 have 60% identity and 74% similarity as determined by the "Blast 2 Sequence" blastp program set at default parameters. (In calculating percent similarity, the blastp program includes both identical and similar amino acids. Similar amino acids are indicated by "+" signs in the alignments below.) The second of the two alignments below demonstrates that SEQ ID NOs:4 and 6 have 59% identity and 72% similarity as determined by the "Blast 2 Sequence" blastp program set at default parameters. In certain embodiments, one or more amino acids that are not conserved in at least one of the alignments below (i.e., amino acids that are not identical or similar) are substituted or deleted to create variants of polypeptides comprising SEQ ID NO:1, SEQ ID NO:4, or SEQ ID NO:6.

sensus sequence. In certain such embodiments, the nucleic acid binding polypeptide has at least one activity of a naturally occurring nucleic acid binding polypeptide.

In certain embodiments, a fragment or variant of a naturally occurring nucleic acid binding polypeptide has nucleic acid binding activity that is less than that of the naturally occurring nucleic acid binding polypeptide. In certain such embodiments, the fragment or variant has from about 10-20%, about 20-30%, about 30-40%, about 40-50%, about 50-60%, about 60-70%, about 70-80%, about 80-90%, or about 90-95% of the nucleic acid binding activity of the naturally occurring nucleic acid binding polypeptide.

In certain embodiments, a polynucleotide comprising a nucleic acid sequence encoding any of the above nucleic acid binding polypeptides is provided. In certain embodiments, a polynucleotide comprises a nucleic acid sequence encoding a polypeptide comprising an amino acid sequence selected from SEQ ID NOs:1, 4, 6, 20, and 21. In certain embodiments, a polynucleotide comprises a nucleic acid sequence encoding a fragment of a polypeptide comprising an amino acid sequence selected from SEQ ID NOs: 1, 4, 6, 20, and 21. In certain such embodiments, the fragment has at least one activity of a naturally occurring nucleic acid binding polypeptide. In certain embodiments, a polynucleotide comprises a nucleic acid sequence encoding a variant of a polypeptide comprising an amino acid sequence selected from SEQ ID NOs:1, 4, 6, 20, and 21. In certain such embodiments, the variant has at least one activity of a naturally occurring nucleic acid binding polypeptide.

In certain embodiments, a polynucleotide comprises a nucleic acid sequence selected from SEQ ID NOs:2, 3, 5, 7, 44, 45, and 46. In certain embodiments, a polynucleotide comprises a fragment of a nucleic acid sequence selected from SEQ ID NOs: 2, 3, 5, 7, 44, 45, and 46, wherein the fragment encodes a polypeptide having at least one activity of a naturally occurring nucleic acid binding polypeptide.

In certain embodiments, a polynucleotide comprises a variant of a nucleic acid sequence selected from SEQ ID NOs:2, 3, 5, 7, 44, 45, and 46, wherein the variant encodes a polypeptide having at least one activity of a naturally occurring nucleic acid binding polypeptide. In certain embodiments, a variant of a nucleic acid sequence selected from SEQ ID NOs:2, 3, 5, 7, 44, 45, and 46 comprises a nucleic acid sequence having from about 60% to about 99% identity to a nucleic acid sequence selected from SEQ ID NOs:2, 3, 5, 7, 44, 45, and 46. For example, in certain embodiments, a vari-

```
SEQ ID NO: 1:1  MSKKQKLKFYDIKAKQAFETDQYEVIEKQTARGPMMFAVAKSPYTGIKVYRLLGKKK 57
                M KK+K+KF+D+ AK+ +ETD YEV  K+T RG    FA AKSPYTG   YR+LGK
SEQ ID NO: 6:1  MPKKEKIKFFDLVAKKYYETDNYEVEIKETKRGKFRFAKAKSPYTGKIFYRVLGKA 55

SEQ ID NO: 4:1   MAKQKLKFYDIKAKQSFETDKYEVIEKETARGPMLFAVATSPYTGIKVYRLLGKKK 56
                 K+K+KF+D+ AK+ +ETD YEV  KET RG    FA A SPYTG   YR+LGK
SEQ ID NO: 6:1  MPKKEKIKFFDLVAKKYYETDNYEVEIKETKRGKFRFAKAKSPYTGKIFYRVLGKA 55
```

Based on the above alignments, a consensus sequence for a Crenarchaeal nucleic acid binding polypeptide is provided as follows:

SEQ ID NO: 28
5' KXKXKFXDXXAKXXXETDXYEVXXKXTXRGXXXFAXAKSPYTGXX XYRXLGK 3'

In the above consensus sequence, "X" is any amino acid. In certain embodiments, a nucleic acid binding polypeptide comprises an amino acid sequence that conforms to that conant of a nucleic acid sequence selected from SEQ ID NOs:2, 3, 5, 7, 44, 45, and 46 comprises a nucleic acid sequence having at least 60%, 65%, 70%, 75%, 80%, 85%, 90%, 95%, 97%, 98%, or 99% identity to a nucleic acid sequence selected from SEQ ID NO:2, 3, 5, 7, 44, 45, and 46. In certain such embodiments, the variant encodes a polypeptide having at least one activity of a naturally occurring nucleic acid binding polypeptide.

In certain embodiments, the length of an isolated polynucleotide is any number of nucleotides less than or equal to 10,000. For example, in certain embodiments, an isolated polynucleotide is less than or equal to 10,000, 9000, 8000, 7000, 6000, 5000, 4000, 3000, 2000, 1000, or 500 nucleotides in length. In certain embodiments, the length of an isolated polynucleotide does not include vector sequences.

In certain embodiments, a polynucleotide encoding a nucleic acid binding polypeptide is obtained by the polymerase chain reaction (PCR). Certain methods employing PCR are known to those skilled in the art. See, e.g., Sambrook et al. (2001) *Molecular Cloning: A Laboratory Manual*, Chapter 8 (3$^{rd}$ ed., Cold Spring Harbor Laboratory Press, NY). In certain embodiments, a polynucleotide comprising all or a portion of the coding sequence of a nucleic acid binding polypeptide is amplified using appropriate primers. In certain embodiments, restriction enzyme sites are included in the primers to facilitate cloning of the amplification product into an appropriate expression vector. In certain embodiments, the polynucleotide is amplified from genomic DNA or from cDNA of a crenarchaeote. The complete genome sequence of certain crenarchaeotes is published and may be used in designing primers for PCR. See, e.g., Fitz-Gibbon et al. (2002) *Proc. Nat'l Acad. Sci. USA* 99:984-989; Kawarabayasi (1999) *DNA Research Supp:*145-152; and She et al. (2001) *Proc. Nat'l Acad. Sci. USA* 98:7835-7840.

In certain embodiments, a polynucleotide encoding a nucleic acid binding polypeptide is obtained by synthesizing individual oligonucleotides which are ligated end-to-end in vitro, with the resulting ligation product comprising the coding sequence of a nucleic acid binding polypeptide. In certain embodiments, the ligation product is amplified by PCR. In certain embodiments, the oligonucleotides overlap in sequence and are extended by PCR, resulting in a PCR product comprising the coding sequence of a nucleic acid binding polypeptide. See, e.g., Stemmer et al. (1995) *Gene* 164:49-53; Gronlund et al. (2003) *J. Biol. Chem.* 278:40144-40151. In certain embodiments, the PCR product is cloned into a suitable vector.

In certain embodiments, a polynucleotide encoding a nucleic acid binding polypeptide is cloned into a suitable vector. In certain such embodiments, the vector is transferred (e.g., transformed or transfected) into a host cell. In certain embodiments, a polynucleotide encoding a nucleic acid binding polypeptide is cloned into an expression vector and, in certain embodiments, expressed in a suitable host cell. Certain exemplary expression vectors are available for use in certain host cells including, but not limited to, prokaryotes, yeast cells, insect cells, plant cells, and mammalian cells. See, e.g., Ausubel et al. (1991) Current Protocols in Molecular Biology, Chapter 16, John Wiley & Sons, New York. Certain expression vectors for the inducible expression of recombinant proteins in prokaryotes are known to those skilled in the art. For example, in certain embodiments, a polynucleotide encoding a nucleic acid binding polypeptide is cloned into an expression vector such that its transcription is under the control of an inducible promoter, such as the T7 bacteriophage promoter, the T5 promoter, or the tac promoter. See, e.g., the pET series of vectors (Invitrogen, Carlsbad, Calif.), the pQE series of vectors (Qiagen, Valencia, Calif.), or the pGEX series of vectors (Amersham Biosciences, Piscataway, N.J.). In certain embodiments, the recombinant expression vector is transformed into bacteria, such as *E. coli*. In certain embodiments, the expression of the nucleic acid binding polypeptide is induced by culturing the bacteria under certain growth conditions. For example, in certain embodiments, expression of the nucleic acid binding polypeptide is induced by addition of isopropylthio-β-galactoside (IPTG) to the culture medium.

In various embodiments of expression vectors, a polynucleotide encoding a tag, such as an affinity tag, is expressed in frame with a polynucleotide encoding a nucleic acid binding polypeptide. In certain embodiments, certain such tags can provide a mechanism for detection or purification of the nucleic acid binding polypeptide. Examples of tags include, but are not limited to, polyhistidine tags, which allow purification using nickel chelating resin, and glutathione S-transferase moieties, which allow purification using glutathione-based chromatography. In certain embodiments, an expression vector further provides a cleavage site between the tag and the nucleic acid binding polypeptide, so that the nucleic acid binding polypeptide may be cleaved from the tag following purification. In certain embodiments, e.g., embodiments using polyhistidine tags, the nucleic acid binding polypeptide is not cleaved from the tag. It has been reported that the presence of a polyhistidine tag on a recombinant DNA binding protein may enhance the interaction of the DNA binding protein with DNA. See, e.g., Buning et al. (1996) *Anal. Biochem.* 234:227-230.

B. Certain DNA Polymerases

Certain polymerases are known to those skilled in the art. For example, DNA polymerases include DNA-dependent polymerases, which use DNA as a template, or RNA-dependent polymerases, such as reverse transcriptase, which use RNA as a template. Currently, DNA-dependent DNA polymerases fall into one of six families (A, B, C, D, X, and Y), with most falling into one of three families (A, B, and C). See, e.g., Ito et al. (1991) *Nucleic Acids Res.* 19:4045-4057; Braithwaite et al. (1993) *Nucleic Acids Res.* 21:787-802; Fileé et al. (2002) *J. Mol. Evol.* 54:763-773; and Albà (2001) *Genome Biol.* 2:3002.1-3002.4. Certain DNA polymerases may be single-chain polypeptides (e.g., certain family A and B polymerases) or multi-subunit enzymes (e.g., certain family C polymerases) with one of the subunits having polymerase activity. Id. In certain embodiments, a fusion protein comprises a DNA polymerase selected from a family A, B, C, D, X, or Y polymerase.

In certain embodiments, a polymerase comprises a fragment or variant of an A, B, C, D, X, or Y polymerase having polymerase activity. In certain embodiments, a polymerase comprises a family A DNA polymerase or a fragment or variant thereof having polymerase activity. In certain such embodiments, the family A polymerase is a bacterial family A polymerase, such as a polymerase from the genus *Bacillus, Thermus, Rhodothermus* or *Thermotoga*. In certain such embodiments, the family A polymerase is Taq DNA polymerase (SEQ ID NO:31) or a fragment or variant thereof having polymerase activity. In certain embodiments, a variant of Taq DNA polymerase comprises an amino acid sequence having at least 80%, 85%, 90%, 95%, 96%, 97%, 98%, or 99% identity to SEQ ID NO:31.

In certain embodiments, a polymerase comprises a family B DNA polymerase or a fragment or variant thereof having polymerase activity. In certain such embodiments, the family B polymerase is an archaeal family B polymerase, such as a polymerase from the genus *Thermococcus, Pyrococcus,* or *Pyrobaculum*. In certain such embodiments, the family B polymerase is Pfu DNA polymerase (SEQ ID NO:30) or a fragment or variant thereof having polymerase activity. In certain embodiments, a variant of Pfu DNA polymerase comprises an amino acid sequence having at least 80%, 85%, 90%, 95%, 96%, 97%, 98%, or 99% identity to SEQ ID NO:30.

In addition to polymerase activity, certain DNA polymerases also possess other activities, such as 3' to 5' exonuclease (proofreading) activity or 5' to 3' exonuclease activity. See, e.g., Filed et al. (2002) *J. Mol. Evol.* 54:763-773; and Pavlov et al. (2004) *Trends in Biotech.* 22:253-260. In certain such DNA polymerases, polymerase activity and exonuclease activity are carried out by separate domains. The domain structure of certain DNA polymerases is known to those skilled in the art. See, e.g., id.; Albà (2001) *Genome Biol.* 2:3002.1-3002.4; and Steitz (1999) *J. Biol. Chem.* 274: 17395-17398.

In certain embodiments, a "chimeric" DNA polymerase is provided. In certain such embodiments, a chimeric DNA polymerase comprises a domain having polymerase activity from a particular DNA polymerase and a domain having exonuclease activity from a different DNA polymerase. See, e.g., U.S. Pat. Nos. 5,795,762 and 5,466,591.

In certain embodiments, a DNA polymerase having both polymerase activity and exonuclease activity is provided. In certain such embodiments, the exonuclease activity is 5' to 3' exonuclease activity. In certain such embodiments, the level of 5' to 3' exonuclease activity is reduced or eliminated relative to the level of 5' to 3' exonuclease activity of a native DNA polymerase. In certain such embodiments, mutation of a DNA polymerase results in reduction or elimination of 5' to 3' exonuclease activity. In certain such embodiments, one or more amino acid substitutions result in reduction or elimination of 5' to 3' exonuclease activity. Certain such substitutions are known to those skilled in the art. For example, substitution of a conserved glycine in certain thermostable DNA polymerases reduces or eliminates 5' to 3' exonuclease activity. See, e.g., U.S. Pat. Nos. 5,795,762 and 5,466,591 (describing the G46D substitution in Taq, Tth, and TZ05 DNA polymerases; the G43D substitution in Tsps17 DNA polymerase; and the G37D substitution in Tma and Taf DNA polymerases).

In certain embodiments, deletion of one or more amino acids from a DNA polymerase results in the reduction or elimination of 5' to 3' exonuclease activity. Certain such deletions are known to those skilled in the art. For example, certain N-terminal deletions of certain thermostable DNA polymerases reduce or eliminate 5' to 3' exonuclease activity. Exemplary N-terminal deletions include, but are not limited to, deletion of about the first 35-50 amino acid residues of a thermostable DNA polymerase. See, e.g., U.S. Pat. Nos. 5,795,762 and 5,466,591 (describing deletion of N-terminal amino acid residues up to and including the conserved glycine residues in Taq, Tth, TZ05, Tsps17, Tma, and Taf, described above). Exemplary N-terminal deletions further include, but are not limited to, deletion of about the first 70-80 amino acid residues of a thermostable DNA polymerase. See, e.g., U.S. Pat. Nos. 5,795,762 and 5,466,591 (describing deletion of N-terminal amino acid residues up to and including the following residues: Ala 77 (Taq DNA polymerase), Ala 78 (Tth DNA polymerase), Ala 78 (TZ05 DNA polymerase), Ala 74 (TSPS17 DNA polymerase), Leu 72 (Tma DNA polymerase), and Ile 73 (Taf DNA polymerase)). Exemplary N-terminal deletions further include, but are not limited to, deletion of the first 139 or the first 283 amino acid residues of Tma DNA polymerase. See, e.g., U.S. Pat. Nos. 5,795,762 and 5,466,591.

In certain embodiments, a DNA polymerase that lacks an exonuclease domain is provided. In certain embodiments, the exonuclease domain is a 5' to 3' exonuclease domain. Exemplary polymerases that lack a 5' to 3' exonuclease domain include, but are not limited to, a family B polymerase such as Pfu DNA polymerase; the large "Klenow" fragment of *E. coli* DNA polymerase I; the "Klentaq235" fragment of Taq DNA polymerase, which lacks the first 235 N-terminal amino acids of full-length Taq; the "Klentaq278" fragment of Taq DNA polymerase, which lacks the first 278 N-terminal amino acids of full-length Taq; and the "Stoffel" fragment of Taq DNA polymerase, which lacks about the first 289-300 N-terminal amino acids of full-length Taq DNA polymerase. See Lawyer et al. (1989) *J. Biol. Chem.* 264:6427-6437 (describing a "Stoffel" fragment); Vainshtein et al. (1996) *Protein Science* 5:1785-1792; Barnes (1992) *Gene* 112:29-35; and U.S. Pat. No. 5,436,149. In certain embodiments, thermostable DNA polymerases that lack a 5' to 3' exonuclease domain show increased thermal stability and/or fidelity relative to their full-length counterparts. See, e.g., Barnes (1992) *Gene* 112: 29-35; and U.S. Pat. No. 5,436,149.

In certain embodiments, mutation of one or more amino acids in a DNA polymerase results in the reduction or elimination of 3' to 5' exonuclease activity. For example, the 3' to 5' exonuclease domain of certain archaeal family B polymerases comprises the consensus sequence FDXE(T/V) (where "X" is any amino acid). See, e.g., amino acid residues 140-144 of SEQ ID NO:30; and Kahler et al. (2000) *J. Bacteriol.* 182:655-663. In certain embodiments, mutation of the consensus sequence to FDXD(T/V) reduces the level of 3' to 5' exonuclease activity to about 10% or less of the activity in the corresponding wild-type polymerase. See, e.g., Southworth et al. (1996) *Proc. Natl. Acad. Sci. USA* 93:5281-5285 (describing a mutant of *Thermococcus* sp. 9° N-7); and Derbyshire et al. (1995) *Methods Enzymol.* 262:363-388. In certain embodiments, mutation of the consensus sequence to FAXA(T/V) substantially eliminates 3' to 5' exonuclease activity. See, e.g., Southworth et al. (1996) *Proc. Natl. Acad. Sci. USA* 93:5281-5285 (describing a mutant of *Thermococcus* sp. 9° N-7); Kong et al. (1993) J. Biol. Chem. 268:1965-1975 (describing a mutant of Tli DNA polymerase); and Derbyshire et al. (1995) *Methods Enzymol.* 262:363-388. In certain embodiments, reducing or eliminating 3' to 5' exonuclease activity may alleviate polymerase "stutter" or slippage, e.g., in the amplification of repetitive DNA. See, e.g., Walsh et al. (1996) *Nucleic Acids Res.* 24:2807-2812. In certain embodiments, reducing or eliminating 3' to 5' exonuclease activity may alleviate primer degradation by the polymerase.

In certain embodiments, a DNA polymerase is provided that comprises one or more mutations adjacent to the exonuclease domain. For example, in certain embodiments, a B family DNA polymerase from a hyperthermophilic Archaeon, such as KOD polymerase from *Thermococcus kodakarensis*, is provided in which the histidine at position 147 (proximal to the conserved Exo-I domain) is changed to glutamic acid (H147E), which results a lowered 3'→5' exonuclease activity while maintaining near wild-type fidelity. The resulting measured ratio of exonuclease activity to polymerase activity is lowered, resulting in higher yields of amplified DNA target from a typical PCR reaction. See, for example, Kuroita et al., J. Mol. Biol., 351:291-298 (2005).

In certain embodiments, a DNA polymerase is provided that comprises one or more mutations such that it retains double stranded exonuclease activity, but it has reduced single stranded exonuclease activity. A nonlimiting example is a polymerase with the Y384F mutation (mutation of tyrosine to phenylalanine) in the conserved YxGG domain of family B DNA polymerases. See, for example, Bohlke et al., Nucl. Acid Res., 28:3910-3917 (2000).

In certain embodiments, a family B DNA polymerase is provided that comprises one or more mutations that allow the polymerase to perform DNA polymerization using a primed RNA template. Exemplary polymerases include, but are not limited to, a family B polymerase, such as Pfu DNA polymerase, with a point mutation L408Y or L408F (leucine to tyrosine or to phenylalane) in the conserved LYP motif, which results in a polymerase that can perform an RNA-templated DNA polymerization reaction. See, for example, U.S. Patent Publication No. US2003/0228616. Exemplary family B polymerases include, but are not limited to, Pfu polymerase, Tgo polymerase (Roche), Vent polymerase (New England Biolabs), Deep Vent polymerase (New England Biolabs), KOD polymerase (Toyo Boseki/EMD Biosciences), and 9°Nm polymerase (New England Biolabs).

In certain embodiments, a DNA polymerase is provided that comprises one or more mutations that reduce the ability of the polymerase to discriminate against the incorporation of dideoxynucleotides. Certain exemplary mutations are described, for example, in U.S. Pat. No. 6,333,183; EP 0 745 676 B1; and U.S. Pat. No. 5,614,365. One such exemplary mutation is the F667Y mutation in Taq DNA polymerase. See, e.g., U.S. Pat. No. 5,614,365.

In certain embodiments, a DNA polymerase is provided that comprises one or more mutations that reduce the ability of the polymerase to discriminate against the incorporation of fluorescently labeled nucleotides into polynucleotides. In certain embodiments, such "discrimination reduction" mutations occur within the nucleotide label interaction region of a DNA polymerase, which is described, for example, in U.S. Pat. No. 6,265,193. Exemplary discrimination reduction mutations are provided in U.S. Pat. No. 6,265,193.

In certain embodiments, a DNA polymerase further comprises one or more mutations in addition to one or more discrimination reduction mutations. Certain exemplary mutations include, but are not limited to, mutations that increase or decrease 3' to 5' exonuclease activity; increase or decrease 5' to 3' exonuclease activity; increase or decrease thermostability; increase or decrease processivity; and increase incorporation of dideoxynucleotides. In certain embodiments, a DNA polymerase comprises one or more discrimination reduction mutations and one or more mutations that decrease 3' to 5' exonuclease activity. In certain embodiments, a DNA polymerase comprises one or more discrimination reduction mutations and one or more mutations that increase incorporation of dideoxynucleotides. Certain such DNA polymerases are described, for example, in U.S. Pat. No. 6,265,193.

In certain embodiments, a polymerase comprises a thermostable DNA polymerase. In certain embodiments, a thermostable DNA polymerase is a naturally occurring thermostable DNA polymerase. In certain embodiments, a thermostable DNA polymerase is a fragment or variant of a naturally occurring thermostable DNA polymerase that possesses polymerase activity. Exemplary guidance for determining certain such fragments and variants is provided in Pavlov et al. (2004) *Trends in Biotech.* 22:253-260.

Certain exemplary thermostable DNA polymerases are known to those skilled in the art. See, e.g., Sambrook et al. (2001)*Molecular Cloning: A Laboratory Manual* (3$^{rd}$ ed., Cold Spring Harbor Laboratory Press, NY) at 8.10-8.11. Certain exemplary thermostable DNA polymerases include, but are not limited to, DNA polymerases from the genus *Thermus, Thermococcus, Thermotoga, Bacillus,* and *Pyrococcus.* Certain exemplary thermostable DNA polymerases include, but are not limited to, DNA polymerases from *Thermus aquaticus* (e.g., Taq DNA polymerase), *Thermus brockianus* (e.g., Tbr polymerase), *Thermus flavus* (e.g., Tfl DNA polymerase), *Thermus caldophilus, Thermus filiformis, Thermus oshimai, Thermus thermophilus* (e.g., Tth DNA polymerase), and *Thermus ubiquitus.* Certain other thermostable DNA polymerases from *Thermus* include, but are not limited to, Tsps17 and TZ05. Certain fragments and variants of Taq, Tfl, Tth, Tsps17, and TZ05 DNA polymerases are known to those skilled in the art. See, e.g., Vainshtein et al. (1996) *Protein Science* 5:1785-1792 (discussing the Taq Stoffel fragment), EP 0 745 676 B1, WO 01/14568, US 2004/0005573 A1, U.S. Pat. Nos. 5,795,762, and 5,466,591.

In certain embodiments, a polymerase comprises a variant of a naturally occurring thermostable DNA polymerase having increased efficiency relative to the naturally occurring thermostable DNA polymerase. Certain such variants of Taq DNA polymerase are known to those skilled in the art. One such exemplary variant is the S543N mutant of Klentaq. That variant synthesizes long DNA molecules with greater efficiency than Klentaq. See, e.g., Ignatov et al. (1999) *FEBS Letters* 425:249-250. It also more efficiently amplifies templates having complex secondary structures (e.g., GC-rich templates) that typically induce polymerase pausing. See, e.g., Ignatov et al.
FEBS Letters 448:145-148.

In certain embodiments, a polymerase comprises a thermostable DNA polymerase from *Thermococcus litoralis* (e.g., Tli polymerase), *Thermococcus* kodakarensis KOD1 (e.g., KOD DNA polymerase), or *Thermococcus gorgonarius* (e.g., Tgo DNA polymerase). See, e.g., Takagi et al. (1997) *Appl. Environ. Microbiol.* 63:4504-4510 (KOD DNA polymerase). Certain fragments and variants of KOD DNA polymerase are known to those skilled in the art. See, e.g., EP 1 154 017 A1 and U.S. Pat. No. 5,436,149. Certain such variants having increased processivity and elongation rates are commercially available from EMD Biosciences—Novagen, San Diego, Calif. In certain embodiments, a thermostable DNA polymerase comprises a DNA polymerase from *Thermotoga neapolitana* (e.g., Tne DNA polymerase) or *Thermotoga maritima* (e.g., Tma DNA polymerase). See, e.g., US 2003/0092018 A1 and US 2003/0162201 A1. In certain embodiments, a thermostable DNA polymerase comprises a DNA polymerase from *Thermosipho africanus* (e.g., Taf DNA polymerase). Certain fragments and variants of Tma, Taf, and Tne DNA polymerases are known to those skilled in the art. See, e.g., US 2003/0092018 A1, US 2003/0162201 A1, U.S. Pat. Nos. 5,795,762, and 5,466,591.

Certain exemplary thermostable DNA polymerases include, but are not limited to, DNA polymerases from *Pyrococcus furiosus* (e.g., Pfu DNA polymerase), *Pyrococcus woesei* (e.g., Pwo polymerase), *Pyrococcus* spp. GB-D, *Pyrococcus abyssi,* and *Pyrolobus fumarius.* See, e.g., U.S. Pat. Nos. 5,834,285, 6,489,150 B1, 6,673,585 B1, 5,948,666, 6,492,511, and EP 0 547 359 B1.

Certain fragments and variants of Pfu polymerase are known to those skilled in the art. See, e.g., U.S. Pat. No. 6,333,183 B1 and US 2004/0219558 A1. In certain embodiments, a variant of Pfu polymerase comprises any of the variants described in US 2004/0219558 A1. In certain embodiments, a variant of Pfu polymerase comprises any one or more of the following mutations: M247R, T265R, K502R, A408S, K485R, and ΔL381 (deletion).

Certain variants of *Pyrococcus* spp. GB-D polymerase are known to those skilled in the art. See, e.g., US 2004/0219558 A1. In certain embodiments, a variant of *Pyrococcus* spp. GB-D polymerase comprises any of the variants described in US 2004/0219558 A1.

In certain embodiments, a variant of a *Pyrococcus* polymerase has one or more mutations in the uracil binding pocket. Certain such polymerases are capable of utilizing uracil containing templates. For example, in certain embodiments, a variant of Pfu DNA polymerase comprises the V93Q mutation. See, e.g., Shuttleworth et al. (2004) *J. Molec. Biol.* 337:621-634; and Fogg et al. (2002) *Nature Struct. Biol.* 9:922-927.

In certain embodiments, a thermostable DNA polymerase comprises a DNA polymerase from *Bacillus stearothermophilus* or a variant or fragment thereof, such as the "large fragment" of Bst DNA polymerase. In certain embodiments, a thermostable DNA polymerase comprises a DNA polymerase from the thermophilic bacterium designated Tsp JS1. See, e.g., US 2004/0005573 A1. Certain fragments and variants of a thermostable DNA polymerase from Tsp JS1 are known to those skilled in the art. Id.

C. Certain Reverse Transcriptases

Reverse transcriptases are polymerases that can use RNA as a template. Thus, reverse transcriptases catalyze the synthesis of DNA using RNA as a template. In certain instances, reverse transcriptases catalyze DNA using DNA as the template. As discussed above, certain DNA polymerases have reverse transcriptase activity as well.

In certain embodiments, a reverse transcriptase is used to synthesize cDNA from messenger RNA. Thus, in certain embodiments, reverse transcriptases are used in methods that measure gene expression. Certain such methods include, but are not limited to, reverse transcriptase PCR (RT-PCR) and microarray analysis. In certain embodiments, reverse transcriptases are used to generate cDNA for sequencing, gene cloning, protein expression, and/or cDNA library construction. In certain embodiments, reverse transcriptases are used in sequence detection when the target(s) are RNA. Certain such targets include, but are not limited, to RNA viruses. In certain embodiments, reverse transcriptases are used in vitro nucleic acid amplification techniques that employ an RNA intermediate. Certain such exemplary techniques include, but are not limited to, Ribo-SPIA (Single Primer Isothermal Amplification; NuGEN, San Carlos, Calif.), NASBA/NucliSense (Nucleic Acid Sequence Based Amplification; bioMerieux USA, Durham, N.C.) and TMA (Transcription Mediated Amplification; GenProbe, San Diego, Calif.) technologies.

Certain exemplary classes of reverse transcriptases include, but are not limited to, reverse transcriptases from avian myeloblastosis virus (AMV), reverse transcriptases from the Moloney murine leukemia virus (MMLV) RT, and Family A DNA polymerases from various bacteria. Exemplary Family A DNA polymerases include, but are not limited to, Tth polymerase from *Thermus thermophilus*; Taq polymerase from *Thermus aquaticus; Thermus thermophilus* Rt41A; Dictyoglomus thermophilum RT46B.1*; Caldicellulosiruptor saccharolyticus* Tok7B.1; *Caldicellulosiruptor* spp. Tok13B.1; *Caldicellulosiruptor* spp. Rt69B.1; *Clostridium thermosulfurogenes; Thermotoga neapolitana; Bacillus caldolyticus* EA1.3; *Clostridium stercorarium*; and *Caldibacillus cellulovorans* CA2. Shandilya et al., *Extremophiles,* 8:243-251 (2004) discusses certain bacterial DNA polymerases with reverse transcriptase activity.

Reverse transcriptases from AMV and MMLV include RNase H domains, which mediate the degradation of the RNA component of RNA:DNA complexes. In certain instances, that RNase H activity can decrease the amount of final product because of the degradation of RNA template. Point mutants in the RNase H domain of MMLV reverse transcriptase (for example, Superscript II and III, Invitrogen; Powerscript, Takara) and a deletion mutant of the MMLV reverse transcriptase RNase H domain (Superscript I, Invitrogen) are available. In certain instances, deletion of the RNase H domain results in severe processivity defects and impaired interaction of the reverse transcriptase with primer-template (see, for example, Telesnitsky et al., Proc. Natl. Acad. Sci. USA, 90:1276-1280 (1993).

In certain instances, an obstacle to generating consistent, full length cDNAs in short time periods arises from the inherent propensity of RNA to form secondary structure. In certain instances, regions of secondary structure in the template RNA can cause reverse transcriptases to stall, fall off the template, or skip over looped out regions. In certain instances, this can be partially alleviated by running the reverse transcriptase reaction at higher temperatures at which secondary structures melt. AMV reverse transcriptases and Tth DNA polymerases have been used for such higher temperature reactions in view of their thermostability. In certain instances, nucleic acid binding polypeptide is added in trans to increase polymerase processivity through regions of RNA secondary structure (see, for example PCT Application WO 0055307).

D. Certain Fusion Proteins

In certain embodiments, fusion proteins are provided. In certain such embodiments, a fusion protein comprises a nucleic acid binding polypeptide and a nucleic acid modification enzyme. In certain such embodiments, the nucleic acid modification enzyme comprises a nucleic acid polymerase. In certain embodiments, the nucleic acid polymerase comprises a DNA polymerase. In certain such embodiments, the nucleic acid modification enzyme comprises a reverse transcriptase. In various embodiments, fusion proteins may comprise any of the nucleic acid binding polypeptides and any of the polymerases or reverse transcriptases discussed herein.

In certain embodiments, fusion proteins comprising a polymerase and a nucleic acid binding polypeptide are provided. In certain such embodiments, fusion proteins have polymerase activity, exhibiting improved performance and/or increased efficiency in nucleic acid amplification reactions compared to polymerase alone. In certain embodiments, methods are provided for using fusion proteins in nucleic acid amplification reactions, such as PCR. In certain such embodiments, fusion proteins demonstrate unexpected properties under fast cycling conditions, having the ability to produce substantial yields of amplification product. In certain embodiments, fusion proteins comprising a polymerase and a nucleic acid binding polypeptide can be used in amplification reactions at high pH, for example, at a pH is equal to or greater than 8.5. In certain embodiments, fusion proteins comprising a polymerase and a nucleic acid binding polypeptide can be used in amplification reactions at high pH, for example, at a pH in the range of 8.5 to 10 (including all pH values between those endpoints). In certain embodiments, fusion proteins comprising a polymerase and a nucleic acid binding polypeptide can be used in amplification reactions at high pH, for example, at a pH in the range of 8.5 to 9.5.

In certain embodiments, fusion proteins comprising a nucleic acid binding protein and a given DNA polymerase can be used for RNA-templated DNA synthesis when the given DNA polymerase alone cannot perform DNA polymerization using a primed RNA template. In certain such embodiments, the DNA polymerase in the fusion protein is a Family B polymerase.

In certain embodiments, fusion proteins comprising a nucleic acid binding protein and a given DNA polymerase that has reverse transcriptase activity have improved properties compared to the given DNA polymerase alone. In certain embodiments, fusion proteins comprising a nucleic acid binding protein and a given reverse transcriptase have improved properties compared to the given reverse transcriptase alone. In certain embodiments, the improved properties include one or more of the following: improved processivity; the ability to produce longer amplification products; increased ability to read through RNA secondary structure; shorter reaction times; increased sensitivity; increased affinity for a primed template; faster product accumulation; and increased salt tolerance.

In various embodiments, a fusion protein comprising a nucleic acid binding polypeptide and a nucleic acid modification enzyme, such as polymerase or reverse transcriptase, is produced using recombinant methods. In certain such embodiments, a polynucleotide encoding a nucleic acid binding polypeptide and a polynucleotide encoding a nucleic acid modification enzyme, such as polymerase or reverse transcriptase, are ligated together in the same reading frame, resulting in a polynucleotide encoding a fusion protein.

In certain embodiments, a polynucleotide encoding a nucleic acid binding polypeptide is obtained as described in Part V.A above.

In certain embodiments, a polynucleotide encoding a polymerase or a reverse transcriptase is obtained by the polymerase chain reaction (PCR). Certain methods employing PCR are known to those skilled in the art. In certain embodiments, a polynucleotide comprising all or a portion of the coding sequence of a polymerase or a reverse transcriptase is amplified using appropriate primers. In certain embodiments, restriction enzyme sites are included in the primers to facilitate cloning of the amplification product into an appropriate vector. Certain polynucleotide sequences encoding certain DNA polymerases are known to those skilled in the art. See, e.g., Ito et al. (1991) *Nuc. Acids. Research* 19:4045-4057; Braithwaite et al. (1993) *Nuc. Acids. Research* 21:787-802; and Fileéet al. (2002) *J. Mol. Evol.* 54:763-773.

In certain embodiments, a polynucleotide encoding a DNA polymerase is a polynucleotide encoding Taq DNA polymerase (SEQ ID NO:31) or a fragment or variant thereof having polymerase activity. In certain embodiments, a polynucleotide encoding a DNA polymerase is a polynucleotide encoding Pfu DNA polymerase (SEQ ID NO:30) or a fragment or variant thereof having polymerase activity. In certain embodiments, a polynucleotide encoding a reverse transcriptase is a polynucleotide encoding the MMLV reverse transcriptase shown in SEQ ID NO:52 or a fragment or variant thereof having polymerase activity.

In various embodiments, a polynucleotide encoding a fusion protein is cloned into a suitable vector. In certain embodiments, a polynucleotide encoding a nucleic acid binding polypeptide and a polynucleotide encoding a nucleic acid modification enzyme, such as polymerase or reverse transcriptase, are ligated together in the same reading frame, and the ligation product is cloned into a suitable vector. In certain embodiments, a polynucleotide encoding a nucleic acid binding polypeptide and a polynucleotide encoding a nucleic acid modification enzyme, such as polymerase or reverse transcriptase, are cloned stepwise into a suitable vector.

In certain embodiments, a vector comprising a polynucleotide encoding a fusion protein is transferred (e.g., transformed or transfected) into a suitable host cell. Certain exemplary host cells include, but are not limited to, prokaryotes, yeast cells, insect cells, plant cells, and mammalian cells. See, e.g., Ausubel et al. (1991) *Current Protocols in Molecular Biology*, Chapter 16, John Wiley & Sons, New York. In certain embodiments, the fusion protein is expressed in the host cell. In certain such embodiments, the fusion protein is isolated from the host cell.

In certain embodiments, a suitable vector is an expression vector. Certain expression vectors for the inducible expression of recombinant proteins are known to those skilled in the art. For example, in certain embodiments, a polynucleotide encoding a fusion protein is cloned into an expression vector such that its transcription is under the control of an inducible promoter, such as the T7 bacteriophage promoter, the T5 promoter, or the tac promoter. See, e.g., the pET series of vectors (Invitrogen, Carlsbad, Calif.), the pQE series of vectors (Qiagen, Valencia, Calif.), or the pGEX series of vectors (Amersham Biosciences, Piscataway, N.J.). Certain such expression vectors are suitable for the expression of a recombinant protein in a prokaryotic organism.

In certain embodiments, a recombinant expression vector is transformed into bacteria, such as *E. coli*. In certain embodiments, expression of the fusion protein is induced by culturing the bacteria under certain growth conditions. For example, in certain embodiments, expression of the fusion protein is induced by addition of isopropylthio-β-galactoside (IPTG) to the culture medium.

In various embodiments of expression vectors, a polynucleotide encoding a tag, such as an affinity tag, is expressed in frame with a polynucleotide encoding a fusion protein. In certain embodiments, certain such tags can provide a mechanism for detection or purification of the fusion protein. Examples of tags include, but are not limited to, polyhistidine tags, which allow purification using nickel chelating resin, and glutathione S-transferase moieties, which allow purification using glutathione-based chromatography. In certain embodiments, a tag is disposed at the N-terminus or C-terminus of a fusion protein. In certain embodiments, a tag is disposed internally within a fusion protein.

In certain embodiments, an expression vector further provides a cleavage site between the tag and the fusion protein, so that the fusion protein may be cleaved from the tag following purification. In certain embodiments, e.g., embodiments using polyhistidine tags, the fusion protein is not cleaved from the tag. It has been reported that the presence of a polyhistidine tag on a recombinant DNA binding protein may enhance the interaction of the DNA binding protein with DNA. See, e.g., Buning et al. (1996) *Anal. Biochem.* 234:227-230. In certain embodiments, a tag comprises from 1 to 15 histidine residues, including all points between those endpoints. In certain such embodiments, an increasing number of histidine residues is unexpectedly correlated with improved performance of the fusion protein in nucleic acid amplification reactions.

In certain embodiments of a fusion protein, a nucleic acid binding polypeptide is joined to the N-terminus of a nucleic acid modification enzyme. In certain embodiments of a fusion protein, a nucleic acid binding polypeptide is joined to the C-terminus of a nucleic acid modification enzyme. In certain embodiments of a fusion protein, a nucleic acid binding polypeptide is disposed internally within a nucleic acid modification enzyme.

In certain embodiments of a fusion protein, a nucleic acid binding polypeptide is joined to the N-terminus of a reverse transcriptase. In certain embodiments of a fusion protein, a nucleic acid binding polypeptide is joined to the C-terminus of a reverse transcriptase. In certain embodiments of a fusion protein, a nucleic acid binding polypeptide is disposed internally within a reverse transcriptase.

In certain embodiments of a fusion protein, a nucleic acid binding polypeptide is joined to the N-terminus of a polymerase. In certain embodiments of a fusion protein, a nucleic acid binding polypeptide is joined to the C-terminus of a polymerase. In certain embodiments of a fusion protein, a nucleic acid binding polypeptide is disposed internally within a polymerase. Certain three dimensional structures of certain DNA polymerases are known to those skilled in the art. See, e.g., Steitz (1999) *J. Biol. Chem.* 274:17395-17398; Albà (2001) *Genome Biol.* 2:3002.1-3002.4. Certain DNA polymerases typically have a "hand-like" three-dimensional structure comprising "finger," "palm," and "thumb" domains. See, e.g., Steitz (1999) *J. Biol. Chem.* 274:17395-17398; Albà (2001) *Genome Biol.* 2:3002.1-3002.4. In certain embodiments of a fusion protein, wherein a nucleic acid binding polypeptide is disposed internally within a DNA polymerase, the nucleic acid binding polypeptide occurs within a loop in the "thumb" domain of the DNA polymerase. See, e.g., U.S. Pat. No. 5,972,603, e.g., FIG. 4.

In certain embodiments, one skilled in the art can routinely determine whether a DNA polymerase retains polymerase activity in the context of a fusion protein by assaying the fusion protein for polymerase activity.

In certain embodiments, a nucleic acid binding polypeptide is joined to a a nucleic acid modification enzyme, such as polymerase or reverse transcriptase, by chemical methods. In certain embodiments, a nucleic acid binding polypeptide is joined to a nucleic acid modification enzyme, such as polymerase or reverse transcriptase, by a chemical coupling agent. Certain such methods are known to those skilled in the art. See, e.g., Hermanson, ed., *Bioconiuqate Techniques* (Academic Press 1996).

In certain embodiments, a nucleic acid binding polypeptide is joined to a a nucleic acid modification enzyme, such as polymerase or reverse transcriptase, by a linker. In certain embodiments, a linker is a peptide, which is joined by peptide bonds to a nucleic acid binding polypeptide and to a nucleic acid modification enzyme, such as polymerase or reverse transcriptase. In certain embodiments, a linker is engineered into a fusion protein by standard recombinant methods. For example, in certain embodiments, a polynucleotide encoding a fusion protein is constructed, wherein a polynucleotide encoding a linker is in frame with and disposed between a polynucleotide encoding a nucleic acid binding polypeptide and a polynucleotide encoding a nucleic acid modification enzyme, such as polymerase or reverse transcriptase.

In certain embodiments, a linker is any whole number of amino acids less than or equal to 25. In certain embodiments, a linker does not form an α-helix or β-strand. In certain such embodiments, a linker forms an extended, or "loop," conformation. In certain embodiments, a linker sequence comprises one or more glycine residues. In certain embodiments, a suitable linker sequence is determined using the LINKER program. See, e.g., Crasto et al. (2000) *Protein Eng.* 13:309-312.

Other exemplary linkers include, but are not limited to, carbohydrate linkers, lipid linkers, fatty acid linkers, and polymeric linkers. Certain exemplary polymeric linkers include, but are not limited to, polyether linkers, such as polyethylene glycol (PEG).

In certain embodiments, full length MMLV reverse transciptase, a fragment of MMLV reverse transcriptase, or other mutant forms of reverse transcriptase are cloned into an expression vector. An nonlimiting exemplary expression vector is pET16b (Novagen/EMD Biosciences, La Jolla, Calif.). Exemplary fragments of MMLV reverse transcriptase include, but are not limited to, forms that contain amino acids 1-516 (an RNase H deletion form), forms that contain amino acids 1-498 (an RNase H deletion form), and forms that contain amino acids 1 to 360 (an RNase H deletion and connectin domain deletion form). Exemplary mutants of MMLV reverse transcriptase include, but are not limited to, a form in which glutamic acid at position 524 is changed to asparagines (D524N) (a form that decreases RNase H activity) (see, for example, Blain et al., J. Biol. Chem., 31:23585-23592 (1993)). FIG. 6 shows the MMLV RT polymerase domain (Pol), the connection domain (Conn), and the RNase H domain (RNaseH) of MMLV reverse transcriptase. Amino acids 2 to 672 correspond to amino acids 122 to 792 of the MMLV pol polyprotein sequence.

In certain embodiments, the full length, fragment, or mutant form of MMLV reverse transcriptase in an expression vector is cloned in frame with a nucleic acid binding polypeptide, such as Pae3192, for expression of a fusion protein. In certain embodiments, the nucleic acid binding polypeptide is placed at the N-terminus of the full length, fragment, or mutant form of MMLV reverse transcriptase. In certain embodiments, the nucleic acid binding polypeptide is placed at the C-terminus of the full length, fragment, or mutant form of MMLV reverse transcriptase. In certain embodiments, the expression vector encoding the fusion protein includes a tag for affinity purification.

In various embodiments, fusion proteins that comprise a nucleic acid binding polypeptide and the full length, fragment, or mutant form of MMLV reverse transcriptase can be subjected to various in vitro assays. Exemplary assays include, but are not limited to, tests for reverse transcriptase activity, including, but not limited to, radioactive nucleotide incorporation and gel analysis of product length and yield. In certain such embodiments, temperature and salt tolerance can also be determined. In certain embodiments, the ability of the fusion protein to read through RNAs with significant secondary structure, such as stem loops containing CUUCGG hairpins, is tested. In certain such embodiments, temperature and salt tolerance is also tested. In certain embodiments, processivity of the fusion protein is assayed using fluorescently-labeled primers and capillary electrophoresis.

E. Certain Methods Using Nucleic Acid Binding Polypeptides

Example K below shows that Pae3192 not only binds to DNA:DNA duplexes, but also binds to DNA:RNA duplexes. Thus, Ape3192, Sso7d, and other nucleic acid binding polypeptides should also bind to both DNA:DNA duplexes and DNA:RNA duplexes. Accordingly, all of the methods discussed in this Part (Part V.E) in various embodiments may involve a DNA:DNA duplex, a DNA:RNA duplex, or both a DNA:DNA duplex and a DNA:RNA duplex.

1. Stabilize Nucleic Acid Duplexes

In certain embodiments, one or more nucleic acid binding polypeptides are used to stabilize a nucleic acid duplex from denaturation at temperatures above the Tm of the nucleic acid duplex, thereby effectively increasing the Tm of the nucleic acid duplex. In certain such embodiments, one or more nucleic acid binding polypeptides are combined with a nucleic acid duplex. In certain such embodiments, the ratio of the concentration of a nucleic acid binding polypeptide to the concentration of the nucleic acid duplex (in nucleotides) is at least about 1:25, 1:10, 1:5, 1:3, 1:1, or any ratio wherein the concentration of the nucleic acid binding polypeptide exceeds that of the nucleic acid duplex.

2. Anneal Complementary Nucleic Acid Strands

In certain embodiments, one or more nucleic acid binding polypeptides are used to promote the annealing of complementary nucleic acid strands. In certain embodiments, annealing takes place with greater rapidity and specificity in the presence of a nucleic acid binding polypeptide than in the absence of a nucleic acid binding polypeptide. In certain embodiments, complementary nucleic acid strands are allowed to anneal in a composition comprising one or more nucleic acid binding polypeptides. In certain such embodiments, a nucleic acid binding polypeptide is present at any concentration from about 1 µg/ml to about 500 µg/ml. In certain embodiments, one or more nucleic acid binding polypeptides are used to favor the annealing of nucleic acid strands that are complementary without mismatches over the annealing of nucleic acid strands that are complementary with mismatches.

In certain embodiments, nucleic acid binding polypeptides are used in hybridization-based detection assays or primer extension assays in which a probe or primer is annealed to a target nucleic acid sequence. Certain examples of the use of nucleic acid binding polypeptides in certain such assays are provided below.

a) Hybridization-Based Detection Assays

In certain embodiments, one or more nucleic acid binding polypeptides are used to increase the efficiency, e.g., the speed and specificity, of a hybridization-based detection assay. Exemplary hybridization-based detection assays include, but are not limited to, assays in which target nucleic acid is immobilized on a solid support and exposed to a labeled probe (see, e.g., Sambrook et al. (2001) *Molecular Cloning: A Laboratory Manual* ($3^{rd}$ ed., Cold Spring Harbor Laboratory Press, NY), e.g., at 6.33-6.58 (describing "Southern" hybridizations). In certain embodiments, exemplary hybridization-based detection assays include microarray-based assays in which target nucleic acid is labeled and exposed to a plurality of polynucleotides immobilized on a solid support. See id. Appendix 10. An example of the use of the nucleic acid binding polypeptide Sso7d in a microarray-based detection assay is described, e.g., in Hatakeyama, US 2003/0022162 A1.

In certain hybridization-based detection assays, a nucleic acid probe is exposed to a mixture of nucleic acids. Within that mixture is a target nucleic acid, which comprises a sequence that is complementary to the probe. The probe specifically anneals to the target nucleic acid to form a hybridization complex under certain conditions, e.g., conditions in which the probe is exposed to the target nucleic acid for an appropriate length of time and at an annealing temperature below that of the predicted Tm of the probe.

In certain embodiments, one or more nucleic acid binding polypeptides are used to increase the Tm of a probe, thereby increasing the temperature at which the annealing may be carried out. In certain such embodiments, the annealing is carried out in the presence of one or more nucleic acid binding polypeptides. In certain such embodiments, the annealing takes place at any temperature from 10° C. below to 40° C. above the predicted Tm of the probe. In certain such embodiments, the annealing takes place at a temperature up to 40° C. above the predicted Tm of the probe. In certain embodiments in which a probe is an oligonucleotide of about 15-35 nucleotides, annealing takes place in the presence of one or more nucleic acid binding polypeptides at any temperature between 40° C. and 85° C.

In certain embodiments, one or more nucleic acid binding polypeptides are used to increase the Tm of a probe, thereby allowing the use of shorter probes. In certain such embodiments, the annealing is carried out in the presence of one or more nucleic acid binding polypeptides. In certain such embodiments, a probe is of any length between 12 and 25 nucleotides. In certain such embodiments, a probe is of any length between 12 and 19 nucleotides. In certain such embodiments, a probe is of any length between 12 and 16 nucleotides.

In certain embodiments, one or more nucleic acid binding polypeptides are used to decrease the duration of time to achieve annealing. In certain such embodiments, the annealing is carried out in the presence of one or more nucleic acid binding polypeptides. In certain such embodiments, the annealing takes place over any amount of time from about 0.5 minute to about three hours. In certain such embodiments, the annealing takes place over any amount of time from about 1 minute to about 30 minutes. In certain such embodiments, the annealing takes place over any amount of time from about 1 minute to about 15 minutes.

In certain embodiments of hybridization-based detection assays, a probe may selectively hybridize to a target nucleic acid that is complementary without mismatches to the probe. In certain embodiments, a probe may also selectively hybridize to a target nucleic acid that is complementary to the probe but that contains one or more mismatches relative to the probe. In certain embodiments, one or more nucleic acid binding polypeptides are used to favor the hybridization of a probe to a target nucleic acid that is complementary without mismatches to the probe over the hybridization of a probe to a target nucleic acid that is complementary but that contains one or more mismatches relative to the probe. Thus, in certain embodiments, the specificity of hybridization is increased. In certain such embodiments, annealing is carried out under any of the conditions of time or temperature described above. In certain such embodiments, annealing is carried out at a temperature greater than the predicted Tm of the probe.

In certain embodiments, because nucleic acid binding polypeptides can substantially increase the speed and specificity of a hybridization-based detection assay, such polypeptides can be used in certain hybridization-based "point-of-use" devices. Point-of-use devices are typically portable devices that allow rapid diagnosis or detection of a physiological or pathological condition, in certain instances, in a non-clinical or small-scale laboratory setting. An exemplary point-of-use device is, for example, a typical pregnancy test. An exemplary point-of-use device that uses hybridization-based detection is, for example, the Affirm VPIII Microbial Identification System (Becton Dickinson and Company—BD Diagnostics, Sparks, Md.), whereby the presence of certain vaginal pathogens is detected in vaginal swab specimens using an oligonucleotide hybirdization assay. See Briselden et al. (1994) *J. Clin. Microbiol.* 32:148-52; Witt et al. (2002) *J. Clin. Microbiol.* 40:3057-3059.

In certain embodiments, one or more nucleic acid binding polypeptides can be used in a hybridization-based point-of-use device that diagnoses a pathological condition, such as an infection, by detecting genetic material from a pathogen in a biological sample from a host. In certain embodiments, the volume of a biological sample to be used with a point-of-use device is reduced in the presence of one or more nucleic acid binding polypeptides. In certain embodiments, the hybridization-based point-of-use device utilizes microarray technology.

In certain embodiments, because nucleic acid binding polypeptides can substantially increase the specificity of a hybridization-based detection assay, one or more nucleic acid binding polypeptides can be used in assays that detect mutations or polymorphisms in a target polynucleotide. For example, one or more nucleic acid binding polypeptides can be used in assays that detect single nucleotide polymorphisms (SNPs). For a review of SNP detection methods, see, e.g., Shi (2001) *Clinical Chem.* 47:164-172. In certain embodiments, one or more nucleic acid binding polypeptides are used in assays that detect rare copies of a target polynucleotide in a complex mixture of nucleic acids. For example, in certain such embodiments, the target polynucleotide comprises genetic material from a pathogen contained within a biological sample from a host.

b) Increase Tm of Primers in Primer Extension Reactions

In certain embodiments, one or more nucleic acid binding polypeptides are used to increase the Tm of a primer in a primer extension reaction. In certain primer extension reactions, such as PCR, one or more primers are annealed to a template nucleic acid. In PCR, e.g., the annealing typically takes place over 30 seconds at about 55° C., a temperature that is less than the predicted Tm of a typical primer of about 20-30 nucleotides. Sambrook et al. (2001) *Molecular Cloning: A Laboratory Manual* (3$^{rd}$ ed., Cold Spring Harbor Laboratory Press, NY) at 8.22.

In certain embodiments, one or more nucleic acid binding polypeptides are used to increase the Tm of a primer in a primer extension reaction, thereby increasing the temperature at which the annealing may be carried out. In certain such embodiments, the annealing is carried out in the presence of one or more nucleic acid binding polypeptides. In certain such embodiments, the annealing is carried out at any temperature from about 55° C. up to about 75° C. In certain such embodiments, the annealing is carried out at any temperature between 60° C. and 70° C. In certain embodiments, increased annealing temperature reduces certain primer artifacts, such as primer dimers and hairpin formation.

In certain embodiments, one or more nucleic acid binding polypeptides are used to increase the Tm of a primer in a primer extension reaction, thereby allowing the use of shorter primers. In certain such embodiments, the annealing is carried out in the presence of one or more nucleic acid binding polypeptides. In certain such embodiments, a primer is of any length between 12 and 19 nucleotides. In certain such embodiments, a primer is of any length between 12 and 16 nucleotides.

3. Enhance Activity of Nucleic Acid Modification Enzymes

In certain embodiments, one or more nucleic acid binding polypeptides are used to enhance the activity of a nucleic acid modification enzyme. In certain such embodiments, one or more nucleic acid binding polypeptides are included in a composition comprising a nucleic acid modification enzyme and a nucleic acid, thus enhancing the activity of the nucleic acid modification enzyme. In various embodiments, the enhancement in the activity of a nucleic acid modification enzyme is demonstrated by comparing the activity of the nucleic acid modification enzyme in the presence of one or more nucleic acid binding polypeptides with its activity in the absence of one or more nucleic acid binding polypeptides. In certain embodiments, the following assays may be used to evaluate the activity of a nucleic acid modification enzyme:

In certain embodiments, the activity of a gyrase or topoisomerase is assessed by determining the change in the supercoiled state of a nucleic acid exposed to the gyrase or topoisomerase in the presence and in the absence of one or more nucleic acid binding polypeptides.

In certain embodiments, the activity of a nuclease is assessed by determining the amount of cleavage product produced by the nuclease in the presence and in the absence of one or more nucleic acid binding polypeptides. In certain such embodiments, the activity of a restriction endonuclease is assessed by exposing a nucleic acid to a restriction endonuclease in the presence and in the absence of one or more nucleic acid binding polypeptides. In certain such embodiments, the extent of digestion by the restriction endonuclease is determined by gel electrophoresis.

In certain embodiments, the activity of a methylase is determined by assessing the methylation state of a nucleic acid exposed to a methylase in the presence and in the absence of one or more nucleic acid binding polypeptides. In certain such embodiments, the methylation state of the nucleic acid is assessed, for example, by determining the extent to which the nucleic acid is cleaved by a methylation sensitive restriction endonuclease, such as MboI.

In certain embodiments, the activity of a ligase is assessed by determining the amount of ligation product produced by the ligase in the presence and in the absence of one or more nucleic acid binding polypeptides. In certain such embodiments, a circularized plasmid is linearized by a restriction endonuclease, isolated from the restriction endonuclease, and exposed to ligase in the presence and in the absence of one or more nucleic acid binding polypeptides. In certain such embodiments, the ligation reaction mixture is used to transform competent bacteria. In certain such embodiments, the number of transformants is proportional to the activity of the ligase.

In certain embodiments, the activity of a polymerase is assessed in the presence and in the absence of one or more nucleic acid binding polypeptides using a polymerase activity assay described above.

4. Increase Processivity of a DNA Polymerase

In certain embodiments, one or more nucleic acid binding polypeptides are used to improve the performance of DNA polymerase. In certain such embodiments, improved performance of DNA polymerase is increased processivity of the DNA polymerase in a primer extension reaction. In certain embodiments, the primer extension reaction is PCR. For example, in certain embodiments, the inclusion of one or more nucleic acid binding polypeptides in a PCR reaction allows for more efficient amplification of targets under suboptimal conditions, such as high salt concentrations. Examples of certain high salt concentrations include from 60 mM KCl to 130 mM KCl for Taq DNA polymerase, and from 40 mM KCl to 130 mM KCl for Pfu polymerase. In certain embodiments, the inclusion of one or more nucleic acid binding polypeptides in a PCR reaction decreases the time of the extension step of PCR to, for example, ≤5 minutes, ≤3 minutes, ≤2 minutes, ≤1 minute, or ≤30 seconds. In certain embodiments, the inclusion of one or more nucleic acid binding polypeptides in a PCR reaction allows for more efficient amplification of long targets, for example, targets from about 5 kb to about 20 kb.

F. Certain Methods Using Fusion Proteins

In certain embodiments, a fusion protein comprising a nucleic acid binding polypeptide and a nucleic acid modification enzyme is used in any method that uses a nucleic acid binding polypeptide (as described, for example, in Part V.E. above), except that the fusion protein replaces the nucleic acid binding polypeptide in the method. In certain embodiments, a fusion protein comprising a nucleic acid binding polypeptide and a nucleic acid modification enzyme is used in any method that uses a nucleic acid binding polypeptide (as described, for example, in Part V.E. above), except that the fusion protein is used in combination with the nucleic acid binding polypeptide in the method.

In certain embodiments, a fusion protein comprising a nucleic acid binding polypeptide and a nucleic acid modification enzyme is used in any reaction in which the nucleic acid modification enzyme alone can be used. In certain embodiments, a fusion protein comprising a nucleic acid binding polypeptide and a nucleic acid modification enzyme is used to improve the efficiency of any reaction in which the nucleic acid modification enzyme alone can be used. In certain such embodiments, a fusion protein comprising a nucleic acid binding polypeptide and a nucleic acid modification enzyme has increased activity relative to the nucleic acid modification enzyme alone. In certain such embodiments, the assays set forth in Part V.E.3 above may be used to evaluate the activity of a nucleic acid modification enzyme or a fusion protein comprising a nucleic acid binding polypeptide and a nucleic acid modification enzyme. In certain embodiments, a fusion protein comprising a nucleic acid binding polypeptide and a DNA polymerase has increased processivity relative to the DNA polymerase alone.

In certain embodiments, a fusion protein comprising a nucleic acid binding polypeptide and a DNA polymerase is used in a primer extension reaction. In certain such embodiments, the fusion protein increases the efficiency of the primer extension reaction. In certain embodiments, a fusion protein comprising a nucleic acid binding polypeptide and a DNA polymerase is included in a primer extension reaction to increase the Tm of one or more primers in the reaction. In certain embodiments, the temperature at which annealing is carried out may be increased. In certain embodiments, shorter primers may be used.

In certain embodiments, a fusion protein comprising a nucleic acid binding polypeptide and a thermostable DNA polymerase is included in a PCR reaction. In certain such embodiments, the fusion protein increases the efficiency of PCR. In certain embodiments, a fusion protein comprising a nucleic acid binding polypeptide and a thermostable DNA polymerase is included in a PCR reaction that is conducted under suboptimal conditions, such as high salt concentrations. Exemplary high salt concentrations are described above in Part V.E.4. In certain embodiments, a fusion protein comprising a nucleic acid binding polypeptide and a thermostable DNA polymerase is included in a PCR reaction to decrease the time of the extension step of PCR. Exemplary extension times are provided above in Part V.E.4. In certain embodiments, a fusion protein comprising a nucleic acid binding polypeptide and a thermostable DNA polymerase is included in a PCR reaction to more efficiently amplify long targets. Exemplary target lengths are provided above in Part V.E.4. In certain embodiments, a fusion protein comprising a nucleic acid binding polypeptide and a thermostable DNA polymerase is included in a PCR reaction to increase the amount of PCR amplification product.

In certain embodiments, a fusion protein comprising a nucleic acid binding polypeptide and a thermostable DNA polymerase is used in "hot start" PCR. In certain embodiments, "hot start" PCR is used to suppress non-specific binding of primer to template. See, e.g., Sambrook et al. (2001) *Molecular Cloning: A Laboratory Manual* ($3^{rd}$ ed., Cold Spring Harbor Laboratory Press, NY) at 8.110 (describing "hot start" PCR). In certain embodiments of "hot start" PCR, one or more components to be used in a PCR are prevented from functioning in the PCR until the reaction mixture reaches or exceeds a temperature at which non-specific priming does not occur. Id. For example, in certain embodiments of "hot start" PCR, an antibody to the thermostable DNA polymerase is used to reversibly block polymerase activity until a suitable temperature is reached. See, e.g., Kellogg et al. (1994) *Biotechniques* 16:1134-1137 (describing the use of antibodies to Taq DNA polymerase). In certain embodiments, a fusion protein comprising a nucleic acid binding polypeptide and a thermostable DNA polymerase is used in "hot start" PCR. In certain such embodiments, an antibody to the nucleic acid binding polypeptide is used to reversibly block nucleic acid binding activity and/or polymerase activity until a suitable temperature is reached.

In certain embodiments, a fusion protein comprising a nucleic acid binding polypeptide and a reverse transcriptase is used in a primer extension reaction. In certain such embodiments, the fusion protein increases the efficiency of the primer extension reaction. In certain embodiments, a fusion protein comprising a nucleic acid binding polypeptide and a reverse transcriptase is included in a primer extension reaction to increase the Tm of one or more primers in the reaction. In certain embodiments, the temperature at which annealing is carried out may be increased. In certain embodiments, shorter primers may be used.

In certain embodiments, a fusion protein comprising a nucleic acid binding polypeptide and a thermostable reverse transcriptase is included in an RT-PCR (reverse transcriptase-PCR) reaction. In certain such embodiments, the fusion protein increases the efficiency of RT-PCR. In certain embodiments, a fusion protein comprising a nucleic acid binding polypeptide and a thermostable reverse transcriptase is included in a RT-PCR reaction that is conducted under suboptimal conditions, such as high salt concentrations. Exemplary high salt concentrations are described above in Part V.E.4. In certain embodiments, a fusion protein comprising a nucleic acid binding polypeptide and a thermostable reverse transcriptase is included in a RT-PCR reaction to decrease the time of the extension step of RT-PCR. Exemplary extension times are provided above in Part V.E.4. In certain embodiments, a fusion protein comprising a nucleic acid binding polypeptide and a thermostable reverse transcriptase is included in a RT-PCR reaction to more efficiently amplify long targets. Exemplary target lengths are provided above in Part V.E.4. In certain embodiments, a fusion protein comprising a nucleic acid binding polypeptide and a thermostable reverse transcriptase is included in a RT-PCR reaction to increase the amount of RT-PCR amplification product.

In certain embodiments, a fusion protein comprising a nucleic acid binding polypeptide and a thermostable reverse transcriptase is used in "hot start" RT-PCR. In certain embodiments, "hot start" RT-PCR is used to suppress non-specific binding of primer to template. See, e.g., Sambrook et al. (2001) *Molecular Cloning: A Laboratory Manual* ($3^{rd}$ ed., Cold Spring Harbor Laboratory Press, NY) at 8.110 (describing "hot start" RT-PCR). In certain embodiments of "hot start" RT-PCR, one or more components to be used in a RT-PCR are prevented from functioning in the RT-PCR until the reaction mixture reaches or exceeds a temperature at which non-specific priming does not occur. Id. For example, in certain embodiments of "hot start" RT-PCR, an antibody to the thermostable reverse transcriptase is used to reversibly block reverse transcriptase activity until a suitable temperature is reached. See, e.g., Kellogg et al. (1994) *Biotechniques* 16:1134-1137 (describing the use of antibodies to Taq DNA polymerase). In certain embodiments, a fusion protein comprising a nucleic acid binding polypeptide and a thermostable reverse transcriptase is used in "hot start" RT-PCR. In certain such embodiments, an antibody to the nucleic acid binding polypeptide is used to reversibly block nucleic acid binding activity and/or reverse transcriptase activity until a suitable temperature is reached.

G. Certain Exemplary Amplification Methods Using Fusion Proteins

In certain embodiments, a fusion protein comprising a nucleic acid binding polypeptide and a polymerase is used to amplify a target nucleic acid sequence, e.g., in a primer extension reaction. In certain such embodiments, the primer extension reaction is PCR. Certain exemplary methods for performing PCR are known to those skilled in the art. See, e.g., Sambrook et al. (2001) *Molecular Cloning: A Laboratory Manual* ($3^{rd}$ ed., Cold Spring Harbor Laboratory Press, NY) at 8.18-8.24; Innis et al. (1990) *PCR Protocols: A Guide to Methods and Applications* (Academic Press, NY).

1. "Fast" PCR

In various instances, a typical PCR cycle comprises denaturing a double-stranded nucleic acid, annealing at least two primers to opposite strands of the denatured nucleic acid, and extending the primers using a thermostable DNA polymerase. In various embodiments, the primers are typically oligodeoxyribonucleotides of about 18-25 nucleotides in length. In various instances, the denaturing step is typically at least 30 seconds in length at a temperature of at least about 90° C. In various instances, the annealing step is typically at least 30 seconds in length at a temperature that is less than the predicted Tm of the primers. In various instances, the annealing is typically conducted at about 55° C. for a primer of about 18-25 nucleotides. In various instances, the extension step typically takes place at 72° C. for one minute per 1000 base pairs of target DNA. In various instances, about 25-30 cycles are typically performed to generate detectable amplification product. For certain typical PCR conditions, see, e.g., Sambrook et al. (2001) *Molecular Cloning: A Laboratory Manual* (3$^{rd}$ ed., Cold Spring Harbor Laboratory Press, NY) at 8.22.

In certain embodiments, a fusion protein comprising a nucleic acid binding polypeptide and a polymerase unexpectedly allows for the amplification of a target nucleic acid using substantially faster cycling conditions, e.g., substantially decreased denaturing, annealing, and/or extension times, as described below.

In certain embodiments, a fusion protein comprising a nucleic acid binding polypeptide and a polymerase stabilizes the primer-template duplex, thereby increasing the Tm of the primers above the predicted Tm. Accordingly, in certain embodiments, the annealing is carried out at a temperature that is greater than the predicted Tm of the primers. In certain such embodiments, it is possible to carry out the annealing and extension at the same temperature in a single step, thus increasing the efficiency of PCR.

In certain embodiments, the annealing is carried out at a temperature that is from about 1° C. to about 40° C. above the predicted Tm of at least one of the primers (including all points between those endpoints). In certain such embodiments, the annealing is carried out at about 5° C., 10° C., 15° C., or 20° C. above the predicted Tm of at least one of the primers.

In certain embodiments, the annealing is carried out at any temperature from about 55° C. up to about 80° C. (including all points between those endpoints). In certain such embodiments, the annealing is carried out at any temperature from about 62° C. to about 78° C.; from about 62° C. to about 75° C.; from about 65° C. to about 72° C.; from about 65° C. to about 75° C.; from about 68° C. to about 72° C.; and from about 68° C. to about 75° C. In certain embodiments, the annealing and extension are carried out at the same temperature.

In certain embodiments, annealing at temperatures higher than the annealing temperatures typically used in PCR may, under certain circumstances, have other beneficial effects. For example, in certain embodiments, annealing at higher temperatures may improve primer specificity (i.e., may alleviate "mispriming"). In certain embodiments, annealing at higher temperatures may allow for more efficient amplification of problematic targets, such as targets having repetitive sequences or targets having complex secondary structure, such as GC-rich targets.

In certain embodiments, a fusion protein comprising a nucleic acid binding polypeptide and a polymerase is used in PCR amplifications having substantially decreased denaturing, annealing, and/or extension times. Generally, the time of the denaturing, annealing, and/or extension step in a PCR cycle is measured as the amount of time that the reaction mixture is held at the denaturing, annealing, and/or extension temperature once the reaction mixture reaches that temperature. In certain embodiments, the time of the denaturing, annealing, and/or extension step is any amount of time that is less than or equal to 30 seconds. For example, in certain embodiments, the time of the denaturing, annealing, and/or extension step is less than or equal to 30, 25, 20, 15, 10, 9, 8, 7, 6, 5, 4, 3, 2, or 1 second. In certain embodiments, the time of the denaturing, annealing, and/or extension step is 0 seconds. In certain embodiments, the annealing and extension are performed in a single step that is of any of the above lengths of time.

Exemplary embodiments of a PCR amplification cycle comprising a denaturing step, an annealing step, and an extension step are as follows. In certain such embodiments, a reaction mixture comprising a target nucleic acid, at least two primers, and a fusion protein comprising a polymerase and a nucleic acid binding polypeptide is brought to a denaturing temperature (a temperature capable of denaturing the target nucleic acid). Bringing the reaction mixture to the denaturing temperature encompasses heating or cooling the reaction mixture to the denaturing temperature, or maintaining the reaction mixture at the denaturing temperature without heating or cooling it. After bringing the reaction mixture to the denaturing temperature, the reaction mixture is cooled to an annealing temperature. At the annealing temperature, the at least two primers are capable of selectively hybridizing to opposite strands of the target nucleic acid. In certain embodiments, the annealing temperature is greater than the Tm of at least one of the primers. After cooling the reaction mixture to the annealing temperature, the reaction mixture is heated to an extension temperature. The extension temperature allows for the extension of the at least two primers by the fusion protein.

In certain embodiments of the above PCR amplification cycle, the reaction mixture is held at the denaturing, annealing, and/or extension temperature for any amount of time that is less than or equal to 30 seconds. For example, in certain embodiments, the reaction mixture is held at the denaturing, annealing, and/or extension temperature for less than or equal to 30, 25, 20, 15, 10, 9, 8, 7, 6, 5, 4, 3, 2, or 1 second. In certain such embodiments, the reaction mixture is held at the denaturing, annealing, and/or extension temperature for 0 seconds. In certain such embodiments, the reaction mixture is cycled from one temperature to the next without holding at any temperature (i.e., the time of the denaturing, annealing, and extension steps is 0 seconds).

Exemplary embodiments of a PCR amplification cycle comprising a denaturing step and a combined annealing/extension step are as follows. In certain such embodiments, a reaction mixture comprising a target nucleic acid, at least two primers, and a fusion protein comprising a polymerase and a nucleic acid binding polypeptide is brought to a denaturing temperature. Bringing the reaction mixture to the denaturing temperature encompasses heating or cooling the reaction mixture to the denaturing temperature, or maintaining the reaction mixture at the denaturing temperature without heating or cooling it. After bringing the reaction mixture to the denaturing temperature, the reaction mixture is cooled to an annealing/extension temperature. In certain embodiments, the annealing/extension temperature is greater than the Tm of at least one of the primers. At the annealing/extension temperature, the at least two primers selectively hybridize to opposite strands of the denatured target nucleic acid and are extended by the fusion protein.

In certain embodiments of the above PCR amplification cycle, the reaction mixture is held at either the denaturing temperature and/or the annealing/extension temperature for any amount of time that is less than or equal to 30 seconds. For example, in certain embodiments, the reaction mixture is held at either the denaturing temperature and/or the annealing/extension temperature for less than or equal to 30, 25, 20, 15, 10, 9, 8, 7, 6, 5, 4, 3, 2, or 1 second. In certain such embodiments, the reaction mixture is held at either the denaturing temperature and/or the annealing/extension temperature for 0 seconds. In certain such embodiments, the reaction mixture is cycled from the denaturing temperature to the annealing/extension temperature without holding at either temperature (i.e., the time of both the denaturing step and the combined annealing/extension step is 0 seconds).

In certain embodiments, a target nucleic acid is denatured by exposing the target nucleic acid to a helicase. See, e.g., Moore (2005) Nature 435:235-238. In certain such embodiments, the denaturing step and the annealing step of a PCR amplification cycle may be performed at the same temperature and/or in a single step. In certain such embodiments, the denaturing step and the combined annealing/extension step of a PCR amplification cycle are performed at the same temperature and/or in a single step.

In certain embodiments, a PCR amplification cycle is repeated multiple times. In various embodiments, the number of cycles may vary. For example, in certain embodiments, the number of cycles may relate to the initial concentration of the target nucleic acid, such that more cycles are performed for targets initially present at lower concentrations. In certain embodiments, the number of cycles performed is sufficient to generate detectable amplification product.

In certain embodiments, the total time to complete a PCR cycle is substantially decreased. The duration of time to complete a single PCR cycle depends, in part, on the amount of time that the reaction is held at the denaturing, annealing, and/or extension temperatures. That amount of time may be user-specified, e.g., based on the denaturing, annealing, and extension times that optimize the specificity and/or yield of amplification product. The duration of time to complete a single PCR cycle also depends, in part, on the amount of time to transition from one temperature to another (i.e., the "ramping" time). That amount of time may be user-specified and/or may depend on the instrumentation used to perform thermal cycling.

The amount of time to complete a single amplification cycle varies among certain known thermal cyclers. For example, certain thermal cyclers are capable of completing a single amplification cycle in about 15 to about 45 seconds for reaction volumes of about 10-30 µl. See, e.g., Applied Biosystems 9800 Fast PCR System, 2004 product overview (Applied Biosystems, Foster City, Calif.); Roche LightCycler®System (Roche Applied Science, Indianapolis, Ind.); the SmartCycler® System (Cepheid, Sunnyvale, Calif.); the RapidCycler instruments (Idaho Technology, Salt Lake City, Utah); and U.S. Pat. No. 6,787,338 B2. Certain thermal cyclers are capable of completing a single amplification cycle in as little as 4 to 6 seconds. See, e.g., the PCRJet, Megabase Research Products, Lincoln, Nebr., patented under U.S. Pat. Nos. 6,472,186; and 6,180,372 B1. For a review of instrumentation capable of rapid cycling times, see, e.g., Moore (2005) Nature 435:235-238.

In certain embodiments, the time to complete a single PCR cycle is any amount of time that is less than or equal to 90 seconds. For example, in certain embodiments, the time to complete a single PCR cycle is less than or equal to 90, 75, 60, 50, 45, 40, 35, 30, 25, 20, 15, 10, or 5 seconds.

In various embodiments, PCR may be carried out in any of a variety of vessels. Certain such vessels include, but are not limited to, microfuge tubes (including thin-walled microfuge tubes); microcapillaries; and multi-well plates (including thin-walled multi-well plates), such as 96-well, 384-well, and 1536-well plates. In certain embodiments, the choice of vessel depends on the thermal cycler used. Certain exemplary thermal cyclers and suitable vessels for such cyclers are known to those skilled in the art, e.g., the GeneAmp® PCR System 9700 and Applied Biosystems 9800 Fast PCR System (Applied Biosystems, Foster City, Calif.). See also Constans (2001) The Scientist 15(24):32 at pp. 1-7 (Dec. 10, 2001); U.S. Pat. Nos. 6,787,338 B2, 6,180,372 B1, 6,640,891 B1, 6,482,615 B2, and 6,271,024 B1.

In certain embodiments, amplification products are detected using any nucleic acid detection method. For example, in certain embodiments, amplification products are detected using certain routine gel electrophoresis methods known to those skilled in the art. In certain embodiments, amplification products are detected using mass spectrometry. See, e.g., U.S. Pat. No. 6,180,372. In certain embodiments, amplification products are detected in the reaction mixture, e.g., either during one or more amplification cycles and/or after completion of one or more amplification cycles. See, e.g., U.S. Pat. Nos. 6,814,934 B1, 6,174,670 B1, and 6,569,627 B2, and Pritham et al. (1998) J. Clin. Ligand Assay 21:404-412. Certain such embodiments are described below, Part V.G.3. In certain embodiments, amplification products are detected using one or more labeled primers or probes. Certain such primers and probes are described below, Part V.G.3.

2. Certain PCR Conditions

In certain embodiments, a fusion protein comprising a nucleic acid binding polypeptide and a polymerase exhibits improved performance relative to polymerase alone. For example, in certain embodiments, a fusion protein comprising a nucleic acid binding polypeptide and a polymerase is capable of amplifying targets in higher salt concentrations than polymerase alone. Thus, in certain embodiments, salt concentrations from about 10 mM to about 130 mM (including all points between those endpoints) may be used. Exemplary salt concentrations include, but are not limited to, about 40, 50, 60, 70, 80, 90, and 100 mM of a monovalent salt, such as KCl.

In certain embodiments, a fusion protein comprising a nucleic acid binding polypeptide and a polymerase is capable of amplifying targets at a higher pH than polymerase alone. Thus, in certain embodiments, the pH may be equal to or greater than 8.5. In certain embodiments, fusion proteins comprising a polymerase and a nucleic acid binding polypeptide can be used in amplification reactions at high pH, for example, at a pH in the range of 8.5 to 10 (including all pH values between those endpoints). In certain embodiments, fusion proteins comprising a polymerase and a nucleic acid binding polypeptide can be used in amplification reactions at high pH, for example, at a pH in the range of 8.5 to 9.5.

In certain embodiments, a fusion protein comprising a nucleic acid binding polypeptide and a polymerase is capable of amplifying long targets more efficiently than polymerase alone. Thus, in certain embodiments, a fusion protein comprising a nucleic acid binding polypeptide and a polymerase is able to more efficiently amplify targets from at least about 5 kb to at least about 20 kb in length (including all points between those endpoints).

In certain embodiments, a fusion protein comprising a nucleic acid binding polypeptide and a polymerase is capable of producing higher yields of amplification product than polymerase alone under the same amplification conditions. In certain such embodiments, the yield (amount of amplification product) produced by the fusion protein is from about 2 to about 500 fold higher (including all points between those endpoints) than the yield produced by polymerase alone under the same conditions. Accordingly, in certain embodiments, a fusion protein comprising a nucleic acid binding polypeptide and a polymerase uses fewer cycles to generate the same amount of amplification product as polymerase alone under the same conditions. In certain embodiments, the number of cycles in a PCR is from about 15 to about 40 (including all points between those endpoints).

In certain embodiments, yield is calculated by the following equation: $N=N_0(1+E)^n$, where N is the number of amplified molecules, $N_0$ is the initial number of molecules, n is the number of amplification cycles, and E is the "amplification efficiency." See Arezi et al. (2003) *Analytical Biochem.* 321: 226-235. "Amplification efficiency" may be determined by the following equation: $E=10^{[-1/slope]}-1$, where "slope" is the slope of the line of the plot of $C_T$ versus the log of the intial target copy number. See id. $C_T$ is the "threshold cycle," or the cycle in which the emission intensity of the amplification product measured by a real-time PCR instrument (such as the 7500 Fast Real-Time PCR System (Applied Biosystems, Foster City, Calif.)) is recorded as statistically significant above background noise when reaction components are not limiting. See id. In certain instances, amplification efficiency for a particular polymerase may vary with target length. See id.

In certain embodiments, the amplification efficiency of a fusion protein comprising a nucleic acid binding polypeptide and a polymerase is from 0.5 to 1.0 (including all points between those endpoints). In certain embodiments, the amplification efficiency of a fusion protein comprising a nucleic acid binding polypeptide and a polymerase is from at least 10% to at least 60% greater than that of polymerase alone under the same conditions.

In certain embodiments, the yield produced by a fusion protein comprising a nucleic acid binding polypeptide and a polymerase is from 85% to 100% (including all points between those endpoints) of the theoretical maximum possible yield, $N=N_0 2^n$, which assumes that the amount of product doubles with each amplification cycle. See id. In certain embodiments, the yield produced by a fusion protein comprising a nucleic acid binding polypeptide and a polymerase in a single amplification cycle is from $1.4N_0$ to $2N_0$, including all points between those endpoints, where $N_0$ is the initial number of molecules (i.e., the number of molecules present at the start of the amplification cycle). In certain embodiments, the yield produced by a fusion protein comprising a nucleic acid binding polypeptide and a polymerase after n amplification cycles is from $N_0(1.4)^n$ to $N_0(2)^n$, including all points between those endpoints.

In certain embodiments, as discussed above, a fusion protein comprising a nucleic acid binding polypeptide and a polymerase increases the Tm of primers above the predicted Tm. In certain embodiments, this allows for the use of primers shorter than those typically used in PCR. For example, in certain embodiments, primers may be used that are about 12 nucleotides in length or longer. In certain embodiments, exemplary primer lengths are from about 12 to about 30 nucleotides (including all points between those endpoints).

In certain embodiments, one or more additives that enhance the performance of a polymerase are added to a PCR. Certain exemplary additives are described, e.g., in Sambrook et al. (2001) *Molecular Cloning: A Laboratory Manual* (3rd ed., Cold Spring Harbor Laboratory Press, NY) at p. 8.9. In certain embodiments, one or more "polymerase enhancing factors" are added to a PCR to enhance the performance of a fusion protein comprising an archaeal family B polymerase (or a fragment or variant thereof) and a nucleic acid binding polypeptide. Certain exemplary archaeal family B polymerase enhancing factors are described, e.g., in U.S. Pat. No. 6,183,997 B1. In certain embodiments, the polymerase enhancing factor is a dUTPase.

Exemplary guidance for certain other PCR conditions (e.g., primer concentration, dNTP concentration, units of polymerase, and target concentration) may be found in the art. Certain exemplary conditions are provided below.

In certain embodiments, the concentration of each PCR primer is from about 0.1 µM to about 2.5 µM (including all points between those endpoints). In certain embodiments, the concentration of each PCR primer is from about 0.5 to about 1 µM. In certain embodiments, the primers are present at different concentrations.

In certain embodiments, at least one primer in a PCR comprises a 3' portion that selectively hybridizes to the target nucleic acid and a 5' portion that does not selectively hybridize to the target nucleic acid. In certain such embodiments, the sequence of the 5' portion is the same as the sequence of a "universal" primer. Those skilled in the art are familiar with certain universal primers and their use in certain amplification reactions. See, e.g., U.S. Pat. No. 6,270,967 B1; Lin et al. (1996) *Proc. Nat'l Acad. Sci. USA* 93:2582-2587. In certain such embodiments, the universal primer may then be used to amplify the amplification products generated by primers that selectively hybridize to the target nucleic acid.

In certain embodiments, primers are used under conditions that favor asymmetric PCR. According to certain embodiments, an asymmetric PCR may occur when (i) at least one primer is in excess relative to the other primer(s); (ii) only one primer is used; (iii) at least one primer is extended under given amplification conditions and another primer is disabled under those conditions; or (iv) both (i) and (iii). Consequently, an excess of one strand of the amplification product (relative to its complement) is generated in asymmetric PCR.

In certain embodiments, primers are used having different Tms. Such embodiments have been called asynchronous PCR (A-PCR). See, e.g., published U.S. Patent Application No. US 2003-0207266 A1, filed Jun. 5, 2001. In certain embodiments, the Tm of a primer is at least 4-15° C. different from the $Tm_{50}$ of another primer.

In certain embodiments, a fusion protein comprising a nucleic acid binding polypeptide and a polymerase has polymerase activity of about 0.25 to about 10 units (including all points between those endpoints). In certain such embodiments, polymerase activity is from about 1 to about 5 units (including all points between those endpoints). In certain such embodiments, polymerase activity is from about 1 to about 2.5 units (including all points between those endpoints).

In certain embodiments, the concentration of each dNTP is from about 20 to about 500 µM (including all points between those endpoints). In certain such embodiments, the concentration of each dNTP is about 250 µM.

In certain embodiments, the target nucleic acid to be amplified may be in double-stranded form. In certain embodiments, the target nucleic acid to be amplified may be in single-stranded form. In certain embodiments in which the target nucleic acid is in single-stranded form, the first amplification cycle can be a linear amplification in which only one primer is extended. In certain embodiments, the target nucleic acid may be present in a sample comprising a complex mixture of nucleic acids and other macromolecules. In certain embodiments, the target nucleic acid may be present in only a few copies. In certain embodiments, the target nucleic acid may be present in a single copy.

3. Certain Real-Time PCR

In certain embodiments, a fusion protein comprising a nucleic acid binding polypeptide and a polymerase is used to amplify a target nucleic acid using "real-time" PCR. For a review of certain real-time PCR, see, e.g., Edwards et al. (ed.) *Real-Time PCR, an Essential Guide* (Horizon Bioscience, 2004). In certain embodiments of real-time PCR, the progress of the PCR is monitored at any point during or after one or more amplification cycles and, optionally, after the completion of all amplification cycles. In certain embodiments, the progress of a PCR is monitored by detecting the presence of amplification products in the reaction. Exemplary methods for performing real-time PCR are described, for example, in U.S. Pat. Nos. 6,814,934 B1, 6,174,670 B1, and 6,569,627 B2, and in Pritham et al. (1998) *J. Clin. Ligand Assay* 21:404-412. Exemplary instruments for performing real-time PCR include, but are not limited to, the ABR PRISM® 7000 Sequence Detection System; the Applied Biosystems 7300 Real-Time PCR System, 7500 Real-Time PCR System, 7500 Fast Real-Time PCR System, and 7900HT Fast Real-Time PCR System (Applied Biosystems, Foster City, Calif.); and certain instrumentation discussed above, Part V.G.1.

In certain embodiments of real-time PCR, the reaction includes an indicator molecule. In certain embodiments, an indicator molecule indicates the amount of double-stranded DNA in the reaction. In certain such embodiments, an indicator molecule is a fluorescent indicator. In certain such embodiments, a fluorescent indicator is a nucleic acid binding dye. Certain such dyes include, but are not limited to, SYBR® Green I (see, e.g., U.S. Pat. No. 6,569,627); SYBR® Gold; thiazole orange; ethidium bromide; pico green; acridine orange; quinolinium 4-[(3-methyl-2(3H)-benzoxazolylidene)methyl]-1-[3-(trimethylammonio) propyl]-diiodide (YOPRO®); quinolinium 4-[(3-methyl-2(3H)-benzothiazolylidene)methyl]-1-[3-(trimethylammonio) propyl]-diiodide (TOPRO®); and chromomycin A3. SYBR® Green I, SYBR® Gold, YOPRO®, and TOPRO® are commercially available from Molecular Probes, Inc., Eugene, Oreg.

In certain embodiments of real-time PCR, a fusion protein comprising a nucleic acid binding polypeptide and a polymerase having 5' to 3' exonuclease activity is used to amplify a target nucleic acid. In certain embodiments of real-time PCR, a fusion protein comprising a nucleic acid binding polypeptide and a polymerase that lacks 5' to 3' exonuclease is used to amplify a target nucleic acid. In certain such embodiments, 5' to 3' exonuclease activity is provided in trans, e.g., by including a polypeptide that has 5' to 3' exonuclease activity. In certain embodiments, a polypeptide that has 5' to 3' exonuclease activity is an enzyme such as a eukaryotic or archaeal "flap" endonuclease, e.g., FEN1. See, e.g., Kaiser et al. (1999) *J. Biol. Chem.* 274:21387-21394. In certain embodiments, a polypeptide that has 5' to 3' exonuclease activity is a polymerase, such as a bacterial family A polymerase. In certain such embodiments, the polymerase is a variant of a bacterial family A polymerase having reduced polymerase activity. In certain embodiments, a polypeptide that has 5' to 3' exonuclease activity is a domain isolated from a polymerase, wherein the domain has 5' to 3' exonuclease activity.

In certain embodiments, real-time PCR is conducted in the presence of an indicator probe. In certain embodiments, an indicator probe produces a detectable signal in the presence of amplification product. In certain embodiments, an indicator probe selectively hybridizes to a strand of an amplification product, resulting in the production of a detectable signal.

In certain embodiments, an indicator probe is an interaction probe comprising two moieties, wherein one of the moieties is capable of influencing the detectable signal from the other moiety depending upon whether the probe is hybridized to a strand of an amplification product. For example, in certain such embodiments, one moiety of an interaction probe is a fluorophore, such that energy from the fluorophore is transferred to the other moiety by the process of fluorescence resonance energy transfer (FRET) depending upon whether the probe is hybridized to a strand of the amplification product. In certain embodiments, FRET occurs when the probe is hybridized to a strand of an amplification product. In certain embodiments, FRET occurs when the probe is not hybridized to a strand of an amplification product.

In certain embodiments, an indicator probe is a 5'-nuclease probe. In certain such embodiments, the probe comprises a fluorophore linked to a quencher moiety through an oligonucleotide link element, wherein energy from the fluorophore is transferred to the quencher moiety in the intact probe through the process of FRET. By this process, fluorescence from the fluorophore is quenched. In certain embodiments, the quencher moiety is a different fluorophore that is capable of fluorescing at a different wavelength. Certain exemplary fluorophores include, but are not limited to, 6FAM™, VIC®, TET™ or NED™ (Applied Biosystems, Foster City, Calif.). Certain exemplary quencher moieties include, but are not limited to, certain non-fluorescent minor groove binders (MGB) and TAMRA™ (which is also a fluorophore) (Applied Biosystems, Foster City, Calif.).

In certain embodiments, the 5'-nuclease probe, when hybridized to a strand of the amplification product, is cleaved by the 5' to 3' exonuclease activity of an extending polymerase and/or by a polypeptide having 5' to 3' exonuclease activity. In certain embodiments, cleavage is detected by a change in fluorescence. Thus, in certain embodiments, the change in fluorescence is related to the amount of amplification product in the reaction. In certain embodiments in which the 5'-nuclease probe comprises a fluorophore linked to a quencher moiety, cleavage of the probe results in an increase in fluorescence from the fluorophore. In certain such embodiments in which the quencher moiety is a different fluorophore, the fluorescence from the quenching moiety is decreased. Certain exemplary methods for using 5'-nuclease probes for the detection of amplification products are known to those skilled in the art. See, e.g., Sambrook et al. (2001) *Molecular Cloning: A Laboratory Manual* (3$^{rd}$ ed., Cold Spring Harbor Laboratory Press, NY) at 8.95; Livak et al. (1995) *PCR Methods Appl.* 4:357-362; and U.S. Pat. No. 5,538,848 and Heid et al. (1996) *Genome Res.* 6:986-994 (discussing T AQ M AN ® probes).

In certain embodiments, real-time PCR is conducted in the presence of two probes that selectively hybridize to adjacent regions of a strand of the amplification product. In certain such embodiments, the 3' end of the first probe is attached to a donor fluorophore. The 5' end of the second probe is attached to an acceptor fluorophore that is capable of fluorescing at a different wavelength than the donor fluorophore. (Alternatively, in certain embodiments, the 3' end of the first probe is attached to an acceptor fluorophore and the 5' end of the second probe is attached to a donor fluorophore.) When the probes are hybridized to a strand of the amplification product, the 3' end of the first probe is in sufficient proximity to the 5' end of the second probe, such that the fluorescence energy from the donor fluorophore is transferred to the acceptor fluorophore via FRET. Accordingly, an increase in fluorescence from the acceptor fluorophore indicates the presence of amplification products.

In certain embodiments, real-time PCR is conducted in the presence of a hybridization-dependent probe. In certain embodiments, a hybridization-dependent probe is a hairpin probe, such as a "molecular beacon." See, e.g., U.S. Pat. Nos. 5,118,801; 5,312,728; and 5,925,517. In certain such embodiments, an oligonucleotide capable of forming a hairpin (stem-loop) structure is linked to a fluorophore at one end of the stem and a quencher moiety at the other end of the stem. The quencher moiety quenches the fluorescence from the fluorophore when the oligonucleotide is in a hairpin configuration. The sequence of the hairpin loop is capable of selectively hybridizing to a strand of the amplification product. When such hybridization takes place, the hairpin configuration is disrupted, separating the fluorophore from the quencher moiety. Accordingly, fluorescence from the fluorophore is increased. Thus, an increase in fluorescence indicates the presence of amplification product.

Other hybridization-dependent probes include, but are not limited to, ECLIPSE™ probes (see, e.g., Afonina et al. (2002) *Biotechniques* 32:940-44, 946-49). Certain quenching moieties for use with hybridization-dependent probes include, but are not limited to, Dabcyl, QSY7, QSY9, QSY22, and QSY35 (commercially available from Molecular Probes, Eugene, Oreg.).

In certain embodiments, real-time PCR is conducted using at least one primer comprising a 5' portion that is not complementary to the target nucleic acid. In certain such embodiments, the 5' portion is capable of forming a hairpin (stem-loop) structure that is linked to a fluorophore at one end of the stem and a quencher moiety at the other end of the stem. The quencher moiety quenches the fluorescence from the fluorophore when the 5' portion is in a hairpin conformation. When the primer becomes incorporated into a double-stranded amplification product, the hairpin conformation is disrupted. Accordingly, fluorescence from the fluorophore is increased. Thus, an increase in fluorescence indicates the presence of amplification product. Certain quenching moieties for use with such primers include, but are not limited to, Dabcyl, QSY7, QSY9, QSY22, and QSY35 (commercially available from Molecular Probes). Certain fluorophores for use with such primers include, but are not limited to, 6-FAM. An example of such a primer is a UNIPRIMER™ (Chemicon International Inc., Temecula, Calif.) or a SCORPION® primer (see, e.g., Whitcombe et al. (1999) *Nat. Biotechnol.* 17:804-807).

4. Certain Hot-Start PCR

In certain embodiments, a fusion protein comprising a nucleic acid binding polypeptide and a thermostable DNA polymerase is used in "hot start" PCR. In certain embodiments known to those skilled in the art, "hot start" PCR is used to suppress non-specific binding of primer to template. See, e.g., Sambrook et al. (2001) *Molecular Cloning: A Laboratory Manual* (3$^{rd}$ ed., Cold Spring Harbor Laboratory Press, NY) at 8.110 (describing "hot start" PCR). In certain embodiments of "hot start" PCR, one or more components to be used in a PCR are prevented from functioning in the PCR until the reaction mixture reaches or exceeds a temperature at which non-specific priming does not occur or is substantially reduced. Id.

In certain embodiments of "hot start" PCR, a thermostable DNA polymerase is reversibly inactivated until a suitable temperature is reached. For example, in certain embodiments, an antibody to a thermostable DNA polymerase is used to reversibly block polymerase activity until a suitable temperature is reached. See, e.g., Kellogg et al. (1994) *Biotechniques* 16:1134-1137 (describing the use of antibodies to Taq DNA polymerase). In certain embodiments, a thermostable DNA polymerase is partially or completely inactivated by a reversible chemical modification. In certain such embodiments, the chemical modification is reversed at a suitable temperature under amplification conditions. See, e.g., U.S. Pat. Nos. 5,773,258; 5,677,152; and 6,183,998. In certain embodiments, a thermostable DNA polymerase is inhibited by the binding of a nucleic acid, such as an oligonucleotide, which dissociates from the thermostable DNA polymerase at a suitable temperature. See, e.g., U.S. Pat. Nos. 6,183,967; 6,020,130; 5,874,557; 5,763,173; and 5,693,502.

In certain embodiments, a fusion protein comprising a nucleic acid binding polypeptide and a thermostable DNA polymerase is used in "hot start" PCR. In certain such embodiments, an antibody to the nucleic acid binding polypeptide is used to reversibly block nucleic acid binding activity and/or polymerase activity until a suitable temperature is reached.

In certain embodiments of "hot start" PCR, the thermostable DNA polymerase comprises a "cold-sensitive" mutant of a thermostable DNA polymerase. In certain such embodiments, the cold-sensitive mutant lacks substantial activity until the reaction mixture reaches or exceeds a temperature at which non-specific priming does not occur or is substantially reduced. Certain exemplary cold-sensitive mutants of Klentaq235, Klentaq278, and naturally occurring Taq are known to those skilled in the art. For example, the W706R, E708D, E626K, and I707L mutations confer cold sensitivity to Klentaq235, Klentaq278, or naturally occurring Taq. See, e.g., Kermekchiev et al. (2003) *Nucleic Acids Res.* 31:6139-6147; U.S. Pat. Nos. 6,333,159, 6,316,202, and 6,214,557; and "Cesium Taq" (commercially available from DNA Polymerase Technology, Inc., St. Louis, Mo.).

5. Certain RT-PCR (Reverse Transcriptase-PCR)

RT-PCR is a modification of PCR in which an RNA template is first reverse transcribed into its DNA complement or cDNA, followed by amplification of the resulting DNA using PCR. In certain embodiments, the reverse transcription reaction and the PCR reaction are carried out with the same reaction mixture. In certain embodiments, the reverse transcription reaction and the PCR reaction proceed in different reaction mixtures.

In certain embodiments in which two separate reaction mixtures are employed, the RNA template is included with appropriate reagents, including a reverse transcriptase, for the reverse transcription reaction. In certain embodiments, the reverse transcription reaction proceeds for 30 minutes. In certain embodiments, the reverse transcription reaction proceeds at 60° C. One skilled in the art can alter times and temperatures as appropriate for various reverse transcriptase reactions. In certain two reaction mixture RT-PCR procedures, a DNA polymerase is then added and PCR is carried out to amplify the cDNA produced in the reverse transcription reaction. In certain two reaction mixture RT-PCR procedures, after the reverse transcription reaction, the cDNA from the reverse transcription reaction is separated out from the rest of the components in the mixture. That cDNA is then included in a second reaction mixture that includes reagents appropriate for amplifying the cDNA, including DNA polymerase, in a PCR reaction.

In certain embodiments, the reverse transcription reaction and the PCR reaction proceed in the same reaction mixture using an enzyme that can serve as both a reverse transcriptase and a DNA polymerase. In certain such embodiments, the reaction mixture including the RNA template are held at an appropriate temperature for an appropriate period of time for the reverse transcription reaction to generate cDNA, and then the PCR cycling is performed to amplify the cDNA. Certain exemplary polymerases that have both reverse transcriptase activity and polymerase activity are discussed in the application, including, but not limited to, the following exemplary Family A DNA polymerases: Tth polymerase from *Thermus thermophilus*; Taq polymerase from *Thermus aquaticus*; *Thermus thermophilus* Rt41A; Dictyoglomus thermophilum RT46B.1; *Caldicellulosiruptor saccharolyticus* Tok7B.1; *Caldicellulosiruptor* spp. Tok13B.1; *Caldicellulosiruptor* spp. Rt69B.1; *Clostridium thermosulfurogenes; Thermotoga neapolitana; Bacillus caldolyticus* EA1.3; *Clostridium stercorarium*; and *Caldibacillus cellulovorans* CA2. Certain exemplary polymerases that have both reverse transcriptase activity and polymerase activity discussed in the application, include, but are not limited to, a family B DNA polymerase that comprises one or more mutations that allow the polymerase to perform DNA polymerization using a primed RNA template, such as Pfu DNA polymerase, with a point mutation L408Y or L408F (leucine to tyrosine or to phenylalane) in the conserved LYP motif. Certain exemplary fusion proteins are discussed in this application that comprise a nucleic acid binding protein and a given DNA polymerase that can be used for RNA-templated DNA synthesis when the given DNA polymerase alone cannot perform DNA polymerization using a primed RNA template. In certain such embodiments, the DNA polymerase in the fusion protein is a Family B polymerase.

In certain embodiments, in which the reverse transcription reaction and the PCR reaction proceed in the same reaction mixture, wax beads containing DNA polymerase for the PCR reaction are included in the initial reaction mixture for the reverse transcription reaction. After the reverse transcription reaction, the temperature is raised to melt the wax to release the DNA polymerase for the PCR reaction.

In certain embodiments, RT-PCR is used to diagnose genetic disease or detect RNA such as viral RNA in a sample. In certain embodiments, RT-PCR is used to determine the abundance of specific RNA molecules within a cell or tissue as a measure of gene expression.

In certain embodiments, a fusion protein comprising a nucleic acid binding protein and a polypeptide with reverse transcriptase activity can be used to shorten the period of time for the reverse transcription reaction. For example, in certain embodiments, a fusion protein generates sufficient cDNA in a reverse transcription reaction that proceeds for three to thirty (and all times between those endpoints) minutes.

In certain embodiments, a fusion protein stabilizes the primer-RNA template duplex, thereby increasing the Tm of the primers above the predicted Tm. Accordingly, in certain embodiments, the reverse transcription reaction is carried out at a temperature that is greater than the predicted Tm of the primers.

In certain embodiments, the reverse transcription reaction is carried out at a temperature that is from about 1° C. to about 40° C. above the predicted Tm of at least one of the primers (including all points between those endpoints). In certain such embodiments, the reverse transcription reaction is carried out at about 5° C., 10° C., 15° C., or 20° C. above the predicted Tm of at least one of the primers.

In certain embodiments, the reverse transcription reaction is carried out at any temperature from about 55° C. up to about 80° C. (including all points between those endpoints). In certain such embodiments, the reverse transcription reaction is carried out at any temperature from about 62° C. to about 78° C.; from about 62° C. to about 75° C.; from about 65° C. to about 72° C.; from about 65° C. to about 75° C.; from about 68° C. to about 72° C.; and from about 68° C. to about 75° C.

In certain embodiments, reverse transcription reaction at temperatures higher than the reverse transcription reaction temperatures typically used in RT-PCR may, under certain circumstances, have beneficial effects. For example, in certain embodiments, reverse transcription reaction at higher temperatures may improve primer specificity (i.e., may alleviate "mispriming"). In certain embodiments, reverse transcription reaction at higher temperatures may allow for more efficient amplification of problematic targets, such as targets having repetitive sequences or targets having complex secondary structure, such as GC-rich targets.

6. Certain Nucleic Acid Sequencing

In certain embodiments, a fusion protein comprising a nucleic acid binding polypeptide and a polymerase is used in a sequencing reaction. In certain embodiments, the sequencing reaction is a "cycle sequencing" reaction. See Sambrook et al. (2001) *Molecular Cloning: A Laboratory Manual* (3$^{rd}$ ed., Cold Spring Harbor Laboratory Press, NY) at 12.51-12.60, 12.94-12.114. In certain such embodiments, a nucleic acid template is subjected to linear amplification using a single primer, thus generating single-stranded amplification products. In certain embodiments, the amplification is conducted in the presence of "chain terminators," e.g., dideoxynucleotides. In certain embodiments, the primer is labeled, e.g., with a radioisotope or fluorescent dye, to allow detection of chain-terminated amplification products. In certain embodiments, the chain terminator is labeled to allow detection of chain-terminated amplification products. Exemplary chain terminators include, but are not limited to, radiolabeled dideoxynucleotide terminators and fluorescently labeled terminators, such as Applied Biosystems' BigDye™ terminators (Applied Biosystems, Foster City, Calif.). In certain embodiments, cycle sequencing may employ any of the PCR cycling conditions described above, with the exception that only one primer is used, instead of at least two primers. In certain embodiments, amplification products are analyzed using an ABI PRISM® 310, 3100, or 3100-Avant Genetic Analyzer, or an Applied Biosystems 3730 or 3730xl DNA Analyzer (Applied Biosystems, Foster City, Calif.).

H. Certain Kits

In certain embodiments, a kit comprises any one or more of the nucleic acid binding polypeptides described above. In certain embodiments, a kit further comprises a nucleic acid modification enzyme. In certain such embodiments the nucleic acid modification enzyme is a DNA polymerase. In certain such embodiments, the DNA polymerase is a thermostable DNA polymerase. In certain such embodiments the nucleic acid modification enzyme is a reverse transcriptase. In certain embodiments, a kit further comprises deoxynucleotides. In certain embodiments, a kit further comprises dideoxynucleotides.

In various embodiments, kits are provided. In certain embodiments, a kit comprises any one or more fusion proteins comprising a nucleic acid binding polypeptide and a polymerase. In certain such embodiments, the fusion protein comprises a nucleic acid binding polypeptide and a thermostable DNA polymerase. In certain embodiments, a kit comprises any one or more fusion proteins comprising a nucleic acid binding polypeptide and a reverse transcriptase. In certain embodiments, a kit further comprises deoxynucleotides. In certain embodiments, a kit further comprises dideoxynucleotides. In certain such embodiments, a kit further comprises fluorescently labeled dideoxynucleotides. In certain embodiments, a kit further comprises primers. In certain embodiments, a kit further comprises one or more primers and/or probes for the detection of amplification products. In certain such embodiments, a kit further comprises a 5' nuclease probe or a hairpin probe. In certain embodiments, a kit further comprises a fluorescent indicator, such as a nucleic acid binding dye.

VI. EXAMPLES

A. Cloning and Expression of Polynucleotides Encoding Nucleic Acid Binding Polypeptides A polynucleotide encoding SEQ ID NO:1 was constructed by ligating the following oligonucleotides (SEQ ID NOs:8-10) end-to-end, such that the 5' end of SEQ ID NO:9 was ligated to the 3' end of SEQ ID NO:8, and the 5' end of SEQ ID NO:10 was ligated to the 3' end of SEQ ID NO:9.

```
                                                    SEQ ID NO: 8
5' atgtccaaga agcagaaact Gaagttctac gacatTaagg cgaagcaggc gtttgag 3'
                                                    SEQ ID NO: 9
5' acCgaccagt acgaggttat tgagaagcag acCgcccgcg gtccgatgat gttcgcc 3'
                                                    SEQ ID NO: 10
5' gtggccaaat cgccgtacac cggcatTaaa gtGtacCgCc tgttaggcaa gaagaaataa 3'
```

The capital letters in SEQ ID NOs:8-10 represent changes from the naturally occurring PAE3192 sequence (SEQ ID NO:2). Those changes were made to generate codons more favorable for the expression of SEQ ID NO:1 in *E. coli*. Those changes do not result in any alterations in the amino acid sequence of SEQ ID NO:1.

To ligate SEQ ID NOs:8-10 together, the following oligonucleotides (SEQ ID NOS:11-12) were first annealed to SEQ ID NOs:8-10 as discussed below.

```
                                                    SEQ ID NO: 11
        5' gtactggtcg gtctcaaacg cctg 3'

SEQ ID NO: 12
        5' cgatttggcc acggcgaaca tcat 3'
```

SEQ ID NO:11 is complementary to the 3' end of SEQ ID NO:8 and the 5' end of SEQ ID NO:9. Thus, the annealing of SEQ ID NO:11 to SEQ ID NOs:8-9 created a region of double-stranded DNA where SEQ ID NO:11 spans the junction of SEQ ID NOS:8-9. This region of double-stranded DNA was a suitable substrate for DNA ligase. Likewise, SEQ ID NO:12 is complementary to the 3' end of SEQ ID NO:9 and the 5' end of SEQ ID NO:10. Thus, the annealing of SEQ ID NO:12 to SEQ ID NOS:9-10 created a region of double-stranded DNA where SEQ ID NO:12 spans the junction of SEQ ID NOS:9-10.

SEQ ID NOs:8-10 were then ligated. The resulting polynucleotide (SEQ ID NO:13) was amplified by PCR.

A polynucleotide encoding SEQ ID NO:6 was constructed by ligating the following oligonucleotides (SEQ ID NOs:14-16) end-to-end:

```
                                                    SEQ ID NO: 14
5' atgccGaaga aggagaagat Taagttcttc gacctGgtcg ccaagaagta ctacgag 3'
                                                    SEQ ID NO: 15
5' actgacaact acgaagtcga gatTaaggag actaagCgCg gcaagtttCg Cttcgcc 3'
                                                    SEQ ID NO: 16
5' aaagccaaga gcccgtacac cggcaagatc ttctatCgCg tgctGggcaa agcctag 3'
```

The capital letters represent changes from the naturally occurring APE3192 sequence (SEQ ID NO:7). Those changes were made to generate codons more favorable for the expression of SEQ ID NO:6 in *E. coli*. Those changes do not result in any alterations in the amino acid sequence of SEQ ID NO:6.

The following oligonucleotides (SEQ ID NOs:17-18) were annealed to SEQ ID NOs:14-16 to create regions of double-stranded DNA spanning the junctions between SEQ ID NOs:14-15 and SEQ ID NOs:15-16.

```
                                                    SEQ ID NO: 17
        5' gtagttgtca gtctcgtagt actt 3'

SEQ ID NO: 18
        5' gctcttggct ttggcgaagc gaaa 3'
```

SEQ ID NOs:14-16 were then ligated. The resulting polynucleotide (SEQ ID NO:19) was amplified by PCR.

SEQ ID NO:13 was cloned into the pET16b vector (Novagen, Milwaukee, Wis.) using standard recombinant methods. That vector allows expression of the cloned sequences from the inducible T7 promoter. It also includes sequences encoding polyhistidine (10×His) followed by a Factor Xa cleavage site upstream of the cloning site. Thus, the encoded proteins are tagged at their N-termini with a polyhistidine moiety. Recombinant vector comprising SEQ ID NO:13 was transformed into competent *E. coli* host cells using standard methods.

SEQ ID NO:19 was also cloned into the pET16b vector using standard recombinant methods. Recombinant vector comprising SEQ ID NO:19 was transformed into competent *E. coli* host cells using standard methods.

Host cells containing a recombinant vector comprising SEQ ID NO:13 are induced to express a tagged polypeptide comprising SEQ ID NO:1 by adding IPTG to the media in which the host cells are grown. The tagged polypeptide is isolated from the host cells by affinity chromatography using nickel-NTA resin. In certain embodiments, the polyhistidine tag is removed from the isolated polypeptide by treatment with Factor Xa.

Host cells containing a recombinant vector comprising SEQ ID NO:19 are induced to express a tagged polypeptide comprising SEQ ID NO:6 by adding IPTG to the media in which the host cells are grown. The tagged polypeptide is isolated from the host cells by affinity chromatography using nickel-NTA resin. In certain embodiments, the polyhistidine tag is removed from the isolated polypeptide by treatment with Factor Xa.

B. Assay for Stabilization of a DNA Duplex from Thermal Denaturation

The ability of a nucleic acid binding polypeptide to stabilize a DNA duplex from thermal denaturation is demonstrated by the following assay, which measures the increase in the Tm of a nucleic acid in the presence of a nucleic acid binding polypeptide. See, e.g., Baumann et al. (1994) *Nature Struct. Biol.* 1:808-819; and McAfee et al. (1995) *Biochem.* 34:10063-10077. Poly(dl-dC) at a concentration of about 70 μM (in nucleotides) is combined with a nucleic acid binding polypeptide at a concentration of about 350 μM in 5 mM Tris.Cl (pH 7.0). Poly(dl-dC) at a concentration of about 70 μM (in nucleotides) in 5 mM Tris.Cl (pH 7.0) without a nucleic acid binding polypeptide is used as a negative control. The absorbance of the poly(dl-dC) with and without a nucleic acid binding polypeptide is measured at 260 nm as a function of temperature using a spectrophotometer. The temperature is increased in steps, and absorbance is measured at each step. For each step, the temperature is raised by 1° C. over 30 seconds, followed by a holding time of 60 seconds prior to the measuring of absorbance. A melting curve is generated based on the increase in absorbance as a function of temperature. The Tm (temperature at which 50% of the poly(dl-dC) is denatured) occurs at the inflection point of the melting curve. The Tm of poly(dl-dC) in the negative control is subtracted from the Tm of poly(dl-dC) in the presence of a nucleic acid binding polypeptide to determine the increase in Tm due to the presence of the nucleic acid binding polypeptide.

The experiment discussed in Example K(2) below can be used to test the ability of a nucleic acid binding polypeptide to stabilize a DNA:RNA duplex from thermal denaturation.

C. Construction and Expression of Fusion Proteins Comprising a Nucleic Acid Binding Polypeptide and a Thermostable DNA Polymerase 1. Fusion Proteins Comprising Pfu DNA Polymerase a) Fusion Proteins Comprising Pfu and Pae3192

A fusion protein comprising Pae3192 (SEQ ID NO:1) joined to the C-terminus of full length Pfu DNA polymerase was constructed as follows. An NdeI-XhoI restriction fragment comprising a polynucleotide sequence encoding full length Pfu DNA polymerase in frame with a polynucleotide sequence encoding Pae3192 (SEQ ID NO:13) was cloned into the NdeI and XhoI sites of the pET16b vector (Novagen, Milwaukee, Wis.) using standard recombinant methods. The resulting recombinant vector (pDS2r) encodes a fusion protein comprising Pae3192 joined to the C-terminus of Pfu DNA polymerase by a Gly-Thr-Gly-Gly-Gly-Gly peptide linker. A 10×His affinity tag is present at the N-terminus of the fusion protein. The fusion protein, designated "10His-Pfu-Pae3192," has the amino acid sequence shown in SEQ ID NO:23. The polynucleotide sequence encoding 10His-Pfu-Pae3192 is shown in SEQ ID NO:22.

The recombinant vector pDS2r was transformed into competent E. coli host cells. Host cells comprising pDS2r were induced to express 10His-Pfu-Pae3192 by adding IPTG to the media in which the host cells were grown. 10His-Pfu-Pae3192 was isolated from the host cells by affinity chromatography using nickel-NTA resin.

In certain embodiments, the polyhistidine tag is removed from 10His-Pfu-Pae3192 by treatment with Factor Xa to yield the fusion protein shown in SEQ ID NO:24. That fusion protein is designated "Pfu-Pae3192."

b) Fusion Proteins Comprising Pfu and Ape3192

A fusion protein comprising Ape3192 (SEQ ID NO:6) joined to the C-terminus of full length Pfu DNA polymerase was constructed as follows: An NdeI-XhoI restriction fragment comprising a polynucleotide sequence encoding full length Pfu DNA polymerase in frame with a polynucleotide sequence encoding Ape3192 (SEQ ID NO:19) was cloned into the NdeI and XhoI sites of the pET16b vector using standard recombinant methods. The resulting recombinant vector (pDS1r) encodes a fusion protein comprising Ape3192 joined to the C-terminus of Pfu DNA polymerase by a Gly-Thr-Gly-Gly-Gly-Gly peptide linker. A 10×His affinity tag is present at the N-terminus of the fusion protein. The fusion protein, designated "10His-Pfu-Ape3192," has the amino acid sequence shown in SEQ ID NO:26. The polynucleotide sequence encoding 10His-Pfu-Ape3192 is shown in SEQ ID NO:25.

The recombinant vector pDS1r was transformed into competent E. coli host cells. Host cells comprising pDS1r were induced to express 10His-Pfu-Ape3192 by adding IPTG to the media in which the host cells were grown. 10His-Pfu-Ape3192 was isolated from the host cells by affinity chromatography using nickel-NTA resin.

In certain embodiments, the polyhistidine tag is removed from 10His-Pfu-Ape3192 by treatment with Factor Xa to yield the fusion protein shown in SEQ ID NO:27. That fusion protein is designated "Pfu-Ape3192."

c) Fusion Proteins Comprising Pfu and Sso7d

A fusion protein comprising Sso7d (SEQ ID NO:20 lacking the first methionine) joined to the C-terminus of full length Pfu DNA polymerase was constructed as follows: An NdeI-XhoI restriction fragment comprising a polynucleotide sequence encoding full length Pfu DNA polymerase in frame with a polynucleotide sequence encoding Sso7d was cloned into the NdeI and XhoI sites of the pET16b vector using standard recombinant methods. The resulting recombinant vector (pDS3r) encodes a fusion protein comprising Sso7d joined to the C-terminus of Pfu DNA polymerase by a Gly-Thr-Gly-Gly-Gly-Gly peptide linker. A 10×His affinity tag is present at the N-terminus of the fusion protein. The fusion protein, designated "10His-Pfu-Sso7d," has the amino acid sequence shown in SEQ ID NO:49. The polynucleotide sequence encoding 10His-Pfu-Sso7d is shown in SEQ ID NO:51.

The recombinant vector pDS3r was transformed into competent E. coli host cells. Host cells comprising pDS3r were induced to express 10His-Pfu-Sso7d by adding IPTG to the media in which the host cells were grown. 10His-Pfu-Sso7d was isolated from the host cells by affinity chromatography using nickel-NTA resin.

In certain embodiments, the polyhistidine tag is removed from 10His-Pfu-Sso7d by treatment with Factor Xa to yield the fusion protein shown in SEQ ID NO:50. That fusion protein is designated "Pfu-Sso7d."

d) Fusion Proteins Comprising Pfu and Pae3192

A fusion protein comprising Pae3192 (SEQ ID NO:1) joined to the C-terminus of full length Pfu DNA polymerase with two mutations D141A and E143A was constructed. The fusion protein was constructed using the same methods described in Example C(1)(a) above, except the polynucleotide sequence encoded full length Pfu DNA polymerase with an alanine at position 141 of Pfu DNA polymerase rather than aspartic acid and with an alanine at position 143 of Pfu DNA polymerase rather than glutamic acid. The fusion protein, designated "10His-Pfu-Pae3192, exo-minus version" has the amino acid sequence shown in SEQ ID NO:23, except the aspartic acid at position 141 is replaced with alanine and the glutamic acid at position 143 is replaced with alanine.

2. Fusion Proteins Comprising Taq DNA Polymerase a) Fusion Proteins Comprising Pae3192 and Taq DNA Polymerase A fusion protein comprising Pae3192 (SEQ ID NO:1) joined to the N-terminus of Taq DNA polymerase (SEQ ID NO:31 lacking the first two amino acid residues) was constructed as follows. A polynucleotide encoding Pae3192 (SEQ ID NO:13) was cloned in frame at the 5' end of a polynucleotide encoding Taq DNA polymerase in the pET16b vector. The resulting recombinant vector (pDS17-7) encodes a fusion protein comprising Pae3192 joined to the N-terminus of Taq DNA polymerase by a Gly-Gly-Val-Thr-Ser peptide linker. A 10×His affinity tag is present at the N-terminus of the fusion protein. The fusion protein, designated "10His-Pae3192-Taq," has the amino acid sequence shown in SEQ ID NO:33. The polynucleotide sequence encoding 10His-Pae3192-Taq is shown in SEQ ID NO:32. The recombinant vector pDS17-7 was transformed into competent host cells.

Expression of 10His-Pae3192-Taq is induced in the host cells using IPTG. 10His-Pae3192-Taq is isolated from the host cells by affinity chromatography using nickel-NTA resin. In certain embodiments, the polyhistidine tag is removed from 10His-Pae3192-Taq by treatment with Factor Xa to yield a fusion protein having the amino acid sequence shown in SEQ ID NO:34. That fusion protein is designated "Pae3192-Taq."

b) Fusion Proteins Comprising Ape3192 and Taq DNA Polymerase

A fusion protein comprising Ape3192 (SEQ ID NO:6) joined to the N-terminus of Taq DNA polymerase (SEQ ID NO:31 lacking the first two amino acid residues) was constructed as follows. A polynucleotide encoding Ape3192 (SEQ ID NO:19) was cloned in frame at the 5' end of a polynucleotide encoding Taq DNA polymerase in the pET16b vector. The resulting recombinant vector (pDS16-3) encodes a fusion protein comprising Ape3192 joined to the N-terminus of Taq DNA polymerase by a Gly-Gly-Val-Thr-Ser peptide linker. A 10×His affinity tag is present at the N-terminus of the fusion protein. The fusion protein, designated "10His-Ape3192-Taq," has the amino acid sequence shown in SEQ ID NO:36. The polynucleotide sequence encoding 10His-Ape3192-Taq is shown in SEQ ID NO:35. The recombinant vector pDS16-3 was transformed into competent host cells.

Expression of 10His-Ape3192-Taq is induced in the host cells using IPTG. 10His-Ape3192-Taq is isolated from the host cells by affinity chromatography using nickel-NTA resin. In certain embodiments, the polyhistidine tag is removed from 10His-Ape3192-Taq by treatment with Factor Xa to yield the fusion protein shown in SEQ ID NO:37. That fusion protein is designated "Ape3192-Taq."

c) Fusion Proteins Comprising Pae3192 and the Stoffel Fragment

A fusion protein comprising Pae3192 (SEQ ID NO:1) joined to the N-terminus of a Stoffel fragment of Taq DNA polymerase (amino acid residues 291-832 of SEQ ID NO:31) was constructed as follows. A polynucleotide encoding Pae3192 (SEQ ID NO:13) was cloned in frame at the 5' end of a polynucleotide encoding the Stoffel fragment in the pET16b vector. The resulting recombinant vector (pDS25-7) encodes a fusion protein comprising Pae3192 joined to the N-terminus of the Stoffel fragment by a Gly-Gly-Val-Thr-Ser peptide linker. A 10×His affinity tag is present at the N-terminus of the fusion protein. The fusion protein, designated "10His-Pae3192-Taq$_{ST}$," has the amino acid sequence shown in SEQ ID NO:39. The polynucleotide sequence encoding 10His-Pae3192-Taq$_{ST}$ is shown in SEQ ID NO:38. The recombinant vector pDS25-7 was transformed into competent host cells.

Expression of 10His-Pae3192-Taq$_{ST}$ is induced in the host cells using IPTG. The fusion protein is isolated from the host cells by affinity chromatography using nickel-NTA resin. In certain embodiments, the polyhistidine tag is removed from 10His-Pae3192-Taq$_{ST}$ by treatment with Factor Xa to yield the fusion protein shown in SEQ ID NO:40. That fusion protein is designated "Pae3192-Taq$_{ST}$."

d) Fusion Proteins Comprising Ape3192 and the Stoffel Fragment

A fusion protein comprising Ape3192 (SEQ ID NO:6) joined to the N-terminus of a Stoffel fragment of Taq DNA polymerase (amino acid residues 291-832 of SEQ ID NO:31) was constructed as follows. A polynucleotide encoding Ape3192 (SEQ ID NO:19) was cloned in frame at the 5' end of a polynucleotide encoding the Stoffel fragment in the pET16b vector. The resulting recombinant vector (pDS24-4) encodes a fusion protein comprising Ape3192 joined to the N-terminus of the Stoffel fragment by a Gly-Gly-Val-Thr-Ser peptide linker. A 10×His affinity tag is present at the N-terminus of the fusion protein. The fusion protein, designated "10His-Ape3192-Taq$_{ST}$," has the amino acid sequence shown in SEQ ID NO:42. The polynucleotide sequence encoding 10His-Ape3192-Taq$_{ST}$ is shown in SEQ ID NO:41. The recombinant vector pDS24-4 was transformed into competent host cells.

Expression of 10His-Ape3192-Taq$_{ST}$ is induced in the host cells using IPTG. The fusion protein is isolated from the host cells by affinity chromatography using nickel-NTA resin. In certain embodiments, the polyhistidine tag is removed from 10His-Ape3192-Taq$_{ST}$ by treatment with Factor Xa to yield the fusion protein shown in SEQ ID NO:43. That fusion protein is designated "Ape3192-Taq$_{ST}$."

D. Use of Fusion Proteins in "Fast" PCR

Fusion proteins were used in PCR reactions having rapid cycling times. A set of five reaction mixtures were prepared as follows:

| Component (stock concentration) | Volume | Final concentration |
|---|---|---|
| Lambda (λ) DNA (10 ng/µl) | 2 µl | 1 ng/µl |
| dNTPs (2.5 mM each) | 2 µl | 250 µM each |
| Buffer (10x or 5x) | 2 or 4 µl | 1x |
| Forward primer (10 µM) | 1 µl | 0.5 µM |
| Reverse primer (10 µM) | 1 µl | 0.5 µM |
| Enzyme | 0.5 µl | ~1 Unit |
| dH$_2$0 | 11.5 or 9.5 µl | |

20 µl final volume

All five reaction mixtures contained the following forward and reverse primers:

```
                                  (SEQ ID NO: 47)
        5'-AGCCAAGGCCAATATCTAAGTAAC-3'
        (Tm = 54.1° C.)

(SEQ ID NO: 48)
        5'-CGAAGCATTGGCCGTAAGTG-3'
        (Tm = 58.4° C.)
```

The reaction mixtures contained one of the following enzyme-buffer combinations, as indicated below:

| Reaction mixture | Enzyme | Buffer (stock concentration) |
|---|---|---|
| A | Cloned Pfu polymerase (Stratagene, La Jolla, CA) | 10x Cloned Pfu polymerase buffer (Stratagene) |
| B | 10His-Pfu-Ape3192 (SEQ ID NO: 26) | 5x Phusion HF buffer (Finnzymes, Espoo, Finland) |
| C | 10His-Pfu-Pae3192 (SEQ ID NO: 23) | 5x Phusion HF buffer (Finnzymes) |
| D | 10His-Pfu-Sso7d (SEQ ID NO: 49) | 5x Phusion HF buffer (Finnzymes) |
| E | AmpliTaq (Roche Molecular Systems, Pleasanton, CA) | 10x AmpliTaq buffer (Roche Molecular Systems) |

The reaction mixtures were subjected to "fast" PCR cycling conditions using an Applied Biosystems 9800 Fas Thermal Cycler (Applied Biosystems, Foster City, Calif.), as follows:

98° C., 30 sec;

99° C., 1 sec; and
65° C., 1 sec. } 30 cycles

After the 30 cycles, the reaction mixtures were analyzed by agarose gel electrophoresis. See FIG. 1, Set 1. Reaction mixtures A and E did not contain detectable amplification product. See lanes A and E of FIG. 1, Set 1. Unexpectedly, reaction mixtures B, C, and D contained substantial amounts of amplification product having the predicted size. See lanes B, C, and D of FIG. 1, Set 1. (Size markers are shown in lane M.) Thus, the fusion proteins 10His-Pfu-Ape3192, 10His-Pfu-Pae3192, and 10His-Pfu-Sso7d efficiently amplified lambda DNA under fast PCR cycling conditions at an annealing temperature of 65° C., whereas the thermostable DNA polymerases Pfu and AmpliTaq did not.

An identical set of reaction mixtures were subjected to fast PCR cycling conditions at a higher annealing/extension temperature, as follows:

98° C., 30 sec;
99° C., 2 sec; and
70° C., 2 sec.     } 30 cycles

After the 30 cycles, the reaction mixtures were analyzed by agarose gel electrophoresis, shown in FIG. 1, Set 2. Reaction mixtures A and E did not contain detectable amplification product. See lanes A and E of FIG. 1, Set 2. Unexpectedly, reaction mixtures B, C, and D contained substantial amounts of amplification product having the predicted size. See lanes B, C, and D of FIG. 1, Set 2. Thus, the fusion proteins 10His-Pfu-Ape3192, 10His-Pfu-Pae3192, and 10His-Pfu-Sso7d efficiently amplified lambda DNA under fast PCR cycling conditions at an annealing temperature of 70° C., whereas the thermostable DNA polymerases Pfu and AmpliTaq did not.

To investigate the effect of a polyhistidine tag on the performance of fusion proteins, two reaction mixtures identical to reaction mixtures B and C above were prepared. A third reaction mixture "F" was prepared as described for reaction mixtures B and C, except that the enzyme used in reaction mixture F was Pfu-Pae3192 (SEQ ID NO:24). Reaction mixtures B, C, and F were subjected to "fast" PCR cycling conditions using an Applied Biosystems 9800 Fast Thermal Cycler (Applied Biosystems, Foster City, Calif.), as follows:

98° C., 30 sec;
99° C., 1 sec; and
65° C., 1 sec.     } 30 cycles

After the 30 cycles, the reaction mixtures were analyzed by agarose gel electrophoresis. All three reaction mixtures contained detectable amplification product. However, reaction mixture F had qualitatively less amplification product than reaction mixtures B and C. Thus, the fusion proteins 10His-Pfu-Ape3192 and 10His-Pfu-Pae3192, which both contain a polyhistidine tag, amplified lambda DNA more efficiently under fast PCR cycling conditions than Pfu-Pae3192, which does not contain a polyhistidine tag.

E. Processivity Assay

The processivity of a DNA polymerase is compared to the processivity of a fusion protein comprising a nucleic acid binding polypeptide and a DNA polymerase using a processivity assay based on that of Wang et al. (2004) Nuc. Acids Res. 32:1197-1207. A 5' FAM-labeled primer of sequence 5' gttttcccagtcacgacgttgtaaaacgacggcc 3' (SEQ ID NO:29) is added to single-stranded M13 mp 18 DNA in a reaction composition comprising 10 mM Tris-HCl pH 8.8, 50 mM KCl, 2.5 mM MgCl$_2$, 250 µm dNTPs, and 0.1% Triton X-100. The concentrations of the primer and M13mp 18 template are 50 nM and 80 nM, respectively. The primer is annealed to the single-stranded M13 mp 18 DNA template by heating the mixture to 90° C. for 5 minutes, cooling to 72° C. at 0.1° C. per second, incubating at 72° C. for 10 minutes, and cooling to 4° C. at 0.1° C. per second.

Two parallel reactions are prepared. In the first reaction, a thermostable DNA polymerase is added to a final concentration of about 1:4000 (DNA polymerase:template) in 20 µl of the above reaction composition. In the second reaction, a fusion protein comprising a thermostable DNA polymerase and a nucleic acid binding polypeptide is added to a final concentration of about 1:4000 (fusion protein:template) in 20 µl of the above reaction composition.

DNA synthesis is initiated in the reactions by incubating them at 72° C. Samples from each reaction are taken at various time points. The samples are diluted in gel loading dye, and the primer extension products in the samples are analyzed by denaturing polyacrylamide gel electrophoresis using an ABI 377 DNA Sequencer (Applied Biosystems, Foster City, Calif.). The median product length is determined based on the integration of all detectable primer extension products. When the median product length does not change with an increase in reaction time or a decrease in polymerase concentration (to ensure that the template is in excess), that length is used as a measure of processivity.

F. Use of Nucleic Acid Binding Polypeptides to Increase Processivity of a DNA Polymerase The ability of a nucleic acid binding polypeptide to increase the processivity of a DNA polymerase is assessed using a processivity assay based on that of Wang et al. (2004) Nuc. Acids Res. 32:1197-1207. A 5' FAM-labeled primer of sequence 5' gttttcccagtcacgacgttgtaaaacgacggcc 3' (SEQ ID NO:29) is added to single stranded M13mp 18 DNA in a reaction composition comprising 10 mM Tris-HCl pH 8.8, 50 mM KCl, 2.5 mM MgCl$_2$, 250 µm dNTPs, and 0.1% Triton X-100. The concentrations of the primer and M13mp 18 template are 50 nM and 80 nM, respectively. The primer is annealed to the single stranded M13mp 18 DNA template by heating the mixture to 90° C. for 5 minutes, cooling to 72° C. at 0.1° C. per second, incubating at 72° C. for 10 minutes, and cooling to 4° C. at 0.1° C. per second. A thermostable DNA polymerase, such as Taq DNA polymerase, is added to the above reaction composition at a concentration of about 1:4000 (DNA polymerase:template).

Two parallel reactions are prepared. In one of the parallel reactions, a nucleic acid binding polypeptide is added to a final concentration of about 70 µg/ml in 20 µl of the above reaction composition. The second parallel reaction contains 20 µl of the above reaction composition with no added nucleic acid binding polypeptide.

DNA synthesis is initiated in the reaction compositions by incubating them at 72° C. Samples from each reaction are taken at various time points. The samples are diluted in gel loading dye, and the primer extension products in the samples are analyzed by denaturing polyacrylamide gel electrophoresis using an ABI 377 DNA Sequencer. The median product length is determined based on the integration of all detectable primer extension products. When the median product length does not change with an increase in reaction time or a decrease in polymerase concentration (to ensure that the template is in excess), that length is used as a measure of processivity.

G. Use of Nucleic Acid Binding Polypeptides to Increase the Efficiency (Speed and Specificity) of a Hybridization-Based Detection Assay 1. Annealing Assay The ability of a nucleic acid binding polypeptide to increase the specificity of a hybridization-based detection assay is measured using an annealing assay based on that of Guagliardi et al. (1997) J. Mol. Biol. 267:841-848. A first set of two reaction compositions is prepared as follows: In a first reaction composition, single stranded M13 mp18 circular DNA (0.05 pmol) is combined with an equal amount of $^{32}$P end-labeled oligonucleotide of sequence 5'-gtaaaacgacggc-cagt-3' (SEQ ID NO:20) in a buffered reaction mixture (20 mM Tris-HCl pH 7.5, 2 mM DTT, 5 mM MgCl2, 100 µg/ml BSA). In a second reaction composition, single stranded M13mp 18 circular DNA (0.05 pmol) is combined with an equal amount of $^{32}$P end-labeled oligonucleotide of sequence 5'-gtaaaacgtcggccagt-3' (SEQ ID NO:21) in a buffered reaction mixture (20 mM Tris-HCl pH 7.5, 2 mM DTT, 5 mM MgCl2, 100 µg/ml BSA). The nucleotide indicated in bold is a mismatch with respect to the M13mp 18 DNA sequence. A nucleic acid binding polypeptide is added separately to both reaction compositions at a final concentration of about 5 µg/ml.

A second set of two reaction compositions is prepared. The second set is the same as the first set of reaction compositions, except that a nucleic acid binding polypeptide is not added to either the first or second reaction composition of the second set of reaction compositions. The final volume of each reaction composition is 10 µl.

The reaction compositions are incubated at 60° C. for three minutes. The reactions are stopped by adding 1% SDS in standard loading dye to each reaction composition. The reactions are analyzed by 1.5% agarose gel electrophoresis followed by autoradiography to visualize annealed product, which can be distinguished from unannealed probe by its slower mobility. Annealed product is quantified for each reaction using standard densitometric methods. An increase in the amount of annealed product in the first reaction compared to the second reaction is determined for both sets of reactions. The ability of a nucleic acid binding polypeptide to increase the specificity of hybridization is demonstrated by a larger increase in the amount of annealed product for the first set of reactions compared to the second set of reactions.

To test the annealing of RNA to DNA, the assay discussed above can be performed by replacing the DNA sequences SEQ ID NO:20 and SEQ ID NO:21 with their RNA sequence counterparts.

2. Microarray-Based Assay

The ability of a nucleic acid binding polypeptide to increase the speed and specificity of a hybridization-based detection assay is also demonstrated by a decrease in the hybridization time (approximately 16 hours) required to perform a typical microarray-based detection assay. A typical microarray-based detection assay may be performed, for example, using the Mouse Genome Survey Microarray system (Applied Biosystems, Foster City, Calif.; P/N 4345065). That system includes reagents, hybridization controls, and reference nucleic acids that can be used to detect selective hybridization of a reference nucleic acid to a probe (i.e., a portion of a mouse cDNA) immobilized on a microarray. In an exemplary assay, a nucleic acid binding polypeptide is added to the hybridization solution at a concentration of about 50 to 250 ug/mL. The hybridization time is from about 1 to 30 minutes at a temperature of about 45° C. to 75° C. The arrays are washed, and hybridization is detected using the Chemiluminescence Detection Kit (Applied Biosystems, Foster City, Calif., P/N 4342142) according to the manufacturer's instructions. The arrays are analyzed using the Applied Biosystems 1700 Chemiluminescent Microarray Analyzer (Applied Biosystems, Foster City, Calif., P/N 4338036). To test hybridization of RNA to the DNA on a microarray, one can use RNA as the reference nucleic acid.

H. Use of Fusion Proteins to Increase Processivity of Taq DNA Polymerase

The increase in processivity of a fusion protein comprising Taq DNA polymerase relative to Taq DNA polymerase alone is assessed using a processivity assay based on that of Wang et al. (2004) *Nuc. Acids Res.* 32:1197-1207. A 5' FAM-labeled primer of sequence 5' gttttcccagtcacgacgttgtaaaacgacggcc 3' (SEQ ID NO:29) is added to single stranded M13mp 18 DNA in a mixture comprising 10 mM Tris-HCl pH 8.8, 50 mM KCl, 2.5 mM MgCl$_2$, 250 µm dNTPs, and 0.1% Triton X-100. The concentrations of the primer and M13mp 18 template are 50 nM and 80 nM, respectively. The primer is annealed to the single stranded M13mp 18 DNA template by heating the mixture to 90° C. for 5 minutes, cooling to 72° C. at 0.1° C. per second, incubating at 72° C. for 10 minutes, and cooling to 4° C. at 0.1° C. per second.

A reaction composition is prepared in which a fusion protein comprising Taq DNA polymerase is added at a molar concentration of about 1:4000 (fusion protein:template) to 20 µl of the above mixture. A control reaction composition is prepared in which Taq DNA polymerase is added at a molar concentration of about 1:4000 (DNA polymerase:template) to 20 µl of the above mixture. DNA synthesis is initiated in the reaction compositions by incubating them at 72° C. Samples from each reaction are taken at various time points. The samples are diluted in gel loading dye, and the primer extension products are analyzed by denaturing polyacrylamide gel electrophoresis using an ABI 377 DNA Sequencer. The median product length is determined based on the integration of all detectable primer extension products. When the median product length does not change with an increase in reaction time or a decrease in polymerase concentration, that length is used as a measure of processivity.

I. Use of Fusion Proteins to Increase Processivity of Pfu DNA Polymerase

The increase in processivity of a fusion protein comprising Pfu DNA polymerase relative to Pfu DNA polymerase alone is assessed using a processivity assay based on that of Wang et al. (2004) *Nuc. Acids Res.* 32:1197-1207. A 5' FAM-labeled primer of sequence 5' gttttcccagtcacgacgttgtaaaacgacggcc 3' (SEQ ID NO:29) is added to single stranded M13mp 18 DNA in a mixture comprising 10 mM Tris-HCl pH 8.8, 50 mM KCl, 2.5 mM MgCl$_2$, 250 µm dNTPs, and 0.1% Triton X-100. The concentrations of the primer and M13mp 18 template are 50 nM and 80 nM, respectively. The primer is annealed to the single stranded M13mp 18 DNA template by heating the mixture to 90° C. for 5 minutes, cooling to 72° C. at 0.1° C. per second, incubating at 72° C. for 10 minutes, and cooling to 4° C. at 0.1° C. per second.

A reaction composition is prepared in which a fusion protein comprising Pfu DNA polymerase is added at a molar concentration of about 1:4000 (fusion protein:template) to 20 µl of the above mixture. A control reaction composition is prepared in which Pfu DNA polymerase is added at a molar concentration of about 1:4000 (DNA polymerase:template) to 20 µl of the above mixture. DNA synthesis is initiated in the reaction compositions by incubating them at 72° C. Samples from each reaction are taken at various time points. The samples are diluted in gel loading dye, and the primer extension products are analyzed by denaturing polyacrylamide gel electrophoresis using an ABI 377 DNA Sequencer. The median product length is determined based on the integration of all detectable primer extension products. When the median product length does not change with an increase in reaction time or a decrease in polymerase concentration, that length is used as a measure of processivity.

One skilled in the art will readily recognize that the above assay may be modified so as to assess the processivity of a fusion protein comprising a DNA polymerase other than Taq or Pfu.

J. Use of Fusion Proteins in PCR

The ability of a fusion protein comprising a nucleic acid binding polypeptide and a thermostable DNA polymerase (e.g., Taq or Pfu) to increase the efficiency of PCR is demonstrated using a typical PCR reaction. An exemplary PCR reaction is prepared which contains PCR buffer (1×), dNTPs (200 μM each), template DNA (250 ng), forward and reverse primers (0.25 μM each) and fusion protein (about 0.5 to 2.5 units) in a final volume of 50 μl. As a control reaction, thermostable DNA polymerase alone is used in place of the fusion protein. The primers used in the PCR reaction are tPAF7 (5'-ggaagtacagctcagagttctgcagcacccctgc-3' (SEQ ID NO:45)) and tPAR10 (5'-gatgcgaaactgaggctggctgtactgtctc-3' (SEQ ID NO:46)). The template DNA is human genomic DNA (Roche, Indianapolis, Ind., P/N 1-691-112). The primers tPAF7 and tPAR10 amplify a product of approximately 5 kb from human genomic DNA. If the fusion protein being used in the PCR reaction comprises Pfu DNA polymerase, then the standard PCR buffer for Pfu (Stratagene; La Jolla, Calif.) is used, except that the KCl concentration is elevated. The final working concentration (1×) of the buffer thus contains 20 mM Tris, pH 8.8; 10 mM $(NH_4)_2SO_4$, 0.1% Triton X-100, 2 mM $MgSO_4$, 100 μg/mL BSA and 60 mM KCl. If the fusion protein being used in the PCR reaction comprises Taq DNA polymerase, the standard PCR buffer for Taq (Applied Biosystems, Foster City, Calif.) is used. Cycling is performed as follows:

initial dentaturation (98° C., 30 sec);

| denaturation (98° C., 10 sec); | |
|---|---|
| annealing (65° C., 10 sec); and | 29 cycles |
| extension (72° C., 2 min); | | and final extension (72° C., 10 min).

An aliquot of the reaction is analyzed by agarose gel electrophoresis along with an appropriate size standard, stained with ethidium bromide, and then visualized by fluorescence.

K. Pae3192 Binding to DNA:DNA Duplexes and DNA:RNA Duplexes

The ability of Pae3192 to bind to DNA:DNA duplexes and DNA:RNA duplexes was tested.

1. Gel-Shift Experiments

Gel shift analysis is an accepted way to assay binding of a polypeptide to a nucleic acid (see, for example, Kamashev et al., EMBO J., 19(23):6527-6535 (2000). Binding of Sso7d to DNA has been shown using gel-shift assays (see, for example, Guagliardi et al., J. Mol. Biol., 267(4):841-848 (1997).

Gel-shift experiments were carried out using 150 nM 42-mer duplex and separate experiments were performed with 0, 1.5, 3, 6 or 12 uM Pae3192 protein. A DNA:DNA duplex was created by annealing DNA oligonucleotides 1a and 2a of Table 1 below. An RNA:RNA duplex was created by annealing RNA oligonucleotides 1b and 2b of Table 1 below. A DNA:RNA duplex was created by annealing DNA oligonucleotide 1a to RNA oligonucleotide 2b of Table 1 below. DNA binding reactions contained 170 mM NaCl, 1 mM $CaCl_2$ and 25 mM Tris, pH 8.0. Pae3192 was incubated separately with each of the three duplexes for 15 minutes at 40° C. before being run on a 1% agarose gel.

TABLE 1

Oligonucleotides

| Name (composition) | Sequence |
|---|---|
| Oligo 1a (DNA) | CAGACTGGAATTCAAGCGCGAGCTCGAAT AAGAGCTACTGTT |
| Oligo 2a (DNA) | AACAGTAGCTCTTATTCGAGCTCGCGCTT GAATTCCAGTCTG |

TABLE 1-continued

Oligonucleotides

| Name (composition) | Sequence |
|---|---|
| Oligo 1b (RNA) | CAGACUGGAAUUCAAGCGCGAGCUCGAAU AAGAGCUACUGUU |
| Oligo 2b (RNA) | AACAGUAGCUCUUAUUCGAGCUCGCGCUU GAAUUCCAGUCUG |
| Oligo 3a (DNA) | GTAAAACGACGGCCAGT-3'-6FAM |
| Oligo 3b (RNA) | GUAAAACGACGGCCAGU-3'-6FAM |
| Oligo 4 (DNA) | 5'-Dabsyl-ACTGGCCGTCGTTTTAC |

The results are shown in FIG. 2. FIG. 2A shows the results for the DNA:DNA duplex and the DNA:RNA duplex. FIG. 2B shows the results for the DNA:DNA duplex and the RNA:RNA duplex in which 20U RNasin Plus (Promega) RNase inhibitor was also included in the binding reaction. Those results show that Pae3192 gel-shifted both the DNA:DNA duplex and the DNA:RNA duplex, but did not gel-shift the RNA:RNA duplex.

2. Tm Experiments

The ability of Pae3192 to stabilize a DNA:DNA duplex and a DNA:RNA duplex at elevated temperatures was tested. The DNA oligonucleotide 3a, RNA nucleotide 3b, and DNA oligonucleotide 4 of Table 1 above were used in this experiment. Oligonucleotides 3a and 3b included a fluorophore (FAM) and oligonucleotide 4 included a quencher (Dabsyl). Annealing of oligonucleotide 4 to either oligonucleotide 3a or oligonucleotide 3b results in quenching of the fluorophore, because the oligonucleotides are brought into close proximity. Melting can thus be monitored in a real-time PCR apparatus as in increase in fluorescence. Tm's were assigned as the minima of the negative derivative of the fluorescence versus temperature curves.

Pae3192 was separately incubated with the DNA:DNA duplex or with the DNA:RNA duplex for 20 minutes at 20° C. in the presence of a protein buffer containing 15 mM NaCl, 88 uM $CaCl_2$ and 50 mM Tris, pH 8.0. Pae3192 was present at 12.5 uM (88 ug/ml), while the duplexes were at 0.25 uM. A dissociation curve (25° C. to 95° C.) was then taken using the AB 7900 apparatus. Negative controls were also monitored in which the protein buffer was added alone or the protein buffer plus 88 ug/ml of bovine serum albumin (BSA) was added. Overall, the addition of BSA had no effect on the Tm's of the duplexes (not shown). The observed differences in Tm between the buffer only samples and the Pae3192-containing samples are indicated in Table 2. Pae3192 stabilized both DNA:DNA duplexes and DNA:RNA hybrids, though stabilization of DNA:RNA duplex occurred to a slightly lesser extent.

TABLE 2

Stabilization of DNA:DNA and DNA:RNA duplexes by Pae3192. Tm's (° C.) for annealed oligos 3a+4 (DNA:DNA) or oligos 3b+4 (DNA:RNA) in the presence or absence of Pae3192 are indicated.

| | $T_m$, buffer alone | $T_m$ + Pae3192 | $\Delta T_m$ |
|---|---|---|---|
| DNA:DNA | 57.5 | 75.9 | 18.4 |
| DNA:RNA | 56.8 | 71.1 | 14.3 |

Sso7d has also been shown to have DNA:DNA duplex stabilization activity (see, for example, McAfee et al, *Biochemistry*, 34(31):10063-10077 (1995).

Together with the data below in Example L that showed that the Pae3192-Pfu fusion protein possessed an acquired reverse transcriptase (RT) activity, these data in Example K(1) and (2) support the conclusion that Pae3192 binds to RNA:DNA duplexes.

L. Use of 10His-Pfu-Pae3192 and 10His-Pfu-Pae3192, exo-minus version in RT-PCR

RT-PCR reactions were performed. All reagents, including RNA template, primers, dNTPs and buffers, were from the GeneAmp EZ rTth RT-PCR Kit (P/N N808-0179; Applied Biosystems, Foster City, Calif.). The enzymes that were tested were Taq DNA polymerase (AmpliTaq; Applied Biosystems, Inc); rTth DNA polymerase (included with the GeneAmp EZ rTth RT-PCR Kit); Phusion DNA polymerase (Finnzymes); 10His-Pfu-Pae3192 (described in Example C(1)(a) above); 10His-Pfu-Pae3192, exo-minus version (described in Example C(1)(d) above (a double mutant of 10His-Pfu-Pae3192 rendering the activity of the 3'45' exonuclease domain essentially inactive)), and P.fu polymerase (without nucleic acid binding polypeptide) (Stratagene).

Each of the enzymes was used in reactions employing the standard RT-PCR cycling conditions recommended by the manufacturer. AmpliTaq, rTth, 10His-Pfu-Pae3192, and 10His-Pfu-Pae3192, exo-minus version, each provided PCR amplification product from the starting RNA template (data not shown). Pfu polymerase (without nucleic acid binding polypeptide) did not amplify a product (data not shown).

A RT-PCR reaction was also performed with each of the enzymes according to the manufacturer's instructions, with the following modifications to the cycling parameters: the initial RT step was shortened from 30 minutes to 5 minutes; the two step PCR cycling program was shortened so that the holding time at both temperatures was reduced to 2 seconds each; and the final extension at 72° C. was omitted. As shown in FIG. 3, when the RT-PCR cycling conditions were significantly shortened as described above, only 10His-Pfu-Pae3192 and 10His-Pfu-Pae3192, exo-minus version, yielded a significant amount of amplification product (lanes 6, 7, 8 in FIG. 3); the rTth enzyme (lane 4) no longer produced a band and AmpliTaq (lane 3) produced a greatly reduced yield.

M. Use of 10His-Pae3192-Taq in PCR

Three sets of PCR reactions were performed. All reaction mixtures contained lambda DNA as the template and the following forward and reverse primers:

```
                                          (SEQ ID NO: 47)
5'-AGCCAAGGCCAATATCTAAGTAAC-3'
(Tm = 54.1° C.)

(SEQ ID NO: 48)
5'-CGAAGCATTGGCCGTAAGTG-3'
(Tm = 58.4° C.)
```

The first set of reaction mixtures was prepared as follows:

| Component (stock concentration) | Volume | Final concentration |
|---|---|---|
| Lambda (λ) DNA (10 ng/µl) | 1 µl | 0.2 ng/µl |
| dNTPs (2.5 mM each) | 1 µl | 200 µM each |
| Buffer* (10x) | 5 µl | 1x |
| Forward primer (10 µM) | 1 µl | 0.2 µM |
| Reverse primer (10 µM) | 1 µl | 0.2 µM |
| Enzyme | 0.5 µl | |
| dH₂0 | 40.5 µl | |
| | 50 µl final volume | |

1× Buffer*: 10 mM Tris-HCl pH 8.3, 50 mM KCl, 1.5 mM $MgCl_2$

In separate reaction mixtures, the enzymes AmpliTaq (Roche Molecular Systems, Pleasanton, Calif.) and 10His-Pae3192-Taq (described in Example C(2)(a) above) were tested. Two-fold serial dilutions of the 10His-Pae3192-Taq were tested in the range of 24, 12, 6, 3, and 1.5 Units per 50 uL reaction. AmpliTaq was tested at 2.5 Units per 50 uL reaction.

The first set of reaction mixtures were subjected to PCR cycling conditions using an Applied Biosystems 9700 Thermal Cycler (Applied Biosystems, Foster City, Calif.), as follows:

95° C., 1 min;

94° C., 30 sec;
55° C., 30 sec; and         30 cycles
72° C., 1 sec.

72° C., 10 min

After the 30 cycles, the reaction mixtures were analyzed by agarose gel electrophoresis. AmpliTaq provided PCR amplification product from the starting template (data not shown). The 10His-Pae3192-Taq did not amplify a product (data not shown).

The second set of reaction mixtures was identical to the first set of reaction mixtures discussed above except that the 1× Buffer* contained 15 mM Tris-HCl pH 8.9, 90 mM KCl, 1.5 mM $MgCl_2$, and 0.05% Tween 20.

The enzyme 10His-Pae3192-Taq (described in Example C(2)(a) above) was tested. Two-fold serial dilutions of the 10His-Pae3192-Taq were tested in the range of 24, 12, 6, 3, and 1.5 Units per 50 uL reaction.

The second set of reaction mixtures were subjected to same PCR cycling conditions discussed above for the first set of reaction mixtures using an Applied Biosystems 9700 Thermal Cycler (Applied Biosystems, Foster City, Calif.).

After the 30 cycles, the reaction mixtures were analyzed by agarose gel electrophoresis. See FIG. 4. The 10His-Pae3192-Taq amplified a product as shown in FIG. 4.

The third set of reaction mixtures was prepared as follows:

| Component (stock concentration) | Volume | Final concentration |
|---|---|---|
| Lambda (λ) DNA (10 ng/µl) | 1 µl | 0.2 ng/µl |
| dNTPs (2.5 mM each) | 1 µl | 200 µM each |
| Buffer* (5x) | 10 µl | 1x |
| Forward primer (10 µM) | 1 µl | 0.2 µM |
| Reverse primer (10 µM) | 1 µl | 0.2 µM |
| Enzyme | 0.5 µl | |
| dH₂0 | 36.5 µl | |
| | 50 µl final volume | |

1× Buffer* for 10His-Pae3192-Taq: 15 mM Tris-HCl at indicated pH, 90 mM KCl, 1.5 mM $MgCl_2$, and some reactions further included 0.05% Tween 20 in the buffer, while others included no Tween 20 in the buffer (pH values of 7.55; 7.7; 8.2; 8.6; 8.7; 9.07; and 9.3 were tested)

1× Buffer* for AmpliTaq: 10 mM Tris-HCl at indicated pH, 50 mM KCl, 1.5 mM $MgCl_2$ (pH values of 7.55; 7.7; 8.2; 8.6; 8.7; 9.07; and 9.3 were tested)

In separate reaction mixtures, the enzymes AmpliTaq (Roche Molecular Systems, Pleasanton, Calif.) and 10His-Pae3192-Taq (described in Example C(2)(a) above were tested. The 10His-Pae3192-Taq was tested at 2.5 Units per 50 uL reaction. AmpliTaq was tested at 2.5 Units per 50 uL reaction.

The third set of reaction mixtures were subjected to same PCR cycling conditions discussed above for the first set of reaction mixtures using an Applied Biosystems 9700 Thermal Cycler (Applied Biosystems, Foster City, Calif.).

After the 30 cycles, the reaction mixtures were analyzed by agarose gel electrophoresis. As shown in FIG. 5, AmpliTaq provided PCR amplification product at the lower pH levels tested, but did not provide PCR amplification product at the higher pH levels tested. As shown in FIG. 5, 10His-Pae3192-Taq with Tween 20 in the buffer provided PCR amplification product at the higher pH levels tested. The 10His-Pae3192-Taq without Tween 20 in the buffer did not provide PCR amplification product The 0.05% Tween can also be substituted with 0.05% NP-40 with similar activity in PCR (data not shown).

| SEQ ID NO: | Brief Description | Sequence |
|---|---|---|
| | | TABLE OF SEQUENCES |
| 1 | Pae3192 (protein) | MSKKQKLKFYDIKAKQAFETDQYEVIEKQTARGPMMFAVAKSPYTGIKVYRLLGKKK |
| 2 | PAE3192 (ORF) | atgcccaaga agcagaaact aaagttctac gacacaaagg cgaagcaggc gtttgagact gaccagtacg aggttattga gaagcagact gcccgcggtc cgatgatgtt cgccgtggcc aaatcgccgt acaccggcat aaaagtatac agactgttag gcaagaagaa ataa |
| 3 | PAE3289 (ORF) | atgtccaaga agcagaaact aaagttctac gacacaaagg cgaagcaggc gtttgagact gaccagtacg aggttattga gaagcagact gcccgcggtc cgatgatgtt cgccgtggcc aaatcgccgt acaccggcat aaaagtatac agactattag gcaagaagaa ataa |
| 4 | Pae0384 (protein) | MAKQKLKFYDIKAKQSFETDKYEVIEKETARGPMLFAVATSPYTGIKVYRLLGKKK |
| 5 | PAE0384 (ORF) | atggccaaac aaaaactaaa gttctacgac ataaaagcga acagtccttc gaaacggac aaatacgagg tcattgagaa agacggcc cgcgggccga tgttatttgc agtggcaacc tcgccgtaca ctggcataaa ggtgtacaga ctgttaggca agaagaaata a |
| 6 | Ape3192 | MPKKEKIKFFDLVAKKYYETDNYEVEIKETKRGKFRFAKAKSPYTGKIFYRVLGKA |
| 7 | APE3192 (ORF) | atgcccaaga aggagaagat aaagttcttc gacctagtcg ccaagaagta ctacgagact gacaactacg aagtcgagat aaaggagact aagaggggca gtttaggtt cgccaaagcc aagagcccgt acaccggcaa gatcttctat agagtgctag gcaaagccta g |
| 8 | p3192-a | atgtccaaga agcagaaact gaagttctac gacattaagg cgaagcaggc gtttgag |
| 9 | p3192-b | accgaccagt acgaggttat tgagaagcag accgcccgcg gtccgatgat gttcgcc |
| 10 | p3192-c | gtggccaaat cgccgtacac cggcattaaa gtgtaccgcc tgttaggcaa gaagaaataa |
| 11 | p3192-y | gtactggtcg gtctcaaacg cctg |
| 12 | p3192-z | cgatttggcc acggcgaaca tcat |
| 13 | 8, 9, and 10 assembled | atgtccaaga agcagaaact gaagttctac gacattaagg cgaagcaggc gtttgagacc gaccagtacg aggttattga gaagcagacc gcccgcggtc cgatgatgtt cgccgtggcc aaatcgccgt acaccggcat taaagtgtac cgcctgttag gcaagaagaa ataa |
| 14 | ap3192-a | atgccgaaga aggagaagat taagttcttc gacctgctcg ccaagaagta ctacqag |
| 15 | ap3192-b | actgacaact acgaagtcga gattaaggag actaagcgcg gcaagtttcg cttcgcc |
| 16 | ap3192-c | aaagccaaga gcccgtacac cggcaagatc ttctatcgcg tgctgggcaa agcctag |
| 17 | ap3192-y | gtagttgtca gtctcgtagt actt |
| 18 | ap3192-z | gctcttggct ttggcgaagc gaaa |
| 19 | 14, 15, and 16 assembled | atgccgaaga aggagaagat taagttcttc gacctggtcg ccaagaagta ctacgagact gacaactacg aagtcgagat taaggagact aagcgcggca gtttcgctt cgccaaagcc aagagcccgt acaccggcaa gatcttctat cgcgtgctgg gcaaagccta g |
| 20 | Sso7d | MATVKFKYKGEEKQVDISKIKKVWRVGKMISFTYDEGGGKTGRGAVSEKDAPKELLQMLEKQKK |
| 21 | Sso7d variant | MEISMATVKFKYKGEEKQVDISKIKKVWRVGKMISFTYDEGGGKTGRGAVSEKDAPKELLQMLEKQKK |

| SEQ ID NO: | Brief Description | Sequence |
|---|---|---|
| 22 | polynucleotide encoding 10His-Pfu-Pae3192 | ccatgggccatcatcatcatcatcatcatcatcatcacagcagcggccatatcgaaggtc gtcatatgattttagatgtggattacataactgaagaaggaaaacctgttattaggctat tcaaaaaagagaacggaaaatttaagatagagcatgatagaactttagaccatacattt acgctcttctcagggatgattcaaagattgaagaagttaagaaaataacgggggaaaggc atggaaagattgtgagaattgttgatgtagagaaggttgagaaaaagtttctcggcaagc ctattaccgtgtggaaacttatttggaacatcccaagatgttccactattagagaaa aagttagagaacatccagcagttgtggacatcttcgaatacgatattccatttgcaaaga gatacctcatcgacaaaggcctaataccaatggagggggaagaagagctaaagattcttg ccttcgatatagaaaccctctatcacgaaggagaagagtttggaaaaggcccaattataa tgattagttatgcagatgaaaatgaagcaaaggtgattacttggaaaaacatagatcttc catacgttgaggttgtatcaagcgagagagagatgataaagagatttctcaggattatca gggagaaggatcctgacattatagttacttataatggagactcattcgacttcccatatt tagccgaaaagggcagaaaaacttgggattaaattaaccattggaagaagtggaagcgagc caagatgcagagaataggcgatatgacggctgtagaagtcaagggaagaatacatttcg acttgtatcatgtaataacaaggacaataaatctcccaacatacacactagaggctgtat atgaagcaattttggaaagccaaggagaaggtatacgccgacgagatagcaaaagcct gggaaagtggagagaaccttgagagagttgccaaatactcgatggaagatgcaaaggcaa cttatgaactcgggaaagaattccttccaatggaaattcagctttcaagattagttggac aacctttatgggatgtttcaaggtcaagcacagggaaccttgtagagtggttcttactta ggaaagcctacgaaagaaacgaagtagctccaaacaagccaagtgaagaggagtatcaaa gaaggctcagggagagctacacaggtggattcgttaaagagccagaaaaggggttgtggg aaaacatagtatacctagattttagagcccatatcccctcgattataattacccacaatg tttctcccgatactctaaatcttgagggatgcaagaactatgatatcgctcctcaagtag gccacaagttctgcaaggacatccctggttttataccaagtctcttgggacatttgttag aggaaagacaaaagattaagacaaaaatgaaggaaactcaagatcctatagaaaaaatac tccttgactatagacaaaaagcgataaaactcttagcaaattctttctacggatattatg gctatgcaaaagcaagatggtactgtaaggagtgtgctgagagcgttactgcctgggaa gaaagtacatcgagttagtatggaaggagctcgaagaaaagtttggatttaaagtcctct acattgacactgatggtctctatgcaactatcccaggaggagaaagtgaggaaataaaga aaaaggctctagaatttgtaaaatacataaattcaaagctccctggactgctagagcttg aatatgaaggggttttataagagggggattcttcgttacgaagaagaggtatgcagtaatag atgaagaggaaaagtcattactcgtggtttagagatagttaggagagattggagtgaaa ttgcaaaagaaactcaagctagagttttggagacaatactaaaacacggagatgttgaag aagctgtgagaatagtaaaagaagtaatacaaaagcttgccaattatgaaattccaccag agaagctcgcaatatatgagcagataaacaagaccattacatgagtataaggcgataggtc ctcacgtagctgttgcaaagaaactagctgctaaaggagttaaaataaagccaggaatgg taattggatacatagtacttagaggcgatggtccaattagcaataggcaattctagctg aggaatacgatcccaaaaagcacaagtatgacgcagaatattacattgagaaccaggttc ttccagcggtacttaggatattggagggatttggatacagaaaggaagacctcagatacc aaaaagacaagacaagtcggcctaacttcctggcttaacattaaaaaatccggtaccggcg gtggcggtatgtccaagaagcagaaactgaagttctacgacattaaggcgaagcggcgt ttgagaccgaccagtacgaggttattgagaagcagaccgcccgcggtccgatgatgttcg ccgtggccaaatcgccgtacaccggcattaaagtgtaccgcctgttaggcaagaagaaat aactcgag |
| 23 | amino acid sequence of 10His-Pfu-Pae3192 | MGHHHHHHHHHHSSGHIEGRHMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE AVRIVKEVIQKLANYEIPPEKLAIYEQITRPLHEYKAIGPHVAVAKKLAAKGVKIKPGMV IGYIVLRGDGPISNRAILAEEYDPKKHKYDAEYYIENQVLPAVLRILEGFGYRKEDLRYQ KTRQVGLTSWLNIKKSGTGGGGMSKKQKLKFYDIKAKQAFETDQYEVIEKQTARGPMMFA VAKSPYTGIKVYRLLGKKK |
| 24 | amino acid sequence of Pfu-Pae3192 | HMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE |

TABLE OF SEQUENCES

| SEQ ID NO: | Brief Description | Sequence |
|---|---|---|
| | | AVRIVKEVIQKLANYEIPPEKLAIYEQITRPLHEYKAIGPHVAVAKKLAAKGVKIKPGMV IGYIVLRGDGPISNRAILAEEYDPKKHKYDAEYYIENQVLPAVLRILEGFGYRKEDLRYQ KTRQVGLTSWLNIKKSGTGGGGMSKKQKLKFYDIKAKQAFETDQYEVIEKQTARGPMMFA VAKSPYTGIKVYRLLGKKK |
| 25 | polynucleotide encoding 10His-Pfu-Ape3192 | ccatgggccatcatcatcatcatcatcatcatcatcatcacagcagcggccatatcgaaggtc gtcatatgattttagatgtggattacataactgaagaaggaaaacctgttattaggctat tcaaaaaagagaacggaaaatttaagatagagcatgatagaacttttagaccatacatttt acgctcttctcagggatgattcaaagattgaagaagttaagaaaataacggggaaaggc atggaaagattgtgagaattgttgatgtagagaaggttgagaaaaagtttctcggcaagc ctattaccgtgtggaaactttatttggaacatcccaagatgttccactattagagaaa aagttagagaacatccagcagttgtggacatcttcgaatacgatattccatttgcaaaga gataccatcgacaaaggcctaataccaatggaggggggaagaagagctaagattcttg cctttcgatatagaaaccctctatcacgaaggagaagagtttggaaaaggcccaattataa tgattagttatgcagatgaaaatgaagcaaaggtgattacttggaaaaacatagatcttc catacgttgaggttgtatcaagcgagagagagatgataaagagatttctcaggattatca gggagaaggatcctgacattatagttacttataatggagactcattcgactttcccatatt tagcgaaaagggcagaaaaacttgggattaaattaaccattggaagatggaagcgagc ccaagatgcagagaataggcgatatgacggctgtagaagtcaagggaagaatacatttcg acttgtatcatgtaataacaaggacaataaatctcccaacatacacactagaggctgtat atgaagcaattttggaaagccaaaggagaaggtatacgccgacgagatagcaaaagcct gggaaagtggagagaaccttgagagagttgccaaatactcgatggaagatgcaaaggcaa cttatgaactcgggaaagaattccttccaatggaaattcagctttcaagattagttggac aacctttatgggatgtttcaaggtcaagcacagggaaccttgtagagtggttcttactta ggaaagcctacgaaagaaacgaagtagctccaaacaagccaagtgaagaggagtatcaaa gaaggctcagggagagctacacaggtggattcgttaaagagccagaaaaggggttgtggg aaaacatagtatacctagatttagagccctatatccctcgattataattacccacaatg tttctcccgatactctaaatcttgagggatgcaagaactatgatatcgctcctcaagtag gccacaagttctgcaaggacatccctggttttataccaagtctcttgggacatttgttag aggaagacaaaagattaagacaaaaatgaaggaaactcaagatcctatagaaaaaatac tccttgactatagacaaaaagcgataaaactcttagcaaattctttctacggatattatg gctatgcaaaagcaagatggtactgtaaggagtgtgctgagagcgttactgcctggggaa gaaagtacatcgagttagtatgaaggagctcgaagaaaagtttggatttaaagtcctct acattgacactgatggtctctatgcaactatcccaggaggagaaagtgaggaaataaaga aaaaggctctagaatttgtaaaatacataaattcaaagctccctggactgctagagcttg aatatgaagggttttataagaggggattcttcgttacgaagaagaggtatgcagtaatag atgaagaaggaaaagtcattactcgtggtttagagatagttaggagagattggagtgaaa ttgcaaaagaaactcaagctagagtttttggagacaatactaaaacacggagatgttgaag aagctgtgagaatagtaaaagaagtaatacaaaagcttgccaattatgaaattccaccag agaagctcgcaatatgagcagataacaagaccattacatgagtataaggcgataggtc ctcacgtagctgttgcaaagaaactagctgctaaaggagttaaaataaagccaggaatgg taattggatacatacttagaggcgatggtccaattagcaataggggcaattctagctg aggaatacgatcccaaaaagcacaagtatgacgcagaatattacattgagaaccaggttc ttccagcggtacttaggatattggagggatttggatacagaaaggaagacctcagatacc aaaagacaagacaagtcggcctaacttcctggcttaacattaaaaaatccggtaccggcg gtggcggtccgaagaaggagaagattaggttcttcgacctggtcgccaagaagtactacg agactgacaactacgaagtcgagattaaggagactaagcgcggcaagtttcgcttcgcca aagccaagagcccgtacaccggcaagatcttctatcgcgtgctgggcaaagcctaactcgag |
| 26 | amino acid sequence of 10His-Pfu-Ape3192 | MGHHHHHHHHHHSSGHIEGRHMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETIKHGDVEE AVRIVKEVIQKLANYEIPPEKLAIYEQITRPLHEYKAIGPHVAVAKKLAAKGVKIKPGMV IGYIVLRGDGPISNRAILAEEYDPKKHKYDAEYYIENQVLPAVLRILEGFGYRKEDLRYQ KTRQVGLTSWLNIKKSGTGGGGPKKEKIRFFDLVAKKYYETDNYEVEIKETKRGKFRFAK AKSPYTGKIFYRVLGKA |
| 27 | amino acid sequence of Pfu-Ape3192 | HMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR |

TABLE OF SEQUENCES

| SEQ ID NO: | Brief Description | Sequence |
|---|---|---|
| | | KYIELVWKELEEKFGFKVLYIDTDGLYATIPGGESEEIKKKALEFVKYINSKLPGLLELE<br>YEGFYKRGFFVTKKRYAVIDEEGKVITRGLEIVRRDWSEIAKETQARVLETILKHGDVEE<br>AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKSGTGGGGPKKEKIRFFDLVAKKYYETDNYEVEIKETKRGKFRFAK<br>AKSPYTGKIFYRVLGKA |
| 28 | Pae/Ape consensus sequence | KXKXKFXDXXAKXXXETDXYEVXXKXTXRGXXXFAXAKSPYTGXXXYRXLGK |
| 29 | oligo for processivity assay | gttttcccagtcacgacgttgtaaaacgacggcc |
| 30 | Pfu DNA polymerase | MILDVDYITEEGKPVIRLFKKENGKFKIEHDRTFRPYIY<br>ALLRDDSKIEEVKKITGERHGKIVRIVDVEKVEKKFLGKPITVWKLYLEHPQDVPTIREK<br>VREHPAVVDIFEYDIPFAKRYLIDKGLIPMEGEEELKILAFDIETLYHEGEEFGKGPIIM<br>ISYADENEAKVITWKNIDLPYVEVVSSEREMIKRFLRIIREKDPDIIVTYNGDSFDFPYL<br>AKRAEKLGIKLTIGRDGSEPKMQRIGDMTAVEVKGRIHFDLYHVITRTINLPTYTLEAVY<br>EAIFGKPKEKVYADEIAKAWESGENLERVAKYSMEDAKATYELGKEFLPMEIQLSRLVGQ<br>PLWDVSRSSTGNLVEWFLLRKAYERNEVAPNKPSEEEYQRRLRESYTGGFVKEPEKGLWE<br>NIVYLDFRALYPSIIITHNVSPDTLNLEGCKNYDIAPQVGHKFCKDIPGFIPSLLGHLLE<br>ERQKIKTKMKETQDPIEKILLDYRQKAIKLLANSFYGYYGYAKARWYCKECAESVTAWGR<br>KYIELVWKELEEKFGEKVLYIDTDGLYATIPGGESEEIKKKALEFVKYINSKLPGLLELE<br>YEGFYKRGFFVTKKRYAVIDEEGKVITRGLEIVRRDWSEIAKETQARVLETILKHGDVEE<br>AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKS |
| 31 | Taq DNA polymerase | MRGMLPLFEPKGRVLLVDGHHLAYRTFHALKGLTTSRGEPVQAVYGFAKSLLKALKEDG<br>DAVIVVFDAKAPSFRHEAYGGYKAGRAPTPEDFPRQLALIKELVDLLGLARLEVPGYEA<br>DDVLASLAKKAEKEGYEVRILTADKDLYQLLSDRIHVLHPEGYLITPAWLWEKYGLRPD<br>QWADYRALTGDESDNLPGVKGIGEKTARKLLEEWGSLEALLKNLDRLKPAIREKILAHM<br>DDLKLSWDLAKVRTDLPLEVDFAKRREPDRERLRAFLERLEFGSLLHEFGLLESPKALE<br>EAPWPPPEGAFVGFVLSRKEPMWADLLALAAARGGRVHRAPEPYKALRDLKEARGLLAK<br>DLSVLALREGLGLPPGDDPMLLAYLLDPSNTTPEGVARRYGGEWTEEAGERAALSERLF<br>ANLWGRLEGEERLLWLYREVERPLSAVLAHMEATGVRLDVAYLRALSLEVAEEIARLEA<br>EVFRLAGHPFNLNSRDQLERVLFDELGLPAIGKTEKTGKRSTSAAVLEALREAHPIVEK<br>ILQYRELTKLKSTYIDPLPDLIHPRTGRLHTRFNQTATATGRLSSSDPNLQNIPVRTPL<br>GQRIRRAFIAEEGWLLVALDYSQIELRVLAHLSGDENLIRVFQEGRDIHTETASWMFGV<br>PREAVDPLMRRAAKTINFGVLYLVGMSAHRLSQELAIPYEEAQAFIERYFQSFPKVRAWIE<br>KTLEEGRRRGYVETLFGRRRYVPDLEARVKSVREAAERMAFNMPVQGTAADLMKLAMVK<br>LEPRLEEMGARMLLQVHDELVLEAPKERAEAVARLAKEVMEGVYPLAVPLEVEVGIGED<br>WLSAKE |
| 32 | polynucleotide encoding 10His-Pae3192-Taq | ATGGGCCATCATCATCATCATCATCATCATCATCATCACAGCAGCGGCCATATCGAAGGTCG<br>TCATATGTCCAAGAAGCAGAAACTGAAGTTCTACGACATTAAGGCGAAGCAGGCGTTTG<br>AGACCGACCAGTACGAGGTTATTGAGAAGCAGACCGCCCGCGGTCCGATGATGTTCGCC<br>GTGGCCAAATCGCCGTACACCGGCATTAAAGTGTACCGCCTGTTAGGCAAGAAGAAAGG<br>CGGCGGTGTCACTAGTGGGATGCTGCCCCTCTTTGAGCCCAAGGGCCGGGTCCTCCTGG<br>TGGACGGCCACCACCTGGCCTACCGCACCTTCCACGCCCTGAAGGGCCTCACCACCAGC<br>CGGGGGGAGCCGGTGCAGGCGGTCTACGGCTTCGCCAAGAGCCTCCTCAAGGCCCTCAA<br>GGAGGACGGGGACGCGGTGATCGTGGTCTTTGACGCCAAGGCCCCCTCCTTCCGCCACG<br>AGGCCTACGGGGGGTACAAGGCGGGCCGGGCCCCCACGCCGGAGGACTTTCCCCGGCAA<br>CTCGCCCTCATCAAGGAGCTGGTGGACCTCCTGGGGCTGGCGCGCCTCGAGGTCCCGGG<br>CTACGAGGCGGACGACGTCCTGGCCAGCCTGGCCAAGAAGGCGGAAAAGGAGGGCTACG<br>AGGTCCGCATCCTCACCGCCGACAAAGACCTTTACCAGCTCCTTTCCGACCGCATCCAC<br>GTCCTCCACCCCGAGGGGTACCTCATCACCCCGGCCTGGCTTTGGGAAAAGTACGGCCT<br>GAGGCCCGACCAGTGGGCCGACTACCGGGCCCTGACCGGGGACGAGTCCGACAACTTC<br>CCCGGGGTCAAGGGCATCGGGGAGAAGACGGCGAGGAAGCTTCTGGAGGAGTGGGGGAGC<br>CTGGAAGCCCTCCTCAAGAACCTGGACCGGCTGAAGCCCGCCATCCGGGAAGATCCT<br>GGCCCACATGGACGATCTGAAGCTCTCCTGGGACCTGGCCAAGGTGCGCACCGACCTGC<br>CCCTGGAGGTGGACTTCGCCAAAAGGCGGGAGCCCGACCGGGAGAGGCTTAGGGCCTTT<br>CTGGAGAGGCTTGAGTTTGGCAGCCTCCTCCACGAGTTCGGCCTTCTGGAAAGCCCCAA<br>GGCCCTGGAGGAGGCCCCTGGCCCCCGCCGGAAGGGGCCTTCGTGGGCTTTGTGCTTT<br>CCCGCAAGGAGCCCATGTGGGCCGATCTTCTGGCCCTGGCCGCCGCAGGGGGGCCGG<br>GTCCACCGGGCCCCCGAGCCTTATAAAGCCTCAGGGACCTGAAGGAGGCGCGGGGCT<br>TCTCGCCAAAGACCTGAGCGTTCTGGCCCTGAGGGAAGGCCTTGGCCTCCCGCCCGGCG<br>ACGACCCCATGCTCCTCGCCTACCTCCTGGACCCTTCCAACACCACCCCCGAGGGGGTG<br>GCCCGGCGCTACGGCGGGAGTGGACGAGGAGGCGGGGAGCGGGCCGCCCTTTCCGA<br>GAGGCTCTTCGCCAACCTGTGGGGGAGGCTTGAGGGGAGGAGAGGCTCCTTTGGCTTT<br>ACCGGGAGGTGGAGAGGCCCCTTTCCGCTGTCCTGGCCCACATGGAGGCCACGGGGTG<br>CGCCTGGACGTGGCCTATCTCAGGGCCTTTGTCCCTGGAGGTGGCCGAGGAGATCGCCCG |

TABLE OF SEQUENCES

| SEQ ID NO: | Brief Description | Sequence |
|---|---|---|
| | | CCTCGAGGCCGAGGTCTTCCGCCTGGCCGGCCACCCCTTCAACCTCAACTCCCGGGACC<br>AGCTGGAAAGGGTCCTCTTTGACGAGCTAGGGCTTCCCGCCATCGGCAAGACGGAGAAG<br>ACCGGCAAGCGCTCCACCAGCGCCGCCGTCCTGGAGGCCCTCCGCGAGGCCCACCCCAT<br>CGTGGAGAAGATCCTGCAGTACCGGGAGCTCACCAAGCTGAAGAGCACCTACATTGACC<br>CCTTGCCGGACCTCATCCACCCCAGGACGGGCCGCCTCCACACCCGCTTCAACCAGACG<br>GCCACGGCCACGGGCAGGCTAAGTAGCTCCGATCCCAACCTCCAGAACATCCCCGTCCG<br>CACCCCGCTTGGGCAGAGGATCCGCCGGGCCTTCATCGCCGAGGAGGGTGGCTATTGG<br>TGGCCCTGGACTATAGCCAGATAGAGCTCAGGGTGCTGGCCCACCTCTCCGGCGACGAG<br>AACCTGATCCGGGTCTTCCAGGAGGGGCGGGACATCCACACGGAGACCGCCAGCTGGAT<br>GTTCGGCGTCCCCCGGGAGGCCGTGGACCCCTGATGCGCCGGGCGGCCAAGACCATCA<br>ACTTCGGGGTCCTCTACGGCATGTCGGCCCACCGCCTCTCCCAGGAGCTAGCCATCCCT<br>TACGAGGAGGCCCAGGCCTTCATTGAGCGCTACTTTCAGAGCTTCCCCAAGGTGCGGGC<br>CTGGATTGAGAAGACCCTGGAGGAGGGCAGGAGGCGGGGGTACGTGGAGACCCTCTTCG<br>GCCGCCGCCGCTACGTGCCAGACCTAGAGGCCCGGGTGAAGAGCGTGCGGGAGGCGGCC<br>GAGCGCATGGCCTTCAACATGCCCGTCCAGGGCACCGCCGCCGACCTCATGAAGCTGAC<br>TATGGTGAAGCTCTTCCCCAGGCTGGAGGAAATGGGGGCCAGGATGCTCCTTCAGGTCC<br>ACGACGAGCTGGTCCTCGAGGCCCCAAAAGAGAGGGCGGAGGCCGTGGCCCGGCTGGCC<br>AAGGAGGTCATGGAGGGGGTGTATCCCCTGGCCGTGCCCCTGGAGGTGGAGGTGGGGAT<br>AGGGGAGGACTGGCTCTCCGCCAAGGAGTGA |
| 33 | amino acid sequence of 10His-Pae3192-Taq | MGHHHHHHHHHHSSGHIEGRHMSKKQKLKFYDIKAKQAFETDQYEVIEKQTARGPMMFA<br>VAKSPYTGIKVYRLLGKKKGGGVTSGMLPLFEPKGRVLLVDGHHLAYRTFHALKGLTTS<br>RGEPVQAVYGFAKSLLKALKEDGDAVIVVFDAKAPSFRHEAYGGYKAGRAPTPEDFPRQ<br>LALIKELVDLLGLARLEVPGYEADDVLASLAKKAEKEGYEVRILTADKDLYQLLSDRIH<br>VLHPEGYLITPAWLWEKYGLRPDQWADYRALTGDESDNLPGVKGIGEKTARKLLEEWGS<br>LEALLKNLDRLKPAIREKILAHMDDLKLSWDLAKVRTDLPLEVDFAKRREPDRERLRAF<br>LERLEFGSLLHEFGLLESPKALEEAPWPPPEGAFVGFVLSRKEPMWADLLALAAARGG<br>VHRAPEPYKALRDLKEARGLLAKDLSVLALREGLGLPPGDDPMLLAYLLDPSNTTPEGV<br>ARRYGGEWTEEAGERAALSERLFANLWGRLEGEERLLWLYREVERPLSAVLAHMEATGV<br>RLDVAYLRALSLEVAEEIARLEAEVFRLAGHPFNLNSRDQLERVLFDELGLPAIGKTEK<br>TGKRSTSAAVLEALREAHPIVEKILQYRELTKLKSTYIDPLPDLIHPRTGRLHTRFNQT<br>ATATGRLSSSDPNLQNIPVRTPLGQRIRRAFIAEEGWLLVALDYSQIELRVLAHLSGDE<br>NLIRVFQEGRDIHTETASWMFGVPREAVDPLMRRAAKTINFGVLYGMSAHRLSQELAIP<br>YEEAQAFIERYFQSFPKVRAWIEKTLEEGRRRGYVETLFGRRRYVPDLEARVKSVREAA<br>ERMAFNMPVQGTAADLMKLAMVKLFPRLEEMGARMLLQVHDELVLEAPKERAEAVARLA<br>KEVMEGVYPLAVPLEVEVGIEDWLSAKE |
| 34 | amino acid sequence of Pae3192-Taq | HMSKKQKLKFYDIKAKQAFETDQYEVIEKQTARGPMMFA<br>VAKSPYTGIKVYRLLGKKKGGGVTSGMLPLFEPKGRVLLVDGHHLAYRTFHALKGLTTS<br>RGEPVQAVYGFAKSLLKALKEDGDAVIVVFDAKAPSFRHEAYGGYKAGRAPTPEDFPRQ<br>LALIKELVDLLGLARLEVPGYEADDVLASLAKKAEKEGYEVRILTADKDLYQLLSDRIH<br>VLHPEGYLITPAWLWEKYGLRPDQWADYRALTGDESDNLPGVKGIGEKTARKLLEEWGS<br>LEALLKNLDRLKPAIREKILAHMDDLKLSWDLAKVRTDLPLEVDFAKRREPDRERLRAF<br>LERLEFGSLLHEFGLLESPKALEEAPWPPPEGAFVGFVLSRKEPMWADLLALAAARGG<br>VHRAPEPYKALRDLKEARGLLAKDLSVLALREGLGLPPGDDPMLLAYLLDPSNTTPEGV<br>ARRYGGEWTEEAGERAALSERLFANLWGRLEGEERLLWLYREVERPLSAVLAHMEATGV<br>RLDVAYLRALSLEVAEEIARLEAEVFRLAGHPFNLNSRDQLERVLFDELGLPAIGKTEK<br>TGKRSTSAAVLEALREAHPIVEKILQYRELTKLKSTYIDPLPDLIHPRTGRLHTRFNQT<br>ATATGRLSSSDPNLQNIPVRTPLGQRIRRAFIAEEGWLLVALDYSQIELRVLAHLSGDE<br>NLIRVFQEGRDIHTETASWMFGVPREAVDPLMRRAAKTINFGVLYGMSAHRLSQELAIP<br>YEEAQAFIERYFQSFPKVRAWIEKTLEEGRRRGYVETLFGRRRYVPDLEARVKSVREAA<br>ERMAFNMPVQGTAADLMKLAMVKLFPRLEEMGARMLLQVHDELVLEAPKERAEAVARLA<br>KEVMEGVYPLAVPLEVEVGIEDWLSAKE |
| 35 | polynucleotide encoding 10-His-Ape3192-Taq | ATGGGCCATCATCATCATCATCATCATCATCATCATCACAGCAGCGGCCATATCGAAG<br>GTCGTCATATGCCGAAGAAGGAGAAGATTAAGTTCTTCGACCTGGTCGCCAAGAAGTAC<br>TACGAGACTGACAACTACGAAGTCGAGATTAAGGAGACTAAGCGCGGCAAGTTTCGCTT<br>CGCCAAAGCCAAGAGCCCGTACACCGGCAAGATCTTCTATCGCGGCTGGGCAAGGCG<br>GCGGCGGTGTCACTAGTGGGATGCTGCCCCTCTTTGAGCCCAAGGGCCGGGTCCTCCTG<br>GTGGACGGCCACCACCTGGCCTACCGCACCTTCCACGCCCTGAAGGGCCTCACCACCAG<br>CCGGGGGGAGCCGGTGCAGGCGGTCTACGGCTTCGCCAAGAGCCTCCTCAAGGCCCTCA<br>AGGAGGACGGGGACGCGGTGATCGTGGTCTTTGACGCCAAGGCCCCCTCCTTCCGCCAC<br>GAGGCCTACGGGGGGTACAAGGCGGGCCGGGCCCCCACGCCGGAGGACTTTCCCCGGCA<br>ACTCGCCCTCATCAAGGAGCTGGTGGACCTCCTGGGGCTGGCGCGCCTCGAGGTCCCGG<br>GCTACGAGGCGGACGACGTCCTGGCCAGCCTGGCCAAGAAGGCGGAAAAGGAGGGCTAC<br>GAGGTCCGCATCCTCACCGCCGACAAAGACCTTTACCAGCTCCTTTCCGACCGCATCCA<br>CGTCCTCCACCCCGAGGGGTACCTCATCACCCCGGCCTGGCTTTGGGAAAAGTACGGCC<br>TGAGGCCCGACCAGTGGGCCGACTACCGGGCCCTGACCGGGGACGAGTCCGACAACCTT<br>CCCGGGGTCAAGGGCATCGGGGAGAAGACGGCGAGGAAGCTTCTGGAGGAGTGGGGGAG<br>CCTGGAAGCCCTCCTCAAGAACCTGGACCGGCTGAAGCCCGCCATCCGGGAGAAGATCC<br>TGGCCCACATGGACGATCTGAAGCTCTCCTGGGACCTGGCCAAGGTGCGCACCGACCTG<br>CCCCTGGAGGTGGACTTCGCCAAAAGGCGGGAGCCCGACCGGGAGAGGCTTAGGGCCTT<br>TCTGGAGAGGCTTGAGTTTGGCAGCCTCCTCCACGAGTTCGGCCTTCTGGAAAGCCCCA<br>AGGCCCTGGAGGAGGCCCCCTGGCCCCCGCCGGAAGGGGCCTTCGTGGGCTTTGTGCTT |

TABLE OF SEQUENCES

| SEQ ID NO: | Brief Description | Sequence |
|---|---|---|
| | | TCCCGCAAGGAGCCCATGTGGGCCGATCTTCTGGCCCTGGCCGCCGCCAGGGGGGCCG<br>GGTCCACCGGGCCCCGAGCCTTATAAAGCCCTCAGGGACCTGAAGGAGGCGCGGGGGC<br>TTCTCGCCAAAGACCTGAGCGTTCTGGCCCTGAGGGAAGGCCTTGGCCTCCCGCCCGGC<br>GACGACCCCATGCTCCTCGCCTACCTCCTGGACCCTTCCAACACCACCCCCGAGGGGGT<br>GGCCCGGCGCTACGGCGGGGAGTGGACGGAGGAGGCGGGGGAGCGGGCCGCCCTTTCCG<br>AGAGGCTCTTCGCCAACCTGTGGGGGAGGCTTGAGGGGGAGGAGAGGCTCCTTTGGCTT<br>TACCGGGAGGTGGAGAGGCCCCTTTCCGCTGTCCTGGCCCACATGGAGGCCACGGGGGT<br>GCGCCTGGACGTGGCCTATCTCAGGGCCTTGTCCCTGGAGGTGGCCGAGGAGATCGCCC<br>GCCTCGAGGCCGAGGTCTTCCGCCTGGCCGGCCACCCCTTCAACCTCAACTCCCGGGAC<br>CAGCTGGAAAGGGTCCTCTTTGACGAGCTAGGGCTTCCCGCCATCGGCAAGACGGAGAA<br>GACCGGCAAGCGCTCCACCAGCGCCGCCGTCCTGGAGGCCCTCCGCGAGGCCCACCCCA<br>TCGTGGAGAAGATCCTGCAGTACCGGGAGCTCACCAAGCTGAAGAGCACCTACATTGAC<br>CCCTTGCCGGACCTCATCCACCCCAGGACGGGCCGCCTCCACACCCGCTTCAACCAGAC<br>GGCCACGGCCACGGGCAGGCTAAGTAGCTCCGATCCCAACCTCCAGAACATCCCCGTCC<br>GCACCCCGCTTGGGCAGAGGATCCGCCGGGCCTTCATCGCCGAGGAGGGTGGCTATTG<br>GTGGCCCTGGACTATAGCCAGATAGAGCTCAGGGTGCTGGCCCACCTCTCCGGCGACGA<br>GAACCTGATCCGGGTCTTCCAGGAGGGGCGGGACATCCACACGGAGACGCCAGCTGGA<br>TGTTCGGCGTCCCCCGGGAGGCCGTGGACCCCTGATGCGCCGGGCGGCCAAGACCATC<br>AACTTCGGGGTCCTCTACGGCATGTCGGCCCACCGCCTCTCCCAGGAGCTAGCCATCCC<br>TTACGAGGAGGCCCAGGCCTTCATTGAGCGCTACTTTCAGAGCTTCCCCAAGGTGCGGG<br>CCTGGATTGAGAAGACCCTGGAGGAGGGCAGGAGGCGGGGGTACGTGGAGACCCTCTTC<br>GGCCGCCGCCGCTACGTGCCAGACCTAGAGGCCCGGGTGAAGAGCGTGCGGGAGGCGGC<br>CGAGCGCATGGCCTTCAACATGCCCGTCCAGGGCACCGCCGCCGACCTCATGAAGCTGG<br>CTATGGTGAAGCTCTTCCCCAGGCTGGAGGAAATGGGGGCCAGGATGCTCCTTCAGGTC<br>CACGACGAGCTGGTCCTCGAGGCCCCAAAAGAGAGGGCGGAGGCCGTGGCCCGGCTGGC<br>CAAGGAGGTCATGGAGGGGGTGTATCCCCTGGCCGTGCCCCTGGAGGTGGAGGTGGGGA<br>TAGGGGAGGACTGGCTCTCCGCCAAGGAGTGA |
| 36 | amino acid sequence of 10-His-Ape3192-Taq | MGHHHHHHHHHHSSGHIEGRHMPKKEKIKFFDLVAKKYYETDNYEVEIKETKRGKFRFA<br>KAKSPYTGKIFYRVLGKAGGGVTSGMLPLFEPKGRVLLVDGHHLAYRTFHALKGLTTSR<br>GEPVQAVYGFAKSLLKALKEDGDAVIVVFDAKAPSFRHEAYGGYKAGRAPTPEDFPRQL<br>ALIKELVDLLGLARLEVPGYEADDVLASLAKKAEKEGYEVRILTADKDLYQLLSDRIHV<br>LHPEGYLITPAWLWEKYGLRPDQWADYRALTGDESDNLPGVKGIGEKTARKLLEEWGSL<br>EALLKNLDRLKPAIREKILAHMDDLKLSWDLAKVRTDLPLEVDFAKRREPDRERLRAFL<br>ERLEFGSLLHEFGLLESPKALEEAPWPPPEGAFVGFVLSRKEPMWADLLALAAARGGRV<br>HRAPEPYKALRDLKEARGLLAKDLSVLALREGLGLPPGDDPMLLAYLLDPSNTTPEGVA<br>RRYGGEWTEEAGERAALSERLFANLWGRLEGEERLLWLYREVERPLSAVLAHMEATGVR<br>LDVAYLRALSLEVAEEIARLEAEVFRLAGHPFNLNSRDQLERVLFDELGLPAIGKTEKT<br>GKRSTSAAVLEALREAHPIVEKILQYRELTKLKSTYIDPLPDLIHPRTGRLHTRFNQTA<br>TATGRLSSSDPNLQNIPVRTPLGQRIRRAFIAEEGWLLVALDYSQIELRVLAHLSGDEN<br>LIRVFQEGRDIHTETASWMFGVPREAVDPLMRRAAKTINFGVLYGMSAHRLSQELAIPY<br>EEAQAFIERYFQSFPKVRAWIEKTLEEGRRRGYVETLFGRRRYVPDLEARVKSVREAAE<br>RMAFNMPVQGTAADLMKLAMVKLFPRLEEMGARMLLQVHDELVLEAPKERAEAVARLAK<br>EVMEGVYPLAVPLEVEVGIGEDWLSAKE |
| 37 | amino acid sequence of Ape3192-Taq | HMPKKEKIKFFDLVAKKYYETDNYEVEIKETKRGKFRFA<br>KAKSPYTGKIFYRVLGKAGGGVTSGMLPLFEPKGRVLLVDGHHLAYRTFHALKGLTTSR<br>GEPVQAVYGFAKSLLKALKEDGDAVIVVFDAKAPSFRHEAYGGYKAGRAPTPEDFPRQL<br>ALIKELVDLLGLARLEVPGYEADDVLASLAKKAEKEGYEVRILTADKDLYQLLSDRIHV<br>LHPEGYLITPAWLWEKYGLRPDQWADYRALTGDESDNLPGVKGIGEKTARKLLEEWGSL<br>EALLKNLDRLKPAIREKILAHMDDLKLSWDLAKVRTDLPLEVDFAKRREPDRERLRAFL<br>ERLEFGSLLHEFGLLESPKALEEAPWPPPEGAFVGFVLSRKEPMWADLLALAAARGGRV<br>HRAPEPYKALRDLKEARGLLAKDLSVLALREGLGLPPGDDPMLLAYLLDPSNTTPEGVA<br>RRYGGEWTEEAGERAALSERLFANLWGRLEGEERLLWLYREVERPLSAVLAHMEATGVR<br>LDVAYLRALSLEVAEEIARLEAEVFRLAGHPFNLNSRDQLERVLFDELGLPAIGKTEKT<br>GKRSTSAAVLEALREAHPIVEKILQYRELTKLKSTYIDPLPDLIHPRTGRLHTRFNQTA<br>TATGRLSSSDPNLQNIPVRTPLGQRIRRAFIAEEGWLLVALDYSQIELRVLAHLSGDEN<br>LIRVFQEGRDIHTETASWMFGVPREAVDPLMRRAAKTINFGVLYGMSAHRLSQELAIPY<br>EEAQAFIERYFQSFPKVRAWIEKTLEEGRRRGYVETLFGRRRYVPDLEARVKSVREAAE<br>RMAFNMPVQGTAADLMKLAMVKLFPRLEEMGARMLLQVHDELVLEAPKERAEAVARLAK<br>EVMEGVYPLAVPLEVEVGIGEDWLSAKE |
| 38 | polynucleotide encoding 10His-Pae3192-Taq$_{ST}$ | ATGGGCCATCATCATCATCATCATCATCATCATCACAGCAGCGGCCATATCGAAGGTCG<br>TCATATGTCCAAGAAGCAGAAACTGAAGTTCTACGACATTAAGGCGAAGCAGGCGTTTG<br>AGACCGACCAGTACGAGGTTATTGAGAAGCAGACCGCCCGCGGTCCGATGATGTTCGCC<br>GTGGCCAAATCGCCGTACACCGGCATTAAAGTGTACCGCCTGTTAGGCAAGAAGAAAGG<br>CGGCGGTGTCACTAGTCCCAAGGCCCTGGAGGAGGCCCCCTGGCCCCCGCCGGAAGGGG<br>CCTTCGTGGGCTTTGTGCTTTCCCGCAAGGAGCCCATGTGGGCCGATCTTCTGGCCCTG<br>GCCGCCGCCAGGGGGGCCGGGTCCACCGGGCCCCGAGCCTTATAAAGCCCTCAGGGA<br>CCTGAAGGAGGCGCGGGGGCTTCTCGCCAAAGACCTGAGCGTTCTGGCCCTGAGGGAAG<br>GCCTTGGCCTCCCGCCCGGCGACGACCCCATGCTCCTCGCCTACCTCCTGGACCCTTCC<br>AACACCACCCCCGAGGGGGTGGCCCGGCGCTACGGCGGGGAGTGGACGGAGGAGGCGGG<br>GGAGCGGGCCGCCCTTTCCGAGAGGCTCTTCGCCAACCTGTGGGGGAGGCTTGAGGGGG<br>AGGAGAGGCTCCTTTGGCTTTACCGGGAGGTGGAGAGGCCCCTTTCCGCTGTCCTGGCC |

TABLE OF SEQUENCES

| SEQ ID NO: | Brief Description | Sequence |
|---|---|---|
| | | CACATGGAGGCCACGGGGGTGCGCCTGGACGTGGCCTATCTCAGGGCCTTGTCCCTGGA<br>GGTGGCCGAGGAGATCGCCCGCCTCGAGGCCGAGGTCTTCCGCCTGGCCGGCCACCCCT<br>TCAACCTCAACTCCCGGGACCAGCTGGAAAGGGTCCTCTTTGACGAGCTAGGGCTTCCC<br>GCCATCGGCAAGACGGAGAAGACCGGCAAGCGCTCCACCAGCGCCGCCGTCCTGGAGGC<br>CCTCCGCGAGGCCCACCCCATCGTGGAGAAGATCCTGCAGTACCGGGAGCTCACCAAGC<br>TGAAGAGCACCTACATTGACCCCTTGCCGGACCTCATCCACCCCAGGACGGGCCGCCTC<br>CACACCCGCTTCAACCAGACGGCCACGGCCACGGGCAGGCTAAGTAGCTCCGATCCCAA<br>CCTCCAGAACATCCCCGTCCGCACCCCGCTTGGGCAGAGGATCCGCCGGGCCTTCATCG<br>CCGAGGAGGGTGGCTATTGGTGGCCCTGGACTATAGCCAGATAGAGCTCAGGGTGCTG<br>GCCCACCTCTCCGGCGACGAGAACCTGATCCGGGTCTTCCAGGAGGGGCGGGACATCCA<br>CACGGAGACCGCCAGCTGGATGTTCGGCGTCCCCGGGAGGCCGTGGACCCCTGATGC<br>GCCGGGCGGCCAAGACCATCAACTTCGGGGTCCTCTACGGCATGTCGGCCCACCGCCTC<br>TCCCAGGAGCTAGCCATCCCTTACGAGGAGGCCCAGGCCTTCATTGAGCGCTACTTTCA<br>GAGCTTCCCCAAGGTGCGGGCCTGGATTGAGAAGACCCTGGAGGAGGGCAGGAGGCGGG<br>GGTACGTGGAGACCCTCTTCGGCCGCCGCCGCTACGTGCCAGACCTAGAGGCCCGGGTG<br>AAGAGCGTGCGGGAGGCGGCCGAGCGCATGGCCTTCAACATGCCCGTCCAGGGCACCGC<br>CGCCGACCTCATGAAGCTGGCTATGGTGAAGCTCTTCCCCAGGCTGGAGGAAATGGGGG<br>CCAGGATGCTCCTTCAGGTCCACGACGAGCTGGTCCTCGAGGCCCCAAAAGAGAGGGCG<br>GAGGCCGTGGCCCGGCTGGCCAAGGAGGTCATGGAGGGGTGTATCCCCTGGCCGTGCC<br>CCTGGAGGTGGAGGTGGGGATAGGGGAGGACTGGCTCTCCGCCAAGGAGTGA |
| 39 | amino acid sequence of 10His-Pae3192-Taq$_{ST}$ | MGHHHHHHHHHHSSGHIEGRHMSKKQKLKFYDIKAKQAFETDQYEVIEKQTARGPMMFA<br>VAKSPYTGIKVYRLLGKKKGGGVTSPKALEEAPWPPPEGAFVGFVLSRKEPMWADLLAL<br>AAARRGGRVHRAPEPYKALRDLKEARGLLAKDLSVLALREGLGLPPGDDPMLLAYLLDPS<br>NTTPEGVARRYGGEWTEEAGERAALSERLFANLWGRLEGEERLLWLYREVERPLSAVLA<br>HMEATGVRLDVAYLRALSLEVAEEIARLEAEVFRLAGHPFNLNSRDQLERVLFDELGLP<br>AIGKTEKTGKRSTSAAVLEALREAHPIVEKILQYRELTKLKSTYIDPLPDLIHPRTGRL<br>HTRFNQTATATGRLSSSDPNLQNIPVRTPLGQRIRRAFIAEEGWLLVALDYSQIELRVL<br>AHLSGDENLIRVFQEGRDIHTETASWMFGVPREAVDPLMRRAAKTINFGVLYGMSAHRL<br>SQELAIPYEEAQAFIERYFQSFPKVRAWIEKTLEEGRRRGYVETLFGRRRYVPDLEARV<br>KSVREAAERMAFNMPVQGTAADLMKLAMVKLFPRLEEMGARMLLQVHDELVLEAPKERA<br>EAVARLAKEVMEGVYPLAVPLEVEVGIGEDWLSAKE |
| 40 | amino acid sequence of Pae3192-Taq$_{ST}$ | HMSKKQKLKFYDIKAKQAFETDQYEVIEKQTARGPMMFA<br>VAKSPYTGIKVYRLLGKKKGGGVTSPKALEEAPWPPPEGAFVGFVLSRKEPMWADLLAL<br>AAARRGGRVHRAPEPYKALRDLKEARGLLAKDLSVLALREGLGLPPGDDPMLLAYLLDPS<br>NTTPEGVARRYGGEWTEEAGERAALSERLFANLWGRLEGEERLLWLYREVERPLSAVLA<br>HMEATGVRLDVAYLRALSLEVAEEIARLEAEVFRLAGHPFNLNSRDQLERVLFDELGLP<br>AIGKTEKTGKRSTSAAVLEALREAHPIVEKILQYRELTKLKSTYIDPLPDLIHPRTGRL<br>HTRFNQTATATGRLSSSDPNLQNIPVRTPLGQRIRRAFIAEEGWLLVALDYSQIELRVL<br>AHLSGDENLIRVFQEGRDIHTETASWMFGVPREAVDPLMRRAAKTINFGVLYGMSAHRL<br>SQELAIPYEEAQAFIERYFQSFPKVRAWIEKTLEEGRRRGYVETLFGRRRYVPDLEARV<br>KSVREAAERMAFNMPVQGTAADLMKLAMVKLFPRLEEMGARMLLQVHDELVLEAPKERA<br>EAVARLAKEVMEGVYPLAVPLEVEVGIGEDWLSAKE |
| 41 | polynucleotide encoding 10His-Ape3192-Taq$_{ST}$ | ATGGGCCATCATCATCATCATCATCATCATCATCATCACAGCAGCGGCCATATCGAAGGTCG<br>TCATATGCCGAAGAAGGAGAAGATTAAGTTCTTCGACCTGGTCGCCAAGAAGTACTACG<br>AGACTGACAACTACGAAGTCGAGATTAAGGAGACTAAGCGCGGCAAGTTTCGCTTCGCC<br>AAAGCCAAGAGCCCGTACACCGGCAAGATCTTCTATCGCGTGCTGGGCAAAGCCGGCGG<br>CGGTGTCACTAGTCCCAAGGCCCTGGAGGAGGCCCCCTGGCCCCCGCCGGAAGGGGCCT<br>TCGTGGGCTTTGTGCTTTCCCGCAAGGAGCCCATGTGGGCCGATCTTCTGGCCCTGGCC<br>GCCGCCAGGGGGGCCGGGTCCACCGGGCCCCCGAGCCTTATAAAGCCCTCAGGGACCT<br>GAAGGAGGCGCGGGGGCTTCTCGCCAAAGACCTGAGCGTTCTGGCCCTGAGGGAAGGCC<br>TTGGCCTCCCCGCCGGCGACGACCCCATGCTTCCTCGCCTACCTCCTGGACCCTTCCAC<br>ACCACCCCCGAGGGGGTGGCCCGGCGCTACGGCGGGGAGTGGACGGAGGAGGCGGGGGA<br>GCGGGCCGCCCTTTCCGAGAGGCTCTTCGCCAACCTGTGGGGGAGGCTTGAGGGGAGG<br>AGAGGCTCCTTTGGCTTTACCGGGAGGTGGAGAGGCCCCTTTCCGCTGTCCTGGCCCAC<br>ATGGAGGCCACGGGGGTGCGCCTGGACGTGGCCTATCTCAGGGCCTTGTCCCTGGAGGT<br>GGCCGAGGAGATCGCCCGCCTCGAGGCCGAGGTCTTCCGCCTGGCCGGCCACCCCTTCA<br>ACCTCAACTCCCGGGACCAGCTGGAAAGGGTCCTCTTTGACGAGCTAGGGCTTCCCGCC<br>ATCGGCAAGACGGAGAAGACCGGCAAGCGCTCCACCAGCGCCGCCGTCCTGGAGGCCCT<br>CCGCGAGGCCCACCCCATCGTGGAGAAGATCCTGCAGTACCGGGAGCTCACCAAGCTGA<br>AGAGCACCTACATTGACCCCTTGCCGGACCTCATCCACCCCAGGACGGGCCGCCTCCAC<br>ACCCGCTTCAACCAGACGGCCACGGCCACGGGCAGGCTAAGTAGCTCCGATCCCAACCT<br>CCAGAACATCCCCGTCCGCACCCCGCTTGGGCAGAGGATCCGCCGGGCCTTCATCGCCG<br>AGGAGGGTGGCTATTGGTGGCCCTGGACTATAGCCAGATAGAGCTCAGGGTGCTGGCC<br>CACCTCTCCGGCGACGAGAACCTGATCCGGGTCTTCCAGGAGGGGCGGGACATCCACAC<br>GGAGACCGCCAGCTGGATGTTCGGCGTCCCCGGGAGGCCGTGGACCCCTGATGCGCCG<br>GGCGGCCAAGACCATCAACTTCGGGGTCCTCTACGGCATGTCGGCCCACCGCCTCTCC<br>CAGGAGCTAGCCATCCCTTACGAGGAGGCCCAGGCCTTCATTGAGCGCTACTTTCAGAG<br>CTTCCCCAAGGTGCGGGCCTGGATTGAGAAGACCCTGGAGGAGGGCAGGAGGCGGGGGT<br>ACGTGGAGACCCTCTTCGGCCGCCGCCGCTACGTGCCAGACCTAGAGGCCCGGGTGAAG<br>AGCGTGCGGGAGGCGGCCGAGCGCATGGCCTTCAACATGCCCGTCCAGGGCACCGCCGC<br>CGACCTCATGAAGCTGGCTATGGTGAAGCTCTTCCCCAGGCTGGAGGAAATGGGGGCCA |

TABLE OF SEQUENCES

| SEQ ID NO: | Brief Description | Sequence |
|---|---|---|
| | | GGATGCTCCTTCAGGTCCACGACGAGCTGGTCCTCGAGGCCCCAAAAGAGAGGGCGGAG GCCGTGGCCCGGCTGGCCAAGGAGGTCATGGAGGGGGTGTATCCCCTGGCCGTGCCCCT GGAGGTGGAGGTGGGGATAGGGGAGGACTGGCTCTCCGCCAAGGAGTGA |
| 42 | amino acid sequence of 10His-Ape3192-Taq$_{ST}$ | MGHHHHHHHHHSSGHIEGRHMPKKEKIKFFDLVAKKYYETDNYEVEIKETKRGKFRFA KAKSPYTGKIFYRVLGKAGGGVTSPKALEEAPWPPPEGAFVGFVLSRKEPMWADLLALA AARGGRVHRAPEPYKALRDLKEARGLLAKDLSVLALREGLGLPPGDDPMLLAYLLDPSN TTPEGVARRYGGEWTEEAGERAALSERLFANLWGRLEGEERLLWLYREVERPLSAVLAH MEATGVRLDVAYLRALSLEVAEEIARLEAEVFRLAGHPFNLNSRDQLERVLFDELGLPA IGKTEKTGKRSTSAAVLEALREAHPIVEKILQYRELTKLKSTYIDPLPDLIHPRTGRLH TRFNQTATATGRLSSSDPNLQNIPVRTPLGQRIRRAFIAEEGWLLVALDYSQIELRVLA HLSGDENLIRVFQEGRDIHTETASWMFGVPREAVDPLMRRAAKTINFGVLYGMSAHRLS QELAIPYEEAQAFIERYFQSFPKVRAWIEKTLEEGRRRGYVETLFGRRRYVPDLEARVK SVREAAERMAFNMPVQGTAADLMKLAMVKLFPRLEEMGARMLLQVHDELVLEAPKERAE AVARLAKEVMEGVYPLAVPLEVEVGIGEDWLSAKE |
| 43 | amino acid sequence of Ape3192-Taq$_{ST}$ | HMPKKEKIKFFDLVAKKYYETDNYEVEIKETKRGKFRFA KAKSPYTGKIFYRVLGKAGGGVTSPKALEEAPWPPPEGAFVGFVLSRKEPMWADLLALA AARGGRVHRAPEPYKALRDLKEARGLLAKDLSVLALREGLGLPPGDDPMLLAYLLDPSN TTPEGVARRYGGEWTEEAGERAALSERLFANLWGRLEGEERLLWLYREVERPLSAVLAH MEATGVRLDVAYLRALSLEVAEEIARLEAEVFRLAGHPFNLNSRDQLERVLFDELGLPA IGKTEKTGKRSTSAAVLEALREAHPIVEKILQYRELTKLKSTYIDPLPDLIHPRTGRLH TRFNQTATATGRLSSSDPNLQNIPVRTPLGQRIRRAFIAEEGWLLVALDYSQIELRVLA HLSGDENLIRVFQEGRDIHTETASWMFGVPREAVDPLMRRAAKTINFGVLYGMSAHRLS QELAIPYEEAQAFIERYFQSFPKVRAWIEKTLEEGRRRGYVETLFGRRRYVPDLEARVK SVREAAERMAFNMPVQGTAADLMKLAMVKLFPRLEEMGARMLLQVHDELVLEAPKERAE AVARLAKEVMEGVYPLAVPLEVEVGIGEDWLSAKE |
| 44 | polynucleotide (1 of 2) encoding Sso7d (SEQ ID NO: 20) | atggcaac agtaaagttc aagtacaaag gagaagagaag caagtagata taagtaagat aaagaaggta tggagagtag gcaaaatgat aagcttcacc tatgatgagg gtggaggaaa gactggtaga ggagctgtaa gcgagaaaga cgctccaaaa gaactactac aaatgttaga gaagcaaaag aagtaa |
| 45 | polynucleotide (2 of 2) encoding Sso7d (SEQ ID NO: 20) | atggcaac agtaaagttc aagtataaag gagaagaaaa caagtagaca taagtaagat aaagaaggta tggagagtcg gaaagatgat aagctttacc tatgatgagg gtggaggaaa gactggtaga ggagcagtaa gcgagaaaga tgctccaaaa gagctattac aaatgttaga gaaacaaaag aagtaa |
| 46 | polynucleotide encoding Sso7d variant (SEQ ID NO: 21) | ttggagatat caatggcaac agtaaagttc aagtacaagg gagaagagaag gaagtagata taagtaagat aaagaaggta tggagagtag gcaaaatgat aagtttcacc tatgatgagg gtggaggaaa gactggtaga ggagctgtaa gcgagaaaga cgctccaaaa gaactactac aaatgttaga gaaagcaaag aaataa |
| 47 | forward primer | AGCCAAGGCCAATATCTAAGTAAC |
| 48 | reverse primer | CGAAGCATTGGCCGTAAGTG |
| 49 | amino acid sequence of 10His-Pfu-Sso7d | MGHHHHHHHHHSSGHIEGRHMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKGPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE AVRIVKEVIQKLANYEIPPEKLAIYEQITRPLHEYKAIGPHVAVAKKLAAKGVKIKPGMV IGYIVLRGDGPISNRAILAEEYDPKKHKYDAEYYIENQVLPAVLRILEGFGYRKEDLRYQ KTRQVGLTSWLNIKKSGTGGGGATVKFKYKGEEKEVDISKIKKVWRVGKMISFTYDEGGG KTGRGAVSEKDAPKELLQMLEKQKK |
| 50 | amino acid sequence of Pfu-Sso7d | HMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPFAKRYLIDKGLIPMEGEEELKILAFDIETLYHEGEEFGKGPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNLEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE |

TABLE OF SEQUENCES

| SEQ ID NO: | Brief Description | Sequence |
|---|---|---|
|  |  | AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKSGTGGGGATVKFKYKGEEKEVDISKIKKVWRVGKMISFTYDEGGG<br>KTGRGAVSEKDAPKELLQMLEKQKK |
| 51 | polynucleotide encoding 10His-Pfu-Sso7d | CCATGGGCCATCATCATCATCATCATCATCATCATCACAGCAGCGGCCATATCGAAGGTCG<br>TCATATGATTTTAGATGTGGATTACATAACTGAAGAAGGAAAACCTGTTATTAGGCTATTC<br>AAAAAAGAGAACGGAAAATTTAAGATAGAGCATGATAGAACTTTTAGACCATACATTTACG<br>CTCTTCTCAGGGATGATTCAAAGATTGAAGAAGTTAAGAAAATAACGGGGGAAAGGCATGG<br>AAAGATTGTGAGAATTGTTGATGTAGAGAAGGTTGAGAAAAGTTTCTCGGCAAGCCTATT<br>ACCGTGTGGAAACTTTATTTGGAACATCCCCAAGATGTTCCCACTATTAGAGAAAAGTTA<br>GAGAACATCCAGCAGTTGTGGACATCTTCGAATACGATATTCCATTTGCAAAGAGATACCT<br>CATCGACAAAGGCCTAATACCAATGGAGGGGGAAGAAGAGCTAAAGATTCTTGCCTTCGAT<br>ATAGAAACCCTCTATCACGAAGGAGAAGAGTTTGGAAAAGGCCCAATTATAATGATTAGTT<br>ATGCAGATGAAAATGAAGCAAAGGTGATTACTTGGAAAAACATAGATCTTCCATACGTTGA<br>GGTTGTATCAAGCGAGAGAGATGATAAAGAGATTTCTCAGGATTATCAGGGAGAAGGAT<br>CCTGACATTATAGTTACTTATAATGGAGACTCATTCGACTTCCCATATTTAGCGAAAAGGG<br>CAGAAAAACTTGGGATTAAATTAACCATTGGAAGAGATGGAAGCGAGCCCAAGATGCAGAG<br>AATAGGCGATATGACGGCTGTAGAAGTCAAGGGAAGAATACATTTCGACTTGTATCATGTA<br>ATAACAAGGACAATAAATCTCCCAACATACACACTAGAGGCTGTATATGAAGCAATTTTTG<br>GAAAGCCAAAGGAGAAGGTATACGCCGACGAGATAGCAAAAGCCTGGGAAAGTGGAGAGAA<br>CCTTGAGAGAGTTGCCAAATACTCGATGGAAGATGCAAAGGCAACTTATGAACTCGGGAAA<br>GAATTCCTTCCAATGGAAATTCAGCTTTCAAGATTAGTTGGACAACCTTTATGGGATGTTT<br>CAAGGTCAAGCACAGGGAACCTTGTAGAGTGGTTCTTACTTAGGAAAGCCTACGAAAGAAA<br>CGAAGTAGCTCCAAACAAGCCAAGTGAAGAGGAGTATCAAAGAAGGCTCAGGGAGAGCTAC<br>ACAGGTGGATTCGTTAAAGAGCCAGAAAAGGGGTTGTGGGAAAACATAGTATACCTAGATT<br>TTAGAGCCCTATATCCCTCGATTATAATTACCCACAATGTTTCTCCCGATACTCTAAATCT<br>TGAGGGATGCAAGAACTATGATATCGCTCCTCAAGTAGGCCACAAGTTCTGCAAGGACATC<br>CCTGGTTTTATACCAAGTCTCTTGGGACATTTGTTAGAGGAAAGACAAAAGATTAAGACAA<br>AAATGAAGGAAACTCAAGATCCTATAGAAAAAATACTCCTTGACTATAGACAAAAAGCGAT<br>AAAACTCTTAGCAAATTCTTTCTACGGATATTATGGCTATGCAAAAGCAAGATGGTACTGT<br>AAGGAGTGTGCTGAGAGCGTTACTGCCTGGGGAAGAAAGTACATCGAGTTAGTATGGAAGG<br>AGCTCGAAGAAAAGTTTGGATTTAAAGTCCTCTACATTGACACTGATGGTCTCTATGCAAC<br>TATCCCAGGAGGAGAAAGTGAGGAAATAAAGAAAAAGGCTCTAGAATTTGTAAAATACATA<br>AATTCAAAGCTCCCTGGACTGCTAGAGCTTGAATATGAAGGGTTTTATAAGAGGGGATTCT<br>TCGTTACGAAGAAGAGGTATGCAGTAATAGATGAAGAAGGAAAAGTCATTACTCGTGGTTT<br>AGAGATAGTTAGGAGAGATTGGAGTGAAATTGCAAAAGAAACTCAAGCTAGAGTTTTGGAG<br>ACAATACTAAAACACGGAGATGTTGAAgAAGCTGTGAGAATAGTAAAAGAAGTAATACAAA<br>AGCTTGCCAATTATGAAATTCCACCAGAGAAGCTCGCAATATATGAGCAGATAACAAGACC<br>ATTACATGAGTATAAGGCGATAGGTCCTCACGTAGCTGTTGCAAAGAAACTAGCTGCTAAA<br>GGAGTTAAAATAAAGCCAGGAATGGTAATTGGATACATAGTACTTAGAGGCGATGGTCCAA<br>TTTCAATAGGGCAATTCTAGCTGAGGAATACGATCCCAAAAAGCACAAGTATGACGCAGA<br>ATATTACATTGAGAACCAGGTTCTTCCAGCGGTACTTAGGATATTGGAGGGATTTGGATAC<br>AGAAAGGAAGACCTCAGATACCAAAAGACAAGACAAGTCGGCCTAACTTCCTGGCTTAACA<br>TTAAAAAATCCGGTACCGGCGGTGGCGGTGCAACCGTAAAGTTCAAGTACAAAGGCGAAGA<br>AAAAGAGGTAGACATCTCCAAGATCAAGAAAGTATGGCGTGTGGGCAAGATGATCTCCTTC<br>ACCTACGACGAGGGCGGTGGCAAGACCGGCCGCGGTGCGGTAAGCGAAAAGGACGCGCCGA<br>AGGAGCTGCTGCAGATGCTGGAGAAGCAGAAAAAGTAACTCGAG |
| 52 | amino acid sequence of MMLV reverse transcriptase | MLNIEDEHRLHETSKEPDVSLGSTWLSDFPQAWAETGGMGLAVRQAPLIIPLKATSTPVSI<br>KQYPMSQEARLGIKPHIQRLLDQGILVPCQSPWNTPLLPVKKPGTNDYRFVQDLREVNKRV<br>EDIHPTVPNPYNLLSGLPPSHQWYTVLDLKDAFFCLRLHPTSQPLFAFEWRDPEMGISGQL<br>TWTRLPQGFKNSPTLFDEALHRDLADFRIQHPDLILLQYVDDLLLAATSELDCQQGTRALL<br>QTLGNLGYRASAKKAQICQKQVKYLGYLLKEGQRWLTEARKETVMGQPTPKTPRQLREFLG<br>TAGFCRLWIPGFAEMAAPLYPLTKTGTLFNWGPDQQKAYQEIKQALLTAPALGLPDLTKPF<br>ELFVDEKQGYAKGVLTQKLGPWRRPVAYLSKKLDPVAAGWPPCLRMVAAIAVLTKDAGKLT<br>MGQPLVILAPHAVEALVKQPPDRWLSNARMTHYQALLLDTDRVQFGPVVALNPATLLPLPE<br>EGLQHDCLDILAEAHGTRSDLTDQPLPDADHTWYTDGSSFLQEGQRKAGAAVTTETEVIWA<br>RALPAGTSAQRAELIALTQALKMAEGEKLNVYTDSRYAFATAHIHGEIYRRRGLLTSEGKE<br>IMIMEILALLKALFLPKRLSIIHCPGHQKGNSAEARGNRMADQAAREVATRETPGTSTLLI |
| 53 | polynucleotide encoding MMLV reverse transcriptase | ATGGAGCATCGGCTACATGAGACCTCAAAAGAGCCAGATGTTTCTCTAGGGTCCACATGGC<br>TGTCTGATTTTCCTCAGGCCTGGGCGGAAACCGGGGGCATGGGACTGGCAGTTCGCCAAGC<br>TCCTCTGATCATACCTCTGAAAGCAACCTCTACCCCCGTGTCCATAAAACAATACCCCATG<br>TCACAAGAGCCAGACTGGGGATCAAGCCCCACATACAGAGACTGTTGGACAGGGAATAC<br>TGGTACCCTGCCAGTCCCCCTGGAACACGCCCCTGCTACCCGTTAAGAAACCAGGGACTAA<br>TGATTATAGGCCTGTCCAGGATCTGAGAGAAGTCAACAAGCGGGTGGAAGACATCCACCCC<br>ACCGTGCCCAACCCTTACAACCTCTTGAGCGGGCTCCCACCGTCCCACCAGTGGTACACTG<br>TGCTTGATTTAAAGGATGCCTTTTTCTGCCTGAGACTCCACCCCACCAGTCAGCCTCTCTT<br>CGCCTTTGAGTGGAGAGATCCAGAGATGGGAATCTCAGGACAATTGACCTGGACCAGACTC<br>CCACAGGGTTTCAAAAACAGTCCCACCCTGTTTGATGAGGCACTGCACAGAGACCTAGCAG |

TABLE OF SEQUENCES

| SEQ ID NO: | Brief Description | Sequence |
|---|---|---|
| | | ACTTCCGGATCCAGCACCCAGACTTGATCCTGCTACAGTACGTGGATGACTTACTGCTGGC |
| | | CGCCACTTCTGAGCTAGACTGCCAACAAGGTACTCGGGCCCTGTTACAAACCCTAGGGAAC |
| | | CTCGGGTATCGGGCCTCGGCCAAGAAAGCCCAAATTTGCCAGAAACAGGTCAAGTATCTGG |
| | | GGTATCTTCTAAAAGAGGGTCAGAGATGGCTGACTGAGGCCAGAAAAGAGACTGTGATGGG |
| | | GCAGCCTACTCCGAAGACCCCTCGACAACTAAGGGAGTTCCTAGGGACGGCAGGCTTCTGT |
| | | CGCCTCTGGATCCCTGGGTTTGCAGAAATGGCAGCCCCCTTGTACCCTCTCACCAAAACGG |
| | | GGACTCTGTTTAATTGGGGCCCAGACCAACAAAAGGCCTATCAAGAAATCAAGCAAGCTCT |
| | | TCTAACTGCCCCAGCCCTGGGGTTGCCAGATTTGACTAAGCCCTTGAACTCTTTGTCGAC |
| | | GAGAAGCAGGGCTACGCCAAAGGCGTCCTAACGCAAAAGCTGGGACCTTGGCGTCGGCCGG |
| | | TGGCCTACCTGTCTAAAAAGCTAGACCCAGTGGCAGCTGGCTGGCCCCCCTGCCTACGGAT |
| | | GGTGGCAGCCATTGCAGTTCTGACAAAAGATGCTGGCAAGCTCACTATGGGACAGCCGTTG |
| | | GTCATTCTGGCCCCCATGCCGTAGAGGCACTAGTTAAGCAACCCCCTGATCGCTGGCTCT |
| | | CCAATGCCCGGATGACCCATTACCAAGCCCTGCTCCTGGACACGGACCGGGTCCAGTTCGG |
| | | GCCAGTAGTGGCCCTAAATCCAGCTACGCTGCTCCCTCTGCCTGAGGAGGGGCTGCAACAT |
| | | GACTGCCTTGACATCTTGGCTGAAGCCCACGGAACTAGATCAGATCTTACGGACCAGCCCC |
| | | TCCCAGACGCCGACCACACCTGGTACACGGATGGGAGCAGCTTCCTGCAAGAAGGGCAGCG |
| | | TAAGGCCGGAGCAGCGGTGACCACTGAGACTGAGGTAATCTGGGCCAGGGCATTGCCAGCC |

---

The invention claimed is:

1. A recombinant fusion protein comprising:
   (a) a first polypeptide having nucleic acid binding activity and comprising an amino acid sequence having at least 90% identity to the amino acid sequence set forth in SEQ ID NO: 1, 4, or 6; and
   (b) a second polypeptide having DNA polymerase activity and/or reverse transcriptase activity.

2. The fusion protein of claim 1, wherein said second polypeptide further comprises 5' to 3' exonuclease activity.

3. The fusion protein of claim 1, wherein said fusion protein exhibits an amplification efficiency that is from 0.8 to 1.0.

4. The fusion protein of claim 1, wherein said first polypeptide and said second polypeptide are joined covalently.

5. The fusion protein of claim 1, wherein said second polypeptide is thermostable.

6. The fusion protein of claim 1, wherein said first polypeptide comprises the amino acid sequence set forth in SEQ ID NOs:1, 4, or 6.

7. The fusion protein of claim 1, wherein said second polypeptide is an archaeal family B polymerase or a bacterial family A polymerase.

8. The fusion protein of claim 1, wherein said second polypeptide is a polymerase selected from the group consisting of Taq polymerase, Pfu polymerase, Tgo polymerase, Vent polymerase, Deep Vent polymerase, KOD polymerase, and 9° Nm polymerase.

9. The fusion protein of claim 8, wherein said polymerase is Pfu polymerase.

10. The fusion protein of claim 9, wherein said Pfu polymerase is Pfu polymerase with a L→Y point mutation or a L→F point mutation at the position corresponding to the amino acid at position 409 of SEQ ID NO:30.

11. The fusion protein of claim 9, wherein said Pfu polymerase is Pfu polymerase with a D→A point mutation at the position corresponding to the amino acid at position 141 of SEQ ID NO:30 and an E→A point mutation at the position corresponding to the amino acid at position 143 of SEQ ID NO:30.

12. The fusion protein of claim 9, wherein said Pfu polymerase is Pfu polymerase with an E→D point mutation at the position corresponding to the amino acid at position 143 of SEQ ID NO:30.

13. The fusion protein of claim 9, wherein said Pfu polymerase is Pfu polymerase with a Y→F point mutation at the position corresponding to the amino acid at position 385 of SEQ ID NO:30.

14. The fusion protein of claim 8, wherein said polymerase is Taq polymerase.

15. A composition comprising:
(a) the recombinant fusion protein of claim 1; and
(b) a buffer.

16. The composition of claim 15, further comprising an antibody that reversibly blocks said nucleic acid binding activity, DNA polymerase activity and/or reverse transcriptase activity at a first temperature.

17. The composition of claim 15, further comprising an oligonucleotide that reversibly blocks said nucleic acid binding activity, DNA polymerase activity and/or reverse transcriptase activity at a first temperature.

18. The composition of claim 16 or 17, wherein said antibody or said oligonucleotide specifically binds said first polypeptide and/or said second polypeptide.

\* \* \* \* \*

SEQUENCE LISTING

<160> NUMBER OF SEQ ID NOS: 69

<210> SEQ ID NO 1
<211> LENGTH: 57
<212> TYPE: PRT
<213> ORGANISM: Pyrobaculum aerophilum

<400> SEQUENCE: 1

Met Ser Lys Lys Gln Lys Leu Lys Phe Tyr Asp Ile Lys Ala Lys Gln
 1               5                  10                  15

Ala Phe Glu Thr Asp Gln Tyr Glu Val Ile Glu Lys Gln Thr Ala Arg
            20                  25                  30

Gly Pro Met Met Phe Ala Val Ala Lys Ser Pro Tyr Thr Gly Ile Lys
        35                  40                  45

Val Tyr Arg Leu Leu Gly Lys Lys Lys
    50                  55

<210> SEQ ID NO 2
<211> LENGTH: 174
<212> TYPE: DNA
<213> ORGANISM: Pyrobaculum aerophilum

<400> SEQUENCE: 2
atgtccaaga agcagaaact aaagttctac gacataaagg cgaagcaggc gtttgagact      60
gaccagtacg aggttattga gaagcagact gcccgcggtc cgatgatgtt cgccgtggcc     120
aaatcgccgt acaccggcat aaaagtatac agactgttag gcaagaagaa ataa           174

<210> SEQ ID NO 3
<211> LENGTH: 174
<212> TYPE: DNA
<213> ORGANISM: Pyrobaculum aerophilum

<400> SEQUENCE: 3
atgtccaaga agcagaaact aaagttctac gacataaagg cgaagcaggc gtttgagact      60
gaccagtacg aggttattga gaagcagact gcccgcggtc cgatgatgtt cgccgtggcc     120
aaatcgccgt acaccggcat aaaagtatac agactattag gcaagaagaa ataa           174

<210> SEQ ID NO 4
<211> LENGTH: 56
<212> TYPE: PRT
<213> ORGANISM: Pyrobaculum aerophilum

<400> SEQUENCE: 4

Met Ala Lys Gln Lys Leu Lys Phe Tyr Asp Ile Lys Ala Lys Gln Ser
1               5                   10                  15

Phe Glu Thr Asp Lys Tyr Glu Val Ile Glu Lys Glu Thr Ala Arg Gly
            20                  25                  30

Pro Met Leu Phe Ala Val Ala Thr Ser Pro Tyr Thr Gly Ile Lys Val
        35                  40                  45

Tyr Arg Leu Leu Gly Lys Lys Lys
        50                  55

<210> SEQ ID NO 5
<211> LENGTH: 171
<212> TYPE: DNA
<213> ORGANISM: Pyrobaculum aerophilum

<400> SEQUENCE: 5
atggccaaac aaaaactaaa gttctacgac ataaaagcga acagtccttc gaaacggac      60 aaatacgagg tcattgagaa agagacggcc cgcgggccga tgttatttgc agtggcaacc    120
tcgccgtaca ctggcataaa ggtgtacaga ctgttaggca agaagaaata a             171

<210> SEQ ID NO 6
<211> LENGTH: 56
<212> TYPE: PRT
<213> ORGANISM: Aeropyrum pernix

<400> SEQUENCE: 6

Met Pro Lys Lys Glu Lys Ile Lys Phe Phe Asp Leu Val Ala Lys Lys
1               5                   10                  15

Tyr Tyr Glu Thr Asp Asn Tyr Glu Val Glu Ile Lys Glu Thr Lys Arg
            20                  25                  30

Gly Lys Phe Arg Phe Ala Lys Ala Lys Ser Pro Tyr Thr Gly Lys Ile
        35                  40                  45

Phe Tyr Arg Val Leu Gly Lys Ala
        50                  55

<210> SEQ ID NO 7
<211> LENGTH: 171
<212> TYPE: DNA
<213> ORGANISM: Aeropyrum pernix

<400> SEQUENCE: 7
atgcccaaga aggagaagat aaagttcttc gacctagtcg ccaagaagta ctacgagact      60
gacaactacg aagtcgagat aaaggagact aagaggggca gtttaggtt cgccaaagcc     120 aagagcccgt acaccggcaa gatcttctat agagtgctag gcaaagccta g             171

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atgtccaaga agcagaaact gaagttctac gacattaagg cgaagcaggc gtttgag        57

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
accgaccagt acgaggttat tgagaagcag accgcccgcg gtccgatgat gttcgcc        57

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtggccaaat cgccgtacac cggcattaaa gtgtaccgcc tgttaggcaa gaagaaataa    60

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtactggtcg gtctcaaacg cctg                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgatttggcc acggcgaaca tcat                                            24

<210> SEQ ID NO 13
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgtccaaga agcagaaact gaagttctac gacattaagg cgaagcaggc gtttgagacc    60
gaccagtacg aggttattga gaagcagacc gcccgcggtc cgatgatgtt cgccgtggcc   120
aaatcgccgt acaccggcat taaagtgtac cgcctgttag gcaagaagaa ataa         174

<210> SEQ ID NO 14
<211> LENGTH: 57
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 14
atgccgaaga aggagaagat taagttcttc gacctggtcg ccaagaagta ctacgag          57

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgacaact acgaagtcga gattaaggag actaagcgcg gcaagtttcg cttcgcc          57

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaagccaaga gcccgtacac cggcaagatc ttctatcgcg tgctgggcaa agcctag          57

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtagttgtca gtctcgtagt actt                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gctcttggct ttggcgaagc gaaa                                              24

<210> SEQ ID NO 19
<211> LENGTH: 171
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atgccgaaga aggagaagat taagttcttc gacctggtcg ccaagaagta ctacgagact       60
gacaactacg aagtcgagat taaggagact aagcgcggca gtttcgctt cgccaaagcc       120 aagagcccgt acaccggcaa gatcttctat cgcgtgctgg gcaaagccta g               171

<210> SEQ ID NO 20
<211> LENGTH: 64
```

```
<212> TYPE: PRT
<213> ORGANISM: Sulfolobus solfataricus

<400> SEQUENCE: 20

Met Ala Thr Val Lys Phe Lys Tyr Lys Gly Glu Glu Lys Gln Val Asp
 1               5                  10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 21
<211> LENGTH: 68
<212> TYPE: PRT
<213> ORGANISM: Sulfolobus solfataricus

<400> SEQUENCE: 21

Met Glu Ile Ser Met Ala Thr Val Lys Phe Lys Tyr Lys Gly Glu Glu
 1               5                  10                  15

Lys Gln Val Asp Ile Ser Lys Ile Lys Lys Val Trp Arg Val Gly Lys
            20                  25                  30

Met Ile Ser Phe Thr Tyr Asp Glu Gly Gly Gly Lys Thr Gly Arg Gly
        35                  40                  45

Ala Val Ser Glu Lys Asp Ala Pro Lys Glu Leu Leu Gln Met Leu Glu
    50                  55                  60

Lys Gln Lys Lys
 65

<210> SEQ ID NO 22
<211> LENGTH: 2588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ccatgggcca tcatcatcat catcatcatc atcatcacag cagcggccat atcgaaggtc    60
gtcatatgat tttagatgtg gattacataa ctgaagaagg aaaacctgtt attaggctat   120
tcaaaaaaga gaacggaaaa tttaagatag agcatgatag aacttttaga ccatacattt   180
acgctcttct cagggatgat tcaaagattg aagaagttaa gaaataacg ggggaaaggc    240 atggaaagat tgtgagaatt gttgatgtag agaaggttga gaaaaagttt ctcggcaagc   300
ctattaccgt gtgaaactt tatttggaac atccccaaga tgttcccact attagagaaa    360
aagttagaga acatccagca gttgtggaca tcttcgaata cgatattcca tttgcaaaga   420
gatacctcat cgacaaaggc ctaataccaa tggaggggga agaagagcta agattcttg    480 ccttcgatat agaaaccctc tatcacgaag gagaagagtt tggaaaaggc ccaattataa   540
tgattagtta tgcagatgaa aatgaagcaa aggtgattac ttggaaaaac atagatcttc   600
catacgttga ggttgtatca agcgagagag agatgataaa gagatttctc aggattatca   660
gggagaagga tcctgacatt atagttactt ataatggaga ctcattcgac ttcccatatt   720
tagcgaaaag ggcagaaaaa cttgggatta aattaaccat ggaagagat ggaagcgagc    780 ccaagatgca gagaataggc gatatgacgg ctgtagaagt caagggaaga atacatttcg   840
```

```
acttgtatca tgtaataaca aggacaataa atctcccaac atacacacta gaggctgtat    900
atgaagcaat ttttggaaag ccaaaggaga aggtatacgc cgacgagata gcaaaagcct    960
gggaaagtgg agagaaccct gagagagttg ccaaatactc gatggaagat gcaaaggcaa   1020
cttatgaact cgggaaagaa ttccttccaa tggaaattca gctttcaaga ttagttggac   1080
aacctttatg ggatgtttca aggtcaagca cagggaacct tgtagagtgg ttcttactta   1140
ggaaagccta cgaaagaaac gaagtagctc caaacaagcc aagtgaagag gagtatcaaa   1200
gaaggctcag ggagagctac acaggtggat tcgttaaaga gccagaaaag gggttgtggg   1260
aaaacatagt ataccctagat tttagagccc tatatccctc gattataatt acccacaatg   1320
tttctcccga tactctaaat cttgagggat gcaagaacta tgatatcgct cctcaagtag   1380
gccacaagtt ctgcaaggac atccctggtt ttataccaag tctcttggga catttgttag   1440
aggaaagaca aagattaag acaaaaatga aggaaactca agatcctata gaaaaaatac    1500
tccttgacta tagacaaaaa gcgataaaac tcttagcaaa ttctttctac ggatattatg   1560
gctatgcaaa agcaagatgg tactgtaagg agtgtgctga gagcgttact gcctgggaa    1620
gaaagtacat cgagttagta tggaaggagc tcgaagaaaa gtttggattt aaagtcctct   1680
acattgacac tgatggtctc tatgcaacta tcccaggagg agaaagtgag gaaataaaga   1740
aaaaggctct agaatttgta aaatacataa attcaaagct ccctggactg ctagagcttg   1800
aatatgaagg ttttataag aggggattct tcgttacgaa gaagaggtat gcagtaatag   1860
atgaagaagg aaaagtcatt actcgtggtt tagagatagt taggagagat tggagtgaaa   1920
ttgcaaaaga aactcaagct agagttttgg agacaatact aaaacacgga gatgttgaag   1980
aagctgtgag aatagtaaaa gaagtaatac aaaagcttgc caattatgaa attccaccag   2040
agaagctcgc aatatatgag cagataacaa gaccattaca tgagtataag gcgataggtc   2100
ctcacgtagc tgttgcaaag aaactagctg ctaaaggagt taaaataaag ccaggaatgg   2160
taattggata catagtactt agaggcgatg gtccaattag caatagggca attctagctg   2220
aggaatacga tcccaaaaag cacaagtatg acgcagaata ttacattgag aaccaggttc   2280
ttccagcggt acttaggata ttggagggat ttggatacag aaaggaagac ctcagatacc   2340
aaaagacaag acaagtcggc ctaacttcct ggcttaacat taaaaaatcc ggtaccggcg   2400
gtggcggtat gtccaagaag cagaaactga agttctacga cattaaggcg aagcaggcgt   2460
ttgagaccga ccagtacgag gttattgaga gcagaccgc ccgcggtccg atgatgttcg    2520
ccgtggccaa atcgccgtac accggcatta agtgtaccg cctgttaggc aagaagaaat    2580
aactcgag                                                             2588
```

<210> SEQ ID NO 23
<211> LENGTH: 859
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 23

Met Gly His His His His His His His His Ser Ser Gly His
 1               5                  10                  15

Ile Glu Gly Arg His Met Ile Leu Asp Val Asp Tyr Ile Thr Glu Glu
            20                  25                  30

Gly Lys Pro Val Ile Arg Leu Phe Lys Lys Glu Asn Gly Lys Phe Lys
        35                  40                  45

```
Ile Glu His Asp Arg Thr Phe Arg Pro Tyr Ile Tyr Ala Leu Leu Arg
 50                  55                  60

Asp Asp Ser Lys Ile Glu Val Lys Lys Ile Thr Gly Glu Arg His
 65                  70                  75                  80

Gly Lys Ile Val Arg Ile Val Asp Val Glu Lys Val Glu Lys Phe
                 85                  90                  95

Leu Gly Lys Pro Ile Thr Val Trp Lys Leu Tyr Leu Glu His Pro Gln
                100                 105                 110

Asp Val Pro Thr Ile Arg Glu Lys Val Arg Glu His Pro Ala Val Val
                115                 120                 125

Asp Ile Phe Glu Tyr Asp Ile Pro Phe Ala Lys Arg Tyr Leu Ile Asp
                130                 135                 140

Lys Gly Leu Ile Pro Met Glu Gly Glu Glu Leu Lys Ile Leu Ala
145                 150                 155                 160

Phe Asp Ile Glu Thr Leu Tyr His Glu Gly Glu Glu Phe Gly Lys Gly
                165                 170                 175

Pro Ile Ile Met Ile Ser Tyr Ala Asp Glu Asn Glu Ala Lys Val Ile
                180                 185                 190

Thr Trp Lys Asn Ile Asp Leu Pro Tyr Val Glu Val Val Ser Ser Glu
                195                 200                 205

Arg Glu Met Ile Lys Arg Phe Leu Arg Ile Ile Arg Glu Lys Asp Pro
                210                 215                 220

Asp Ile Ile Val Thr Tyr Asn Gly Asp Ser Phe Asp Phe Pro Tyr Leu
225                 230                 235                 240

Ala Lys Arg Ala Glu Lys Leu Gly Ile Lys Leu Thr Ile Gly Arg Asp
                245                 250                 255

Gly Ser Glu Pro Lys Met Gln Arg Ile Gly Asp Met Thr Ala Val Glu
                260                 265                 270

Val Lys Gly Arg Ile His Phe Asp Leu Tyr His Val Ile Thr Arg Thr
                275                 280                 285

Ile Asn Leu Pro Thr Tyr Thr Leu Glu Ala Val Tyr Glu Ala Ile Phe
                290                 295                 300

Gly Lys Pro Lys Glu Lys Val Tyr Ala Asp Glu Ile Ala Lys Ala Trp
305                 310                 315                 320

Glu Ser Gly Glu Asn Leu Glu Arg Val Ala Lys Tyr Ser Met Glu Asp
                325                 330                 335

Ala Lys Ala Thr Tyr Glu Leu Gly Lys Glu Phe Leu Pro Met Glu Ile
                340                 345                 350

Gln Leu Ser Arg Leu Val Gly Gln Pro Leu Trp Asp Val Ser Arg Ser
                355                 360                 365

Ser Thr Gly Asn Leu Val Glu Trp Phe Leu Leu Arg Lys Ala Tyr Glu
                370                 375                 380

Arg Asn Glu Val Ala Pro Asn Lys Pro Ser Glu Glu Glu Tyr Gln Arg
385                 390                 395                 400

Arg Leu Arg Glu Ser Tyr Thr Gly Gly Phe Val Lys Glu Pro Glu Lys
                405                 410                 415

Gly Leu Trp Glu Asn Ile Val Tyr Leu Asp Phe Arg Ala Leu Tyr Pro
                420                 425                 430

Ser Ile Ile Ile Thr His Asn Val Ser Pro Asp Thr Leu Asn Leu Glu
                435                 440                 445

Gly Cys Lys Asn Tyr Asp Ile Ala Pro Gln Val Gly His Lys Phe Cys
450                 455                 460
```

```
Lys Asp Ile Pro Gly Phe Ile Pro Ser Leu Leu Gly His Leu Leu Glu
465                 470                 475                 480

Glu Arg Gln Lys Ile Lys Thr Lys Met Lys Glu Thr Gln Asp Pro Ile
            485                 490                 495

Glu Lys Ile Leu Leu Asp Tyr Arg Gln Lys Ala Ile Lys Leu Leu Ala
                500                 505                 510

Asn Ser Phe Tyr Gly Tyr Tyr Gly Tyr Ala Lys Ala Arg Trp Tyr Cys
            515                 520                 525

Lys Glu Cys Ala Glu Ser Val Thr Ala Trp Gly Arg Lys Tyr Ile Glu
            530                 535                 540

Leu Val Trp Lys Glu Leu Glu Glu Lys Phe Gly Phe Lys Val Leu Tyr
545                 550                 555                 560

Ile Asp Thr Asp Gly Leu Tyr Ala Thr Ile Pro Gly Gly Glu Ser Glu
                565                 570                 575

Glu Ile Lys Lys Lys Ala Leu Glu Phe Val Lys Tyr Ile Asn Ser Lys
                580                 585                 590

Leu Pro Gly Leu Leu Glu Leu Glu Tyr Glu Gly Phe Tyr Lys Arg Gly
            595                 600                 605

Phe Phe Val Thr Lys Lys Arg Tyr Ala Val Ile Asp Glu Glu Gly Lys
610                 615                 620

Val Ile Thr Arg Gly Leu Glu Ile Val Arg Arg Asp Trp Ser Glu Ile
625                 630                 635                 640

Ala Lys Glu Thr Gln Ala Arg Val Leu Glu Thr Ile Leu Lys His Gly
                645                 650                 655

Asp Val Glu Glu Ala Val Arg Ile Val Lys Glu Val Ile Gln Lys Leu
            660                 665                 670

Ala Asn Tyr Glu Ile Pro Pro Glu Lys Leu Ala Ile Tyr Glu Gln Ile
            675                 680                 685

Thr Arg Pro Leu His Glu Tyr Lys Ala Ile Gly Pro His Val Ala Val
690                 695                 700

Ala Lys Lys Leu Ala Ala Lys Gly Val Lys Ile Lys Pro Gly Met Val
705                 710                 715                 720

Ile Gly Tyr Ile Val Leu Arg Gly Asp Gly Pro Ile Ser Asn Arg Ala
                725                 730                 735

Ile Leu Ala Glu Glu Tyr Asp Pro Lys Lys His Lys Tyr Asp Ala Glu
            740                 745                 750

Tyr Tyr Ile Glu Asn Gln Val Leu Pro Ala Val Leu Arg Ile Leu Glu
            755                 760                 765

Gly Phe Gly Tyr Arg Lys Glu Asp Leu Arg Tyr Gln Lys Thr Arg Gln
770                 775                 780

Val Gly Leu Thr Ser Trp Leu Asn Ile Lys Lys Ser Gly Thr Gly Gly
785                 790                 795                 800

Gly Gly Met Ser Lys Lys Gln Lys Leu Lys Phe Tyr Asp Ile Lys Ala
                805                 810                 815

Lys Gln Ala Phe Glu Thr Asp Gln Tyr Glu Val Ile Glu Lys Gln Thr
            820                 825                 830

Ala Arg Gly Pro Met Met Phe Ala Val Ala Lys Ser Pro Tyr Thr Gly
            835                 840                 845

Ile Lys Val Tyr Arg Leu Leu Gly Lys Lys Lys
            850                 855

<210> SEQ ID NO 24
<211> LENGTH: 839
<212> TYPE: PRT
```

<213> ORGANISM: Artificial Sequence
<220> FEATURE:
<223> OTHER INFORMATION: Description of Artificial Sequence: Synthetic fusion protein

<400> SEQUENCE: 24

```
His Met Ile Leu Asp Val Asp Tyr Ile Thr Glu Glu Gly Lys Pro Val
 1               5                  10                  15

Ile Arg Leu Phe Lys Lys Glu Asn Gly Lys Phe Lys Ile Glu His Asp
            20                  25                  30

Arg Thr Phe Arg Pro Tyr Ile Tyr Ala Leu Leu Arg Asp Asp Ser Lys
        35                  40                  45

Ile Glu Glu Val Lys Lys Ile Thr Gly Glu Arg His Gly Lys Ile Val
 50                  55                  60

Arg Ile Val Asp Val Glu Lys Val Glu Lys Lys Phe Leu Gly Lys Pro
 65                  70                  75                  80

Ile Thr Val Trp Lys Leu Tyr Leu Glu His Pro Gln Asp Val Pro Thr
            85                  90                  95

Ile Arg Glu Lys Val Arg Glu His Pro Ala Val Val Asp Ile Phe Glu
        100                 105                 110

Tyr Asp Ile Pro Phe Ala Lys Arg Tyr Leu Ile Asp Lys Gly Leu Ile
    115                 120                 125

Pro Met Glu Gly Glu Glu Leu Lys Ile Leu Ala Phe Asp Ile Glu
130                 135                 140

Thr Leu Tyr His Glu Gly Glu Phe Gly Lys Gly Pro Ile Ile Met
145                 150                 155                 160

Ile Ser Tyr Ala Asp Glu Asn Glu Ala Lys Val Ile Thr Trp Lys Asn
            165                 170                 175

Ile Asp Leu Pro Tyr Val Glu Val Val Ser Ser Glu Arg Glu Met Ile
        180                 185                 190

Lys Arg Phe Leu Arg Ile Ile Arg Glu Lys Asp Pro Asp Ile Ile Val
    195                 200                 205

Thr Tyr Asn Gly Asp Ser Phe Asp Phe Pro Tyr Leu Ala Lys Arg Ala
210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
            245                 250                 255

Ile His Phe Asp Leu Tyr His Val Ile Thr Arg Thr Ile Asn Leu Pro
        260                 265                 270

Thr Tyr Thr Leu Glu Ala Val Tyr Glu Ala Ile Phe Gly Lys Pro Lys
    275                 280                 285

Glu Lys Val Tyr Ala Asp Glu Ile Ala Lys Ala Trp Glu Ser Gly Glu
290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
            325                 330                 335

Leu Val Gly Gln Pro Leu Trp Asp Val Ser Arg Ser Ser Thr Gly Asn
        340                 345                 350

Leu Val Glu Trp Phe Leu Leu Arg Lys Ala Tyr Glu Arg Asn Glu Val
    355                 360                 365

Ala Pro Asn Lys Pro Ser Glu Glu Tyr Gln Arg Arg Leu Arg Glu
370                 375                 380
```

```
Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
            405                 410                 415

Thr His Asn Val Ser Pro Asp Thr Leu Asn Leu Glu Gly Cys Lys Asn
        420                 425                 430

Tyr Asp Ile Ala Pro Gln Val Gly His Lys Phe Cys Lys Asp Ile Pro
    435                 440                 445

Gly Phe Ile Pro Ser Leu Leu Gly His Leu Leu Glu Glu Arg Gln Lys
450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
            515                 520                 525

Glu Leu Glu Glu Lys Phe Gly Phe Lys Val Leu Tyr Ile Asp Thr Asp
530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
            580                 585                 590

Lys Lys Arg Tyr Ala Val Ile Asp Glu Glu Gly Lys Val Ile Thr Arg
            595                 600                 605

Gly Leu Glu Ile Val Arg Arg Asp Trp Ser Glu Ile Ala Lys Glu Thr
    610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
            660                 665                 670

His Glu Tyr Lys Ala Ile Gly Pro His Val Ala Val Ala Lys Lys Leu
        675                 680                 685

Ala Ala Lys Gly Val Lys Ile Lys Pro Gly Met Val Ile Gly Tyr Ile
690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
            740                 745                 750

Arg Lys Glu Asp Leu Arg Tyr Gln Lys Thr Arg Gln Val Gly Leu Thr
        755                 760                 765

Ser Trp Leu Asn Ile Lys Lys Ser Gly Thr Gly Gly Gly Met Ser
        770                 775                 780

Lys Lys Gln Lys Leu Lys Phe Tyr Asp Ile Lys Ala Lys Gln Ala Phe
785                 790                 795                 800

Glu Thr Asp Gln Tyr Glu Val Ile Glu Lys Gln Thr Ala Arg Gly Pro
```

```
                805                 810                 815
Met Met Phe Ala Val Ala Lys Ser Pro Tyr Thr Gly Ile Lys Val Tyr
            820                 825                 830
Arg Leu Leu Gly Lys Lys Lys
        835

<210> SEQ ID NO 25
<211> LENGTH: 2582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ccatgggcca tcatcatcat catcatcatc atcatcacag cagcggccat atcgaaggtc      60
gtcatatgat tttagatgtg gattacataa ctgaagaagg aaaacctgtt attaggctat     120
tcaaaaaaga gaacggaaaa tttaagatag agcatgatag aactttttaga ccatacattt    180 acgctcttct cagggatgat tcaaagattg aagaagttaa gaaaataacg ggggaaaggc     240
atggaaagat tgtgagaatt gttgatgtag agaaggttga gaaaaagttt ctcggcaagc     300
ctattaccgt gtggaaactt tatttggaac atccccaaga tgttcccact attagagaaa     360
aagttagaga acatccagca gttgtggaca tcttcgaata cgatattcca tttgcaaaga     420 gataccctcat cgacaaaggc ctaataccaa tggaggggga agaagagcta aagattcttg     480
ccttcgatat agaaaccctc tatcacgaag gagaagagtt tggaaaaggc ccaattataa     540
tgattagtta tgcagatgaa aatgaagcaa aggtgattac ttggaaaaac atagatcttc     600
catacgttga ggttgtatca agcgagagag agatgataaa gagatttctc aggattatca     660
gggagaagga tcctgacatt atagttactt ataatggaga ctcattcgac ttcccatatt     720
tagcgaaaag ggcagaaaaa cttgggatta aattaaccat tggaagagat ggaagcgagc     780
ccaagatgca gagaataggc gatatgacgg ctgtagaagt caagggaaga atacatttcg     840
acttgtatca tgtaataaca aggacaataa atctcccaac atacacacta gaggctgtat     900
atgaagcaat ttttggaaag ccaaaggaga aggtatacgc cgacgagata gcaaaagcct     960
gggaaagtgg agagaacctt gagagagttg ccaaatactc gatggaagat gcaaaggcaa    1020
cttatgaact cgggaaagaa ttccttccaa tggaaattca gctttcaaga ttagttggac    1080
aacctttatg ggatgtttca aggtcaagca cagggaacct tgtagagtgg ttcttactta    1140
ggaaagccta cgaaagaaac gaagtagctc caaacaagcc aagtgaagag gagtatcaaa    1200
gaaggctcag ggagagctac acaggtggat tcgttaaaga gccagaaaag gggttgtggg    1260
aaaacatagt atacctagat tttagagccc tatatccctc gattataatt acccacaatg    1320
tttctcccga tactctaaat cttgagggat gcaagaacta tgatatcgct cctcaagtag    1380
gccacaagtt ctgcaaggac atccctggtt ttataccaag tctcttggga catttgttag    1440
aggaaagaca aaagattaag acaaaaatga aggaaactca agatcctata gaaaaaatac    1500
tccttgacta tagacaaaaa gcgataaaac tcttagcaaa ttcttttctac ggatattatg    1560 gctatgcaaa agcaagatgg tactgtaagg agtgtgctga gagcgttact gcctggggaa    1620
gaaagtacat cgagttagta tggaaggagc tcgaagaaaa gtttggattt aaagtcctct    1680
acattgacac tgatggtctc tatgcaacta tcccaggagg agaaagtgag gaaataaaga    1740
aaaaggctct agaatttgta aaatacataa attcaaagct ccctggactg ctagagcttg    1800
```

-continued

```
aatatgaagg gttttataag aggggattct tcgttacgaa gaagaggtat gcagtaatag   1860
atgaagaagg aaaagtcatt actcgtggtt tagagatagt taggagagat tggagtgaaa   1920
ttgcaaaaga aactcaagct agagttttgg agacaatact aaaacacgga gatgttgaag   1980
aagctgtgag aatagtaaaa gaagtaatac aaaagcttgc caattatgaa attccaccag   2040
agaagctcgc aatatatgag cagataacaa gaccattaca tgagtataag gcgataggtc   2100
ctcacgtagc tgttgcaaag aaactagctg ctaaaggagt taaaataaag ccaggaatgg   2160
taattggata catagtactt agaggcgatg gtccaattag caatagggca attctagctg   2220
aggaatacga tcccaaaaag cacaagtatg acgcagaata ttacattgag aaccaggttc   2280
ttccagcggt acttaggata ttggagggat ttggatacag aaaggaagac ctcagatacc   2340
aaaagacaag acaagtcggc ctaacttcct ggcttaacat taaaaaatcc ggtaccggcg   2400
gtggcggtcc gaagaaggag aagattaggt tcttcgacct ggtcgccaag aagtactacg   2460
agactgacaa ctacgaagtc gagattaagg agactaagcg cggcaagttt cgcttcgcca   2520
aagccaagag cccgtacacc ggcaagatct tctatcgcgt gctgggcaaa gcctaactcg   2580
ag                                                                 2582
```

<210> SEQ ID NO 26
<211> LENGTH: 857
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 26

```
Met Gly His His His His His His His His His Ser Ser Gly His
 1               5                  10                  15

Ile Glu Gly Arg His Met Ile Leu Asp Val Asp Tyr Ile Thr Glu Glu
            20                  25                  30

Gly Lys Pro Val Ile Arg Leu Phe Lys Lys Glu Asn Gly Lys Phe Lys
        35                  40                  45

Ile Glu His Asp Arg Thr Phe Arg Pro Tyr Ile Tyr Ala Leu Leu Arg
    50                  55                  60

Asp Asp Ser Lys Ile Glu Glu Val Lys Lys Ile Thr Gly Glu Arg His
65                  70                  75                  80

Gly Lys Ile Val Arg Ile Val Asp Val Glu Lys Val Glu Lys Lys Phe
                85                  90                  95

Leu Gly Lys Pro Ile Thr Val Trp Lys Leu Tyr Leu Glu His Pro Gln
            100                 105                 110

Asp Val Pro Thr Ile Arg Glu Lys Val Arg Glu His Pro Ala Val Val
        115                 120                 125

Asp Ile Phe Glu Tyr Asp Ile Pro Phe Ala Lys Arg Tyr Leu Ile Asp
    130                 135                 140

Lys Gly Leu Ile Pro Met Glu Gly Glu Glu Leu Lys Ile Leu Ala
145                 150                 155                 160

Phe Asp Ile Glu Thr Leu Tyr His Glu Gly Glu Glu Phe Gly Lys Gly
                165                 170                 175

Pro Ile Ile Met Ile Ser Tyr Ala Asp Glu Asn Glu Ala Lys Val Ile
            180                 185                 190

Thr Trp Lys Asn Ile Asp Leu Pro Tyr Val Glu Val Val Ser Ser Glu
        195                 200                 205

Arg Glu Met Ile Lys Arg Phe Leu Arg Ile Ile Arg Glu Lys Asp Pro
```

```
                210                 215                 220
Asp Ile Ile Val Thr Tyr Asn Gly Asp Ser Phe Asp Phe Pro Tyr Leu
225                 230                 235                 240

Ala Lys Arg Ala Glu Lys Leu Gly Ile Lys Leu Thr Ile Gly Arg Asp
                245                 250                 255

Gly Ser Glu Pro Lys Met Gln Arg Ile Gly Asp Met Thr Ala Val Glu
                260                 265                 270

Val Lys Gly Arg Ile His Phe Asp Leu Tyr His Val Ile Thr Arg Thr
                275                 280                 285

Ile Asn Leu Pro Thr Tyr Thr Leu Glu Ala Val Tyr Glu Ala Ile Phe
                290                 295                 300

Gly Lys Pro Lys Glu Lys Val Tyr Ala Asp Glu Ile Ala Lys Ala Trp
305                 310                 315                 320

Glu Ser Gly Glu Asn Leu Glu Arg Val Ala Lys Tyr Ser Met Glu Asp
                325                 330                 335

Ala Lys Ala Thr Tyr Glu Leu Gly Lys Glu Phe Leu Pro Met Glu Ile
                340                 345                 350

Gln Leu Ser Arg Leu Val Gly Gln Pro Leu Trp Asp Val Ser Arg Ser
                355                 360                 365

Ser Thr Gly Asn Leu Val Glu Trp Phe Leu Leu Arg Lys Ala Tyr Glu
                370                 375                 380

Arg Asn Glu Val Ala Pro Asn Lys Pro Ser Glu Glu Tyr Gln Arg
385                 390                 395                 400

Arg Leu Arg Glu Ser Tyr Thr Gly Gly Phe Val Lys Glu Pro Glu Lys
                405                 410                 415

Gly Leu Trp Glu Asn Ile Val Tyr Leu Asp Phe Arg Ala Leu Tyr Pro
                420                 425                 430

Ser Ile Ile Ile Thr His Asn Val Ser Pro Asp Thr Leu Asn Leu Glu
                435                 440                 445

Gly Cys Lys Asn Tyr Asp Ile Ala Pro Gln Val Gly His Lys Phe Cys
                450                 455                 460

Lys Asp Ile Pro Gly Phe Ile Pro Ser Leu Leu Gly His Leu Leu Glu
465                 470                 475                 480

Glu Arg Gln Lys Ile Lys Thr Lys Met Lys Glu Thr Gln Asp Pro Ile
                485                 490                 495

Glu Lys Ile Leu Leu Asp Tyr Arg Gln Lys Ala Ile Lys Leu Leu Ala
                500                 505                 510

Asn Ser Phe Tyr Gly Tyr Tyr Gly Tyr Ala Lys Ala Arg Trp Tyr Cys
                515                 520                 525

Lys Glu Cys Ala Glu Ser Val Thr Ala Trp Gly Arg Lys Tyr Ile Glu
                530                 535                 540

Leu Val Trp Lys Glu Leu Glu Glu Lys Phe Gly Phe Lys Val Leu Tyr
545                 550                 555                 560

Ile Asp Thr Asp Gly Leu Tyr Ala Thr Ile Pro Gly Gly Glu Ser Glu
                565                 570                 575

Glu Ile Lys Lys Lys Ala Leu Glu Phe Val Lys Tyr Ile Asn Ser Lys
                580                 585                 590

Leu Pro Gly Leu Leu Glu Leu Glu Tyr Glu Gly Phe Tyr Lys Arg Gly
                595                 600                 605

Phe Phe Val Thr Lys Lys Arg Tyr Ala Val Ile Asp Glu Glu Gly Lys
                610                 615                 620

Val Ile Thr Arg Gly Leu Glu Ile Val Arg Arg Asp Trp Ser Glu Ile
625                 630                 635                 640
```

-continued

```
Ala Lys Glu Thr Gln Ala Arg Val Leu Glu Thr Ile Leu Lys His Gly
            645                 650                 655

Asp Val Glu Glu Ala Val Arg Ile Val Lys Glu Val Ile Gln Lys Leu
            660                 665                 670

Ala Asn Tyr Glu Ile Pro Pro Glu Lys Leu Ala Ile Tyr Glu Gln Ile
            675                 680                 685

Thr Arg Pro Leu His Glu Tyr Lys Ala Ile Gly Pro His Val Ala Val
            690                 695                 700

Ala Lys Lys Leu Ala Ala Lys Gly Val Lys Ile Lys Pro Gly Met Val
705                 710                 715                 720

Ile Gly Tyr Ile Val Leu Arg Gly Asp Gly Pro Ile Ser Asn Arg Ala
            725                 730                 735

Ile Leu Ala Glu Glu Tyr Asp Pro Lys Lys His Lys Tyr Asp Ala Glu
            740                 745                 750

Tyr Tyr Ile Glu Asn Gln Val Leu Pro Ala Val Leu Arg Ile Leu Glu
            755                 760                 765

Gly Phe Gly Tyr Arg Lys Glu Asp Leu Arg Tyr Gln Lys Thr Arg Gln
            770                 775                 780

Val Gly Leu Thr Ser Trp Leu Asn Ile Lys Lys Ser Gly Thr Gly Gly
785                 790                 795                 800

Gly Gly Pro Lys Lys Glu Lys Ile Arg Phe Phe Asp Leu Val Ala Lys
            805                 810                 815

Lys Tyr Tyr Glu Thr Asp Asn Tyr Glu Val Glu Ile Lys Glu Thr Lys
            820                 825                 830

Arg Gly Lys Phe Arg Phe Ala Lys Ala Lys Ser Pro Tyr Thr Gly Lys
            835                 840                 845

Ile Phe Tyr Arg Val Leu Gly Lys Ala
            850                 855
```

<210> SEQ ID NO 27
<211> LENGTH: 837
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 27

```
His Met Ile Leu Asp Val Asp Tyr Ile Thr Glu Glu Gly Lys Pro Val
  1               5                  10                  15

Ile Arg Leu Phe Lys Lys Glu Asn Gly Lys Phe Lys Ile Glu His Asp
             20                  25                  30

Arg Thr Phe Arg Pro Tyr Ile Tyr Ala Leu Leu Arg Asp Asp Ser Lys
         35                  40                  45

Ile Glu Glu Val Lys Lys Ile Thr Gly Glu Arg His Gly Lys Ile Val
     50                  55                  60

Arg Ile Val Asp Val Glu Lys Val Glu Lys Lys Phe Leu Gly Lys Pro
 65                  70                  75                  80

Ile Thr Val Trp Lys Leu Tyr Leu Glu His Pro Gln Asp Val Pro Thr
             85                  90                  95

Ile Arg Glu Lys Val Arg Glu His Pro Ala Val Val Asp Ile Phe Glu
        100                 105                 110

Tyr Asp Ile Pro Phe Ala Lys Arg Tyr Leu Ile Asp Lys Gly Leu Ile
    115                 120                 125

Pro Met Glu Gly Glu Glu Glu Leu Lys Ile Leu Ala Phe Asp Ile Glu
```

```
            130                 135                 140
Thr Leu Tyr His Glu Gly Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
                180                 185                 190

Lys Arg Phe Leu Arg Ile Ile Arg Glu Lys Asp Pro Asp Ile Ile Val
                195                 200                 205

Thr Tyr Asn Gly Asp Ser Phe Asp Phe Pro Tyr Leu Ala Lys Arg Ala
                210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
                260                 265                 270

Thr Tyr Thr Leu Glu Ala Val Tyr Glu Ala Ile Phe Gly Lys Pro Lys
                275                 280                 285

Glu Lys Val Tyr Ala Asp Glu Ile Ala Lys Ala Trp Glu Ser Gly Glu
                290                 295                 300

Asn Leu Glu Arg Val Ala Lys Tyr Ser Met Glu Asp Ala Lys Ala Thr
305                 310                 315                 320

Tyr Glu Leu Gly Lys Glu Phe Leu Pro Met Glu Ile Gln Leu Ser Arg
                325                 330                 335

Leu Val Gly Gln Pro Leu Trp Asp Val Ser Arg Ser Ser Thr Gly Asn
                340                 345                 350

Leu Val Glu Trp Phe Leu Leu Arg Lys Ala Tyr Glu Arg Asn Glu Val
                355                 360                 365

Ala Pro Asn Lys Pro Ser Glu Glu Tyr Gln Arg Arg Leu Arg Glu
370                 375                 380

Ser Tyr Thr Gly Gly Phe Val Lys Glu Pro Glu Lys Gly Leu Trp Glu
385                 390                 395                 400

Asn Ile Val Tyr Leu Asp Phe Arg Ala Leu Tyr Pro Ser Ile Ile Ile
                405                 410                 415

Thr His Asn Val Ser Pro Asp Thr Leu Asn Leu Glu Gly Cys Lys Asn
                420                 425                 430

Tyr Asp Ile Ala Pro Gln Val Gly His Lys Phe Cys Lys Asp Ile Pro
                435                 440                 445

Gly Phe Ile Pro Ser Leu Leu Gly His Leu Leu Glu Glu Arg Gln Lys
                450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
                515                 520                 525

Glu Leu Glu Glu Lys Phe Gly Phe Lys Val Leu Tyr Ile Asp Thr Asp
                530                 535                 540

Gly Leu Tyr Ala Thr Ile Pro Gly Gly Glu Ser Glu Glu Ile Lys Lys
545                 550                 555                 560
```

```
Lys Ala Leu Glu Phe Val Lys Tyr Ile Asn Ser Lys Leu Pro Gly Leu
            565                 570                 575

Leu Glu Leu Glu Tyr Glu Gly Phe Tyr Lys Arg Gly Phe Phe Val Thr
        580                 585                 590

Lys Lys Arg Tyr Ala Val Ile Asp Glu Glu Gly Lys Val Ile Thr Arg
    595                 600                 605

Gly Leu Glu Ile Val Arg Arg Asp Trp Ser Glu Ile Ala Lys Glu Thr
    610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
            660                 665                 670

His Glu Tyr Lys Ala Ile Gly Pro His Val Ala Val Ala Lys Lys Leu
        675                 680                 685

Ala Ala Lys Gly Val Lys Ile Lys Pro Gly Met Val Ile Gly Tyr Ile
    690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
            740                 745                 750

Arg Lys Glu Asp Leu Arg Tyr Gln Lys Thr Arg Gln Val Gly Leu Thr
        755                 760                 765

Ser Trp Leu Asn Ile Lys Lys Ser Gly Thr Gly Gly Gly Pro Lys
    770                 775                 780

Lys Glu Lys Ile Arg Phe Phe Asp Leu Val Ala Lys Lys Tyr Tyr Glu
785                 790                 795                 800

Thr Asp Asn Tyr Glu Val Glu Ile Lys Glu Thr Lys Arg Gly Lys Phe
                805                 810                 815

Arg Phe Ala Lys Ala Lys Ser Pro Tyr Thr Gly Lys Ile Phe Tyr Arg
            820                 825                 830

Val Leu Gly Lys Ala
        835

<210> SEQ ID NO 28
<211> LENGTH: 52
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
```

-continued

```
<220> FEATURE:
<221> NAME/KEY: MOD_RES
<222> LOCATION: (13)..(15)
<223> OTHER INFORMATION: Variable amino acid
<220> FEATURE:
<221> NAME/KEY: MOD_RES
<222> LOCATION: (19)
<223> OTHER INFORMATION: Variable amino acid
<220> FEATURE:
<221> NAME/KEY: MOD_RES
<222> LOCATION: (23)..(24)
<223> OTHER INFORMATION: Variable amino acid
<220> FEATURE:
<221> NAME/KEY: MOD_RES
<222> LOCATION: (26)
<223> OTHER INFORMATION: Variable amino acid
<220> FEATURE:
<221> NAME/KEY: MOD_RES
<222> LOCATION: (28)
<223> OTHER INFORMATION: Variable amino acid
<220> FEATURE:
<221> NAME/KEY: MOD_RES
<222> LOCATION: (31)..(33)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (44)..(46)
<223> OTHER INFORMATION: Variable amino acid
<220> FEATURE:
<221> NAME/KEY: MOD_RES
<222> LOCATION: (49)
<223> OTHER INFORMATION: Variable amino acid

<400> SEQUENCE: 28

Lys Xaa Lys Xaa Lys Phe Xaa Asp Xaa Xaa Ala Lys Xaa Xaa Xaa Glu
 1               5                  10                  15

Thr Asp Xaa Tyr Glu Val Xaa Xaa Lys Xaa Thr Xaa Arg Gly Xaa Xaa
                20                  25                  30

Xaa Phe Ala Xaa Ala Lys Ser Pro Tyr Thr Gly Xaa Xaa Xaa Tyr Arg
            35                  40                  45

Xaa Leu Gly Lys
        50

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttttcccag tcacgacgtt gtaaaacgac ggcc                              34

<210> SEQ ID NO 30
<211> LENGTH: 775
<212> TYPE: PRT
<213> ORGANISM: Pyrococcus furiosus

<400> SEQUENCE: 30

Met Ile Leu Asp Val Asp Tyr Ile Thr Glu Glu Gly Lys Pro Val Ile
 1               5                  10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
```

```
                 35                  40                  45
Glu Glu Val Lys Lys Ile Thr Gly Glu Arg His Gly Lys Ile Val Arg
             50                  55                  60
Ile Val Asp Val Glu Lys Val Glu Lys Lys Phe Leu Gly Lys Pro Ile
 65                  70                  75                  80
Thr Val Trp Lys Leu Tyr Leu Glu His Pro Gln Asp Val Pro Thr Ile
                 85                  90                  95
Arg Glu Lys Val Arg Glu His Pro Ala Val Asp Ile Phe Glu Tyr
            100                 105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
            130                 135                 140
Leu Tyr His Glu Gly Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Tyr Gln Arg Arg Leu Arg Glu Ser
            370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
```

```
Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
        770                 775

<210> SEQ ID NO 31
<211> LENGTH: 832
<212> TYPE: PRT
<213> ORGANISM: Thermus aquaticus

<400> SEQUENCE: 31

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
```

-continued

```
            50                  55                  60
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Asp Val Leu Ala Ser Leu Ala Lys Lys
                115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                    165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
                210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                    245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
                275                 280                 285

Glu Ser Pro Lys Ala Leu Glu Glu Ala Pro Trp Pro Pro Glu Gly
                290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                    325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                    405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
                450                 455                 460

Glu Glu Ile Ala Arg Leu Glu Ala Glu Val Phe Arg Leu Ala Gly His
465                 470                 475                 480
```

Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
        500                 505                 510
Ser Thr Ser Ala Ala Val Leu Glu Ala Leu Arg Glu Ala His Pro Ile
    515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830

<210> SEQ ID NO 32
<211> LENGTH: 2745
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgggccatc atcatcatca tcatcatcat catcacagca gcggccatat cgaaggtcgt    60

```
catatgtcca agaagcagaa actgaagttc tacgacatta aggcgaagca ggcgtttgag      120
accgaccagt acgaggttat tgagaagcag accgcccgcg gtccgatgat gttcgccgtg      180
gccaaatcgc cgtacaccgg cattaaagtg taccgcctgt taggcaagaa gaaaggcggc      240
ggtgtcacta gtgggatgct gcccctcttt gagcccaagg gccgggtcct cctggtggac      300
ggccaccacc tggcctaccg caccttccac gccctgaagg gcctcaccac cagccggggg      360
gagccggtgc aggcggtcta cggcttcgcc aagagcctcc tcaaggccct caaggaggac      420
ggggacgcgg tgatcgtggt ctttgacgcc aaggccccct ccttccgcca cgaggcctac      480
ggggggtaca aggcgggccg ggcccccacg ccggaggact tcccccggca actcgccctc      540
atcaaggagc tggtggacct cctggggctg cgcgcctcg aggtcccggg ctacgaggcg       600
gacgacgtcc tggccagcct ggccaagaag gcggaaaagg agggctacga ggtccgcatc      660
ctcaccgccg acaaagacct ttaccagctc ctttccgacc gcatccacgt cctccacccc      720
gaggggtacc tcatcacccc ggcctggctt tgggaaaagt acggcctgag gcccgaccag      780
tgggccgact accgggccct gaccggggac gagtccgaca accttcccgg ggtcaagggc      840
atcggggaga gacggcgag gaagcttctg gaggagtggg ggagcctgga agccctcctc       900
aagaacctgg accggctgaa gccgccatc cgggagaaga tcctggccca catggacgat       960
ctgaagctct cctgggacct ggccaaggtg cgcaccgacc tgcccctgga ggtggacttc     1020
gccaaaaggc gggagcccga ccgggagagg cttagggcct ttctggagag gcttgagttt     1080
ggcagcctcc tccacgagtt cggccttctg gaaagcccca aggccctgga ggaggccccc     1140
tggcccccgc cggaaggggc cttcgtgggc tttgtgcttt cccgcaagga gcccatgtgg     1200
gccgatcttc tggccctggc cgccgccagg ggggccgggg tccaccgggc ccccgagcct     1260
tataaagccc tcagggacct gaaggaggcg cgggggcttc tcgccaaaga cctgagcgtt     1320
ctggccctga gggaaggcct tggcctcccg cccggcgacg acccatgct cctcgcctac      1380
ctcctggacc cttccaacac cacccccgag ggggtggccc ggcgctacgg cggggagtgg     1440
acggaggagg cgggggagcg ggccgcccctt tccgagaggc tcttcgccaa cctgtggggg     1500
aggcttgagg gggaggagag gctccttttgg ctttaccggg aggtggagag gcccctttcc    1560
gctgtcctgg cccacatgga ggccacgggg gtgcgcctgg acgtggccta tctcagggcc     1620
ttgtccctgg aggtggccga ggagatcgcc cgcctcgagg ccgaggtctt ccgcctggcc     1680
ggccacccct tcaacctcaa ctcccgggac cagctggaaa gggtcctctt tgacgagcta     1740
gggcttcccg ccatcggcaa gacggagaag accggcaagc gctccaccag cgccgccgtc     1800
ctggaggccc tccgcgaggc ccaccccatc gtggagaaga tcctgcagta ccgggagctc     1860
accaagctga agagcaccta cattgacccc ttgccggacc tcatccaccc caggacgggc     1920
cgcctccaca cccgcttcaa ccagacggcc acggccacgg gcaggctaag tagctccgat     1980
cccaacctcc agaacatccc cgtccgcacc ccgcttgggc agaggatccg ccgggccttc     2040
atcgccgagg agggggtggct attggtggcc ctggactata ccagataga gctcagggtg    2100
ctggcccacc tctccggcga cgagaacctg atccgggtct tccaggaggg gcgggacatc     2160
cacacggaga ccgccagctg gatgttcggc gtccccccggg aggccgtgga ccccctgatg   2220
cgccgggcgg ccaagaccat caacttcggg gtcctctacg gcatgtcggc ccaccgcctc     2280
tcccaggagc tagccatccc ttacgaggag gcccaggcct tcattgagcg ctactttcag     2340
agcttcccca aggtgcgggc ctggattgag aagaccctgg aggagggcag gaggcggggg     2400
```

```
tacgtggaga ccctcttcgg ccgccgccgc tacgtgccag acctagaggc ccgggtgaag    2460
agcgtgcggg aggcggccga gcgcatggcc ttcaacatgc ccgtccaggg caccgccgcc    2520
gacctcatga agctgactat ggtgaagctc ttccccaggc tggaggaaat gggggccagg    2580
atgctccttc aggtccacga cgagctggtc ctcgaggccc caaaagagag gcggaggcc     2640 gtggcccggc tggccaagga ggtcatggag ggggtgtatc ccctggccgt gcccctggag    2700
gtggaggtgg ggatagggga ggactggctc tccgccaagg agtga                   2745
```

<210> SEQ ID NO 33
<211> LENGTH: 914
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 33

```
Met Gly His His His His His His His His Ser Ser Gly His
 1               5                  10                  15

Ile Glu Gly Arg His Met Ser Lys Lys Gln Lys Leu Lys Phe Tyr Asp
            20                  25                  30

Ile Lys Ala Lys Gln Ala Phe Glu Thr Asp Gln Tyr Glu Val Ile Glu
        35                  40                  45

Lys Gln Thr Ala Arg Gly Pro Met Met Phe Ala Val Ala Lys Ser Pro
    50                  55                  60

Tyr Thr Gly Ile Lys Val Tyr Arg Leu Leu Gly Lys Lys Gly Gly
65                  70                  75                  80

Gly Val Thr Ser Gly Met Leu Pro Leu Phe Glu Pro Lys Gly Arg Val
                85                  90                  95

Leu Leu Val Asp Gly His His Leu Ala Tyr Arg Thr Phe His Ala Leu
            100                 105                 110

Lys Gly Leu Thr Thr Ser Arg Gly Glu Pro Val Gln Ala Val Tyr Gly
        115                 120                 125

Phe Ala Lys Ser Leu Leu Lys Ala Leu Lys Glu Asp Gly Asp Ala Val
    130                 135                 140

Ile Val Val Phe Asp Ala Lys Ala Pro Ser Phe Arg His Glu Ala Tyr
145                 150                 155                 160

Gly Gly Tyr Lys Ala Gly Arg Ala Pro Thr Pro Glu Asp Phe Pro Arg
                165                 170                 175

Gln Leu Ala Leu Ile Lys Glu Leu Val Asp Leu Leu Gly Leu Ala Arg
            180                 185                 190

Leu Glu Val Pro Gly Tyr Glu Ala Asp Asp Val Leu Ala Ser Leu Ala
        195                 200                 205

Lys Lys Ala Glu Lys Glu Gly Tyr Glu Val Arg Ile Leu Thr Ala Asp
    210                 215                 220

Lys Asp Leu Tyr Gln Leu Leu Ser Asp Arg Ile His Val Leu His Pro
225                 230                 235                 240

Glu Gly Tyr Leu Ile Thr Pro Ala Trp Leu Trp Glu Lys Tyr Gly Leu
                245                 250                 255

Arg Pro Asp Gln Trp Ala Asp Tyr Arg Ala Leu Thr Gly Asp Glu Ser
            260                 265                 270

Asp Asn Leu Pro Gly Val Lys Gly Ile Gly Glu Lys Thr Ala Arg Lys
        275                 280                 285

Leu Leu Glu Glu Trp Gly Ser Leu Glu Ala Leu Leu Lys Asn Leu Asp
    290                 295                 300
```

```
Arg Leu Lys Pro Ala Ile Arg Glu Lys Ile Leu Ala His Met Asp Asp
305                 310                 315                 320

Leu Lys Leu Ser Trp Asp Leu Ala Lys Val Arg Thr Asp Leu Pro Leu
            325                 330                 335

Glu Val Asp Phe Ala Lys Arg Arg Glu Pro Asp Arg Glu Arg Leu Arg
            340                 345                 350

Ala Phe Leu Glu Arg Leu Glu Phe Gly Ser Leu Leu His Glu Phe Gly
            355                 360                 365

Leu Leu Glu Ser Pro Lys Ala Leu Glu Glu Ala Pro Trp Pro Pro Pro
370                 375                 380

Glu Gly Ala Phe Val Gly Phe Val Leu Ser Arg Lys Pro Met Trp
385                 390                 395                 400

Ala Asp Leu Leu Ala Leu Ala Ala Arg Gly Gly Arg Val His Arg
            405                 410                 415

Ala Pro Glu Pro Tyr Lys Ala Leu Arg Asp Leu Lys Glu Ala Arg Gly
            420                 425                 430

Leu Leu Ala Lys Asp Leu Ser Val Leu Ala Leu Arg Glu Gly Leu Gly
            435                 440                 445

Leu Pro Pro Gly Asp Asp Pro Met Leu Leu Ala Tyr Leu Leu Asp Pro
450                 455                 460

Ser Asn Thr Thr Pro Glu Gly Val Ala Arg Arg Tyr Gly Gly Glu Trp
465                 470                 475                 480

Thr Glu Glu Ala Gly Glu Arg Ala Ala Leu Ser Glu Arg Leu Phe Ala
            485                 490                 495

Asn Leu Trp Gly Arg Leu Glu Gly Glu Arg Leu Leu Trp Leu Tyr
            500                 505                 510

Arg Glu Val Glu Arg Pro Leu Ser Ala Val Leu Ala His Met Glu Ala
            515                 520                 525

Thr Gly Val Arg Leu Asp Val Ala Tyr Leu Arg Ala Leu Ser Leu Glu
            530                 535                 540

Val Ala Glu Glu Ile Ala Arg Leu Glu Ala Glu Val Phe Arg Leu Ala
545                 550                 555                 560

Gly His Pro Phe Asn Leu Asn Ser Arg Asp Gln Leu Glu Arg Val Leu
                565                 570                 575

Phe Asp Glu Leu Gly Leu Pro Ala Ile Gly Lys Thr Glu Lys Thr Gly
            580                 585                 590

Lys Arg Ser Thr Ser Ala Ala Val Leu Glu Ala Leu Arg Glu Ala His
            595                 600                 605

Pro Ile Val Glu Lys Ile Leu Gln Tyr Arg Glu Leu Thr Lys Leu Lys
            610                 615                 620

Ser Thr Tyr Ile Asp Pro Leu Pro Asp Leu Ile His Pro Arg Thr Gly
625                 630                 635                 640

Arg Leu His Thr Arg Phe Asn Gln Thr Ala Thr Ala Thr Gly Arg Leu
            645                 650                 655

Ser Ser Ser Asp Pro Asn Leu Gln Asn Ile Pro Val Arg Thr Pro Leu
            660                 665                 670

Gly Gln Arg Ile Arg Arg Ala Phe Ile Ala Glu Glu Gly Trp Leu Leu
            675                 680                 685

Val Ala Leu Asp Tyr Ser Gln Ile Glu Leu Arg Val Leu Ala His Leu
            690                 695                 700

Ser Gly Asp Glu Asn Leu Ile Arg Val Phe Gln Glu Gly Arg Asp Ile
705                 710                 715                 720
```

His Thr Glu Thr Ala Ser Trp Met Phe Gly Val Pro Arg Glu Ala Val
                725                 730                 735

Asp Pro Leu Met Arg Arg Ala Ala Lys Thr Ile Asn Phe Gly Val Leu
            740                 745                 750

Tyr Gly Met Ser Ala His Arg Leu Ser Gln Glu Leu Ala Ile Pro Tyr
        755                 760                 765

Glu Glu Ala Gln Ala Phe Ile Glu Arg Tyr Phe Gln Ser Phe Pro Lys
    770                 775                 780

Val Arg Ala Trp Ile Glu Lys Thr Leu Glu Glu Gly Arg Arg Arg Gly
785                 790                 795                 800

Tyr Val Glu Thr Leu Phe Gly Arg Arg Arg Tyr Val Pro Asp Leu Glu
                805                 810                 815

Ala Arg Val Lys Ser Val Arg Glu Ala Ala Glu Arg Met Ala Phe Asn
            820                 825                 830

Met Pro Val Gln Gly Thr Ala Ala Asp Leu Met Lys Leu Ala Met Val
        835                 840                 845

Lys Leu Phe Pro Arg Leu Glu Glu Met Gly Ala Arg Met Leu Leu Gln
    850                 855                 860

Val His Asp Glu Leu Val Leu Glu Ala Pro Lys Glu Arg Ala Glu Ala
865                 870                 875                 880

Val Ala Arg Leu Ala Lys Glu Val Met Glu Gly Val Tyr Pro Leu Ala
                885                 890                 895

Val Pro Leu Glu Val Glu Val Gly Ile Gly Glu Asp Trp Leu Ser Ala
            900                 905                 910

Lys Glu

<210> SEQ ID NO 34
<211> LENGTH: 894
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 34

His Met Ser Lys Lys Gln Lys Leu Lys Phe Tyr Asp Ile Lys Ala Lys
  1               5                  10                  15

Gln Ala Phe Glu Thr Asp Gln Tyr Glu Val Ile Glu Lys Gln Thr Ala
                 20                  25                  30

Arg Gly Pro Met Met Phe Ala Val Ala Lys Ser Pro Tyr Thr Gly Ile
             35                  40                  45

Lys Val Tyr Arg Leu Leu Gly Lys Lys Gly Gly Val Thr Ser
 50                  55                  60

Gly Met Leu Pro Leu Phe Glu Pro Lys Gly Arg Val Leu Leu Val Asp
 65                  70                  75                  80

Gly His His Leu Ala Tyr Arg Thr Phe His Ala Leu Lys Gly Leu Thr
                 85                  90                  95

Thr Ser Arg Gly Glu Pro Val Gln Ala Val Tyr Gly Phe Ala Lys Ser
            100                 105                 110

Leu Leu Lys Ala Leu Lys Glu Asp Gly Asp Ala Val Ile Val Val Phe
        115                 120                 125

Asp Ala Lys Ala Pro Ser Phe Arg His Glu Ala Tyr Gly Gly Tyr Lys
    130                 135                 140

Ala Gly Arg Ala Pro Thr Pro Glu Asp Phe Pro Arg Gln Leu Ala Leu
145                 150                 155                 160

-continued

```
Ile Lys Glu Leu Val Asp Leu Leu Gly Leu Ala Arg Leu Glu Val Pro
                165                 170                 175
Gly Tyr Glu Ala Asp Val Leu Ala Ser Leu Ala Lys Lys Ala Glu
            180                 185                 190
Lys Glu Gly Tyr Glu Val Arg Ile Leu Thr Ala Asp Lys Asp Leu Tyr
            195                 200                 205
Gln Leu Leu Ser Asp Arg Ile His Val Leu His Pro Glu Gly Tyr Leu
            210                 215                 220
Ile Thr Pro Ala Trp Leu Trp Glu Lys Tyr Gly Leu Arg Pro Asp Gln
225                 230                 235                 240
Trp Ala Asp Tyr Arg Ala Leu Thr Gly Asp Glu Ser Asp Asn Leu Pro
                245                 250                 255
Gly Val Lys Gly Ile Gly Glu Lys Thr Ala Arg Lys Leu Leu Glu Glu
            260                 265                 270
Trp Gly Ser Leu Glu Ala Leu Leu Lys Asn Leu Asp Arg Leu Lys Pro
            275                 280                 285
Ala Ile Arg Glu Lys Ile Leu Ala His Met Asp Asp Leu Lys Leu Ser
            290                 295                 300
Trp Asp Leu Ala Lys Val Arg Thr Asp Leu Pro Leu Glu Val Asp Phe
305                 310                 315                 320
Ala Lys Arg Arg Glu Pro Asp Arg Glu Arg Leu Arg Ala Phe Leu Glu
                325                 330                 335
Arg Leu Glu Phe Gly Ser Leu Leu His Glu Phe Gly Leu Leu Glu Ser
            340                 345                 350
Pro Lys Ala Leu Glu Glu Ala Pro Trp Pro Pro Pro Glu Gly Ala Phe
            355                 360                 365
Val Gly Phe Val Leu Ser Arg Lys Glu Pro Met Trp Ala Asp Leu Leu
            370                 375                 380
Ala Leu Ala Ala Ala Arg Gly Gly Arg Val His Arg Ala Pro Glu Pro
385                 390                 395                 400
Tyr Lys Ala Leu Arg Asp Leu Lys Glu Ala Arg Gly Leu Leu Ala Lys
                405                 410                 415
Asp Leu Ser Val Leu Ala Leu Arg Glu Gly Leu Gly Leu Pro Pro Gly
            420                 425                 430
Asp Asp Pro Met Leu Leu Ala Tyr Leu Leu Asp Pro Ser Asn Thr Thr
            435                 440                 445
Pro Glu Gly Val Ala Arg Arg Tyr Gly Gly Glu Trp Thr Glu Glu Ala
            450                 455                 460
Gly Glu Arg Ala Ala Leu Ser Glu Arg Leu Phe Ala Asn Leu Trp Gly
465                 470                 475                 480
Arg Leu Glu Gly Glu Glu Arg Leu Leu Trp Leu Tyr Arg Glu Val Glu
                485                 490                 495
Arg Pro Leu Ser Ala Val Leu Ala His Met Glu Ala Thr Gly Val Arg
            500                 505                 510
Leu Asp Val Ala Tyr Leu Arg Ala Leu Ser Leu Glu Val Ala Glu Glu
            515                 520                 525
Ile Ala Arg Leu Glu Ala Glu Val Phe Arg Leu Ala Gly His Pro Phe
            530                 535                 540
Asn Leu Asn Ser Arg Asp Gln Leu Glu Arg Val Leu Phe Asp Glu Leu
545                 550                 555                 560
Gly Leu Pro Ala Ile Gly Lys Thr Glu Lys Thr Gly Lys Arg Ser Thr
                565                 570                 575
Ser Ala Ala Val Leu Glu Ala Leu Arg Glu Ala His Pro Ile Val Glu
```

```
                580             585                 590
Lys Ile Leu Gln Tyr Arg Glu Leu Thr Lys Leu Lys Ser Thr Tyr Ile
                595                 600                 605
Asp Pro Leu Pro Asp Leu Ile His Pro Arg Thr Gly Arg Leu His Thr
            610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Val Arg Thr Pro Leu Gly Gln Arg Ile
                645                 650                 655
Arg Arg Ala Phe Ile Ala Glu Glu Gly Trp Leu Leu Val Ala Leu Asp
                660                 665                 670
Tyr Ser Gln Ile Glu Leu Arg Val Leu Ala His Leu Ser Gly Asp Glu
                675                 680                 685
Asn Leu Ile Arg Val Phe Gln Glu Gly Arg Asp Ile His Thr Glu Thr
            690                 695                 700
Ala Ser Trp Met Phe Gly Val Pro Arg Glu Ala Val Asp Pro Leu Met
705                 710                 715                 720
Arg Arg Ala Ala Lys Thr Ile Asn Phe Gly Val Leu Tyr Gly Met Ser
                725                 730                 735
Ala His Arg Leu Ser Gln Glu Leu Ala Ile Pro Tyr Glu Glu Ala Gln
                740                 745                 750
Ala Phe Ile Glu Arg Tyr Phe Gln Ser Phe Pro Lys Val Arg Ala Trp
                755                 760                 765
Ile Glu Lys Thr Leu Glu Glu Gly Arg Arg Gly Tyr Val Glu Thr
            770                 775                 780
Leu Phe Gly Arg Arg Tyr Val Pro Asp Leu Glu Ala Arg Val Lys
785                 790                 795                 800
Ser Val Arg Glu Ala Ala Glu Arg Met Ala Phe Asn Met Pro Val Gln
                805                 810                 815
Gly Thr Ala Ala Asp Leu Met Lys Leu Ala Met Val Lys Leu Phe Pro
            820                 825                 830
Arg Leu Glu Glu Met Gly Ala Arg Met Leu Leu Gln Val His Asp Glu
            835                 840                 845
Leu Val Leu Glu Ala Pro Lys Glu Arg Ala Glu Ala Val Ala Arg Leu
    850                 855                 860
Ala Lys Glu Val Met Glu Gly Val Tyr Pro Leu Ala Val Pro Leu Glu
865                 870                 875                 880
Val Glu Val Gly Ile Gly Glu Asp Trp Leu Ser Ala Lys Glu
                885                 890

<210> SEQ ID NO 35
<211> LENGTH: 2742
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgggccatc atcatcatca tcatcatcat catcacagca gcggccatat cgaaggtcgt      60
catatgccga agaaggagaa gattaagttc ttcgacctgg tcgccaagaa gtactacgag     120
actgacaact acgaagtcga gattaaggag actaagcgcg gcaagtttcg cttcgccaaa     180
gccaagagcc cgtacaccgg caagatcttc tatcgcgtgc tgggcaaagc cggcggcggt     240
gtcactagtg ggatgctgcc cctctttgag cccaagggcc gggtcctcct ggtggacggc     300
```

```
caccacctgg cctaccgcac cttccacgcc ctgaagggcc tcaccaccag ccggggggag    360
ccggtgcagg cggtctacgg cttcgccaag agcctcctca aggccctcaa ggaggacggg    420
gacgcggtga tcgtggtctt tgacgccaag gcccctcct tccgccacga ggcctacggg     480
gggtacaagg cgggccgggc ccccacgccg gaggactttc ccggcaact cgccctcatc     540 aaggagctgg tggacctcct ggggctggcg cgcctcgagg tcccgggcta cgaggcggac    600
gacgtcctgc cagcctggc caagaaggcg aaaaggagg gctacgaggt ccgcatcctc      660
accgccgaca agacccttta ccagctcctt ccgaccgca tccacgtcct ccaccccgag     720
gggtacctca tcaccccggc ctggcttttgg aaaagtacg gcctgaggcc cgaccagtgg    780
gccgactacc gggccctgac cggggacgag tccgacaacc ttcccggggt caagggcatc    840
ggggagaaga cggcgaggaa gcttctggag gagtggggga gcctggaagc cctcctcaag    900
aacctggacc ggctgaagcc cgccatccgg gagaagatcc tggcccacat ggacgatctg    960
aagctctcct gggacctggc caaggtgcgc accgacctgc ccctggaggt ggacttcgcc   1020
aaaaggcggg agcccgaccg ggagaggctt agggcctttc tggagaggct tgagtttggc   1080
agcctcctcc acgagttcgg ccttctggaa agccccaagg ccctggagga ggcccccctgg  1140 cccccgccgg aaggggcctt cgtgggcttt gtgctttccc gcaaggagcc catgtgggcc   1200
gatcttctgg ccctggccgc cgccaggggg ggccgggtcc accggccccc cgagccttat   1260
aaagccctca gggacctgaa ggaggcgcgg ggcttctcg ccaaagacct gagcgttctg     1320
gccctgaggg aaggccttgg cctcccgccc ggcgacgacc ccatgctcct cgcctacctc   1380 ctggacccctt ccaacaccac ccccgagggg gtggcccggc gctacggcgg ggagtggacg  1440
gaggaggcgg gggagcgggc cgcccttttcc gagaggctct cgccaacct gtggggagg    1500 cttgaggggg aggagaggct cctttggctt taccgggagg tggagaggcc cctttccgct   1560
gtcctggccc acatggaggc cacggggtg cgcctgacg tggcctatct cagggccttg      1620
tccctggagg tggccgagga gatcgcccgc ctcgaggccg aggtcttccg cctggccggc   1680
caccccttca acctcaactc ccgggaccag ctggaaaggg tcctctttga cgagctaggg   1740
cttcccgcca tcggcaagac ggagaagacc ggcaagcgct ccaccagcgc cgccgtcctg   1800
gaggccctcc gcgaggccca ccccatcgtg gagaagatcc tgcagtaccg ggagctcacc   1860
aagctgaaga gcacctacat tgacccctttg ccggacctca tccaccccag gacgggccgc   1920
ctccacaccc gcttcaacca gacggccacg gccacgggca ggctaagtag ctccgatccc   1980
aacctccaga acatccccgt ccgcaccccg cttgggcaga ggatccgccg ggccttcatc   2040
gccgaggagg ggtggctatt ggtggccctg gactatagcc agatagagct cagggtgctg   2100
gcccacctct ccgcgacga gaacctgatc cgggtcttcc aggaggggcg ggacatccac   2160
acggagaccg ccagctggat gttcggcgtc cccgggagg ccgtggaccc cctgatgcgc    2220
cgggcggcca agaccatcaa cttcggggtc tctacggca tgtcggccca ccgcctctcc    2280
caggagctag ccatccctta cgaggaggcc caggccttca ttgagcgcta ctttcagagc   2340
ttccccaagg tgcgggcctg gattgagaag accctggagg agggcaggag gcgggggtac   2400
gtggagaccc tcttcggccg ccgccgctac gtgccagacc tagaggcccg ggtgaagagc   2460
gtgcgggagg cggccgagcg catggccttc aacatgcccg tccagggcac cgccgccgac   2520
ctcatgaagc tggctatggt gaagctcttc ccaggctggg aggaaatggg ggccaggatg   2580
ctccttcagg tccacgacga gctggtcctc gaggccccaa aagagagggc ggaggccgtg   2640
```

```
gcccggctgg ccaaggaggt catggagggg gtgtatcccc tggccgtgcc cctggaggtg    2700
gaggtgggga tagggagga ctggctctcc gccaaggagt ga                        2742
```

<210> SEQ ID NO 36
<211> LENGTH: 913
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 36

```
Met Gly His His His His His His His His Ser Ser Gly His
1               5                   10                  15

Ile Glu Gly Arg His Met Pro Lys Glu Lys Ile Lys Phe Phe Asp
            20                  25                  30

Leu Val Ala Lys Lys Tyr Tyr Glu Thr Asp Asn Tyr Glu Val Glu Ile
        35                  40                  45

Lys Glu Thr Lys Arg Gly Lys Phe Arg Phe Ala Lys Ala Lys Ser Pro
    50                  55                  60

Tyr Thr Gly Lys Ile Phe Tyr Arg Val Leu Gly Lys Ala Gly Gly Gly
65                  70                  75                  80

Val Thr Ser Gly Met Leu Pro Leu Phe Glu Pro Lys Gly Arg Val Leu
                85                  90                  95

Leu Val Asp Gly His His Leu Ala Tyr Arg Thr Phe His Ala Leu Lys
            100                 105                 110

Gly Leu Thr Thr Ser Arg Gly Glu Pro Val Gln Ala Val Tyr Gly Phe
        115                 120                 125

Ala Lys Ser Leu Leu Lys Ala Leu Lys Glu Asp Gly Asp Ala Val Ile
    130                 135                 140

Val Val Phe Asp Ala Lys Ala Pro Ser Phe Arg His Glu Ala Tyr Gly
145                 150                 155                 160

Gly Tyr Lys Ala Gly Arg Ala Pro Thr Pro Glu Asp Phe Pro Arg Gln
                165                 170                 175

Leu Ala Leu Ile Lys Glu Leu Val Asp Leu Leu Gly Leu Ala Arg Leu
            180                 185                 190

Glu Val Pro Gly Tyr Glu Ala Asp Asp Val Leu Ala Ser Leu Ala Lys
        195                 200                 205

Lys Ala Glu Lys Glu Gly Tyr Glu Val Arg Ile Leu Thr Ala Asp Lys
    210                 215                 220

Asp Leu Tyr Gln Leu Leu Ser Asp Arg Ile His Val Leu His Pro Glu
225                 230                 235                 240

Gly Tyr Leu Ile Thr Pro Ala Trp Leu Trp Glu Lys Tyr Gly Leu Arg
                245                 250                 255

Pro Asp Gln Trp Ala Asp Tyr Arg Ala Leu Thr Gly Asp Glu Ser Asp
            260                 265                 270

Asn Leu Pro Gly Val Lys Gly Ile Gly Glu Lys Thr Ala Arg Lys Leu
        275                 280                 285

Leu Glu Glu Trp Gly Ser Leu Glu Ala Leu Leu Lys Asn Leu Asp Arg
    290                 295                 300

Leu Lys Pro Ala Ile Arg Glu Lys Ile Leu Ala His Met Asp Asp Leu
305                 310                 315                 320

Lys Leu Ser Trp Asp Leu Ala Lys Val Arg Thr Asp Leu Pro Leu Glu
                325                 330                 335

Val Asp Phe Ala Lys Arg Arg Glu Pro Asp Arg Glu Arg Leu Arg Ala
```

-continued

```
            340                 345                 350
Phe Leu Glu Arg Leu Glu Phe Gly Ser Leu Leu His Glu Phe Gly Leu
            355                 360                 365

Leu Glu Ser Pro Lys Ala Leu Glu Ala Pro Trp Pro Pro Glu
        370                 375                 380

Gly Ala Phe Val Gly Phe Val Leu Ser Arg Lys Glu Pro Met Trp Ala
385                 390                 395                 400

Asp Leu Leu Ala Leu Ala Ala Arg Gly Gly Arg Val His Arg Ala
                405                 410                 415

Pro Glu Pro Tyr Lys Ala Leu Arg Asp Leu Lys Glu Ala Arg Gly Leu
                420                 425                 430

Leu Ala Lys Asp Leu Ser Val Leu Ala Leu Arg Glu Gly Leu Gly Leu
            435                 440                 445

Pro Pro Gly Asp Asp Pro Met Leu Leu Ala Tyr Leu Leu Asp Pro Ser
        450                 455                 460

Asn Thr Thr Pro Glu Gly Val Ala Arg Arg Tyr Gly Gly Glu Trp Thr
465                 470                 475                 480

Glu Glu Ala Gly Glu Arg Ala Ala Leu Ser Glu Arg Leu Phe Ala Asn
                485                 490                 495

Leu Trp Gly Arg Leu Glu Gly Glu Glu Arg Leu Leu Trp Leu Tyr Arg
            500                 505                 510

Glu Val Glu Arg Pro Leu Ser Ala Val Leu Ala His Met Glu Ala Thr
        515                 520                 525

Gly Val Arg Leu Asp Val Ala Tyr Leu Arg Ala Leu Ser Leu Glu Val
        530                 535                 540

Ala Glu Glu Ile Ala Arg Leu Glu Ala Glu Val Phe Arg Leu Ala Gly
545                 550                 555                 560

His Pro Phe Asn Leu Asn Ser Arg Asp Gln Leu Glu Arg Val Leu Phe
                565                 570                 575

Asp Glu Leu Gly Leu Pro Ala Ile Gly Lys Thr Glu Lys Thr Gly Lys
            580                 585                 590

Arg Ser Thr Ser Ala Ala Val Leu Glu Ala Leu Arg Glu Ala His Pro
        595                 600                 605

Ile Val Glu Lys Ile Leu Gln Tyr Arg Glu Leu Thr Lys Leu Lys Ser
        610                 615                 620

Thr Tyr Ile Asp Pro Leu Pro Asp Leu Ile His Pro Arg Thr Gly Arg
625                 630                 635                 640

Leu His Thr Arg Phe Asn Gln Thr Ala Thr Ala Thr Gly Arg Leu Ser
                645                 650                 655

Ser Ser Asp Pro Asn Leu Gln Asn Ile Pro Val Arg Thr Pro Leu Gly
            660                 665                 670

Gln Arg Ile Arg Arg Ala Phe Ile Ala Glu Glu Gly Trp Leu Leu Val
        675                 680                 685

Ala Leu Asp Tyr Ser Gln Ile Glu Leu Arg Val Leu Ala His Leu Ser
        690                 695                 700

Gly Asp Glu Asn Leu Ile Arg Val Phe Gln Glu Gly Arg Asp Ile His
705                 710                 715                 720

Thr Glu Thr Ala Ser Trp Met Phe Gly Val Pro Arg Glu Ala Val Asp
                725                 730                 735

Pro Leu Met Arg Arg Ala Ala Lys Thr Ile Asn Phe Gly Val Leu Tyr
            740                 745                 750

Gly Met Ser Ala His Arg Leu Ser Gln Glu Leu Ala Ile Pro Tyr Glu
        755                 760                 765
```

```
Glu Ala Gln Ala Phe Ile Glu Arg Tyr Phe Gln Ser Phe Pro Lys Val
        770                 775                 780
Arg Ala Trp Ile Glu Lys Thr Leu Glu Glu Gly Arg Arg Arg Gly Tyr
785                 790                 795                 800
Val Glu Thr Leu Phe Gly Arg Arg Tyr Val Pro Asp Leu Glu Ala
                805                 810                 815
Arg Val Lys Ser Val Arg Glu Ala Ala Glu Arg Met Ala Phe Asn Met
                820                 825                 830
Pro Val Gln Gly Thr Ala Ala Asp Leu Met Lys Leu Ala Met Val Lys
                835                 840                 845
Leu Phe Pro Arg Leu Glu Glu Met Gly Ala Arg Met Leu Leu Gln Val
        850                 855                 860
His Asp Glu Leu Val Leu Glu Ala Pro Lys Glu Arg Ala Glu Ala Val
865                 870                 875                 880
Ala Arg Leu Ala Lys Glu Val Met Glu Gly Val Tyr Pro Leu Ala Val
                885                 890                 895
Pro Leu Glu Val Glu Val Gly Ile Gly Glu Asp Trp Leu Ser Ala Lys
                900                 905                 910
Glu

<210> SEQ ID NO 37
<211> LENGTH: 893
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 37

His Met Pro Lys Lys Glu Lys Ile Lys Phe Phe Asp Leu Val Ala Lys
  1               5                  10                  15
Lys Tyr Tyr Glu Thr Asp Asn Tyr Glu Val Glu Ile Lys Glu Thr Lys
                20                  25                  30
Arg Gly Lys Phe Arg Phe Ala Lys Ala Lys Ser Pro Tyr Thr Gly Lys
            35                  40                  45
Ile Phe Tyr Arg Val Leu Gly Lys Ala Gly Gly Val Thr Ser Gly
        50                  55                  60
Met Leu Pro Leu Phe Glu Pro Lys Gly Arg Val Leu Leu Val Asp Gly
 65                  70                  75                  80
His His Leu Ala Tyr Arg Thr Phe His Ala Leu Lys Gly Leu Thr Thr
                 85                  90                  95
Ser Arg Gly Glu Pro Val Gln Ala Val Tyr Gly Phe Ala Lys Ser Leu
            100                 105                 110
Leu Lys Ala Leu Lys Glu Asp Gly Asp Ala Val Ile Val Val Phe Asp
        115                 120                 125
Ala Lys Ala Pro Ser Phe Arg His Glu Ala Tyr Gly Gly Tyr Lys Ala
    130                 135                 140
Gly Arg Ala Pro Thr Pro Glu Asp Phe Pro Arg Gln Leu Ala Leu Ile
145                 150                 155                 160
Lys Glu Leu Val Asp Leu Leu Gly Leu Ala Arg Leu Glu Val Pro Gly
                165                 170                 175
Tyr Glu Ala Asp Asp Val Leu Ala Ser Leu Ala Lys Lys Ala Glu Lys
            180                 185                 190
Glu Gly Tyr Glu Val Arg Ile Leu Thr Ala Asp Lys Asp Leu Tyr Gln
        195                 200                 205
```

```
Leu Leu Ser Asp Arg Ile His Val Leu His Pro Glu Gly Tyr Leu Ile
    210                 215                 220

Thr Pro Ala Trp Leu Trp Glu Lys Tyr Gly Leu Arg Pro Asp Gln Trp
225                 230                 235                 240

Ala Asp Tyr Arg Ala Leu Thr Gly Asp Glu Ser Asp Asn Leu Pro Gly
                245                 250                 255

Val Lys Gly Ile Gly Glu Lys Thr Ala Arg Lys Leu Leu Glu Glu Trp
            260                 265                 270

Gly Ser Leu Glu Ala Leu Leu Lys Asn Leu Asp Arg Leu Lys Pro Ala
        275                 280                 285

Ile Arg Glu Lys Ile Leu Ala His Met Asp Asp Leu Lys Leu Ser Trp
290                 295                 300

Asp Leu Ala Lys Val Arg Thr Asp Leu Pro Leu Glu Val Asp Phe Ala
305                 310                 315                 320

Lys Arg Arg Glu Pro Asp Arg Glu Arg Leu Arg Ala Phe Leu Glu Arg
                325                 330                 335

Leu Glu Phe Gly Ser Leu Leu His Glu Phe Gly Leu Leu Glu Ser Pro
            340                 345                 350

Lys Ala Leu Glu Glu Ala Pro Trp Pro Pro Glu Gly Ala Phe Val
        355                 360                 365

Gly Phe Val Leu Ser Arg Lys Glu Pro Met Trp Ala Asp Leu Leu Ala
370                 375                 380

Leu Ala Ala Arg Gly Gly Arg Val His Arg Ala Pro Glu Pro Tyr
385                 390                 395                 400

Lys Ala Leu Arg Asp Leu Lys Glu Ala Arg Gly Leu Leu Ala Lys Asp
                405                 410                 415

Leu Ser Val Leu Ala Leu Arg Glu Gly Leu Gly Leu Pro Pro Gly Asp
            420                 425                 430

Asp Pro Met Leu Leu Ala Tyr Leu Leu Asp Pro Ser Asn Thr Thr Pro
        435                 440                 445

Glu Gly Val Ala Arg Arg Tyr Gly Gly Glu Trp Thr Glu Glu Ala Gly
        450                 455                 460

Glu Arg Ala Ala Leu Ser Glu Arg Leu Phe Ala Asn Leu Trp Gly Arg
465                 470                 475                 480

Leu Glu Gly Glu Glu Arg Leu Leu Trp Leu Tyr Arg Glu Val Glu Arg
                485                 490                 495

Pro Leu Ser Ala Val Leu Ala His Met Glu Ala Thr Gly Val Arg Leu
            500                 505                 510

Asp Val Ala Tyr Leu Arg Ala Leu Ser Leu Glu Val Ala Glu Glu Ile
        515                 520                 525

Ala Arg Leu Glu Ala Glu Val Phe Arg Leu Ala Gly His Pro Phe Asn
530                 535                 540

Leu Asn Ser Arg Asp Gln Leu Glu Arg Val Leu Phe Asp Glu Leu Gly
545                 550                 555                 560

Leu Pro Ala Ile Gly Lys Thr Glu Lys Thr Gly Lys Arg Ser Thr Ser
                565                 570                 575

Ala Ala Val Leu Glu Ala Leu Arg Glu Ala His Pro Ile Val Glu Lys
            580                 585                 590

Ile Leu Gln Tyr Arg Glu Leu Thr Lys Leu Lys Ser Thr Tyr Ile Asp
        595                 600                 605

Pro Leu Pro Asp Leu Ile His Pro Arg Thr Gly Arg Leu His Thr Arg
610                 615                 620
```

```
Phe Asn Gln Thr Ala Thr Ala Thr Gly Arg Leu Ser Ser Ser Asp Pro
625                 630                 635                 640

Asn Leu Gln Asn Ile Pro Val Arg Thr Pro Leu Gly Gln Arg Ile Arg
            645                 650                 655

Arg Ala Phe Ile Ala Glu Glu Gly Trp Leu Leu Val Ala Leu Asp Tyr
            660                 665                 670

Ser Gln Ile Glu Leu Arg Val Leu Ala His Leu Ser Gly Asp Glu Asn
            675                 680                 685

Leu Ile Arg Val Phe Gln Glu Gly Arg Asp Ile His Thr Glu Thr Ala
690                 695                 700

Ser Trp Met Phe Gly Val Pro Arg Glu Ala Val Asp Pro Leu Met Arg
705                 710                 715                 720

Arg Ala Ala Lys Thr Ile Asn Phe Gly Val Leu Tyr Gly Met Ser Ala
                725                 730                 735

His Arg Leu Ser Gln Glu Leu Ala Ile Pro Tyr Glu Glu Ala Gln Ala
            740                 745                 750

Phe Ile Glu Arg Tyr Phe Gln Ser Phe Pro Lys Val Arg Ala Trp Ile
            755                 760                 765

Glu Lys Thr Leu Glu Glu Gly Arg Arg Arg Gly Tyr Val Glu Thr Leu
770                 775                 780

Phe Gly Arg Arg Arg Tyr Val Pro Asp Leu Glu Ala Arg Val Lys Ser
785                 790                 795                 800

Val Arg Glu Ala Ala Glu Arg Met Ala Phe Asn Met Pro Val Gln Gly
                805                 810                 815

Thr Ala Ala Asp Leu Met Lys Leu Ala Met Val Lys Leu Phe Pro Arg
            820                 825                 830

Leu Glu Glu Met Gly Ala Arg Met Leu Leu Gln Val His Asp Glu Leu
            835                 840                 845

Val Leu Glu Ala Pro Lys Glu Arg Ala Glu Ala Val Ala Arg Leu Ala
850                 855                 860

Lys Glu Val Met Glu Gly Val Tyr Pro Leu Ala Val Pro Leu Glu Val
865                 870                 875                 880

Glu Val Gly Ile Gly Glu Asp Trp Leu Ser Ala Lys Glu
                885                 890

<210> SEQ ID NO 38
<211> LENGTH: 1881
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atgggccatc atcatcatca tcatcatcat catcacagca gcggccatat cgaaggtcgt      60
catatgtcca agaagcagaa actgaagttc tacgacatta aggcgaagca ggcgtttgag     120
accgaccagt acgaggttat tgagaagcag accgcccgcg gtccgatgat gttcgccgtg     180
gccaaatcgc cgtacaccgg cattaaagtg taccgcctgt aggcaagaa gaaaggcggc     240 ggtgtcacta gtcccaaggc cctggaggag cccccctggc cccgccgga gggggccttc     300 gtgggctttg tgctttcccg caaggagccc atgtgggccg atcttctggc cctggccgcc     360
gccagggggg ccgggtcca ccgggccccc gagcctttata agccctcag ggacctgaag     420 gaggcgcggg gcttctcgc caagacctg agcgttctgg ccctgaggga aggccttggc     480
ctcccgcccg cgacgaccc catgctcctc gcctacctcc tggacccttc aacaccacc     540
```

```
cccgagggg   tggcccggcg   ctacggcggg   gagtggacgg   aggaggcggg   ggagcgggcc    600
gcccttccg   agaggctctt   cgccaacctg   tgggggaggc   ttgaggggga   ggagaggctc    660
ctttggcttt  accgggaggt   ggagaggccc   ctttccgctg   tcctggccca   catggaggcc    720
acggggtgc   gcctggacgt   ggcctatctc   agggccttgt   ccctggaggt   ggccgaggag    780
atcgcccgcc  tcgaggccga   ggtcttccgc   ctggccggcc   acccttcaa    cctcaactcc    840
cgggaccagc  tggaaagggt   cctctttgac   gagctagggc   ttcccgccat   cggcaagacg    900
gagaagaccg  gcaagcgctc   caccagcgcc   gccgtcctgg   aggccctccg   cgaggcccac    960
cccatcgtgg  agaagatcct   gcagtaccgg   gagctcacca   agctgaagag   cacctacatt   1020
gaccccttgc  cggacctcat   ccaccccagg   acgggccgcc   tccacacccg   cttcaaccag   1080
acggccacgg  ccacgggcag   gctaagtagc   tccgatccca   acctccagaa   catccccgtc   1140
cgcacccccgc ttgggcagag   gatccgccgg   gccttcatcg   ccgaggaggg   gtggctattg   1200
gtggccctgg  actatagcca   gatagagctc   agggtgctgg   cccacctctc   cggcgacgag   1260
aacctgatcc  gggtcttcca   ggaggggcgg   gacatccaca   cggagaccgc   cagctggatg   1320
ttcggcgtcc  cccgggaggc   cgtggacccc   ctgatgcgcc   gggcggccaa   gaccatcaac   1380
ttcggggtcc  tctacggcat   gtcggcccac   cgcctctccc   aggagctagc   catcccttac   1440
gaggaggccc  aggccttcat   tgagcgctac   tttcagagct   tccccaaggt   gcgggcctgg   1500
attgagaaga  ccctggagga   gggcaggagg   cgggggtacg   tggagaccct   cttcggccgc   1560
cgccgctacg  tgccagacct   agaggccgg    gtgaagagcg   tgcggaggc   ggccgagcgc   1620
atggccttca  acatgcccgt   ccagggcacc   gccgccgacc   tcatgaagct   ggctatggtg   1680
aagctcttcc  ccaggctgga   ggaaatgggg   gccaggatgc   tccttcaggt   ccacgacgag   1740
ctggtcctcg  aggccccaaa   agagagggcg   gaggccgtgg   cccggctggc   caaggaggtc   1800
atggagggg   tgtatcccct   ggccgtgccc   ctggaggtgg   aggtggggat   aggggaggac   1860
tggctctccg  ccaaggagtg   a                                                   1881
```

<210> SEQ ID NO 39
<211> LENGTH: 626
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 39

```
Met Gly His His His His His His His His Ser Ser Gly His
 1               5                   10                  15

Ile Glu Gly Arg His Met Ser Lys Lys Gln Lys Leu Lys Phe Tyr Asp
                20                  25                  30

Ile Lys Ala Lys Gln Ala Phe Glu Thr Asp Gln Tyr Glu Val Ile Glu
        35                  40                  45

Lys Gln Thr Ala Arg Gly Pro Met Met Phe Ala Val Ala Lys Ser Pro
    50                  55                  60

Tyr Thr Gly Ile Lys Val Tyr Arg Leu Leu Gly Lys Lys Lys Gly Gly
65                  70                  75                  80

Gly Val Thr Ser Pro Lys Ala Leu Glu Glu Ala Pro Trp Pro Pro
                85                  90                  95

Glu Gly Ala Phe Val Gly Phe Val Leu Ser Arg Lys Glu Pro Met Trp
            100                 105                 110
```

-continued

```
Ala Asp Leu Leu Ala Leu Ala Ala Arg Gly Gly Arg Val His Arg
            115                 120                 125
Ala Pro Glu Pro Tyr Lys Ala Leu Arg Asp Leu Lys Glu Ala Arg Gly
        130                 135                 140
Leu Leu Ala Lys Asp Leu Ser Val Leu Ala Leu Arg Glu Gly Leu Gly
145                 150                 155                 160
Leu Pro Pro Gly Asp Pro Met Leu Leu Ala Tyr Leu Leu Asp Pro
                165                 170                 175
Ser Asn Thr Thr Pro Glu Gly Val Ala Arg Arg Tyr Gly Gly Glu Trp
            180                 185                 190
Thr Glu Glu Ala Gly Glu Arg Ala Ala Leu Ser Glu Arg Leu Phe Ala
        195                 200                 205
Asn Leu Trp Gly Arg Leu Glu Gly Glu Glu Arg Leu Leu Trp Leu Tyr
    210                 215                 220
Arg Glu Val Glu Arg Pro Leu Ser Ala Val Leu Ala His Met Glu Ala
225                 230                 235                 240
Thr Gly Val Arg Leu Asp Val Ala Tyr Leu Arg Ala Leu Ser Leu Glu
                245                 250                 255
Val Ala Glu Glu Ile Ala Arg Leu Glu Ala Glu Val Phe Arg Leu Ala
            260                 265                 270
Gly His Pro Phe Asn Leu Asn Ser Arg Asp Gln Leu Glu Arg Val Leu
        275                 280                 285
Phe Asp Glu Leu Gly Leu Pro Ala Ile Gly Lys Thr Glu Lys Thr Gly
    290                 295                 300
Lys Arg Ser Thr Ser Ala Ala Val Leu Glu Ala Leu Arg Glu Ala His
305                 310                 315                 320
Pro Ile Val Glu Lys Ile Leu Gln Tyr Arg Glu Leu Thr Lys Leu Lys
                325                 330                 335
Ser Thr Tyr Ile Asp Pro Leu Pro Asp Leu Ile His Pro Arg Thr Gly
            340                 345                 350
Arg Leu His Thr Arg Phe Asn Gln Thr Ala Thr Ala Thr Gly Arg Leu
        355                 360                 365
Ser Ser Ser Asp Pro Asn Leu Gln Asn Ile Pro Val Arg Thr Pro Leu
    370                 375                 380
Gly Gln Arg Ile Arg Arg Ala Phe Ile Ala Glu Glu Gly Trp Leu Leu
385                 390                 395                 400
Val Ala Leu Asp Tyr Ser Gln Ile Glu Leu Arg Val Leu Ala His Leu
                405                 410                 415
Ser Gly Asp Glu Asn Leu Ile Arg Val Phe Gln Glu Gly Arg Asp Ile
            420                 425                 430
His Thr Glu Thr Ala Ser Trp Met Phe Gly Val Pro Arg Glu Ala Val
        435                 440                 445
Asp Pro Leu Met Arg Arg Ala Ala Lys Thr Ile Asn Phe Gly Val Leu
    450                 455                 460
Tyr Gly Met Ser Ala His Arg Leu Ser Gln Glu Leu Ala Ile Pro Tyr
465                 470                 475                 480
Glu Glu Ala Gln Ala Phe Ile Glu Arg Tyr Phe Gln Ser Phe Pro Lys
                485                 490                 495
Val Arg Ala Trp Ile Glu Lys Thr Leu Glu Glu Gly Arg Arg Arg Gly
            500                 505                 510
Tyr Val Glu Thr Leu Phe Gly Arg Arg Arg Tyr Val Pro Asp Leu Glu
        515                 520                 525
Ala Arg Val Lys Ser Val Arg Glu Ala Ala Glu Arg Met Ala Phe Asn
```

```
                    530                 535                 540
Met Pro Val Gln Gly Thr Ala Ala Asp Leu Met Lys Leu Ala Met Val
545                 550                 555                 560

Lys Leu Phe Pro Arg Leu Glu Glu Met Gly Ala Arg Met Leu Leu Gln
                565                 570                 575

Val His Asp Glu Leu Val Leu Glu Ala Pro Lys Glu Arg Ala Glu Ala
            580                 585                 590

Val Ala Arg Leu Ala Lys Glu Val Met Glu Gly Val Tyr Pro Leu Ala
            595                 600                 605

Val Pro Leu Glu Val Glu Val Gly Ile Gly Glu Asp Trp Leu Ser Ala
            610                 615                 620

Lys Glu
625

<210> SEQ ID NO 40
<211> LENGTH: 606
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 40

His Met Ser Lys Lys Gln Lys Leu Lys Phe Tyr Asp Ile Lys Ala Lys
 1               5                  10                  15

Gln Ala Phe Glu Thr Asp Gln Tyr Glu Val Ile Glu Lys Gln Thr Ala
                20                  25                  30

Arg Gly Pro Met Met Phe Ala Val Ala Lys Ser Pro Tyr Thr Gly Ile
            35                  40                  45

Lys Val Tyr Arg Leu Leu Gly Lys Lys Gly Gly Val Thr Ser
    50                  55                  60

Pro Lys Ala Leu Glu Glu Ala Pro Trp Pro Pro Glu Gly Ala Phe
65                  70                  75                  80

Val Gly Phe Val Leu Ser Arg Lys Glu Pro Met Trp Ala Asp Leu Leu
                85                  90                  95

Ala Leu Ala Ala Arg Gly Gly Arg Val His Arg Ala Pro Glu Pro
            100                 105                 110

Tyr Lys Ala Leu Arg Asp Leu Lys Glu Ala Arg Gly Leu Leu Ala Lys
        115                 120                 125

Asp Leu Ser Val Leu Ala Leu Arg Glu Gly Leu Gly Leu Pro Pro Gly
    130                 135                 140

Asp Asp Pro Met Leu Leu Ala Tyr Leu Leu Asp Pro Ser Asn Thr Thr
145                 150                 155                 160

Pro Glu Gly Val Ala Arg Arg Tyr Gly Gly Glu Trp Thr Glu Glu Ala
                165                 170                 175

Gly Glu Arg Ala Ala Leu Ser Glu Arg Leu Phe Ala Asn Leu Trp Gly
            180                 185                 190

Arg Leu Glu Gly Glu Glu Arg Leu Leu Trp Leu Tyr Arg Glu Val Glu
        195                 200                 205

Arg Pro Leu Ser Ala Val Leu Ala His Met Glu Ala Thr Gly Val Arg
    210                 215                 220

Leu Asp Val Ala Tyr Leu Arg Ala Leu Ser Leu Glu Val Ala Glu Glu
225                 230                 235                 240

Ile Ala Arg Leu Glu Ala Glu Val Phe Arg Leu Ala Gly His Pro Phe
                245                 250                 255
```

```
Asn Leu Asn Ser Arg Asp Gln Leu Glu Arg Val Leu Phe Asp Glu Leu
            260                 265                 270

Gly Leu Pro Ala Ile Gly Lys Thr Glu Lys Thr Gly Lys Arg Ser Thr
        275                 280                 285

Ser Ala Ala Val Leu Glu Ala Leu Arg Glu Ala His Pro Ile Val Glu
    290                 295                 300

Lys Ile Leu Gln Tyr Arg Glu Leu Thr Lys Leu Lys Ser Thr Tyr Ile
305                 310                 315                 320

Asp Pro Leu Pro Asp Leu Ile His Pro Arg Thr Gly Arg Leu His Thr
                325                 330                 335

Arg Phe Asn Gln Thr Ala Thr Ala Thr Gly Arg Leu Ser Ser Ser Asp
            340                 345                 350

Pro Asn Leu Gln Asn Ile Pro Val Arg Thr Pro Leu Gly Gln Arg Ile
        355                 360                 365

Arg Arg Ala Phe Ile Ala Glu Glu Gly Trp Leu Leu Val Ala Leu Asp
    370                 375                 380

Tyr Ser Gln Ile Glu Leu Arg Val Leu Ala His Leu Ser Gly Asp Glu
385                 390                 395                 400

Asn Leu Ile Arg Val Phe Gln Glu Gly Arg Asp Ile His Thr Glu Thr
                405                 410                 415

Ala Ser Trp Met Phe Gly Val Pro Arg Glu Ala Val Asp Pro Leu Met
            420                 425                 430

Arg Arg Ala Ala Lys Thr Ile Asn Phe Gly Val Leu Tyr Gly Met Ser
        435                 440                 445

Ala His Arg Leu Ser Gln Glu Leu Ala Ile Pro Tyr Glu Glu Ala Gln
    450                 455                 460

Ala Phe Ile Glu Arg Tyr Phe Gln Ser Phe Pro Lys Val Arg Ala Trp
465                 470                 475                 480

Ile Glu Lys Thr Leu Glu Glu Gly Arg Arg Arg Gly Tyr Val Glu Thr
                485                 490                 495

Leu Phe Gly Arg Arg Arg Tyr Val Pro Asp Leu Glu Ala Arg Val Lys
            500                 505                 510

Ser Val Arg Glu Ala Ala Glu Arg Met Ala Phe Asn Met Pro Val Gln
        515                 520                 525

Gly Thr Ala Ala Asp Leu Met Lys Leu Ala Met Val Lys Leu Phe Pro
    530                 535                 540

Arg Leu Glu Glu Met Gly Ala Arg Met Leu Leu Gln Val His Asp Glu
545                 550                 555                 560

Leu Val Leu Glu Ala Pro Lys Glu Arg Ala Glu Ala Val Ala Arg Leu
                565                 570                 575

Ala Lys Glu Val Met Glu Gly Val Tyr Pro Leu Ala Val Pro Leu Glu
            580                 585                 590

Val Glu Val Gly Ile Gly Glu Asp Trp Leu Ser Ala Lys Glu
        595                 600                 605

<210> SEQ ID NO 41
<211> LENGTH: 1878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgggccatc atcatcatca tcatcatcat catcacagca gcggccatat cgaaggtcgt      60
```

```
catatgccga agaaggagaa gattaagttc ttcgacctgg tcgccaagaa gtactacgag    120
actgacaact acgaagtcga gattaaggag actaagcgcg gcaagtttcg cttcgccaaa    180
gccaagagcc cgtacaccgg caagatcttc tatcgcgtgc tgggcaaagc cggcggcggt    240
gtcactagtc ccaaggccct ggaggaggcc cctggcccc cgccgaagg ggccttcgtg     300 ggctttgtgc tttcccgcaa ggagcccatg tgggccgatc ttctggccct ggccgccgcc    360 aggggggggcc gggtccaccg gccccccgag ccttataaag ccctcaggga cctgaaggag    420 gcgcggggc ttctcgccaa agacctgagc gttctggccc tgagggaagg ccttggcctc    480
ccgcccggcg acgaccccat gctcctcgcc tacctcctgg acccttccaa caccacccc    540 gaggggggtgg cccggcgcta cggcggggag tggacggagg aggcggggga gcgggccgcc    600
ctttccgaga ggctcttcgc caacctgtgg ggaggcttg aggggagga gaggctcctt    660 tggctttacc gggaggtgga gaggcccctt tccgctgtcc tggcccacat ggaggccacg    720
ggggtgcgcc tggacgtggc ctatctcagg gccttgtccc tggaggtggc cgaggagatc    780
gcccgcctcg aggccgaggt cttccgcctg ccggccacc ccttcaacct caactcccgg    840
gaccagctgg aaagggtcct ctttgacgag ctagggcttc cgccatcgg caagacggag    900 aagaccggca agcgctccac cagcgccgcc gtcctggagg ccctccgcga ggcccacccc    960
atcgtggaga gatcctgca gtaccgggag ctcaccaagc tgaagagcac ctacattgac   1020
cccttgccgg acctcatcca ccccaggacg ggccgcctcc acacccgctt caaccagacg   1080
gccacggcca cgggcaggct aagtagctcc gatcccaacc tccagaacat cccgtccgc   1140 accccgcttg gcagaggat ccgccggcc ttcatcgccg aggaggggtg gctattggtg   1200
gccctggact atagccagat agagctcagg gtgctggccc acctctccgg cgacgagaac   1260
ctgatccggg tcttccagga ggggcgggac atccacacgg agaccgccag ctggatgttc   1320
ggcgtccccc gggaggccgt ggacccctg atgcgccggg cggccaagac catcaacttc   1380
ggggtcctct acggcatgtc ggcccaccgc ctctcccagg agctagccat cccttacgag   1440
gaggcccagg ccttcattga gcgctacttt cagagcttcc ccaaggtgcg ggcctggatt   1500
gagaagaccc tggaggaggg caggaggcgg gggtacgtgg agaccctctt cggccgccgc   1560
cgctacgtgc cagacctaga ggcccgggtg aagagcgtgc gggaggcggc cgagcgcatg   1620
gccttcaaca tgcccgtcca gggcaccgcc gccgacctca tgaagctggc tatggtgaag   1680
ctcttcccca ggctggagga aatgggggcc aggatgctcc ttcaggtcca cgacgagctg   1740
gtcctcgagg ccccaaaaga gagggcggag ccgtggccc ggctggccaa ggaggtcatg   1800 gaggggtgt atcccctggc cgtgcccctg gaggtggagg tggggatagg ggaggactgg   1860
ctctccgcca aggagtga                                                 1878
```

<210> SEQ ID NO 42
<211> LENGTH: 625
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 42

```
Met Gly His His His His His His His His His Ser Ser Gly His
 1               5                  10                  15

Ile Glu Gly Arg His Met Pro Lys Lys Glu Lys Ile Lys Phe Phe Asp
            20                  25                  30
```

Leu Val Ala Lys Lys Tyr Tyr Glu Thr Asp Asn Tyr Val Glu Ile
    35                  40                  45

Lys Glu Thr Lys Arg Gly Lys Phe Arg Phe Ala Lys Ala Lys Ser Pro
 50                  55                  60

Tyr Thr Gly Lys Ile Phe Tyr Arg Val Leu Gly Lys Ala Gly Gly Gly
 65                  70                  75                  80

Val Thr Ser Pro Lys Ala Leu Glu Glu Ala Pro Trp Pro Pro Pro Glu
                 85                  90                  95

Gly Ala Phe Val Gly Phe Val Leu Ser Arg Lys Glu Pro Met Trp Ala
                100                 105                 110

Asp Leu Leu Ala Leu Ala Ala Arg Gly Gly Arg Val His Arg Ala
    115                 120                 125

Pro Glu Pro Tyr Lys Ala Leu Arg Asp Leu Lys Glu Ala Arg Gly Leu
    130                 135                 140

Leu Ala Lys Asp Leu Ser Val Leu Ala Leu Arg Glu Gly Leu Gly Leu
145                 150                 155                 160

Pro Pro Gly Asp Asp Pro Met Leu Leu Ala Tyr Leu Leu Asp Pro Ser
                165                 170                 175

Asn Thr Thr Pro Glu Gly Val Ala Arg Arg Tyr Gly Gly Glu Trp Thr
                180                 185                 190

Glu Glu Ala Gly Glu Arg Ala Ala Leu Ser Glu Arg Leu Phe Ala Asn
                195                 200                 205

Leu Trp Gly Arg Leu Glu Gly Glu Glu Arg Leu Leu Trp Leu Tyr Arg
    210                 215                 220

Glu Val Glu Arg Pro Leu Ser Ala Val Leu Ala His Met Glu Ala Thr
225                 230                 235                 240

Gly Val Arg Leu Asp Val Ala Tyr Leu Arg Ala Leu Ser Leu Glu Val
                245                 250                 255

Ala Glu Glu Ile Ala Arg Leu Glu Ala Glu Val Phe Arg Leu Ala Gly
                260                 265                 270

His Pro Phe Asn Leu Asn Ser Arg Asp Gln Leu Glu Arg Val Leu Phe
    275                 280                 285

Asp Glu Leu Gly Leu Pro Ala Ile Gly Lys Thr Glu Lys Thr Gly Lys
    290                 295                 300

Arg Ser Thr Ser Ala Ala Val Leu Glu Ala Leu Arg Glu Ala His Pro
305                 310                 315                 320

Ile Val Glu Lys Ile Leu Gln Tyr Arg Glu Leu Thr Lys Leu Lys Ser
                325                 330                 335

Thr Tyr Ile Asp Pro Leu Pro Asp Leu Ile His Pro Thr Gly Arg
                340                 345                 350

Leu His Thr Arg Phe Asn Gln Thr Ala Thr Ala Thr Gly Arg Leu Ser
    355                 360                 365

Ser Ser Asp Pro Asn Leu Gln Asn Ile Pro Val Arg Thr Pro Leu Gly
370                 375                 380

Gln Arg Ile Arg Arg Ala Phe Ile Ala Glu Glu Gly Trp Leu Leu Val
385                 390                 395                 400

Ala Leu Asp Tyr Ser Gln Ile Glu Leu Arg Val Leu Ala His Leu Ser
                405                 410                 415

Gly Asp Glu Asn Leu Ile Arg Val Phe Gln Glu Gly Arg Asp Ile His
                420                 425                 430

Thr Glu Thr Ala Ser Trp Met Phe Gly Val Pro Arg Glu Ala Val Asp
                435                 440                 445

Pro Leu Met Arg Arg Ala Ala Lys Thr Ile Asn Phe Gly Val Leu Tyr

```
                450                 455                 460
Gly Met Ser Ala His Arg Leu Ser Gln Glu Leu Ala Ile Pro Tyr Glu
465                 470                 475                 480

Glu Ala Gln Ala Phe Ile Glu Arg Tyr Phe Gln Ser Phe Pro Lys Val
                485                 490                 495

Arg Ala Trp Ile Glu Lys Thr Leu Glu Gly Arg Arg Gly Tyr
            500                 505                 510

Val Glu Thr Leu Phe Gly Arg Arg Tyr Val Pro Asp Leu Glu Ala
            515                 520                 525

Arg Val Lys Ser Val Arg Glu Ala Ala Glu Arg Met Ala Phe Asn Met
            530                 535                 540

Pro Val Gln Gly Thr Ala Ala Asp Leu Met Lys Leu Ala Met Val Lys
545                 550                 555                 560

Leu Phe Pro Arg Leu Glu Glu Met Gly Ala Arg Met Leu Leu Gln Val
                565                 570                 575

His Asp Glu Leu Val Leu Glu Ala Pro Lys Glu Arg Ala Glu Ala Val
                580                 585                 590

Ala Arg Leu Ala Lys Glu Val Met Glu Gly Val Tyr Pro Leu Ala Val
            595                 600                 605

Pro Leu Glu Val Glu Val Gly Ile Gly Glu Asp Trp Leu Ser Ala Lys
            610                 615                 620

Glu
625

<210> SEQ ID NO 43
<211> LENGTH: 605
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 43

His Met Pro Lys Lys Glu Lys Ile Lys Phe Phe Asp Leu Val Ala Lys
1               5                  10                  15

Lys Tyr Tyr Glu Thr Asp Asn Tyr Glu Val Glu Ile Lys Glu Thr Lys
            20                  25                  30

Arg Gly Lys Phe Arg Phe Ala Lys Ala Lys Ser Pro Tyr Thr Gly Lys
        35                  40                  45

Ile Phe Tyr Arg Val Leu Gly Lys Ala Gly Gly Val Thr Ser Pro
    50                  55                  60

Lys Ala Leu Glu Glu Ala Pro Trp Pro Pro Glu Gly Ala Phe Val
65                  70                  75                  80

Gly Phe Val Leu Ser Arg Lys Glu Pro Met Trp Ala Asp Leu Leu Ala
                85                  90                  95

Leu Ala Ala Ala Arg Gly Gly Arg Val His Arg Ala Pro Glu Pro Tyr
            100                 105                 110

Lys Ala Leu Arg Asp Leu Lys Glu Ala Arg Gly Leu Leu Ala Lys Asp
            115                 120                 125

Leu Ser Val Leu Ala Leu Arg Glu Gly Leu Gly Leu Pro Pro Gly Asp
            130                 135                 140

Asp Pro Met Leu Leu Ala Tyr Leu Leu Asp Pro Ser Asn Thr Thr Pro
145                 150                 155                 160

Glu Gly Val Ala Arg Arg Tyr Gly Gly Glu Trp Thr Glu Glu Ala Gly
                165                 170                 175
```

```
Glu Arg Ala Ala Leu Ser Glu Arg Leu Phe Ala Asn Leu Trp Gly Arg
            180                 185                 190

Leu Glu Gly Glu Glu Arg Leu Leu Trp Leu Tyr Arg Glu Val Glu Arg
        195                 200                 205

Pro Leu Ser Ala Val Leu Ala His Met Glu Ala Thr Gly Val Arg Leu
    210                 215                 220

Asp Val Ala Tyr Leu Arg Ala Leu Ser Leu Glu Val Ala Glu Glu Ile
225                 230                 235                 240

Ala Arg Leu Glu Ala Glu Val Phe Arg Leu Ala Gly His Pro Phe Asn
                245                 250                 255

Leu Asn Ser Arg Asp Gln Leu Glu Arg Val Leu Phe Asp Glu Leu Gly
            260                 265                 270

Leu Pro Ala Ile Gly Lys Thr Glu Lys Thr Gly Lys Arg Ser Thr Ser
        275                 280                 285

Ala Ala Val Leu Glu Ala Leu Arg Glu Ala His Pro Ile Val Glu Lys
    290                 295                 300

Ile Leu Gln Tyr Arg Glu Leu Thr Lys Leu Lys Ser Thr Tyr Ile Asp
305                 310                 315                 320

Pro Leu Pro Asp Leu Ile His Pro Arg Thr Gly Arg Leu His Thr Arg
                325                 330                 335

Phe Asn Gln Thr Ala Thr Ala Thr Gly Arg Leu Ser Ser Ser Asp Pro
            340                 345                 350

Asn Leu Gln Asn Ile Pro Val Arg Thr Pro Leu Gly Gln Arg Ile Arg
        355                 360                 365

Arg Ala Phe Ile Ala Glu Glu Gly Trp Leu Leu Val Ala Leu Asp Tyr
    370                 375                 380

Ser Gln Ile Glu Leu Arg Val Leu Ala His Leu Ser Gly Asp Glu Asn
385                 390                 395                 400

Leu Ile Arg Val Phe Gln Gly Arg Asp Ile His Thr Glu Thr Ala
                405                 410                 415

Ser Trp Met Phe Gly Val Pro Arg Glu Ala Val Asp Pro Leu Met Arg
            420                 425                 430

Arg Ala Ala Lys Thr Ile Asn Phe Gly Val Leu Tyr Gly Met Ser Ala
        435                 440                 445

His Arg Leu Ser Gln Glu Leu Ala Ile Pro Tyr Glu Glu Ala Gln Ala
    450                 455                 460

Phe Ile Glu Arg Tyr Phe Gln Ser Phe Pro Lys Val Arg Ala Trp Ile
465                 470                 475                 480

Glu Lys Thr Leu Glu Glu Gly Arg Arg Gly Tyr Val Glu Thr Leu
                485                 490                 495

Phe Gly Arg Arg Arg Tyr Val Pro Asp Leu Glu Ala Arg Val Lys Ser
            500                 505                 510

Val Arg Glu Ala Ala Glu Arg Met Ala Phe Asn Met Pro Val Gln Gly
        515                 520                 525

Thr Ala Ala Asp Leu Met Lys Leu Ala Met Val Lys Leu Phe Pro Arg
    530                 535                 540

Leu Glu Glu Met Gly Ala Arg Met Leu Leu Gln Val His Asp Glu Leu
545                 550                 555                 560

Val Leu Glu Ala Pro Lys Glu Arg Ala Glu Ala Val Ala Arg Leu Ala
                565                 570                 575

Lys Glu Val Met Glu Gly Val Tyr Pro Leu Ala Val Pro Leu Glu Val
            580                 585                 590

Glu Val Gly Ile Gly Glu Asp Trp Leu Ser Ala Lys Glu
```

<210> SEQ ID NO 44
<211> LENGTH: 195
<212> TYPE: DNA
<213> ORGANISM: Sulfolobus solfataricus

<400> SEQUENCE: 44

| | | | | |
|---|---|---|---|---|
| atggcaacag taaagttcaa gtacaaagga gaagagaagc aagtagatat aagtaagata | | | | 60 |
| aagaaggtat ggagagtagg caaaatgata agcttcacct atgatgaggg tggaggaaag | | | | 120 |
| actggtagag gagctgtaag cgagaaagac gctccaaaag aactactaca atgttagag | | | | 180 |
| aagcaaaaga agtaa | | | | 195 |

<210> SEQ ID NO 45
<211> LENGTH: 195
<212> TYPE: DNA
<213> ORGANISM: Sulfolobus solfataricus

<400> SEQUENCE: 45

| | | | | |
|---|---|---|---|---|
| atggcaacag taaagttcaa gtataaagga gaagaaaaac aagtagacat aagtaagata | | | | 60 |
| aagaaggtat ggagagtcgg aaagatgata agctttacct atgatgaggg tggaggaaag | | | | 120 |
| actggtagag gagcagtaag cgagaaagat gctccaaaag agctattaca atgttagag | | | | 180 |
| aaacaaaaga agtaa | | | | 195 |

<210> SEQ ID NO 46
<211> LENGTH: 207
<212> TYPE: DNA
<213> ORGANISM: Sulfolobus solfataricus

<400> SEQUENCE: 46

| | | | | |
|---|---|---|---|---|
| ttggagatat caatggcaac agtaaagttc aagtacaagg gagaagagaa ggaagtagat | | | | 60 |
| ataagtaaga taaagaaggt atggagagta ggcaaaatga taagtttcac ctatgatgag | | | | 120 |
| ggtggaggaa agactggtag aggagctgta agcgagaaag acgctccaaa agaactacta | | | | 180 |
| caatgttag aaaagcaaaa gaaataa | | | | 207 |

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agccaaggcc aatatctaag taac                                              24

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgaagcattg gccgtaagtg                                                   20

<210> SEQ ID NO 49
<211> LENGTH: 865

```
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 49

Met Gly His His His His His His His His Ser Ser Gly His
 1               5                  10                  15

Ile Glu Gly Arg His Met Ile Leu Asp Val Asp Tyr Ile Thr Glu Glu
             20                  25                  30

Gly Lys Pro Val Ile Arg Leu Phe Lys Lys Glu Asn Gly Lys Phe Lys
         35                  40                  45

Ile Glu His Asp Arg Thr Phe Arg Pro Tyr Ile Tyr Ala Leu Leu Arg
     50                  55                  60

Asp Asp Ser Lys Ile Glu Glu Val Lys Lys Ile Thr Gly Glu Arg His
 65                  70                  75                  80

Gly Lys Ile Val Arg Ile Val Asp Val Glu Lys Val Glu Lys Lys Phe
                 85                  90                  95

Leu Gly Lys Pro Ile Thr Val Trp Lys Leu Tyr Leu Glu His Pro Gln
            100                 105                 110

Asp Val Pro Thr Ile Arg Glu Lys Val Arg Glu His Pro Ala Val Val
        115                 120                 125

Asp Ile Phe Glu Tyr Asp Ile Pro Phe Ala Lys Arg Tyr Leu Ile Asp
    130                 135                 140

Lys Gly Leu Ile Pro Met Glu Gly Glu Glu Leu Lys Ile Leu Ala
145                 150                 155                 160

Phe Asp Ile Glu Thr Leu Tyr His Glu Gly Glu Glu Phe Gly Lys Gly
                165                 170                 175

Pro Ile Ile Met Ile Ser Tyr Ala Asp Glu Asn Glu Ala Lys Val Ile
            180                 185                 190

Thr Trp Lys Asn Ile Asp Leu Pro Tyr Val Glu Val Val Ser Ser Glu
        195                 200                 205

Arg Glu Met Ile Lys Arg Phe Leu Arg Ile Ile Arg Glu Lys Asp Pro
    210                 215                 220

Asp Ile Ile Val Thr Tyr Asn Gly Asp Ser Phe Asp Phe Pro Tyr Leu
225                 230                 235                 240

Ala Lys Arg Ala Glu Lys Leu Gly Ile Lys Leu Thr Ile Gly Arg Asp
                245                 250                 255

Gly Ser Glu Pro Lys Met Gln Arg Ile Gly Asp Met Thr Ala Val Glu
            260                 265                 270

Val Lys Gly Arg Ile His Phe Asp Leu Tyr His Val Ile Thr Arg Thr
        275                 280                 285

Ile Asn Leu Pro Thr Tyr Thr Leu Glu Ala Val Tyr Glu Ala Ile Phe
    290                 295                 300

Gly Lys Pro Lys Glu Lys Val Tyr Ala Asp Glu Ile Ala Lys Ala Trp
305                 310                 315                 320

Glu Ser Gly Glu Asn Leu Glu Arg Val Ala Lys Tyr Ser Met Glu Asp
                325                 330                 335

Ala Lys Ala Thr Tyr Glu Leu Gly Lys Glu Phe Leu Pro Met Glu Ile
            340                 345                 350

Gln Leu Ser Arg Leu Val Gly Gln Pro Leu Trp Asp Val Ser Arg Ser
        355                 360                 365

Ser Thr Gly Asn Leu Val Glu Trp Phe Leu Leu Arg Lys Ala Tyr Glu
    370                 375                 380
```

-continued

Arg Asn Glu Val Ala Pro Asn Lys Pro Ser Glu Glu Tyr Gln Arg
385                 390                 395                 400

Arg Leu Arg Glu Ser Tyr Thr Gly Gly Phe Val Lys Glu Pro Glu Lys
            405                 410                 415

Gly Leu Trp Glu Asn Ile Val Tyr Leu Asp Phe Arg Ala Leu Tyr Pro
        420                 425                 430

Ser Ile Ile Ile Thr His Asn Val Ser Pro Asp Thr Leu Asn Leu Glu
            435                 440                 445

Gly Cys Lys Asn Tyr Asp Ile Ala Pro Gln Val Gly His Lys Phe Cys
        450                 455                 460

Lys Asp Ile Pro Gly Phe Ile Pro Ser Leu Leu Gly His Leu Leu Glu
465                 470                 475                 480

Glu Arg Gln Lys Ile Lys Thr Lys Met Lys Glu Thr Gln Asp Pro Ile
            485                 490                 495

Glu Lys Ile Leu Leu Asp Tyr Arg Gln Lys Ala Ile Lys Leu Leu Ala
        500                 505                 510

Asn Ser Phe Tyr Gly Tyr Tyr Gly Tyr Ala Lys Ala Arg Trp Tyr Cys
            515                 520                 525

Lys Glu Cys Ala Glu Ser Val Thr Ala Trp Gly Arg Lys Tyr Ile Glu
530                 535                 540

Leu Val Trp Lys Glu Leu Glu Glu Lys Phe Gly Phe Lys Val Leu Tyr
545                 550                 555                 560

Ile Asp Thr Asp Gly Leu Tyr Ala Thr Ile Pro Gly Gly Glu Ser Glu
            565                 570                 575

Glu Ile Lys Lys Lys Ala Leu Glu Phe Val Lys Tyr Ile Asn Ser Lys
        580                 585                 590

Leu Pro Gly Leu Leu Glu Leu Glu Tyr Glu Gly Phe Tyr Lys Arg Gly
    595                 600                 605

Phe Phe Val Thr Lys Lys Arg Tyr Ala Val Ile Asp Glu Glu Gly Lys
610                 615                 620

Val Ile Thr Arg Gly Leu Glu Ile Val Arg Arg Asp Trp Ser Glu Ile
625                 630                 635                 640

Ala Lys Glu Thr Gln Ala Arg Val Leu Glu Thr Ile Leu Lys His Gly
            645                 650                 655

Asp Val Glu Glu Ala Val Arg Ile Val Lys Glu Val Ile Gln Lys Leu
        660                 665                 670

Ala Asn Tyr Glu Ile Pro Pro Glu Lys Leu Ala Ile Tyr Glu Gln Ile
    675                 680                 685

Thr Arg Pro Leu His Glu Tyr Lys Ala Ile Gly Pro His Val Ala Val
        690                 695                 700

Ala Lys Lys Leu Ala Ala Lys Gly Val Lys Ile Lys Pro Gly Met Val
705                 710                 715                 720

Ile Gly Tyr Ile Val Leu Arg Gly Asp Gly Pro Ile Ser Asn Arg Ala
            725                 730                 735

Ile Leu Ala Glu Glu Tyr Asp Pro Lys Lys His Lys Tyr Asp Ala Glu
        740                 745                 750

Tyr Tyr Ile Glu Asn Gln Val Leu Pro Ala Val Leu Arg Ile Leu Glu
        755                 760                 765

Gly Phe Gly Tyr Arg Lys Glu Asp Leu Arg Tyr Gln Lys Thr Arg Gln
    770                 775                 780

Val Gly Leu Thr Ser Trp Leu Asn Ile Lys Lys Ser Gly Thr Gly Gly
785                 790                 795                 800

```
Gly Gly Ala Thr Val Lys Phe Lys Tyr Lys Gly Glu Glu Lys Glu Val
                805                 810                 815

Asp Ile Ser Lys Ile Lys Lys Val Trp Arg Val Gly Lys Met Ile Ser
            820                 825                 830

Phe Thr Tyr Asp Glu Gly Gly Lys Thr Gly Arg Gly Ala Val Ser
            835                 840                 845

Glu Lys Asp Ala Pro Lys Glu Leu Leu Gln Met Leu Glu Lys Gln Lys
850                 855                 860

Lys
865

<210> SEQ ID NO 50
<211> LENGTH: 845
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 50

His Met Ile Leu Asp Val Asp Tyr Ile Thr Glu Glu Gly Lys Pro Val
  1               5                  10                  15

Ile Arg Leu Phe Lys Lys Glu Asn Gly Lys Phe Lys Ile Glu His Asp
                 20                  25                  30

Arg Thr Phe Arg Pro Tyr Ile Tyr Ala Leu Leu Arg Asp Asp Ser Lys
             35                  40                  45

Ile Glu Glu Val Lys Lys Ile Thr Gly Glu Arg His Gly Lys Ile Val
         50                  55                  60

Arg Ile Val Asp Val Glu Lys Val Glu Lys Lys Phe Leu Gly Lys Pro
 65                  70                  75                  80

Ile Thr Val Trp Lys Leu Tyr Leu Glu His Pro Gln Asp Val Pro Thr
                 85                  90                  95

Ile Arg Glu Lys Val Arg Glu His Pro Ala Val Val Asp Ile Phe Glu
            100                 105                 110

Tyr Asp Ile Pro Phe Ala Lys Arg Tyr Leu Ile Asp Lys Gly Leu Ile
        115                 120                 125

Pro Met Glu Gly Glu Glu Leu Lys Ile Leu Ala Phe Asp Ile Glu
    130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175

Ile Asp Leu Pro Tyr Val Glu Val Val Ser Ser Glu Arg Glu Met Ile
            180                 185                 190

Lys Arg Phe Leu Arg Ile Ile Arg Glu Lys Asp Pro Asp Ile Ile Val
        195                 200                 205

Thr Tyr Asn Gly Asp Ser Phe Asp Phe Pro Tyr Leu Ala Lys Arg Ala
    210                 215                 220

Glu Lys Leu Gly Ile Lys Leu Thr Ile Gly Arg Asp Gly Ser Glu Pro
225                 230                 235                 240

Lys Met Gln Arg Ile Gly Asp Met Thr Ala Val Glu Val Lys Gly Arg
                245                 250                 255

Ile His Phe Asp Leu Tyr His Val Ile Thr Arg Thr Ile Asn Leu Pro
            260                 265                 270

Thr Tyr Thr Leu Glu Ala Val Tyr Glu Ala Ile Phe Gly Lys Pro Lys
        275                 280                 285
```

-continued

```
Glu Lys Val Tyr Ala Asp Glu Ile Ala Lys Ala Trp Glu Ser Gly Glu
    290                 295                 300
Asn Leu Glu Arg Val Ala Lys Tyr Ser Met Glu Asp Ala Lys Ala Thr
305                 310                 315                 320
Tyr Glu Leu Gly Lys Glu Phe Leu Pro Met Glu Ile Gln Leu Ser Arg
                325                 330                 335
Leu Val Gly Gln Pro Leu Trp Asp Val Ser Arg Ser Ser Thr Gly Asn
            340                 345                 350
Leu Val Glu Trp Phe Leu Leu Arg Lys Ala Tyr Glu Arg Asn Glu Val
        355                 360                 365
Ala Pro Asn Lys Pro Ser Glu Glu Tyr Gln Arg Arg Leu Arg Glu
370                 375                 380
Ser Tyr Thr Gly Gly Phe Val Lys Glu Pro Glu Lys Gly Leu Trp Glu
385                 390                 395                 400
Asn Ile Val Tyr Leu Asp Phe Arg Ala Leu Tyr Pro Ser Ile Ile Ile
                405                 410                 415
Thr His Asn Val Ser Pro Asp Thr Leu Asn Leu Glu Gly Cys Lys Asn
            420                 425                 430
Tyr Asp Ile Ala Pro Gln Val Gly His Lys Phe Cys Lys Asp Ile Pro
        435                 440                 445
Gly Phe Ile Pro Ser Leu Leu Gly His Leu Leu Glu Glu Arg Gln Lys
450                 455                 460
Ile Lys Thr Lys Met Lys Glu Thr Gln Asp Pro Ile Glu Lys Ile Leu
465                 470                 475                 480
Leu Asp Tyr Arg Gln Lys Ala Ile Lys Leu Leu Ala Asn Ser Phe Tyr
                485                 490                 495
Gly Tyr Tyr Gly Tyr Ala Lys Ala Arg Trp Tyr Cys Lys Glu Cys Ala
            500                 505                 510
Glu Ser Val Thr Ala Trp Gly Arg Lys Tyr Ile Glu Leu Val Trp Lys
        515                 520                 525
Glu Leu Glu Glu Lys Phe Gly Phe Lys Val Leu Tyr Ile Asp Thr Asp
530                 535                 540
Gly Leu Tyr Ala Thr Ile Pro Gly Gly Glu Ser Glu Glu Ile Lys Lys
545                 550                 555                 560
Lys Ala Leu Glu Phe Val Lys Tyr Ile Asn Ser Lys Leu Pro Gly Leu
                565                 570                 575
Leu Glu Leu Glu Tyr Glu Gly Phe Tyr Lys Arg Gly Phe Phe Val Thr
            580                 585                 590
Lys Lys Arg Tyr Ala Val Ile Asp Glu Glu Gly Lys Val Ile Thr Arg
        595                 600                 605
Gly Leu Glu Ile Val Arg Arg Asp Trp Ser Glu Ile Ala Lys Glu Thr
610                 615                 620
Gln Ala Arg Val Leu Glu Thr Ile Leu Lys His Gly Asp Val Glu Glu
625                 630                 635                 640
Ala Val Arg Ile Val Lys Glu Val Ile Gln Lys Leu Ala Asn Tyr Glu
                645                 650                 655
Ile Pro Pro Glu Lys Leu Ala Ile Tyr Glu Gln Ile Thr Arg Pro Leu
            660                 665                 670
His Glu Tyr Lys Ala Ile Gly Pro His Val Ala Val Ala Lys Lys Leu
        675                 680                 685
Ala Ala Lys Gly Val Lys Ile Lys Pro Gly Met Val Ile Gly Tyr Ile
690                 695                 700
```

```
Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
            725                 730                 735

Asn Gln Val Leu Pro Ala Val Leu Arg Ile Leu Glu Gly Phe Gly Tyr
        740                 745                 750

Arg Lys Glu Asp Leu Arg Tyr Gln Lys Thr Arg Gln Val Gly Leu Thr
    755                 760                 765

Ser Trp Leu Asn Ile Lys Lys Ser Gly Thr Gly Gly Gly Ala Thr
770                 775                 780

Val Lys Phe Lys Tyr Lys Gly Glu Glu Lys Glu Val Asp Ile Ser Lys
785                 790                 795                 800

Ile Lys Lys Val Trp Arg Val Gly Lys Met Ile Ser Phe Thr Tyr Asp
                805                 810                 815

Glu Gly Gly Gly Lys Thr Gly Arg Gly Ala Val Ser Glu Lys Asp Ala
                820                 825                 830

Pro Lys Glu Leu Leu Gln Met Leu Glu Lys Gln Lys Lys
            835                 840                 845

<210> SEQ ID NO 51
<211> LENGTH: 2606
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ccatgggcca tcatcatcat catcatcatc atcatcacag cagcggccat atcgaaggtc        60
gtcatatgat tttagatgtg gattacataa ctgaagaagg aaaacctgtt attaggctat       120
tcaaaaaaga gaacggaaaa tttaagatag agcatgatag aacttttaga ccatacattt       180
acgctcttct cagggatgat tcaaagattg aagaagttaa gaaaataacg ggggaaaggc       240
atggaaagat tgtgagaatt gttgatgtag agaaggttga gaaaaagttt ctcggcaagc       300
ctattaccgt gtggaaactt tatttggaac atccccaaga tgttcccact attagagaaa       360
aagttagaga acatccagca gttgtggaca tcttcgaata cgatattcca tttgcaaaga       420
gatacctcat cgacaaaggc ctaataccaa tggaggggga agaagagcta aagattcttg       480
ccttcgatat agaaacctc tatcacgaag agaagagtt tggaaaaggc ccaattataa        540
tgattagtta tgcagatgaa aatgaagcaa aggtgattac ttggaaaaac atagatcttc       600
catacgttga ggttgtatca agcgagagag agatgataaa gagatttctc aggattatca       660
gggagaagga tcctgacatt atagttactt ataatggaga ctcattcgac ttcccatatt       720
tagcgaaaag ggcagaaaaa cttgggatta aattaaccat tggaagagat ggaagcgagc       780
ccaagatgca gagaataggc gatatgacgg ctgtagaagt caagggaaga atacatttcg       840
acttgtatca tgtaataaca aggacaataa atctcccaac atacacacta gaggctgtat       900
atgaagcaat ttttggaaag ccaaaggaga aggtatacgc cgacgagata gcaaaagcct       960
gggaaagtgg agagaacctt gagagagttg ccaaatactc gatggaagat gcaaaggcaa      1020
cttatgaact cgggaaagaa ttccttccaa tggaaattca gctttcaaga ttagttggac      1080
aacctttatg ggatgtttca aggtcaagca cagggaacct tgtagagtgg ttcttactta      1140
ggaaagccta cgaagaaac gaagtagctc caaacaagcc aagtgaagag gagtatcaaa       1200
gaaggctcag ggagagctac acaggtggat tcgttaaaga gccagaaaag gggttgtggg      1260
```

```
aaaacatagt ataccctagat tttagagccc tatatccctc gattataatt acccacaatg   1320
tttctcccga tactctaaat cttgagggat gcaagaacta tgatatcgct cctcaagtag   1380
gccacaagtt ctgcaaggac atccctggtt ttataccaag tctcttggga catttgttag   1440
aggaaagaca aaagattaag acaaaaatga aggaaactca agatcctata gaaaaaatac   1500
tccttgacta tagacaaaaa gcgataaaac tcttagcaaa ttctttctac ggatattatg   1560
gctatgcaaa agcaagatgg tactgtaagg agtgtgctga gagcgttact gcctggggaa   1620
gaaagtacat cgagttagta tggaaggagc tcgaagaaaa gtttggattt aaagtcctct   1680
acattgacac tgatggtctc tatgcaacta tcccaggagg agaaagtgag gaaataaaga   1740 aaaggctct agaatttgta aaatacataa attcaaagct ccctggactg ctagagcttg   1800
aatatgaagg gttttataag aggggattct tcgttacgaa gaagaggtat gcagtaatag   1860
atgaagaagg aaaagtcatt actcgtggtt tagagatagt taggagagat tggagtgaaa   1920
ttgcaaaaga aactcaagct agagttttgg agacaatact aaaacacgga gatgttgaag   1980
aagctgtgag aatagtaaaa gaagtaatac aaaagcttgc caattatgaa attccaccag   2040
agaagctcgc aatatatgag cagataacaa gaccattaca tgagtataag gcgataggtc   2100
ctcacgtagc tgttgcaaag aaactagctg ctaaaggagt taaaataaag ccaggaatgg   2160
taattggata catagtactt agaggcgatg gtccaattag caatagggca attctagctg   2220
aggaatacga tcccaaaaag cacaagtatg acgcagaata ttacattgag aaccaggttc   2280
ttccagcggt acttaggata ttggagggat ttggatacag aaaggaagac ctcagatacc   2340
aaaagacaag acaagtcggc ctaacttcct ggcttaacat taaaaaatcc ggtaccggcg   2400
gtggcggtgc aaccgtaaag ttcaagtaca aggcgaagaa aaaagaggta gacatctcca   2460
agatcaagaa agtatggcgt gtgggcaaga tgatctcctt cacctacgac gagggcggtg   2520
gcaagaccgg ccgcggtgcg gtaagcgaaa aggacgcgcc gaaggagctg ctgcagatgc   2580
tggagaagca gaaaaagtaa ctcgag                                       2606
```

<210> SEQ ID NO 52
<211> LENGTH: 672
<212> TYPE: PRT
<213> ORGANISM: Moloney murine leukemia virus

<400> SEQUENCE: 52

```
Met Leu Asn Ile Glu Asp Glu His Arg Leu His Glu Thr Ser Lys Glu
  1               5                  10                  15

Pro Asp Val Ser Leu Gly Ser Thr Trp Leu Ser Asp Phe Pro Gln Ala
                 20                  25                  30

Trp Ala Glu Thr Gly Gly Met Gly Leu Ala Val Arg Gln Ala Pro Leu
             35                  40                  45

Ile Ile Pro Leu Lys Ala Thr Ser Thr Pro Val Ser Ile Lys Gln Tyr
         50                  55                  60

Pro Met Ser Gln Glu Ala Arg Leu Gly Ile Lys Pro His Ile Gln Arg
     65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125
```

```
Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asp Cys Leu
                485                 490                 495

Asp Ile Leu Ala Glu Ala His Gly Thr Arg Ser Asp Leu Thr Asp Gln
            500                 505                 510

Pro Leu Pro Asp Ala Asp His Thr Trp Tyr Thr Asp Gly Ser Ser Phe
        515                 520                 525

Leu Gln Glu Gly Gln Arg Lys Ala Gly Ala Ala Val Thr Thr Glu Thr
    530                 535                 540

Glu Val Ile Trp Ala Arg Ala Leu Pro Ala Gly Thr Ser Ala Gln Arg
```

```
             545                 550                 555                 560
Ala Glu Leu Ile Ala Leu Thr Gln Ala Leu Lys Met Ala Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Gly Leu Leu Thr Ser Glu Gly
                595                 600                 605

Lys Glu Ile Lys Asn Lys Asp Glu Ile Leu Ala Leu Lys Ala Leu
            610                 615                 620

Phe Leu Pro Lys Arg Leu Ser Ile Ile His Cys Pro Gly His Gln Lys
625                 630                 635                 640

Gly Asn Ser Ala Glu Ala Arg Gly Asn Arg Met Ala Asp Gln Ala Ala
                645                 650                 655

Arg Glu Val Ala Thr Arg Glu Thr Pro Gly Thr Ser Thr Leu Leu Ile
                660                 665                 670

<210> SEQ ID NO 53
<211> LENGTH: 1647
<212> TYPE: DNA
<213> ORGANISM: Moloney murine leukemia virus

<400> SEQUENCE: 53
atggagcatc ggctacatga gacctcaaaa gagccagatg tttctctagg gtccacatgg      60
ctgtctgatt ttcctcaggc ctgggcggaa accgggggca tgggactggc agttcgccaa     120
gctcctctga tcatacctct gaaagcaacc tctacccccg tgtccataaa acaataccoc     180 atgtcacaag aagccagact ggggatcaag ccccacatac agagactgtt ggaccaggga     240
atactggtac cctgccagtc ccctggaac acgcccctgc tacccgttaa gaaaccaggg      300
actaatgatt ataggcctgt ccaggatctg agagaagtca caagcgggt ggaagacatc      360 caccccaccg tgcccaaccc ttacaacctc ttgagcgggc tcccaccgtc caccagtgg      420 tacactgtgc ttgatttaaa ggatgccttt ttctgcctga gactccaccc caccagtcag     480
cctctcttcg cctttgagtg gagagatcca gagtgggaa tctcaggaca attgacctgg      540
accagactcc cacagggttt caaaaacagt cccaccctgt tgatgaggc actgcacaga      600 gacctagcag acttccggat ccagcaccca gacttgatcc tgctacagta cgtggatgac     660
ttactgctgg ccgccacttc tgagctagac tgccaacaag gtactcgggc cctgttacaa     720
accctaggga acctcgggta tcgggcctcg gccaagaaag cccaaatttg ccagaaacag     780
gtcaagtatc tggggtatct tctaaaagag ggtcagagat ggctgactga ggccagaaaa     840
gagactgtga tggggcagcc tactccgaag acccctcgac aactaaggga gttcctaggg     900
acggcaggct tctgtcgcct ctggatccct gggtttgcag aaatggcagc cccccttgtac    960 cctctcacca aaacggggac tctgtttaat tggggcccag accaacaaaa ggcctatcaa    1020
gaaatcaagc aagctcttct aactgcccca gccctgggt tgccagattt gactaagccc    1080
tttgaactct ttgtcgacga aagcagggc tacgccaaag cgtcctaac gcaaaagctg     1140 ggaccttggc gtcggccggt ggcctacctg tctaaaaagc tagacccagt ggcagctggc    1200
tggcccccct gcctacggat ggtggcagcc attgcagttc tgacaaaaga tgctggcaag    1260
ctcactatgg gacagccgtt ggtcattctg gcccccatg ccgtagaggc actagttaag     1320
caaccccctg atcgctggct ctccaatgcc cggatgaccc attaccaagc cctgctcctg    1380
gacacggacc gggtccagtt cgggccagta gtggccctaa atccagctac gctgctccct    1440
```

```
ctgcctgagg aggggctgca acatgactgc cttgacatct tggctgaagc ccacggaact    1500
agatcagatc ttacggacca gcccctccca gacgccgacc acacctggta cacggatggg    1560
agcagcttcc tgcaagaagg cagcgtaag gccggagcag cggtgaccac tgagactgag    1620
gtaatctggg ccagggcatt gccagcc                                        1647
```

```
<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Gln Lys Lys
  1

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Thr Gly Gly Gly Gly
  1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Val Thr Ser
  1               5

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtaaaacgac ggccagt                                                    17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gtaaaacgtc ggccagt                                                    17

<210> SEQ ID NO 59
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggaagtacag ctcagagttc tgcagcaccc ctgc                                34

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatgcgaaac tgaggctggc tgtactgtct c                                   31

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cagactggaa ttcaagcgcg agctcgaata agagctactg tt                       42

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
aacagtagct cttattcgag ctcgcgcttg aattccagtc tg                       42

<210> SEQ ID NO 63
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cagacuggaa uucaagcgcg agcucgaaua agagcuacug uu                       42

<210> SEQ ID NO 64
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aacaguagcu cuuauucgag cucgcgcuug aauuccaguc ug                       42

<210> SEQ ID NO 65
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 65
gtaaaacgac ggccagt                                                    17

<210> SEQ ID NO 66
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
guaaaacgac ggccagu                                                    17

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
actggccgtc gttttac                                                    17

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 68

His His His His His His His His His His
  1               5                  10

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Lys Gln Lys
  1
```